(12) United States Patent
Chen et al.

(10) Patent No.: US 8,058,269 B2
(45) Date of Patent: Nov. 15, 2011

(54) OXINDOLE DERIVATIVES

(75) Inventors: Li Chen, Shanghai (CN); Song Yang, Shanghai (CN); Jing Zhang, Parsippany, NJ (US); Zhuming Zhang, Hillsborough, NJ (US)

(73) Assignee: Hoffman-La Roche Inc., Nutley, NJ (US)

( * ) Notice: Subject to any disclaimer, the term of this patent is extended or adjusted under 35 U.S.C. 154(b) by 322 days.

(21) Appl. No.: 11/856,197

(22) Filed: Sep. 17, 2007

(65) Prior Publication Data

US 2008/0081810 A1    Apr. 3, 2008

Related U.S. Application Data

(60) Provisional application No. 60/846,201, filed on Sep. 21, 2006.

(51) Int. Cl.
| | |
|---|---|
| A61K 31/5377 | (2006.01) |
| A61K 31/541 | (2006.01) |
| A61K 31/496 | (2006.01) |
| A61K 31/498 | (2006.01) |
| A61K 31/454 | (2006.01) |
| A61K 31/4178 | (2006.01) |
| A61K 31/404 | (2006.01) |
| C07D 417/04 | (2006.01) |
| C07D 413/12 | (2006.01) |
| C07D 405/12 | (2006.01) |
| C07D 401/04 | (2006.01) |
| C07D 401/14 | (2006.01) |
| C07D 403/12 | (2006.01) |
| C07D 403/04 | (2006.01) |
| C07D 209/34 | (2006.01) |
| C07D 209/38 | (2006.01) |
| C07D 209/401 | (2006.01) |

(52) U.S. Cl. .......... 514/228.2; 514/235.2; 514/249; 514/253.09; 514/254.09; 514/323; 514/397; 514/418; 544/58.1; 544/144; 544/354; 544/364; 544/373; 546/201; 548/312.1; 548/485; 548/486

(58) Field of Classification Search .................. None
See application file for complete search history.

(56) References Cited

U.S. PATENT DOCUMENTS 3,441,570 A * 4/1969 Meyer .................. 548/483

FOREIGN PATENT DOCUMENTS

| EP | 0947511 | 10/1999 |
| WO | WO 00/15657 | 3/2000 |
| WO | WO 2006/136606 | 12/2006 |

OTHER PUBLICATIONS

Hellmann et al. Chemical Abstracts vol. 49, abstract No. 8230 (1955) Abstract for Chemische Berichte vol. 86, pp. 1346-1361 (1953).*
Alarcon-Vargas, D et al, *Carcinogenesis*, 23(4):541-547 (2002) XP002481521.
Hellmann, H et al, Cheische Berichte, ISSN.009-2440, vol. 86, 1346-1361 (1953) XP002481520.
Shigemori, H. et al., Database accession No. 2003:27172, 59(1), Heterocycles, 275-281, Chemical abstracts Service, Columbus, OH XP002481522.

\* cited by examiner

*Primary Examiner* — Emily Bernhardt
(74) *Attorney, Agent, or Firm* — George W. Johnston; Patricia S. Rocha-Tramaloni

(57) ABSTRACT

There is provided compounds of the formula

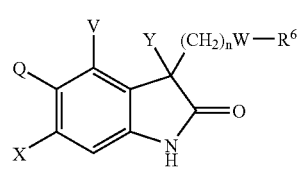

I wherein $R^6$, V, W, X, Y, Q and n are as described. The compounds exhibit activity as anticancer agents.

17 Claims, No Drawings

OXINDOLE DERIVATIVES

PRIORITY TO RELATED APPLICATION(S)

This application claims the benefit of U.S. Provisional Application No. 60/846,201, filed Sep. 21, 2006, which is hereby incorporated by reference in its entirety.

BACKGROUND OF THE INVENTION p53 is a tumor suppresser protein that plays a central role in protection against development of cancer. It guards cellular integrity and prevents the propagation of permanently damaged clones of cells by the induction of growth arrest or apoptosis. At the molecular level, p53 is a transcription factor that can activate a panel of genes implicated in the regulation of cell cycle and apoptosis. p53 is a potent cell cycle inhibitor which is tightly regulated by MDM2 at the cellular level. MDM2 and p53 form a feedback control loop. MDM2 can bind p53 and inhibit its ability to transactivate p53-regulated genes. In addition, MDM2 mediates the ubiquitin-dependent degradation of p53. p53 can activate the expression of the MDM2 gene, thus raising the cellular level of MDM2 protein. This feedback control loop insures that both MDM2 and p53 are kept at a low level in normal proliferating cells. MDM2 is also a cofactor for E2F, which plays a central role in cell cycle regulation.

The ratio of MDM2 to p53 (E2F) is dysregulated in many cancers. Frequently occurring molecular defects in the p16INK4/p19ARF locus, for instance, have been shown to affect MDM2 protein degradation. Inhibition of MDM2-p53 interaction in tumor cells with wild-type p53 should lead to accumulation of p53, cell cycle arrest and/or apoptosis. MDM2 antagonists, therefore, can offer a novel approach to cancer therapy as single agents or in combination with a broad spectrum of other antitumor therapies. The feasibility of this strategy has been shown by the use of different macromolecular tools for inhibition of MDM2-p53 interaction (e.g. antibodies, antisense oligonucleotides, peptides). MDM2 also binds E2F through a conserved binding region as p53 and activates E2F-dependent transcription of cyclin A, suggesting that MDM2 antagonists might have effects in p53 mutant cells.

SUMMARY OF THE INVENTION

The present invention relates to oxindole derivatives which act as antagonists of mdm2 interactions and hence are useful as potent and selective anticancer agents. The present compounds are of the general formula

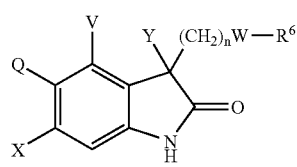

wherein $R^6$, W, X, Y, V, Q and n are as hereinafter described.

DETAILED DESCRIPTION OF THE INVENTION

The present invention relates to compounds of the formula

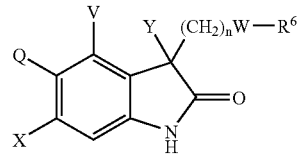

wherein X is selected from the group consisting of hydrogen, halogen, cyano, lower alkyl, lower alkenyl, lower alkynyl, lower alkoxy, nitro, methyl sulfonyl, sulfonamide and cyclopropyl, V is hydrogen, Q is hydrogen or halogen, Y is selected from

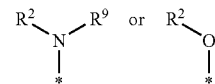

$R^2$ is selected from the group consisting of lower alkyl, substituted lower alkyl, aryl, substituted aryl, heteroaryl, substituted heteroaryl, cycloalkyl, substituted cycloalkyl, cycloalkenyl, substituted alkenyl, heterocycle, substituted heterocycle, $R^6$ is selected from the group consisting of aryl, substituted aryl, heteroaryl, and substituted heteroaryl, $R^9$ is selected from the group consisting of hydrogen, lower alkyl, substituted lower alkyl, lower alkoxy and substituted lower alkoxy, and in the case of $R^2$ and $R^9$ they may independently link to form a cyclic structure selected from substituted or unsubstituted heteroaryl, or substituted or unsubstituted heterocycle, said heteroaryl or heterocycle selected from the group consisting of

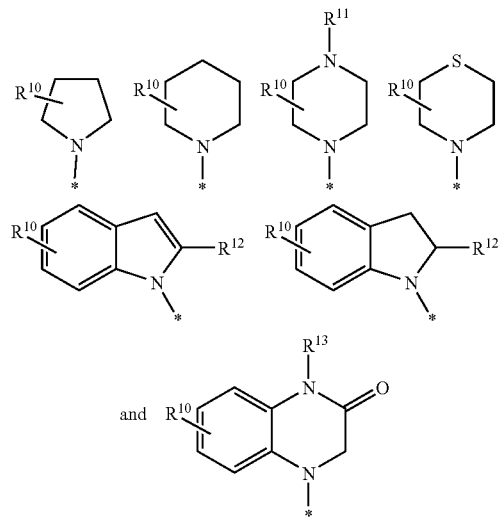

wherein $R^{10}$ is selected from the group consisting of hydrogen, lower alkyl, lower-alkenyl, lower-alkynyl, dioxo-lower-alkylene (forming e.g. a benzodioxyl group), halogen, hydroxy, CN, $CF_3$, $NH_2$, heterocycloalkyl, N(H, lower-alkyl), N(lower-alkyl)$_2$, aminocarbonyl, carboxy, $NO_2$, lower-alkoxy, thio-lower-alkoxy, lower-alkylsulfonyl, aminosulfonyl, lower-alkylcarbonyl, lower-alkylcarbonyloxy, lower-alkoxycarbonyl, lower-alkyl-carbonyl-NH, fluoro-lower-alkyl, fluoro-lower-alkoxy, lower-alkoxy-carbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)$_2$-lower-alkoxy, benzyloxy-lower-alkoxy, mono- or di-lower alkyl substituted amino-sulfonyl and lower-alkyl which can optionally be substituted with halogen, hydroxy, $NH_2$, N(H, lower-alkyl) or N(lower-alkyl)$_2$, $R^{11}$ is selected from the group consisting of hydrogen, lower alkyl, lower-alkenyl, lower-alkynyl, dioxo-lower-alkylene (forming e.g. a benzodioxyl group), hydroxy, CN, $CF_3$, $NH_2$, N(H, lower-alkyl), N(lower-alkyl)$_2$, lower-alkoxy, thio-lower-alkoxy, lower-alkylsulfonyl, aminosulfonyl, lower-alkylcarbonyl, lower-alkylcarbonyloxy, lower-alkoxycarbonyl, fluoro-lower-alkyl, fluoro-lower-alkoxy, lower-alkoxy-carbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)-$_2$-lower-alkoxy, benzyloxy-lower-alkoxy, mono- or di-lower alkyl substituted amino-sulfonyl and lower-alkyl which can optionally be substituted with halogen, hydroxy, $NH_2$, N(H, lower-alkyl) or N(lower-alkyl)$_2$, N(H, lower-alkyl)-carbonyl, N(lower-alkyl)$_2$-carbonyl, $R^{12}$ is selected from the group consisting of hydrogen, lower alkyl, aminocarbonyl, lower-alkylsulfonyl, aminosulfonyl, lower-alkylcarbonyl, lower-alkoxycarbonyl, fluoro-lower-alkyl, N(H, lower-alkyl)-carbonyl, N(lower-alkyl)$_2$-carbonyl, mono- or di-lower alkyl substituted amino-sulfonyl and lower-alkyl which can optionally be substituted with halogen, hydroxy, $NH_2$, N(H, lower-alkyl) or N(lower-alkyl)$_2$, $R^{13}$ is selected from the group consisting of hydrogen, lower alkyl, lower-alkenyl, lower-alkynyl, dioxo-lower-alkylene (forming e.g. a benzodioxyl group), hydroxy, CN, $NH_2$, heterocycloalkyl, N(H, lower-alkyl), N(lower-alkyl)$_2$, lower-alkoxy, thio-lower-alkoxy, lower-alkylcarbonyloxy, fluoro-lower-alkyl, fluoro-lower-alkoxy, lower-alkoxy-carbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)$_2$-lower-alkoxy, benzyloxy-lower-alkoxy, lower-alkyl which can optionally be substituted with halogen, hydroxy, $NH_2$, N(H, lower-alkyl) or N(lower-alkyl)$_2$, N(H, lower-alkyl)-carbonyl, N(lower-alkyl)$_2$-carbonyl, W is O, N or a single bond, n is 1-3 and the pharmaceutically acceptable salts thereof.

Preferred are compounds wherein Y is

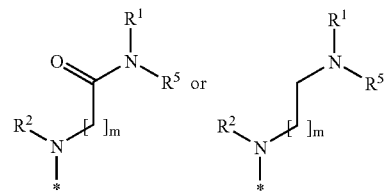

$R^1$ and $R^5$ are independently selected from the group consisting of hydrogen, lower alkyl, substituted lower alkyl, lower alkenyl, substituted lower alkenyl, lower alkynyl, substituted lower alkynyl, lower alkoxy, substituted lower alkoxy, aryl, substituted aryl, heteroaryl, substituted heteroaryl, cycloalkyl, substituted cycloalkyl, cycloalkenyl, substituted cycloalkenyl, heterocycle and substituted heterocycle and in the case of $R^1$ and $R^5$ they may independently link to form a cyclic structure selected from substituted or unsubstituted heteroaryl, substituted or unsubstituted cycloalkyl, substituted or unsubstituted cycloalkenyl or substituted or unsubstituted heterocycle, $R^2$ is selected from lower alkyl, cycloalkyl, phenyl, or substituted cycloalkyl, $R^6$ is a meta halogen substituted phenyl, X is Cl or Br, V is hydrogen, W is a bond, n is 1 and m is 1-3.

Also preferred are compounds wherein Y is

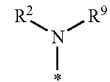

$R^2$ is

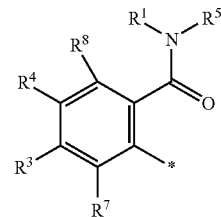

$R^1$ and $R^5$ are independently selected from the group consisting of hydrogen, lower alkyl, substituted lower alkyl, lower alkenyl, substituted lower alkenyl, lower alkynyl, substituted lower alkynyl, lower alkoxy, substituted lower alkoxy, aryl, substituted aryl, heteroaryl, substituted heteroaryl, cycloalkyl, substituted cycloalkyl, cycloalkenyl, substituted cycloalkenyl, heterocycle and substituted heterocycle and in the case of $R^1$ and $R^5$ they may independently link to form a cyclic structure selected from substituted or unsubstituted heteroaryl, substituted or unsubstituted cycloalkyl, substituted or unsubstituted cycloalkenyl or substituted or unsubstituted heterocycle, $R^3$, $R^4$, $R^7$ and $R^8$ are selected from the group consisting of hydrogen, halogen, lower alkyl, lower alkenyl, lower alkynyl, lower alkoxy and cycloalkyl, $R^9$ is hydrogen.
$R^6$ is a meta halogen substituted phenyl,
X is Cl or Br,
V is hydrogen,
W is a bond,
n is 1 and
m is 1-3.

Further preferred of the compounds immediately above are those wherein
$R^7$ is hydrogen
$R^8$ is hydrogen,
$R^3$ is selected from halogen, lower alkyl, lower alkoxy, and
$R^4$ is selected from hydrogen, halogen, lower alkyl and lower alkoxy Especially preferred are compounds of the formula
rac-6-chloro-3-(3-chloro-benzyl)-3-(3-isopropoxy-phenylamino)-1,3-dihydro-indol-2-one,
rac-6-chloro-3-(3-chloro-benzyl)-3-(2,6-difluoro-phenylamino)-1,3-dihydro-indol-2-one,
rac-3-(benzo[1,3]dioxol-5-ylamino)-6-chloro-3-(3-chlorobenzyl)-1,3-dihydro-indol-2-one,
rac-6-chloro-3-(3-chloro-benzyl)-3-(4-fluoro-phenylamino)-1,3-dihydro-indol-2-one,
rac-6-chloro-3-(3-chloro-benzyl)-3-(2,4-difluoro-phenylamino)-1,3-dihydro-indol-2-one,
rac-6-chloro-3-(3-chloro-benzyl)-3-(4-chloro-2-fluoro-phenylamino)-1,3-dihydro-indol-2-one,
rac-3-(4-bromo-2-fluoro-phenylamino)-6-chloro-3-(3-chloro-benzyl)-1,3-dihydro-indol-2-one,
rac-6-chloro-3-(3-chloro-benzyl)-3-(3-ethyl-phenylamino)-1,3-dihydro-indol-2-one,
rac-6-chloro-3-(3-chloro-benzyl)-3-(4-isopropoxy-phenylamino)-1,3-dihydro-indol-2-one,
rac-6-chloro-3-(3-chloro-benzyl)-3-(3,4-difluoro-phenylamino)-1,3-dihydro-indol-2-one,
rac-6-chloro-3-(3-chloro-benzyl)-3-(3-hydroxymethyl-phenylamino)-1,3-dihydro-indol-2-one,
rac-6-chloro-3-(3-chloro-benzyl)-3-(4-difluoromethoxyphenylamino)-1,3-dihydro-indol-2-one,
rac-6-chloro-3-(3-chloro-benzyl)-3-(3-difluoromethoxyphenylamino)-1,3-dihydro-indol-2-one,
rac-6-chloro-3-(3-chloro-benzyl)-3-(4-trifluoromethyl-phenylamino)-1,3-dihydro-indol-2-one,
rac-3-(3-acetyl-phenylamino)-6-chloro-3-(3-chloro-benzyl)-1,3-dihydro-indol-2-one,
rac-6-chloro-3-(3-chloro-benzyl)-3-phenylamino-1,3-dihydro-indol-2-one,
rac-6-chloro-3-(3-chloro-benzyl)-3-(4-methoxy-phenylamino)-1,3-dihydro-indol-2-one,
rac-3-[6-chloro-3-(3-chloro-benzyl)-2-oxo-2,3-dihydro-indol-3-ylamino]-benzonitrile,
rac-6-chloro-3-(3-chloro-benzyl)-3-(3-chloro-phenylamino)-1,3-dihydro-indol-2-one,
rac-3-(4-bromo-2-methyl-phenylamino)-6-chloro-3-(3-chloro-benzyl)-1,3-dihydro-indol-2-one,
rac-6-chloro-3-(3-chloro-benzyl)-3-(5-fluoro-2-methyl-phenylamino)-1,3-dihydro-indol-2-one,
rac-6-chloro-3-(3-chloro-benzyl)-3-(2-trifluoromethyl-phenylamino)-1,3-dihydro-indol-2-one,
rac-6-chloro-3-(3-chloro-benzyl)-3-(2-fluoro-phenylamino)-1,3-dihydro-indol-2-one,
rac-6-chloro-3-(3-chloro-benzyl)-3-(4-fluoro-2-methyl-phenylamino)-1,3-dihydro-indol-2-one,
rac-6-chloro-3-(3-chloro-benzyl)-3-(4-chloro-3-methyl-phenylamino)-1,3-dihydro-indol-2-one,
rac-6-chloro-3-(3-chloro-benzyl)-3-(3,4,5-trifluoro-phenylamino)-1,3-dihydro-indol-2-one,
rac-6-chloro-3-(3-chloro-benzyl)-3-(2-chloro-phenylamino)-1,3-dihydro-indol-2-one,
rac-6-chloro-3-(3-chloro-benzyl)-3-(3-hydroxy-phenylamino)-1,3-dihydro-indol-2-one,
rac-6-chloro-3-(3-chloro-benzyl)-3-(3-methoxy-phenylamino)-1,3-dihydro-indol-2-one,
rac-6-chloro-3-(3-chloro-benzyl)-3-cyclohexylamino-1,3-dihydro-indol-2-one,
rac-6-chloro-3-(3-chloro-benzyl)-3-(2-methyl-pyrrolidin-1-yl)-1,3-dihydro-indol-2-one,
rac-6-chloro-3-(3-chloro-benzyl)-3-cyclobutylamino-1,3-dihydro-indol-2-one,
rac-1-[6-chloro-3-(3-chloro-benzyl)-2-oxo-2,3-dihydrol-indol-3-yl]-piperidine-3-carboxylic acid amide,
rac-6-chloro-3-(3-chloro-benzyl)-3-(3-hydroxy-pyrrolidin-1-yl)-1,3-dihydro-indol-2-one,
rac-6-chloro-3-(3-chloro-benzyl)-3-(isopropyl-methyl-amino)-1,3-dihydro-indol-2-one,
rac-6-chloro-3-(3-chloro-benzyl)-3-[(1R)-hydroxymethyl-2,2-dimethyl-propylamino]-1,3-dihydro-indol-2-one,
rac-1-[6-chloro-3-(3-chloro-benzyl)-2-oxo-2,3-dihydrol-1H-indol-3-yl]-piperidine-4-carboxylic acid amide,
rac-6-chloro-3-(3-chloro-benzyl)-3-[4-(2-fluoro-phenyl)-piperazin-1-yl]-1,3-dihydro-indol-2-one,
rac-6-chloro-3-(3-chloro-benzyl)-3-[4-(3-trifluoromethyl-pyridin-2-yl)-piperazin-1-yl]-1,3-dihydro-indol-2-one,
rac-6-chloro-3-(3-chloro-benzyl)-3-[2-(2-hydroxy-ethoxy)-ethylamino]-1,3-dihydro-indol-2-one,
rac-6-chloro-3-(3-chloro-benzyl)-3-thiomorpholin-4-yl-1,3-dihydro-indol-2-one,
rac-6-chloro-3-(3-chloro-benzyl)-3-cyclopropylamino-1,3-dihydro-indol-2-one,
rac-6-chloro-3-(3-chloro-benzyl)-3-(3-hydroxy-piperidin-1-yl)-1,3-dihydro-indol-2-one,
rac-6-chloro-3-(3-chloro-benzyl)-3-(2-hydroxy-cyclohexylamino)-1,3-dihydro-indol-2-one,
rac-6-chloro-3-(3-chloro-benzyl)-3-(1-hydroxymethyl-2-methyl-propylamino)-1,3-dihydro-indol-2-one,
rac-6-chloro-3-(3-chloro-benzyl)-3-(2-hydroxy-1-hydroxymethyl-1-methyl-ethylamino)-1,3-dihydro-indol-2-one,
rac-(2S)-[6-chloro-3-(3-chloro-benzyl)-2-oxo-2,3-dihydro-1H-indol-3-ylamino]-4-methyl-pentanoic acid tert-butyl ester,
rac-{[6-chloro-3-(3-chloro-benzyl)-2-oxo-2,3-dihydro-1H-indol-3-yl]-phenyl-amino}-acetic acid,
rac-6-chloro-3-(4-chloro-benzyl)-3-cyclohexylamino-1,3-dihydro-indol-2-one,
rac-5-bromo-6-chloro-3-(4-chloro-benzyl)-3-cyclohexylamino-1,3-dihydro-indol-2-one,
rac-6-chloro-3-(4-chloro-benzyl)-3-cyclohexylamino-1-(2-oxo-2-piperidin-1-yl-ethyl)-1,3-dihydro-indol-2-one,
rac-5-bromo-6-chloro-3-(4-chloro-benzyl)-3-cyclohexylamino-1-(2-oxo-2-piperidin-1-yl-ethyl)-1,3-dihydro-indol-2-one,
rac-{[6-chloro-3-(3-chloro-benzyl)-2-oxo-2,3-dihydro-1H-indol-3-yl]-cyclohexyl-amino}-acetic acid ethyl ester,
rac-{[6-chloro-3-(3-chloro-benzyl)-2-oxo-2,3-dihydro-1H-indol-3-yl]-cyclohexyl-amino}-acetic acid,
rac-3-{[2-(4-acetyl-piperazin-1-yl)-2-oxo-ethyl]-cyclohexyl-amino}-6-chloro-3-(3-chloro-benzyl)-1,3-dihydro-indol-2-one,
rac-1-(2-{[6-chloro-3-(3-chloro-benzyl)-2-oxo-2,3-dihydro-1H-indol-3-yl]-cyclohexyl-amino}-acetyl)-1,3-diisopropyl-urea, rac-6-chloro-3-(3-chloro-benzyl)-3-{cyclohexyl-[2-oxo-2-(3-oxo-piperazin-1-yl)-ethyl]-amino}-1,3-dihydro-indol-2-one, rac-6-chloro-3-(3-chloro-benzyl)-3-{cyclohexyl-[2-(4-isopropyl-piperazin-1-yl)-2-oxo-ethyl]-amino}-1,3-dihydro-indol-2-one, rac-6-chloro-3-(3-chloro-benzyl)-3-(cyclohexyl-{2-[4-(3-hydroxy-propyl)-piperazin-1-yl]-2-oxo-ethyl}-amino)-1,3-dihydro-indol-2-one, rac-2-{[6-chloro-3-(3-chloro-benzyl)-2-oxo-2,3-dihydro-1H-indol-3-yl]-cyclohexyl-amino}-N-(2-morpholin-4-yl-ethyl)-acetamide, rac-2-{[6-chloro-3-(3-chloro-benzyl)-2-oxo-2,3-dihydro-1H-indol-3-yl]-cyclohexyl-amino}-N-[2-(3H-imidazol-4-yl)-ethyl]-acetamide, rac-2-{[6-chloro-3-(3-chloro-benzyl)-2-oxo-2,3-dihydro-1H-indol-3-yl]-cyclohexyl-amino}-N-cyclobutyl-acetamide, rac-2-{[6-chloro-3-(3-chloro-benzyl)-2-oxo-2,3-dihydro!-1H-indol-3-yl]-cyclohexyl-amino}-N-(1,1-dimethyl-propyl)-acetamide, rac-2-{[6-chloro-3-(3-chloro-benzyl)-2-oxo-2,3-dihydro-1H-indol-3-yl]-cyclohexyl-amino}-N-(2-dimethylamino-1-methyl-ethyl)-acetamide, rac-2-{[6-chloro-3-(3-chloro-benzyl)-2-oxo-2,3-dihydro-1H-indol-3-yl]-cyclohexyl-amino}-N-piperidin-1-yl-acetamide, rac-2-{[6-chloro-3-(3-chloro-benzyl)-2-oxo-2,3-dihydro-1H-indol-3-yl]-cyclohexyl-amino}-N-furan-2-ylmethyl-acetamide, rac-2-{[6-chloro-3-(3-chloro-benzyl)-2-oxo-2,3-dihydro-1H-indol-3-yl]-cyclohexyl-amino}-N-(2-hydroxy-1,1-dimethyl-ethyl)-acetamide, rac-6-chloro-3-(3-chloro-benzyl)-3-[cyclohexyl-(2-oxo-2-piperazin-1-yl-ethyl)-amino]-1,3-dihydro-indol-2-one, rac-(2R)-[6-chloro-3-(3-chloro-benzyl)-2-oxo-2,3-dihydro-1H-indol-3-ylamino]-3-methyl-butyric acid, rac-1-(2-{[6-chloro-3-(3-chloro-benzyl)-2-oxo-2,3-dihydro-1H-indol-3-yl]-phenyl-amino}-acetyl)-piperidine-4-carboxylic acid amide, rac-6-chloro-3-(3-chloro-benzyl)-3-{[2-(4-hydroxy-piperidin-1-yl)-2-oxo-ethyl]-phenyl-amino}-1,3-dihydro-indol-2-one, rac-2-{[6-chloro-3-(3-chloro-benzyl)-2-oxo-2,3-dihydro-1H-indol-3-yl]-phenyl-amino}-N-(4-hydroxy-cyclohexyl)-acetamide, rac-6-chloro-3-(3-chloro-benzyl)-3-({2-[4-(2-hydroxy-ethyl)-piperazin-1-yl]-2-oxo-ethyl}-phenyl-amino)-1,3-dihydro-indol-2-one, rac-6-chloro-3-(3-chloro-benzyl)-3-{[2-(3-hydroxy-pyrrolidin-1-yl)-2-oxo-ethyl]-phenyl-amino}-1,3-dihydro-indol-2-one, rac-2-{[6-chloro-3-(3-chloro-benzyl)-2-oxo-2,3-dihydro-1H-indol-3-yl]-phenyl-amino}-N-(2-hydroxy-ethyl)-acetamide, rac-{(2S)-[6-chloro-3-(3-chloro-benzyl)-2-oxo-2,3-dihydro-1H-indol-3-ylamino]-4-methyl-pentanoyl}-piperidine-4-carboxylic acid amide, rac-6-chloro-3-(3-chloro-benzyl)-3-[(1S)-(3-hydroxy-pyrrolidine-1-carbonyl)-3-methyl-butylamino]-1,3-dihydro-indol-2-one, rac-6-chloro-3-(3-chloro-benzyl)-3-{(1S)-[4-(2-hydroxy-ethyl)-piperazine-1-carbonyl]-3-methyl-butylamino}-1,3-dihydro-indol-2-one, rac-(2S)-[6-chloro-3-(3-chloro-benzyl)-2-oxo-2,3-dihydro-1H-indol-3-ylamino]-4-methyl-pentanoic acid (2-hydroxy-ethyl)-amide, rac-6-chloro-3-(3-chloro-benzyl)-3-[(1S)-(4-hydroxy-piperidine-1-carbonyl)-3-methyl-butylamino]-1,3-dihydro-indol-2-one, rac-2-{[6-chloro-3-(3-chloro-benzyl)-2-oxo-2,3-dihydro-1H-indol-3-yl]-cyclohexyl-amino}-N-cyclohexyl-acetamide, rac-2-{[6-chloro-3-(3-chloro-benzyl)-2-oxo-2,3-dihydro-1H-indol-3-yl]-cyclohexyl-amino}-N-phenyl-acetamide, rac-N-tert-butyl-2-{[6-chloro-3-(3-chloro-benzyl)-2-oxo-2,3-dihydro-1H-indol-3-yl]-cyclohexyl-amino}-acetamide rac-2-{[6-chloro-3-(3-chloro-benzyl)-2-oxo-2,3-dihydro-1H-indol-3-yl]-cyclohexyl-amino}-N-cyclopropyl-acetamide, rac-(2S)-[6-chloro-3-(3-chloro-benzyl)-2-oxo-2,3-dihydro-1H-indol-3-ylamino]-4-methyl-pentanoic acid methyl ester, rac-6-chloro-3-(3-chloro-benzyl)-3-[4-(4-trifluoromethyl-phenyl)-piperazin-1-yl]-1,3-dihydro-indol-2-one, rac-6-chloro-3-(3-chloro-benzyl)-3-[4-(3-chloro-phenyl)-piperazin-1-yl]-1,3-dihydro-indol-2-one, rac-6-chloro-3-(3-chloro-benzyl)-3-(4-phenyl-piperazin-1-yl)-1,3-dihydro-indol-2-one, rac-2-{[6-chloro-3-(3-chloro-benzyl)-2-oxo-2,3-dihydro-1H-indol-3-yl]-phenyl-amino}-N-cyclohexy -acetamide, rac-2-{[6-chloro-3-(3-chloro-benzyl)-2-oxo-2,3-dihydro-1H-indol-3-yl]-phenyl-amino}-N-isopropoyl -acetamide, rac-2-{[6-chloro-3-(3-chloro-benzyl)-2-oxo-2,3-dihydro-1H-indol-3-yl]-phenyl-amino}-N-cyclopentyl -acetamide, rac-2-{[6-chloro-3-(3-chloro-benzyl)-2-oxo-2,3-dihydro-1H-indol-3-yl]-phenyl-amino}-N-cyclopropyl -acetamide, rac-2-{[6-chloro-3-(3-chloro-benzyl)-2-oxo-2,3-dihydro-1H-indol-3-yl]-phenyl-amino}-N-phenyl -acetamide, rac-6-chloro-3-(3-chloro-benzyl)-3-({2-[4-(3-hydroxy-propyl)-piperazin-1-yl]-2-oxo-ethyl}-phenyl-amino)-1,3-dihydro-indol-2-one, rac-2-{[6-chloro-3-(3-chloro-benzyl)-2-oxo-2,3-dihydro-1H-indol-3-yl]-phenyl-amino}-N-cyclobutyl -acetamide, rac-2-{[6-chloro-3-(3-chloro-benzyl)-2-oxo-2,3-dihydro-1H-indol-3-yl]-phenyl-amino}-N-[2-(3H-imidazol-4-yl)-ethyl]-acetamide, rac-4-(2-{[6-chloro-3-(3-chloro-benzyl)-2-oxo-2,3-dihydro-1H-indol-3-yl]-phenyl-amino}-acetyl)-piperazine-1-carboxylic acid tert-butyl ester, rac-2-{[6-chloro-3-(3-chloro-benzyl)-2-oxo-2,3-dihydro-1H-indol-3-yl]-phenyl-amino}-N-piperidin-1-yl-acetamide, rac-(2S)-[6-chloro-3-(3-chloro-benzyl)-2-oxo-2,3-dihydro-1H-indol-3-ylamino]-N-(4-hydroxy-cyclohexyl)-3-phenyl-propionamide, rac-(2S)-[6-chloro-3-(3-chloro-benzyl)-2-oxo-2,3-dihydro-1H-indol-3-ylamino]-N-(2-hydroxy-ethyl)-3-phenyl-propionamide, rac-6-chloro-3-(3-chloro-benzyl)-3-[(2-oxo-2-piperazin-1-yl-ethyl)-phenyl-amino]-1,3-dihydro-indol-2-one, rac-6-chloro-3-(3-chloro-benzyl)-3-piperazin-1-yl-1,3-dihydro-indol-2-one, rac-3-(4-benzenesulfonyl-piperazin-1-yl)-6-chloro-3-(3-chloro-benzyl)-1,3-dihydro-indol-2-one, rac-6-chloro-3-(3-chloro-benzyl)-3-[4-(thiophene-2-sulfonyl)-piperazin-1-yl]-1,3-dihydro-indol-2-one, rac-2-[6-chloro-3-(3-chloro-benzyl)-2-oxo-2,3-dihydro-1H-indol-3-ylamino]-benzoic acid, rac-1-[6-chloro-3-(3-chloro-benzyl)-2-oxo-2,3-dihydro-1H-indol-3-yl]-piperidine-3-carboxylic acid, rac-6-chloro-3-(3-chloro-benzyl)-3-[3-(4-methyl-piperazine-1-carbonyl)-phenylamino]-1,3-dihydro-indol-2-one,
rac-3-[3-(4-acetyl-piperazine-1-carbonyl)-phenylamino]-6-chloro-3-(3-chloro-benzyl)-1,3-dihydro-indol-2-one,
rac-6-chloro-3-(3-chloro-benzyl)-3-{2-[4-(2-hydroxyethyl)-piperazine-1-carbonyl]-phenylamino}-1,3-dihydro-indol-2-one,
rac-3-[2-(4-acetyl-piperazine-1-carbonyl)-phenylamino]-6-chloro-3-(3-chloro-benzyl)-1,3-dihydro-indol-2-one,
rac-1-{1-[6-Chloro-3-(3-chloro-benzyl)-2-oxo-2,3-dihydro-1H-indol-3-yl]-piperidine-3-carbonyl}-piperidine-4-carboxylic acid amide,
rac-3-[3-(4-acetyl-piperazine-1-carbonyl)-piperidin-1-yl]-6-chloro-3-(3-chloro-benzyl)-1,3-dihydro-indol-2-one,
rac-6-chloro-3-(3-chloro-benzyl)-3-[3-(morpholine-4-carbonyl)-piperidin-1-yl]-1,3-dihydro-indol-2-one,
rac-6-chloro-3-(3-chloro-benzyl)-3-{3-[4-(2-hydroxyethyl)-piperazine-1-carbonyl]-phenylamino}-1,3-dihydro-indol-2-one,
rac-6-chloro-3-(3-chloro-benzyl)-3-[3-(4-methyl-piperazine-1-carbonyl)-piperidin-1-yl]-1,3-dihydro-indol-2-one,
rac-6-chloro-3-(3-chloro-benzyl)-3-{3-[4-(2-hydroxyethyl)-piperazine-1-carbonyl]-piperidin-1-yl}-1,3-dihydro-indol-2-one,
rac-6-chloro-3-(3-chloro-benzyl)-3-[2-(morpholine-4-carbonyl)-phenylamino]-1,3-dihydro-indol-2-one,
rac-6-(4-{1-[6-chloro-3-(3-chloro-benzyl)-2-oxo-2,3-dihydro-1H-indol-3-yl]-piperidine-3-carbonyl}-piperazin-1-yl)-nicotinonitrile,
rac-6-chloro-3-(3-chloro-benzyl)-3-[3-(4-pyridin-2-yl-piperazine-1-carbonyl)-piperidin-1-yl]-1,3-dihydro-indol-2-one,
rac-6-chloro-3-(3-chloro-benzyl)-3-[3-(4-pyrimidin-2-yl-piperazine-1-carbonyl)-piperidin-1-yl]-1,3-dihydro-indol-2-one,
rac-6-chloro-3-(3-chloro-benzyl)-3-{3-[4-(3-hydroxy-propyl)-piperazine-1-carbonyl]-piperidin-1-yl}-1,3-dihydro-indol-2-on,
rac-1-[6-chloro-3-(3-chloro-benzyl)-2-oxo-2,3-dihydro-1H-indol-3-yl]-piperidine-3-carboxylic acid (2-hydroxy-1-hydroxymethyl-ethyl)-amide,
rac-1-[6-chloro-3-(3-chloro-benzyl)-2-oxo-2,3-dihydro-1H-indol-3-yl]-piperidine-3-carboxylic acid (2-morpholin-4-yl-ethyl)-amide,
rac-({1-[6-chloro-3-(3-chloro-benzyl)-2-oxo-2,3-dihydro-1H-indol-3-yl]-piperidine-3-carbonyl}-amino)-acetic acid ethyl ester,
rac-1-{2-[6-chloro-3-(3-chloro-benzyl)-2-oxo-2,3-dihydro-1H-indol-3-ylamino]-benzoyl}-piperidine-4-carboxylic acid amide,
rac-1-{3-[6-chloro-3-(3-chloro-benzyl)-2-oxo-2,3-dihydro-1H-indol-3-ylamino]-benzoyl}-piperidine-4-carboxylic acid amide,
rac-6-chloro-3-(3-chloro-benzyl)-3-{3-[4-(2-methoxyethyl)-piperazine-1-carbonyl]-phenylamino}-1,3-dihydro-indol-2-one,
rac-6-chloro-3-(3-chloro-benzyl)-3-[3-(morpholine-4-carbonyl)-phenylamino]-1,3-dihydro-indol-2-one,
rac-(4-methyl-piperazine-1-carboxylic acid{1-[6-chloro-3-(3-chloro-benzyl)-2-oxo-2,3-dihydro-1H-indol-3-yl]-piperidin-(3S)-yl}-amide,
rac-4-(2-hydroxy-ethyl)-piperazine-1-carboxylic acid{1-[6-chloro-3-(3-chloro-benzyl)-2-oxo-2,3-dihydro-1H-indol-3-yl]-piperidin-(3S)-yl}-amide,
rac-morpholine-4-carboxylic acid{1-[6-chloro-3-(3-chloro-benzyl)-2-oxo-2,3-dihydro-1H-indol-3-yl]-piperidin-(3S)-yl}-amide,
rac-4-(2-methoxy-ethyl)-piperazine-1-carboxylic acid{1-[6-chloro-3-(3-chloro-benzyl)-2-oxo-2,3-dihydro-1H-indol-3-yl]-piperidin-(3S)-yl}-amide,
rac-4-acetyl-piperazine-1-carboxylic acid{1-[6-chloro-3-(3-chloro-benzyl)-2-oxo-2,3-dihydro-1H-indol-3-yl]-piperidin-(3S)-yl}-amide,
rac-6-chloro-3-(3-chloro-benzyl)-3-(cyclopropylmethyl-amino)-1,3-dihydro-indol-2-one,
rac-6-chloro-3-(3-chloro-benzyl)-3-[cyclohexyl-(2-morpholin-4-yl-2-oxo-ethyl)-amino]-1,3-dihydro-indol-2-one,
rac-6-chloro-3-(3-chloro-benzyl)-3-{cyclohexyl-[2-(4-methyl-piperazin-1-yl)-2-oxo-ethyl]-amino}-1,3-dihydro-indol-2-one,
rac-1-(2-{[6-chloro-3-(3-chloro-benzyl)-2-oxo-2,3-dihydro-1H-indol-3-yl]-cyclohexyl-amino}-acetyl)-piperidine-4-carboxylic acid amide,
rac-6-chloro-3-(3-chloro-benzyl)-3-(cyclohexyl-{2-[4-(2-hydroxy-ethyl)-piperazin-1-yl]-2-oxo-ethyl}-amino)-1,3-dihydro-indol-2-one,
rac-6-chloro-3-(3-chloro-benzyl)-3-(cyclohexyl-{2-[4-(2-methoxy-ethyl)-piperazin-1-yl]-2-oxo-ethyl}-amino)-1,3-dihydro-indol-2-one,
rac-4-chloro-2-[6-chloro-3-(3-chloro-benzyl)-2-oxo-2,3-dihydro-1H-indol-3-ylamino]-benzoic acid,
rac-6-chloro-3-(3-chloro-benzyl)-3-[5-chloro-2-(morpholine-4-carbonyl)-phenylamino]-1,3-dihydro-indol-2-one,
rac-1-{4-chloro-2-[6-chloro-3-(3-chloro-benzyl)-2-oxo-2,3-dihydro-1H-indol-3-ylamino]-benzoyl}-piperidine-4-carboxylic acid amide,
rac-6-chloro-3-(3-chloro-benzyl)-3-[5-chloro-2-(4-methyl-piperazine-1-carbonyl)-phenylamino]-1,3-dihydro-indol-2-one,
rac-6-chloro-3-(3-chloro-benzyl)-3-{5-chloro-2-[4-(2-hydroxy-ethyl)-piperazine-1-carbonyl]-phenylamino}-1,3-dihydro-indol-2-one,
rac-6-chloro-3-(3-chloro-benzyl)-3-{5-chloro-2-[4-(2-methoxy-ethyl)piperazine-1-carbonyl]-phenylamino}-1,3-dihydro-indol-2-one,
rac-3-[2-(4-acetyl-piperazine-1-carbonyl)-5-chloro-phenylamino]-6-chloro-3-(3-chloro-benzyl)-1,3-dihydro-indol-2-one,
rac-6-chloro-3-(3-chloro-benzyl)-3-[(2-hydroxy-ethyl)-phenyl-amino]-1,3-dihydro-indol-2-one,
rac-2-{[6-chloro-3-(3-chloro-benzyl)-2-oxo-2,3-dihydro-1H-indol-3-yl]-phenyl-amino}-acetamide,
rac-[[6-chloro-3-(3-chloro-benzyl)-2-oxo-2,3-dihydro-1-H-indol-3-yl]-(3-methoxy-phenyl)-amino]-acetic acid ethyl ester,
rac-6-Chloro-3-(3-chloro-benzyl)-3-[4-(2-ethoxy-phenyl)-piperazin-1-yl]-1,3-dihydro-indol-2-one,
rac-2-[6-Chloro-3-(3-chloro-benzyl)-2-oxo-2,3-dihydro-1H-indol-3-ylamino]-4,5-difluoro-benzoic acid,
rac-2-[6-Chloro-3-(3-chloro-benzyl)-2-oxo-2,3-dihydro-1H-indol-3-ylamino]-4,5-dimethoxyl-benzoic acid,
rac-2-[6-Chloro-3-(3-chloro-benzyl)-2-oxo-2,3-dihydro-1H-indol-3-ylamino]-4-methoxyl-benzoic acid,
rac-6-Chloro-3-(3-chloro-benzyl)-3-[4,5-difluoro-2-(morpholine-4-carbonyl)-phenylamino]-1,3-dihydro-indol-2-one,
rac-6-Chloro-3-(3-chloro-benzyl)-3-[4,5-dimethoxy-2-(morpholine-4-carbonyl)-phenylamino]-1,3-dihydro-indol-2-one, rac-6-Chloro-3-(3-chloro-benzyl)-3-[4-methoxy-2-(morpholine-4-carbonyl)-phenylamino]-1,3-dihydro-indol-2-one,
rac-2-[6-Chloro-3-(3-chloro-benzyl)-2-oxo-2,3-dihydro-1H-indol-3-ylamino]-4,5-difluoro-N,N!-dimethyl-benzamide,
rac-2-[6-Chloro-3-(3-chloro-benzyl)-2-oxo-2,3-dihydro-1H-indol-3-ylamino]-4,5-difluoro-N-methyl-benzamide,
rac-2-[6-Chloro-3-(3-chloro-benzyl)-2-oxo-2,3-dihydro-1H-indol-3-ylamino]-4,5-difluoro-N-(2-morpholin-4-yl-ethyl)-benzamide,
rac-2-[6-Chloro-3-(3-chloro-benzyl)-2-oxo-2,3-dihydro-1H-indol-3-ylamino]-4,5-difluoro-N-(2-morpholin-4-yl-propyl)-benzamide,
rac-4-Chloro-2-[6-chloro-3-(3-chloro-benzyl)-2-oxo-2,3-dihydro-1H-indol-3-ylamino]-N-cyclobutyl-benzamide,
rac-1-[6-Chloro-3-(3-chloro-benzyl)-2-oxo-2,3-dihydro-1H-indol-3-yl]-piperidine-3-carboxylic acid cyclobutylamide,
rac-6-Methoxy-2,3-dihydro-1H-indole-2-carboxylic acid ethyl ester,
rac-6'-Chloro-3'-(3-chloro-benzyl)-6-methoxy-2'-oxo-2,3,2',3'-tetrahydro-1'H-[1,3']biindolyl-2-carboxylic acid ethyl ester,
rac-6'-Chloro-3'-(3-chloro-benzyl)-6-methoxy-2'-oxo-2,3,2',3'-tetrahydro-1'H-[1,3']biindolyl-2-carboxylic acid,
rac-6,6'-Dichloro-3'-(3-chloro-benzyl)-2-(morpholine-4-carbonyl)-2,3,1',3'-tetrahydro-[1,3']biindolyl-2'-one,
rac-6,6'-Dichloro-3'-(3-chloro-benzyl)-2'-oxo-2,3,2',3'-tetrahydro-1'H-[1,3']biindolyl-2-carboxylic acid cyclobutylamide,
rac-2-(4-Acetyl-piperazine-1-carbonyl)-6,6'-dichloro-3'-(3-chloro-benzyl)-2,3,1',3'-tetrahydro-[1,3']biindolyl-2'-one,
rac-6,6'-Dichloro-3'-(3-chloro-benzyl)-2'-oxo-2',3'-dihydro-1'H-[1,3']biindolyl-2-carboxylic acid cyclobutylamide,
rac-2-(4-Acetyl-piperazine-1-carbonyl)-6,6'-dichloro-3'-(3-chloro-benzyl)-1',3'-dihydro-[1,3']biindolyl-2'-one,
rac-2-[6-Chloro-3-(3-chloro-benzyl)-2-oxo-2,3-dihydro-1H-indol-3-ylamino]-4-ethynyl-benzoic acid,
rac-4-Bromo-2-[6-chloro-3-(3-chloro-benzyl)-2-oxo-2,3-dihydro-1H-indol-3-ylamino]-benzoic acid,
rac-3-[5-Bromo-2-(morpholine-4-carbonyl)-phenylamino]-6-chloro-3-(3-chloro-benzyl)-1,3-dihydro-indol-2-one,
rac-6-Chloro-3-(3-chloro-benzyl)-3-[5-ethynyl-2-(morpholine-4-carbonyl)-phenylamino]-1,3-dihydro-indol-2-one,
rac-2-[6-Chloro-3-(3-chloro-benzyl)-2-oxo-2,3-dihydro-1H-indol-3-yloxy]-3-isopropyl-benzoic acid,
rac-3-[2-(4-Acetyl-piperazine-1-carbonyl)-5-ethynyl-phenylamino]-6-chloro-3-(3-chloro-benzyl)-1,3-dihydro-indol-2-one,
rac-3-[2-(4-Acetyl-piperazine-1-carbonyl)-5-bromo-phenylamino]-6-chloro-3-(3-chloro-benzyl)-1,3-dihydro-indol-2-one,
rac-6-Chloro-3-(3-chloro-benzyl)-3-[2-isopropyl-6-(morpholine-4-carbonyl)-phenoxy]-1,3-dihydro-indol-2-one,
rac-3-[2-(4-Acetyl-piperazine-1-carbonyl)-6-isopropyl-phenoxy]-6-chloro-3-(3-chloro-benzyl)-1,3-dihydro-indol-2-one,
rac-6-Chloro-3-(3-chloro-benzyl)-3-[3-(morpholine-4-sulfonyl)-phenylamino]-1,3-dihydro-indol-2-one,
rac-4-{4-Chloro-2-[6-chloro-3-(3-chloro-benzyl)-2-oxo-2,3-dihydro-1H-indol-3-ylamino]-benzenesulfonylamino}-piperidine-1-carboxylic acid tert-butyl ester,
rac-4-Chloro-2-[6-chloro-3-(3-chloro-benzyl)-2-oxo-2,3-dihydro-1H-indol-3-yloxy]-benzoic acid,
rac-4-{4-Bromo-2-[6-chloro-3-(3-chloro-benzyl)-2-oxo-2,3-dihydro-1H-indol-3-ylamino]-benzoylamino}-piperidine-1-carboxylic acid tert-butyl ester,
rac-6-Chloro-3-(3-chloro-benzyl)-3-[5-chloro-2-(morpholine-4-carbonyl)-phenoxy]-1,3-dihydro-indol-2-one,
rac-3-[2-(4-Acetyl-piperazine-1-carbonyl)-5-chloro-phenoxy]-6-chloro-3-(3-chloro-benzyl)-1,3-dihydro-indol-2-one,
rac-4-Bromo-2-[6-chloro-3-(3-chloro-benzyl)-2-oxo-2,3-dihydro-1H-indol-3-ylamino]-N-piperidin-4-yl-benzamide,
rac-4-Bromo-2-[6-chloro-3-(3-chloro-benzyl)-2-oxo-2,3-dihydro-1H-indol-3-ylamino]-N-(3-morpholin-4-yl-propyl)-benzamide,
rac-2-{[6-Chloro-3-(3-chloro-benzyl)-2-oxo-2,3-dihydro-1H-indol-3-yl]-isopropyl-amino}-acetamide,
rac-3-[(2-Amino-ethyl)-isopropyl-amino]-6-chloro-3-(3-chloro-benzyl)-1,3-dihydro-indol-2-one
rac-N-(2-{[6-Chloro-3-(3-chloro-benzyl)-2-oxo-2,3-dihydro-1H-indol-3-yl]-isopropyl-amino}-ethyl)-methanesulfonamide,
rac-N-(2-{[6-Chloro-3-(3-chloro-benzyl)-2-oxo-2,3-dihydro-1H-indol-3-yl]-isopropyl-amino}-ethyl)-acetamide,
rac-3-(2-{[6-Chloro-3-(3-chloro-benzyl)-2-oxo-2,3-dihydro-1H-indol-3-yl]-isopropyl-amino}-ethyl)-1,1-dimethyl-urea,
rac-4-Acetyl-piperazine-1-carboxylic acid (2-{[6-chloro-3-(3-chloro-benzyl)-2-oxo-2,3-dihydro-1H-indol-3-yl]-isopropyl-amino}-ethyl)-amide,
rac-Morpholine-4-carboxylic acid (2-{[6-chloro-3-(3-chloro-benzyl)-2-oxo-2,3-dihydro-1H-indol-3-yl]-isopropyl-amino}-ethyl)-amide,
rac-Cyclobutanecarboxylic acid (2-{[6-chloro-3-(3-chloro-benzyl)-2-oxo-2,3-dihydro-1H-indol-3-yl]-isopropyl-amino}-ethyl)-amide,
rac-1-Acetyl-piperidine-4-carboxylic acid (2-{[6-chloro-3-(3-chloro-benzyl)-2-oxo-2,3-dihydro-1H-indol-3-yl]-isopropyl-amino}-ethyl)-amide,
rac-N-(2-Acetylamino-ethyl)-2-[6-chloro-3-(3-chloro-benzyl)-2-oxo-2,3-dihydro-1H-indol-3-ylamino]-4-methoxy-benzamide,
rac-2-[6-Chloro-3-(3-chloro-benzyl)-2-oxo-2,3-dihydro-1H-indol-3-ylamino]-N-(3-dimethylamino-propyl)-4-methoxy-benzamide,
rac-6-Chloro-3-(3-chloro-benzyl)-3-[5-methoxy-2-(morpholine-4-carbonyl)-phenylamino]-1,3-dihydro-indol-2-one,
rac-N-(2-Acetylamino-ethyl)-2,4-dichloro-6-[6-chloro-3-(3-chloro-benzyl)-2-oxo-2,3-dihydro-1H-indol-3-ylamino]-benzamide,
rac-2,4-Dichloro-6-[6-chloro-3-(3-chloro-benzyl)-2-oxo-2,3-dihydro-1H-indol-3-ylamino]-N-(3-dimethylamino-propyl)-benzamide,
rac-6-Chloro-3-(3-chloro-benzyl)-3-[3,5-dichloro-2-(morpholine-4-carbonyl)-phenylamino]-1,3-dihydro-indol-2-one,
rac-3-Chloro-2-[6-chloro-3-(3-chloro-benzyl)-2-oxo-2,3-dihydro-1H-indol-3-ylamino]-N-cyclohexyl-benzamide,
rac-3-Chloro-2-[6-chloro-3-(3-chloro-benzyl)-2-oxo-2,3-dihydro-1H-indol-3-ylamino]-N-cyclobutyl-benzamide,
rac-6-Chloro-3-(3-chloro-benzyl)-3-{2-chloro-6-[4-(2-hydroxy-ethyl)-piperazine-1-carbonyl]-phenylamino}-1,3-dihydro-indol-2-one,
rac-2-[6-Chloro-3-(3-chloro-benzyl)-2-oxo-2,3-dihydro-1H-indol-3-ylamino]-N -cyclohexyl-3-methoxy-benzamide, rac-2-[6-Chloro-3-(3-chloro-benzyl)-2-oxo-2,3-dihydro-1H-indol-3-ylamino]-N-cyclobutyl-3-methoxy-benzamide,
rac-6-Chloro-3-(3-chloro-benzyl)-3-{2-[4-(2-hydroxy-ethyl)-piperazine-1-carbonyl]-6-methoxy-phenylamino}-1,3-dihydro-indol-2-one,
rac-1-{2-[6-Chloro-3-(3-chloro-benzyl)-2-oxo-2,3-dihydro-1H-indol-3-ylamino]-3-methoxy-benzoyl}-piperidine-4-carboxylic acid amide,
rac-1-{2-[[6-Chloro-3-(3-chloro-benzyl)-2-oxo-2,3-dihydro-1H-indol-3-yl]-(3-chloro-phenyl)-amino]-acetyl}-piperidine-4-carboxylic acid amide,
rac-6-Chloro-3-(3-chloro-benzyl)-3-((3-chloro-phenyl)-{2-[4-(2-hydroxy-ethyl)-piperazin-1-yl]-2-oxo-ethyl}-amino)-1,3-dihydro-indol-2-one,
rac-1-{2-[[6-Chloro-3-(3-chloro-benzyl)-2-oxo-2,3-dihydro-1H-indol-3-yl]-(1-ethyl-propyl) -amino]-acetyl}-piperidine-4-carboxylic acid amide,
rac-1-(2-{[6-Chloro-3-(3-chloro-benzyl)-2-oxo-2,3-dihydro-1H-indol-3-yl]-isopropyl-amino}-acetyl)-piperidine-4-carboxylic acid amide,
rac-2-[[6-Chloro-3-(3-chloro-benzyl)-2-oxo-2,3-dihydro-1H-indol-3-yl]-(1-ethyl-propyl)-amino]-N-cyclobutyl-acetamide,
rac-6-Chloro-3-(3-chloro-benzyl)-3-({2-[4-(2-hydroxy-ethyl)-piperazin-1-yl]-2-oxo-ethyl}-isopropyl-amino)-1,3-dihydro-indol-2-one,
rac-2-{[6-Chloro-3-(3-chloro-benzyl)-2-oxo-2,3-dihydro-1H-indol-3-yl]-isopropyl-amino}-N-cyclohexyl-acetamide,
rac-[[6-Chloro-3-(3-chloro-benzyl)-2-oxo-2,3-dihydro-1H-indol-3-yl]-(1-ethyl-propyl)-amino]-acetic acid ethyl ester,
rac-2-{[6-Chloro-3-(3-chloro-benzyl)-2-oxo-2,3-dihydro-1H-indol-3-yl]-isopropyl-amino}-N-cyclobutyl-acetamide,
rac-2-[[6-Chloro-3-(3-chloro-benzyl)-2-oxo-2,3-dihydro-1H-indol-3-yl]-(1-ethyl-propyl)-amino]-N-cyclohexyl-acetamide,
rac-[[6-Chloro-3-(3-chloro-benzyl)-2-oxo-2,3-dihydro-1H-indol-3-yl]-(3-chloro-phenyl)-amino]-acetic acid,
rac-{[6-Chloro-3-(3-chloro-benzyl)-2-oxo-2,3-dihydro-1H-indol-3-yl]-isopropyl-amino}-acetic acid ethyl ester,
rac-{[6-Chloro-3-(3-chloro-benzyl)-2-oxo-2,3-dihydro-1H-indol-3-yl]-isopropyl-amino}-acetic acid,
rac-[[6-Chloro-3-(3-chloro-benzyl)-2-oxo-2,3-dihydro-1H-indol-3-yl]-(1-ethyl-propyl)-amino]-acetic acid,
rac-6'-Chloro-3'-(3-chloro-benzyl)-2-(morpholine-4-carbonyl)-1',3'-dihydro-[1,3']biindolyl-2'-one,
rac-2-(4-Acetyl-piperazine-1-carbonyl)-6'-chloro-3'-(3-chloro-benzyl)-1',3'-dihydro-[1,3']biindolyl-2'-one,
rac-6'-Chloro-3'-(3-chloro-benzyl)-2'-oxo-2',3'-dihydro-1'H-[1,3']biindolyl-2-carboxylic acid cyclobutylamide,
rac-2-(4-Acetyl-piperazine-1-carbonyl)-6'-chloro-3'-(3-chloro-benzyl)-2,3,1',3'-tetrahydro-[1,3']biindolyl-2'-one,
rac-2-(4-Acetyl-piperazine-1-carbonyl)-6'-chloro-3'-(3-chloro-benzyl)-2,3,1',3'-tetrahydro-[1,3']biindolyl-2'-one,
rac-6'-Chloro-3'-(3-chloro-benzyl)-2-(morpholine-4-carbonyl)-2,3,1',3'-tetrahydro-[1,3']biindolyl-2'-one,
rac-3-[2-(4-Acetyl-piperazine-1-carbonyl)-6-ethoxy-phenylamino]-6-chloro-3-(3-chloro-benzyl)-1,3-dihydro-indol-2-one,
rac-6-Chloro-3-(3-chloro-benzyl)-3-[2-ethoxy-6-(morpholine-4-carbonyl)-phenylamino]-1,3-dihydro-indol-2-one,
rac-2-[6-Chloro-3-(3-chloro-benzyl)-2-oxo-2,3-dihydro-1H-indol-3-ylamino]-3-ethoxy-benzoic acid,
rac-5-Chloro-2-[6-chloro-3-(3-chloro-benzyl)-2-oxo-2,3-dihydro-1H-indol-3-ylamino]-benzoic acid,
rac-2-[6-Chloro-3-(3-chloro-benzyl)-2-oxo-2,3-dihydro-1H-indol-3-ylamino]-5-methyl-benzoic acid,
rac-2-[6-Chloro-3-(3-chloro-benzyl)-2-oxo-2,3-dihydro-1H-indol-3-ylamino]-3,5-dimethyl-benzoic acid,
rac-6'-Chloro-3'-(3-chloro-benzyl)-2'-oxo-2,3,2',3'-tetrahydro-1'H-[1,3']biindolyl-2-carboxylic acid,
rac-2-{[6-Chloro-3-(3-chloro-benzyl)-2-oxo-2,3-dihydro-1H-indol-3-yl]-piperidin-4-yl-amino}-N-cyclobutyl-acetamide,
rac-4-{[6-Chloro-3-(3-chloro-benzyl)-2-oxo-2,3-dihydro-1H-indol-3-yl]-cyclobutylcarbamoylmethyl-amino}-piperidine-1-carboxylic acid dimethylamide,
rac-2-{(1-Acetyl-piperidin-4-yl)-[6-chloro-3-(3-chloro-benzyl)-2-oxo-2,3-dihydro-1H-indol-3-yl]-amino}-N-cyclobutyl-acetamide,
rac-4-{[6-Chloro-3-(3-chloro-benzyl)-2-oxo-2,3-dihydro-1H-indol-3-yl]-cyclobutylcarbamoylmethyl-amino}-piperidine-1-carboxylic acid tert-butyl ester,
rac-3-[2-(4-Acetyl-piperazine-1-carbonyl)-6-isopropyl-phenylamino]-6-chloro-3-(3-chloro-benzyl)-1,3-dihydro-indol-2-one,
rac-2-{[6-Chloro-3-(3-chloro-benzyl)-2-oxo-2,3-dihydro-1H-indol-3-yl]-isopropyl-amino}-N-(1-methanesulfonyl-piperidin-4-yl)-acetamide,
rac-N-(1-Acetyl-piperidin-4-yl)-2-{[6-chloro-3-(3-chloro-benzyl)-2-oxo-2,3-dihydro-1H-indol-3-yl]-isopropyl-amino}-acetamide,
rac-2-{[6-Chloro-3-(3-chloro-benzyl)-2-oxo-2,3-dihydro-1H-indol-3-yl]-isopropyl-amino}-N-piperidin-4-yl-acetamide,
rac-4-(2-{[6-Chloro-3-(3-chloro-benzyl)-2-oxo-2,3-dihydro-1H-indol-3-yl]-isopropyl-amino}-acetylamino)-piperidine-1-carboxylic acid tert-butyl ester,
rac-3-{2-[(1-Acetyl-piperidin-4-ylamino)-methyl]-5-bromo-phenylamino}-6-chloro-3-(3-chloro-benzyl)-1,3-dihydro-indol-2-one,
rac-3-[2-(4-Acetyl-piperazin-1-ylmethyl)-5-bromo-phenylamino]-6-chloro-3-(3-chloro-benzyl)-1,3-dihydro-indol-2-one,
rac-3-{5-Bromo-2-[(1-methanesulfonyl-piperidin-4-ylamino)-methyl]-phenylamino}-6-chloro-3-(3-chloro-benzyl)-1,3-dihydro-indol-2-one,
rac-4-{4-Bromo-2-[6-chloro-3-(3-chloro-benzyl)-2-oxo-2,3-dihydro-1H-indol-3-ylamino]-benzylamino}-piperidine-1-carboxylic acid tert-butyl ester,
rac-3-(5-Bromo-2-cyclobutylaminomethyl-phenylamino)-6-chloro-3-(3-chloro-benzyl)-1,3-dihydro-indol-2-one,
rac-3-(5-Bromo-2-morpholin-4-ylmethyl-phenylamino)-6-chloro-3-(3-chloro-benzyl)-1,3-dihydro-indol-2-one,
rac-3-(5-Bromo-2-hydroxymethyl-phenylamino)-6-chloro-3-(3-chloro-benzyl)-1,3-dihydro-indol-2-one,
rac-4-Bromo-2-[6-chloro-3-(3-chloro-benzyl)-2-oxo-2,3-dihydro-1H-indol-3-ylamino]-N-(2-morpholin-4-yl-ethyl)-benzamide,
rac-N-(2-{4-Bromo-2-[6-chloro-3-(3-chloro-benzyl)-2-oxo-2,3-dihydro-1H-indol-3-ylamino]-benzylamino}-ethyl)-acetamide,
rac-3-{5-Bromo-2-[(2,2-difluoro-ethylamino)-methyl]-phenylamino}-6-chloro-3-(3-chloro-benzyl)-1,3-dihydro-indol-2-one,
rac-3-{5-Bromo-2-[(3-imidazol-1-yl-propylamino)-methyl]-phenylamino}-6-chloro-3-(3-chloro-benzyl)-1,3-dihydro-indol-2-one, rac-3-{5-Bromo-2-[(2,2,2-trifluoro-ethylamino)-methyl]-phenylamino}-6-chloro-3-(3-chloro-benzyl)-1,3-dihydro-indol-2-one,
rac-N-(2-Acetylamino-ethyl)-4-bromo-2-[6-chloro-3-(3-chloro-benzyl)-2-oxo-2,3-dihydro-1H-indol-3-ylamino]-benzamide,
rac-4-Bromo-2-[6-chloro-3-(3-chloro-benzyl)-2-oxo-2,3-dihydro-1H-indol-3-ylamino]-N-(2,2-difluoro-ethyl)-benzamide,
rac-4-Bromo-2-[6-chloro-3-(3-chloro-benzyl)-2-oxo-2,3-dihydro-1H-indol-3-ylamino]-N-(3-imidazol-1-yl-propyl)-benzamide,
rac-4-Bromo-2-[6-chloro-3-(3-chloro-benzyl)-2-oxo-2,3-dihydro-1H-indol-3-ylamino]-N-(3-dimethylamino-propyl)-benzamide,
rac-4-Bromo-2-[6-chloro-3-(3-chloro-benzyl)-2-oxo-2,3-dihydro-1H-indol-3-ylamino]-N-(2,2,2-trifluoro-ethyl)-benzamide,
rac-3-{5-Bromo-2-[(3-morpholin-4-yl-propylamino)-methyl]-phenylamino}-6-chloro-3-(3-chloro-benzyl)-1,3-dihydro-indol-2-one,
rac-3-{5-Bromo-2-[(2-morpholin-4-yl-ethylamino)-methyl]-phenylamino}-6-chloro-3-(3-chloro-benzyl)-1,3-dihydro-indol-2-one,
rac-3-{5-Bromo-2-[4-(2-methanesulfonyl-ethyl)-piperazine-1-carbonyl]-phenylamino}-6-chloro-3-(3-chloro-benzyl)-1,3-dihydro-indol-2-one,
rac-4-Chloro-2-{[6-chloro-3-(3-chloro-benzyl)-2-oxo-2,3-dihydro-1H-indol-3-yl]-methyl-amino}-benzoic acid,
rac-6-Chloro-3-(3-chloro-benzyl)-3-{[5-chloro-2-(morpholine-4-carbonyl)-phenyl]-methyl-amino}-1,3-dihydro-indol-2-one,
rac-4-Chloro-2-{[6-chloro-3-(3-chloro-benzyl)-2-oxo-2,3-dihydro-1H-indol-3-yl]-methyl-amino}-N-(3-imidazol-1-yl-propyl)-benzamide,
rac-N-(2-Acetylamino-ethyl)-4-chloro-2-{[6-chloro-3-(3-chloro-benzyl)-2-oxo-2,3-dihydro-1H-indol-3-yl]-methyl-amino}-benzamide,
rac-4-Chloro-2-{[6-chloro-3-(3-chloro-benzyl)-2-oxo-2,3-dihydro-1H-indol-3-yl]-methyl-amino}-N-(3-dimethylamino-propyl)-benzamide,
rac-2-{[6-Chloro-3-(3-chloro-benzyl)-2-oxo-2,3-dihydro-1H-indol-3-yl]-cyclohexyl-amino}-N-cyclopentyl-acetamide,
rac-{[6-Chloro-3-(3-chloro-benzyl)-2-oxo-2,3-dihydro-1H-indol-3-yl]-cyclopentyl-amino}-acetic acid,
rac-{[6-Chloro-3-(3-chloro-benzyl)-2-oxo-2,3-dihydro-1H-indol-3-yl]-cyclobutyl-amino}-acetic acid,
rac-2-{[6-Chloro-3-(3-chloro-benzyl)-2-oxo-2,3-dihydro-1H-indol-3-yl]-cyclobutyl-amino}-N-cyclobutyl-acetamide,
rac-2-{[6-Chloro-3-(3-chloro-benzyl)-2-oxo-2,3-dihydro-1H-indol-3-yl]-cyclobutyl-amino}-N-cyclopentyl-acetamide,
rac-2-{[6-Chloro-3-(3-chloro-benzyl)-2-oxo-2,3-dihydro-1H-indol-3-yl]-cyclobutyl-amino}-N-cyclohexyl-acetamide,
rac-2-{[6-Chloro-3-(3-chloro-benzyl)-2-oxo-2,3-dihydro-1H-indol-3-yl]-cyclobutyl-amino}-N-cyclopropyl-acetamide,
rac-6-Chloro-3-(3-chloro-benzyl)-3-(cyclobutyl-{2-[4-(2-hydroxy-ethyl)-piperazin-1-yl]-2-oxo-ethyl}-amino)-1,3-dihydro-indol-2-one,
rac-1-(2-{[6-Chloro-3-(3-chloro-benzyl)-2-oxo-2,3-dihydro-1H-indol-3-yl]-cyclobutyl-amino}-acetyl)-piperidine-4-carboxylic acid amide,
rac-2-{[6-Chloro-3-(3-chloro-benzyl)-2-oxo-2,3-dihydro-1H-indol-3-yl]-cyclopentyl-amino}-N-cyclopropyl-acetamide,
rac-2-{[6-Chloro-3-(3-chloro-benzyl)-2-oxo-2,3-dihydro-1H-indol-3-yl]-cyclopentyl-amino}-N-cyclobutyl-acetamide,
rac-2-{[6-Chloro-3-(3-chloro-benzyl)-2-oxo-2,3-dihydro-1H-indol-3-yl]-cyclopentyl-amino}-N-cyclopentyl-acetamide,
rac-2-{[6-Chloro-3-(3-chloro-benzyl)-2-oxo-2,3-dihydro-1H-indol-3-yl]-cyclopentyl-amino}-N-cyclohexyl-acetamide,
rac-6-Chloro-3-(3-chloro-benzyl)-3-(cyclopentyl-{2-[4-(2-hydroxy-ethyl)-piperazin-1-yl]-2-oxo-ethyl}-amino)-1,3-dihydro-indol-2-one,
rac-1-(2-{[6-Chloro-3-(3-chloro-benzyl)-2-oxo-2,3-dihydro-1H-indol-3-yl]-cyclopentyl-amino}-acetyl)-piperidine-4-carboxylic acid amide,
rac-2-{[6-Chloro-3-(3-chloro-benzyl)-2-oxo-2,3-dihydro-1H-indol-3-yl]-cycloheptyl-amino}-N-cyclopropyl-acetamide,
rac-2-{[6-Chloro-3-(3-chloro-benzyl)-2-oxo-2,3-dihydro-1H-indol-3-yl]-cycloheptyl-amino}-N-cyclobutyl-acetamide,
rac-2-{[6-Chloro-3-(3-chloro-benzyl)-2-oxo-2,3-dihydro-1H-indol-3-yl]-cycloheptyl-amino}-N-cyclopentyl-acetamide,
rac-2-{[6-Chloro-3-(3-chloro-benzyl)-2-oxo-2,3-dihydro-1H-indol-3-yl]-cycloheptyl-amino}-N-cyclohexyl-acetamide,
rac-6-Chloro-3-(3-chloro-benzyl)-3-(cycloheptyl-{2-[4-(2-hydroxy-ethyl)-piperazin-1-yl]-2-oxo-ethyl}-amino)-1,3-dihydro-indol-2-one,
rac-1-(2-{[6-Chloro-3-(3-chloro-benzyl)-2-oxo-2,3-dihydro-1H-indol-3-yl]-cycloheptyl-amino}-acetyl)-piperidine-4-carboxylic acid amide,
rac-(S)-2-[6-Chloro-3-(3-chloro-benzyl)-2-oxo-2,3-dihydro-1H-indol-3-ylamino]-2,4-dimethyl-pentanoic acid cyclopropylamide,
rac-(S)-2-[6-Chloro-3-(3-chloro-benzyl)-2-oxo-2,3-dihydro-1H-indol-3-ylamino]-4-methyl-pentanoic acid cyclobutylamide,
rac-(S)-2-[6-Chloro-3-(3-chloro-benzyl)-2-oxo-2,3-dihydro-1H-indol-3-ylamino]-4-methyl-pentanoic acid cyclopentylamide,
rac-(S)-2-[6-Chloro-3-(3-chloro-benzyl)-2-oxo-2,3-dihydro-1H-indol-3-ylamino]-4-methyl-pentanoic acid cyclohexylamide,
rac-2-{[6-Chloro-3-(3-chloro-benzyl)-2-oxo-2,3-dihydro-1H-indol-3-yl]-cyclohexyl-amino}-acetamide,
rac-6'-Chloro-3'-(3-chloro-benzyl)-6-methoxy-2'-oxo-2',3'-dihydro-1'H-[1,3']biindolyl-2-carboxylic acid methyl ester,
rac-{[6-Chloro-3-(3-chloro-benzyl)-2-oxo-2,3-dihydro-1H-indol-3-yl]-cycloheptyl-amino}-acetic acid,
rac-6'-Chloro-3'-(3-chloro-benzyl)-6-methoxy-2'-oxo-2',3'-dihydro-1'H-[1,3']biindolyl-2-carboxylic acid,
rac-2-{[6-Chloro-3-(3-chloro-benzyl)-2-oxo-2,3-dihydro-1H-indol-3-yl]-cyclohexyl-amino}-N,N-dimethyl-acetamide,
rac-2-{[6-Chloro-3-(3-chloro-benzyl)-2-oxo-2,3-dihydro-1H-indol-3-yl]-cyclohexyl-amino}-N-methyl-acetamide,
rac-6'-Chloro-3'-(3-chloro-benzyl)-6-methoxy-2'-oxo-2',3'-dihydro-1'H-[1,3']biindolyl-2-carboxylic acid cyclobutylamide, rac-6'-Chloro-3'-(3-chloro-benzyl)-6-methoxy-2'-oxo-2',3'-dihydro-1'H-[1,3']biindolyl-2-carboxylic acid cyclohexylamide, rac-1-[6'-Chloro-3'-(3-chloro-benzyl)-6-methoxy-2'-oxo-2',3'-dihydro-1'H-[1,3']biindolyl-2-carbonyl]-piperidine-4-carboxylic acid amide, rac-6'-Chloro-3'-(3-chloro-benzyl)-2-[4-(2-hydroxy-ethyl)-piperazine-1-carbonyl]-6-methoxy-1',3'-dihydro-[1,3']biindolyl-2'-one, rac-6'-Chloro-3'-(3-chloro-benzyl)-6-methoxy-2-(morpholine-4-carbonyl)-1',3'-dihydro-[1,3']biindolyl-2'-one, rac-2-[6-Chloro-3-(3-chloro-benzyl)-2-oxo-2,3-dihydro-1H-indol-3-ylamino]-3-methyl-benzoic acid, rac-2-[6-Chloro-3-(3-chloro-benzyl)-2-oxo-2,3-dihydro-1H-indol-3-ylamino]-4-fluoro-benzoic acid, rac-6-Chloro-3-(3-chloro-benzyl)-3-[2-methyl-6-(morpholine-4-carbonyl)-phenylamino]-1,3-dihydro-indol-2-one, rac-2-[6-Chloro-3-(3-chloro-benzyl)-2-oxo-2,3-dihydro-1H-indol-3-ylamino]-N-cyclobutyl-4-fluoro-benzamide, rac-6-Chloro-3-(3-chloro-benzyl)-3-[5-fluoro-2-(morpholine-4-carbonyl)-phenylamino]-1,3-dihydro-indol-2-one, rac-3-[2-(4-Acetyl-piperazine-1-carbonyl)-5-fluoro-phenylamino]-6-chloro-3-(3-chloro-benzyl)-1,3-dihydro-indol-2-one, rac-2-[[6-Chloro-3-(3-chloro-benzyl)-2-oxo-2,3-dihydro-1H-indol-3-yl]-((R)-3-methyl-cyclohexyl)-amino]-N-cyclobutyl-acetamide, rac-2-[[6-Chloro-3-(3-chloro-benzyl)-2-oxo-2,3-dihydro-1H-indol-3-yl]-((R)-3-methyl-cyclohexyl)-amino]-N-cyclohexyl-acetamide, rac-2-[[6-Chloro-3-(3-chloro-benzyl)-2-oxo-2,3-dihydro-1H-indol-3-yl]-((R)-3-methyl-cyclohexyl)-amino]-N-morpholin-4-yl-acetamide, rac-6-Chloro-3-(3-chloro-benzyl)-3-[((R)-3-methyl-cyclohexyl)-(2-morpholin-4-yl-2-oxo-ethyl)-amino]-1,3-dihydro-indol-2-one, rac-[[6-Chloro-3-(3-chloro-benzyl)-2-oxo-2,3-dihydro-1H-indol-3-yl]-((R)-3-methyl-cyclopentyl)-amino]-acetic acid, rac-2-[[6-Chloro-3-(3-chloro-benzyl)-2-oxo-2,3-dihydro-1H-indol-3-yl]-((R)-3-methyl-cyclopentyl)-amino]-N-cyclobutyl-acetamide, rac-2-[[6-Chloro-3-(3-chloro-benzyl)-2-oxo-2,3-dihydro-1H-indol-3-yl]-((R)-3-methyl-cyclopentyl)-amino]-N-cyclohexyl-acetamide, rac-2-[[6-Chloro-3-(3-chloro-benzyl)-2-oxo-2,3-dihydro-1H-indol-3-yl]-((R)-3-methyl-cyclopentyl)-amino]-N-morpholin-4-yl-acetamide, rac-6-Chloro-3-(3-chloro-benzyl)-3-[((R)-3-methyl-cyclopentyl)-(2-morpholin-4-yl-2-oxo-ethyl)-amino]-1,3-dihydro-indol-2-one, rac-1-[6-Chloro-3-(3-chloro-benzyl)-2-oxo-2,3-dihydro-1H-indol-3-ylamino]-cyclohexanecarboxylic acid, rac-2-[[6-Chloro-3-(3-chloro-benzyl)-2-oxo-2,3-dihydro-1H-indol-3-yl]-(2-methyl-cyclohexyl)-amino]-N-cyclobutyl-acetamide, rac-1-[6-Chloro-3-(3-chloro-benzyl)-2-oxo-2,3-dihydro-1H-indol-3-ylamino]-cyclohexanecarboxylic acid cyclobutylamide, rac-3-[1-(4-Acetyl-piperazine-1-carbonyl)-cyclohexylamino]-6-chloro-3-(3-chloro-benzyl)-1,3-dihydro-indol-2-one, rac-2-{[6-Chloro-3-(3-chloro-benzyl)-2-oxo-2,3-dihydro-1H-indol-3-yl]-cyclopropylmethyl-amino}-N-cyclobutyl-acetamide, rac-2-[[6-Chloro-3-(3-chloro-benzyl)-2-oxo-2,3-dihydro-1H-indol-3-yl]-(3,3,5,5-tetramethyl-cyclohexyl)-amino]-N-cyclobutyl-acetamide, rac-2-{(R)-Bicyclo[2.2.1]hept-2-yl-[6-chloro-3-(3-chloro-benzyl)-2-oxo-2,3-dihydro-1H-indol-3-yl]-amino}-N-cyclobutyl-acetamide, rac-2-[(6-Chloro-3-cyclohexyl methyl-2-oxo-2,3-dihydro-1H-indol-3-yl)-cyclohexyl-amino]-N-cyclobutyl-acetamide, rac-6-Chloro-3-(3-chloro-benzyl)-3-[cyclohexyl-(2-morpholin-4-yl-ethyl)-amino]-1,3-dihydro-indol-2-one, rac-6-Chloro-3-(3-chloro-benzyl)-3-[cyclohexyl-(3-morpholin-4-yl-propyl)-amino]-1,3-dihydro-indol-2-one, rac-6-Chloro-3-(3-chloro-benzyl)-3-[isopropyl-(2-morpholin-4-yl-ethyl)-amino]-1,3-dihydro-indol-2-one, rac-6-Chloro-3-(3-chloro-benzyl)-3-[isopropyl-(3-morpholin-4-yl-propyl)-amino]-1,3-dihydro-indol-2-one, rac-2-[4-(2-{[6-Chloro-3-(3-chloro-benzyl)-2-oxo-2,3-dihydro-1H-indol-3-yl]-isopropyl-amino}-acetyl)-piperazin-1-yl]-N,N-dimethyl-2-oxo-acetamide, rac-1-(2-{[6-Chloro-3-(3-chloro-benzyl)-2-oxo-2,3-dihydro-1H-indol-3-yl]-isopropyl-amino}-acetyl)-piperidine-4-carboxylic acid dimethylamide, rac-2-{sec-Butyl-[6-chloro-3-(3-chloro-benzyl)-2-oxo-2,3-dihydro-1H-indol-3-yl]-amino}-N-cyclobutyl-acetamide, rac-6-Chloro-3-(3-chloro-benzyl)-3-(isopropyl-{2-[4-(2-methanesulfonyl-ethyl)-piperazin-1-yl]-2-oxo-ethyl}-amino)-1,3-dihydro-indol-2-one, rac-2-{[6-Chloro-3-(3-chloro-benzyl)-2-oxo-2,3-dihydro-1H-indol-3-yl]-isopropyl-amino}-N-[1-(propane-2-sulfonyl)-piperidin-4-yl]-acetamide, rac-2-{[6-Chloro-3-(3-chloro-benzyl)-2-oxo-2,3-dihydro-1H-indol-3-yl]-isopropyl-amino}-N-(2,2,2-trifluoro-ethyl)-acetamide, rac-6-Chloro-3-(3-chloro-benzyl)-3-[cyclohexyl-(2-methanesulfonyl-ethyl)-amino]-1,3-dihydro-indol-2-one, rac-6-Chloro-3-(3-chloro-benzyl)-3-[isopropyl-(2-methanesulfonyl-ethyl)-amino]-1,3-dihydro-indol-2-one, rac-6-Chloro-3-(3-chloro-benzyl)-3-{isopropyl-[2-(4-methanesulfonyl-piperazin-1-yl)-2-oxo-ethyl]-amino}-1,3-dihydro-indol-2-one, rac-2-{tert-Butyl-[6-chloro-3-(3-chloro-benzyl)-2-oxo-2,3-dihydro-1H-indol-3-yl]-amino}-N-cyclobutyl-acetamide, rac-N-[1-(2-{[6-Chloro-3-(3-chloro-benzyl)-2-oxo-2,3-dihydro-1H-indol-3-yl]-isopropyl-amino}-acetyl)-piperidin-4-yl]-methanesulfonamide, rac-2-[[6-Chloro-3-(3-chloro-benzyl)-2-oxo-2,3-dihydro-1H-indol-3-yl]-(1,2-dimethyl-propyl)-amino]-N-cyclobutyl-acetamide, rac-6-Chloro-3-(3-chloro-benzyl)-3-((1,2-dimethyl-propyl)-{2-[4-(2-methanesulfonyl-ethyl)-piperazin-1-yl]-2-oxo-ethyl}-amino)-1,3-dihydro-indol-2-one, rac-2-[[6-Chloro-3-(3-chloro-benzyl)-2-oxo-2,3-dihydro-1H-indol-3-yl]-(1,2-dimethyl-propyl)-amino]-N-(1-methanesulfonyl-piperidin-4-yl)-acetamide, rac-2-[[6-Chloro-3-(3-chloro-benzyl)-2-oxo-2,3-dihydro-1H-indol-3-yl]-(2,2-dimethyl-propyl)-amino]-N-cyclobutyl-acetamide, rac-6-Chloro-3-(3-chloro-benzyl)-3-((2,2-dimethyl-propyl)-{2-[4-(2-methanesulfonyl-ethyl)-piperazin-1-yl]-2-oxo-ethyl}-amino)-1,3-dihydro-indol-2-one and rac-1-{2-[[6-Chloro-3-(3-chloro-benzyl)-2-oxo-2,3-dihydro-1H-indol-3-yl]-(2,2-dimethyl-propyl)-amino]-acetyl}-piperidine-4-carboxylic acid amide.

In the specification, where indicated, the various groups may be substituted by 1-5 or, preferably, 1-3 substituents independently selected from the group consisting of lower alkyl, lower-alkenyl, lower-alkynyl, dioxo-lower-alkylene (forming e.g. a benzodioxyl group), halogen, hydroxy, CN, $CF_3$, $NH_2$, N(H, lower-alkyl), N(lower-alkyl)$_2$, aminocarbonyl, carboxy, $NO_2$, lower-alkoxy, thio-lower-alkoxy, lower-alkylsulfonyl, aminosulfonyl, lower-alkylcarbonyl, lower-alkylcarbonyloxy, lower-alkoxycarbonyl, lower-alkyl-carbonyl-NH, fluoro-lower-alkyl, fluoro-lower-alkoxy, lower-alkoxy-carbonyl-lower-alkoxy, carboxy-lower-alkoxy, carbamoyl-lower-alkoxy, carbamoyl-lower cycloalkyl, hydroxy-lower-alkoxy, $NH_2$-lower-alkoxy, N(H, lower-alkyl)-lower-alkoxy, N(lower-alkyl)$_2$-lower-alkoxy, benzyloxy-lower-alkoxy, mono- or di-lower alkyl substituted amino-sulfonyl and lower-alkyl which can optionally be substituted with halogen, hydroxy, $NH_2$, N(H, lower-alkyl) or N(lower-alkyl)$_2$. Preferred substituents for the alkyl, aryl, heteroaryl and heterocycle rings are halogen, lower alkoxy, lower alkyl and amino.

The term "alkyl" refers to straight- or branched-chain saturated hydrocarbon groups having from 1 to about 20 carbon atoms, including groups having from 1 to about 7 carbon atoms. In certain embodiments, alkyl substituents may be lower alkyl substituents. The term "lower alkyl" refers to alkyl groups having from 1 to 6 carbon atoms, and in certain embodiments from 1 to 4 carbon atoms. Examples of alkyl groups include, but are not limited to, methyl, ethyl, n-propyl, i-propyl, n-butyl, s-butyl, t-butyl, n-pentyl, and s-pentyl.

As used herein, "cycloalkyl" is intended to refer to any stable monocyclic or polycyclic system which consists of carbon atoms only, any ring of which being saturated, and the term "cycloalkenyl" is intended to refer to any stable monocyclic or polycyclic system which consists of carbon atoms only, with at least one ring thereof being partially unsaturated. Examples of cycloalkyls include, but are not limited to, cyclopropyl, cyclobutyl, cyclopentyl, cyclohexyl, cycloheptyl, adamantyl, cyclooctyl, bicycloalkyls, including bicyclooctanes such as [2.2.2]bicyclooctane or [3.3.0]bicyclooctane, bicyclononanes such as [4.3.0]bicyclononane, and bicyclodecanes such as [4.4.0]bicyclodecane (decalin), or spiro compounds. Examples of cycloalkenyls include, but are not limited to, cyclopentenyl or cyclohexenyl.

The term "alkenyl" as used herein means an unsaturated straight-chain or branched aliphatic hydrocarbon group containing one double bond and having 2 to 6, preferably 2 to 4 carbon atoms. Examples of such "alkenyl group" are vinyl (ethenyl), allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

The term "alkynyl" as used herein means an unsaturated straight-chain or branched aliphatic hydrocarbon group containing one triple bond and having 2 to 6, preferably 2 to 4 carbon atoms. Examples of such "alkynyl group" are ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

The term "halogen" as used in the definitions means fluorine, chlorine, bromine, or iodine, preferably fluorine and chlorine.

"Aryl" means a monovalent, monocyclic or bicyclic, aromatic carbocyclic hydrocarbon radical, preferably a 6-10 member aromatic ring system. Preferred aryl groups include, but are not limited to, phenyl, naphthyl, tolyl, and xylyl.

"Heteroaryl" means an aromatic heterocyclic ring system containing up to two rings. Preferred heteroaryl groups include, but are not limited to, thienyl, furyl, indolyl, pyrrolyl, pyridinyl, pyrazinyl, oxazolyl, thiaxolyl, quinolinyl, pyrimidinyl, imidazole and tetrazolyl.

In the case of aryl or heteroaryl which are bicyclic it should be understood that one ring may be aryl while the other is heteroaryl and both being substituted or unsubstituted.

"Heterocycle" or "heterocycloalkyl" means a substituted or unsubstituted 5 to 8 membered, mono- or bicyclic, non-aromatic hydrocarbon, wherein 1 to 3 carbon atoms are replaced by a hetero atom selected from nitrogen, oxygen or sulfur atom. Examples include pyrrolidin-2-yl; pyrrolidin-3-yl; piperidinyl; morpholin-4-yl and the like.

"Hetero atom" means an atom selected from N, O and S.

"Alkoxy, alkoxyl or lower alkoxy" refers to any of the above lower alkyl groups attached to an oxygen atom. Typical lower alkoxy groups include methoxy, ethoxy, isopropoxy or propoxy, butyloxy and the like. Further included within the meaning of alkoxy are multiple alkoxy side chains, e.g. ethoxy ethoxy, methoxy ethoxy, methoxy ethoxy ethoxy and the like and substituted alkoxy side chains, e.g., dimethylamino ethoxy, diethylamino ethoxy, dimethoxy-phosphoryl methoxy and the like.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoro acetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (6th Ed. 1995) at pp. 196 and 1456-1457.

The compounds of formula I as well as their salts that have at least one asymmetric carbon atom may be present as racemic mixtures or different stereoisomers. The various isomers can be isolated by known separation methods, e.g., chromatography.

Compounds disclosed herein and covered by formula I above may exhibit tautomerism or structural isomerism. It is intended that the invention encompasses any tautomeric or structural isomeric form of these compounds, or mixtures of such forms, and is not limited to any one tautomeric or structural isomeric form depicted in formula I above.

The compounds of the present invention are useful in the treatment or control of cell proliferative disorders, in particular oncological disorders. These compounds and formulations containing said compounds may be useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, as well as the particular mode of administration. The amount of active ingredient which can be combined with a carrier material to produce a single dosage form will generally be that amount of a formula I compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, sachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

"Effective amount" means an amount that is effective to prevent, alleviate or ameliorate symptoms of disease or prolong the survival of the subject being treated.

"$IC_{50}$" refers to the concentration of a particular compound required to inhibit 50% of a specific measured activity. $IC_{50}$ can be measured, inter alia, as is described subsequently.

Compounds of this invention can be synthesized according to the following general schemes. It will be readily apparent to those of ordinary skill in the art that compounds in formula I can be prepared by substitution of the reagents or agents in the general synthesis routes. The starting materials are either commercially available or can be synthesized by well-established literature methods known to those of ordinary skill in the art. For example, the 6-substituted oxindole I starting materials were either commercially available or prepared from the corresponding 4-substituted 2-nitro-fluoro or chlorobenzene according to Kraynack, E. A.; Dalgard, J. E.; Gaeta, F. C. A. *Tetrahedron Letters,* 1998, 39, 7679-7682. 4, 6-disubstituted oxindole I can be synthesized similar to the procedures exemplified in EP0869122A1, or Sun, L.; Liang, C.; Shirazian, S.; Zhou, Y. et al, *J. Med. Chem.* 2003, 46, 1116-1119, or Crestini, C.; Saladino, R. *Synthetic Communications,* 1994, 24, 2835-2841. 3-Mono-substituted 1,3-dihydro-indol-2-one II can be synthesized by multiple methods. These include, among others, the methods of Hewawasam, P.; Erway, M.; Moon, S. L.; Knipe, J.; Weiner, H.; Boissard, C. G.; Post-Munson, D. J.; Gao, Q.; Huang, S.; Gribkoff, V. K.; Meanwell, N. A. *J. Med. Chem.* 2002, 45, 1487-1499 or Elliott, I. W.; Rivers, P. *J. Org. Chem.* 1964, 29, 2438-2440 and Andreani, A.; Rambaldi, M.; Locatelli, A.; Bossa, R.; Galatulas, I.; Ninci, M. *Eur. J. Med. Chem.* 1990, 25, 187-190 (Scheme 1). Oxindole I can be reacted with an appropriately substituted aldehyde in the presence of base under heated condition in either a protic like methanol, ethanol to give intermediate II. The commonly used base is either pyrrolidine or piperidine. Intermediate II can then be readily reduced by $NaBH_4$ in methanol or ethanol to afford intermediate IV. Bromination of 3-position by pyridinium tribromide can be achieved in tert-butanol at room temperature. Subsequent nucleophilic displacement of bromide by $R_2R_9NH$ or $R_2OH$ leads to the desired product V or VI.

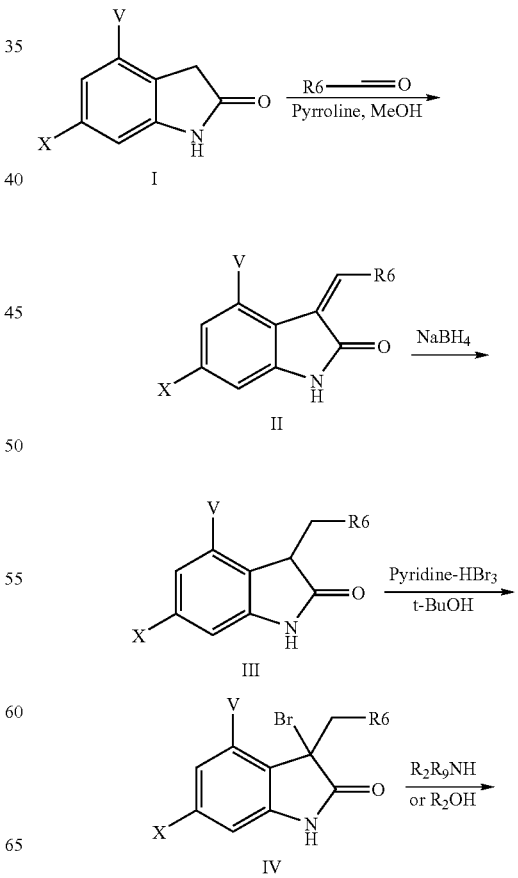

Scheme 1

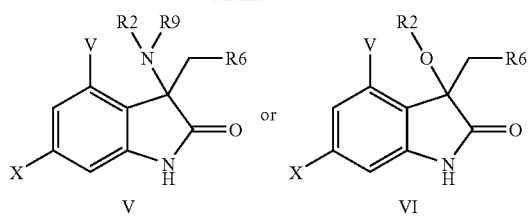

Modified glycine intermediate VIII can be prepared by reductive amination of glycine starting material VII with varied aldehyde or ketone using $NaCNBH_3$. Nucleophilic substitution of bromide in V by intermediate VIII generate IX. Hydrolysis of IX lead to the formation of carboxylic acid intermediate X. Derivatized compound XI can be prepared starting from acid X by using well-known coupling methods for carboxamide formation.

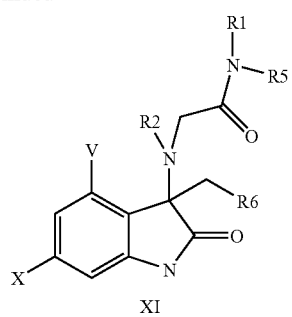

In a similar manner to the method described in Scheme 1, anthranilic acid XIII can be prepared from intermediate V and anthranilic acid XII. XII is either commercially available or readily prepared according to the well-established literature procedure. Various compounds XIV can be prepared from acid XIII and amine $R_1R_6NH$ by using well-known coupling methods for carboxamide formation.

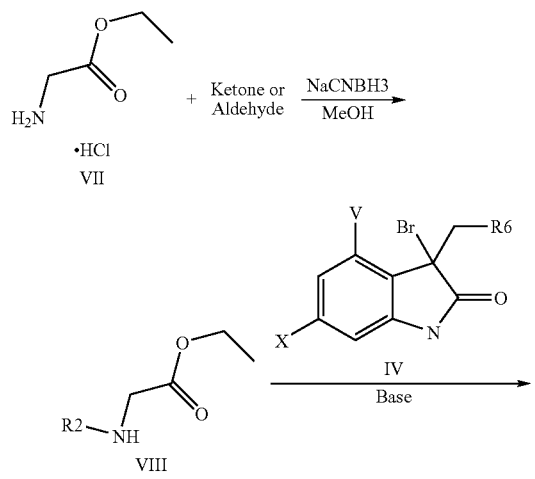

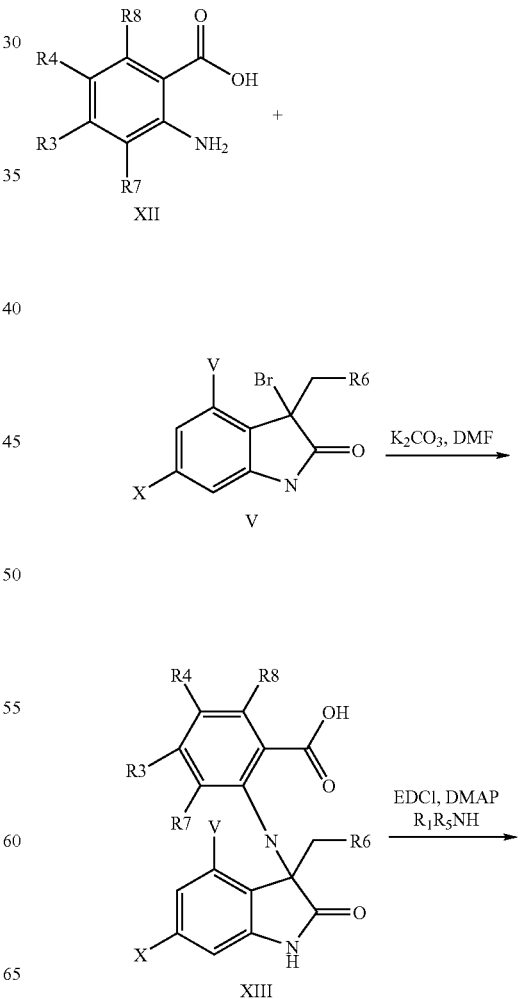

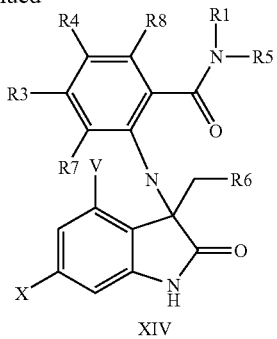

XIV

Sulfone analogue XVII can be formed from intermediates XVI and XVIII in a similar fashion as V in Scheme 1 (Scheme 4). Intermediate XVI is synthesized from commercially available, α,β-unsaturated XV and varied amine R₂NH₂ in one step by a Michael addition type reaction.

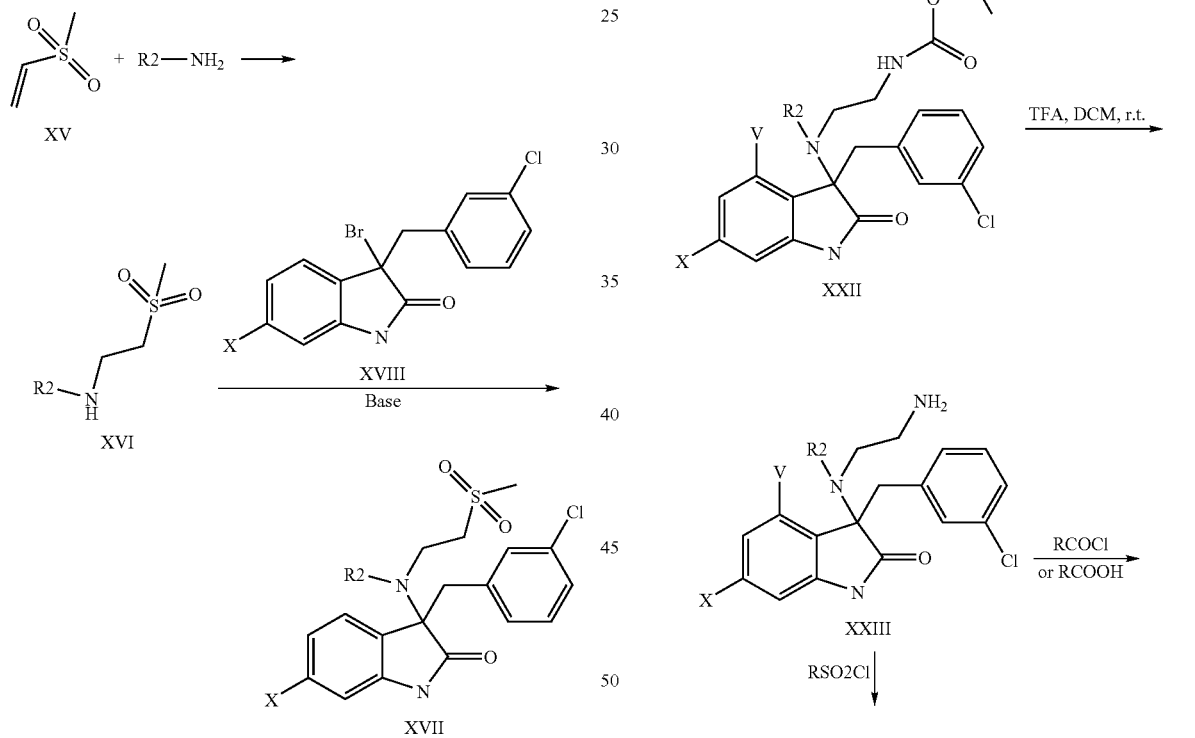

Diverse derivatives XXIV and XXV can be achieved according to the general Scheme 5. Intermediate XXI is prepared in two steps starting from commercially available compound XIX. Similar to the method in Scheme 1, compound XXII is formed by the nucleophilic displacement of Br by XXI. Deprotection of Boc group by trifluoroacid acid leads to amine intermediate XXIII. Subsequently compound XXIV or XXV can be prepared by selectively attaching a derivatized acyl or sulfonyl group on the R₂NH. R is lower alkyl, substituted lower alkyl, aryl, substituted aryl, heteroaryl, substituted heteroaryl, cycloalkyl, substituted cycloalkyl, cycloalkenyl, substituted alkenyl, heterocycle or substituted heterocycle.

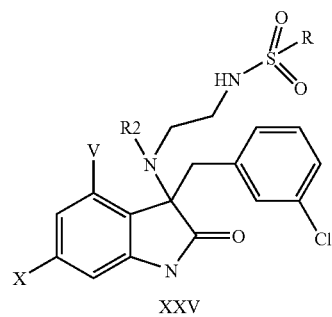

XXV

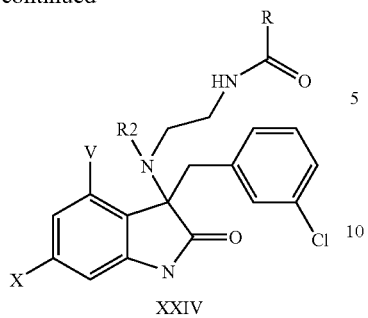

XXIV

The following examples and references are provided to aid the understanding of the present invention, the true scope of which is set forth in the appended claims.

EXAMPLE 1a

Preparation of Intermediate E/Z-6-chloro-3-(3-chloro-benzylidene)-1,3-dihydro-indol-2-one

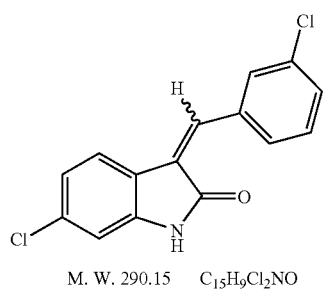

M. W. 290.15   $C_{15}H_9Cl_2NO$

To the mixture of 6-chlorooxindole (16.7 g, 0.1 mol) (Crescent) and 3-chlorobenzaldehyde (14.1 g, 0.1 mol) (Aldrich) in methanol (100 mL) was added pyrrolidine (7.1 g, 0.1 mol) (Aldrich) dropwisely. The mixture was then heated at 70° C. for 3 h. After cooling to 4° C., the resulting precipitate was collected and dried to give 20 g of E/Z-6-chloro-3-(3-chloro-benzylidene)-1,3-dihydro-indol-2-one as a bright yellow solid. MS: 291 $(M+H)^+$.

EXAMPLE 1b

Preparation of Intermediate rac-6-chloro-3-(3-chloro-benzyl)-1,3-dihydro-indol-2-one

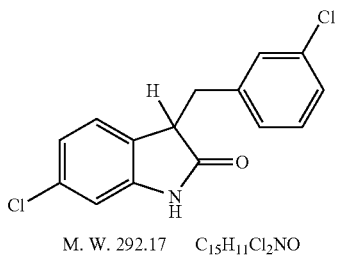

M. W. 292.17   $C_{15}H_{11}Cl_2NO$

Sodium borohydride (3.0 g, 79 mmol) (Aldrich) was added in small portions to a suspension of E/Z-6-chloro-3-(3-chloro-benzylidene)-1,3-dihydro-indol-2-one (19 g, 66 mmol) (from example 1a supra) in methanol (200 mL) and DMSO (50 mL) at such a rate that gas evolution was not too vigorous. When the addition was complete, mixture was stirred at room temperature for 0.5 hr-1 hr. After adding to water (200 mL), the resulting precipitate was collected and dried to give 18 g of rac-6-chloro-3-(3-chloro-benzyl)-1,3-dihydro-indol-2-one as a light yellow solid. MS: 293 $(M+H)^+$.

EXAMPLE 1c

Preparation of Intermediate rac-3-bromo-6-chloro-3-(3-chloro-benzyl)-1,3-dihydro-indol-2-one

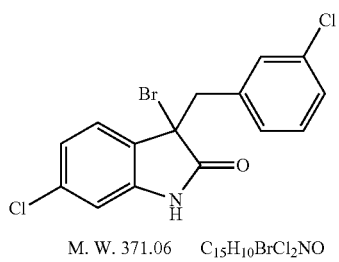

M. W. 371.06   $C_{15}H_{10}BrCl_2NO$

Pyridinium bromide perbromide (21.7 g, 68 mmol) (Aldrich) was added in one portion to a solution of rac-6-chloro-3-(3-chloro-benzyl)-1,3-dihydro-indol-2-one (18 g, 62 mmol) (from example 1b supra) in t-BuOH (400 mL) and water (2 mL) at room temperature with stirring. After stirring at room temperature for 4 h, the mixture was diluted with water (500 mL) and stirred for 1 h. The resulting precipitate was collected and dried to give 22 g of rac-3-bromo-6-chloro-3-(3-chloro-benzyl)-1,3-dihydro-indol-2-one as a pale yellow solid. MS: 371 $(M+H)^+$.

EXAMPLE 1d

Preparation of rac-6-chloro-3-(3-chloro-benzyl)-3-(4-propoxy-phenylamino)-1,3-dihydro-indol-2-one

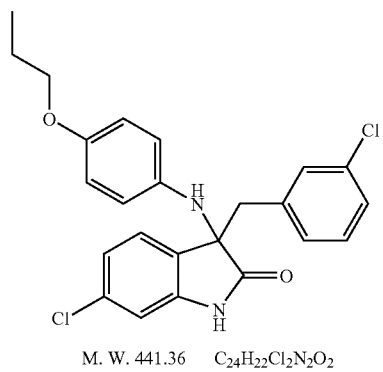

M. W. 441.36   $C_{24}H_{22}Cl_2N_2O_2$

The mixture of rac-3-bromo-6-chloro-3-(3-chloro-benzyl)-1,3-dihydro-indol-2-one (100 mg, 0.27 mmol) (from example 1c supra), 4-propoxy-phenylamine (61 mg, 0.41 mmol) and DIPEA (104.5 mg, 0.81 mmol) in propan-2-ol (10 mL) was stirred at room temperature for 2 h. Then water (10 mL) was added and the desired product was precipitated out, then filtrated and dried to give 98 mg of rac-6-chloro-3-(3-chloro-benzyl)-3-(4-propoxy-phenylamino)-1,3-dihydro-indol-2-one as a white solid. MS: 441 $(M+H)^+$.

EXAMPLE 2

Preparation of rac-6-chloro-3-(3-chloro-benzyl)-3-(2,4-dichloro-phenylamino)-1,3-dihydro-indol-2-one

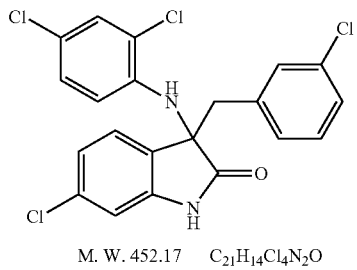

M. W. 452.17    $C_{21}H_{14}Cl_4N_2O$

The title compound was prepared by the same procedure for rac-6-chloro-3-(3-chloro-benzyl)-3-(4-propoxy-phenylamino)-1,3-dihydro-indol-2-one. MS: 452 (M+H)$^+$.

EXAMPLE 3

Preparation of rac-6-chloro-3-(3-chloro-benzyl)-3-(3,4-dimethoxy-phenylamino)-1,3-dihydro-indol-2-one

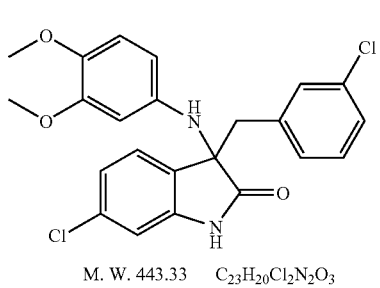

M. W. 443.33    $C_{23}H_{20}Cl_2N_2O_3$

The title compound was prepared by the same procedure for rac-6-chloro-3-(3-chloro-benzyl)-3-(4-propoxy-phenylamino)-1,3-dihydro-indol-2-one. MS: 443 (M+H)$^+$.

EXAMPLE 4

Preparation of rac-6-chloro-3-(3-chloro-benzyl)-3-(3,5-dimethoxy-phenylamino)-1,3-dihydro-indol-2-one

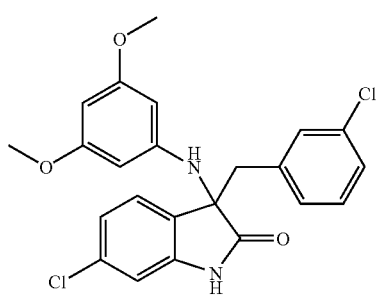

M. W. 443.33    $C_{23}H_{20}Cl_2N_2O_3$

The title compound was prepared by the same procedure for rac-6-chloro-3-(3-chloro-benzyl)-3-(4-propoxy-phenylamino)-1,3-dihydro-indol-2-one. MS: 443 (M+H)$^+$.

EXAMPLE 5

Preparation of rac-6-chloro-3-(3-chloro-benzyl)-3-(3-isopropoxy-phenylamino)-1,3-dihydro-indol-2-one

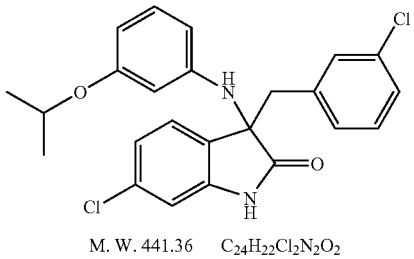

M. W. 441.36    $C_{24}H_{22}Cl_2N_2O_2$

The title compound was prepared by the same procedure for rac-6-chloro-3-(3-chloro-benzyl)-3-(4-propoxy-phenylamino)-1,3-dihydro-indol-2-one. MS: 441 (M+H)$^+$.

EXAMPLE 6

Preparation of rac-6-chloro-3-(3-chloro-benzyl)-3-(2,6-difluoro-phenylamino)-1,3-dihydro-indol-2-one

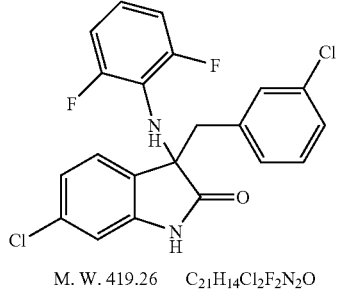

M. W. 419.26    $C_{21}H_{14}Cl_2F_2N_2O$

The title compound was prepared by the same procedure for rac-6-chloro-3-(3-chloro-benzyl)-3-(4-propoxy-phenylamino)-1,3-dihydro-indol-2-one. MS: 419 (M+H)$^+$.

EXAMPLE 7

Preparation of rac-3-(benzo[1,3]dioxol-5-ylamino)-6-chloro-3-(3-chloro-benzyl)-1,3-dihydro-indol-2-one

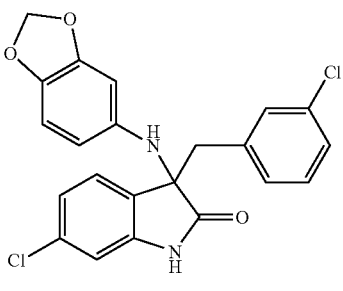

M. W. 427.29    $C_{22}H_{16}Cl_2N_2O_3$

The title compound was prepared by the same procedure for rac-6-chloro-3-(3-chloro-benzyl)-3-(4-propoxy-phenylamino)-1,3-dihydro-indol-2-one. MS: 427 (M+H)$^+$.

EXAMPLE 8

Preparation of rac-6-chloro-3-(3-chloro-benzyl)-3-(4-fluoro-phenylamino)-1,3-dihydro-indol-2-one

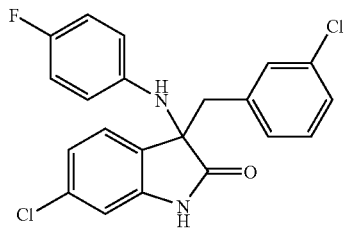

M. W. 401.27    $C_{21}H_{15}Cl_2FN_2O$

The title compound was prepared by the same procedure for rac-6-chloro-3-(3-chloro-benzyl)-3-(4-propoxy-phenylamino)-1,3-dihydro-indol-2-one. MS: 401 (M+H)$^+$.

EXAMPLE 9

Preparation of rac-6-chloro-3-(3-chloro-benzyl)-3-(2,4-difluoro-phenylamino)-1,3-dihydro-indol-2-one

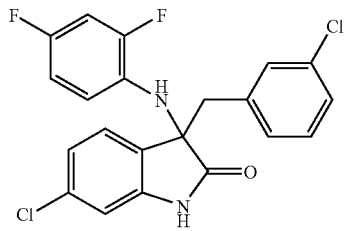

M. W. 419.26    $C_{21}H_{14}Cl_2F_2N_2O$

The title compound was prepared by the same procedure for rac-6-chloro-3-(3-chloro-benzyl)-3-(4-propoxy-phenylamino)-1,3-dihydro-indol-2-one. MS: 419 (M+H)$^+$.

EXAMPLE 10

Preparation of rac-6-chloro-3-(3-chloro-benzyl)-3-(4-chloro-2-fluoro-phenylamino)-1,3-dihydro-indol-2-one

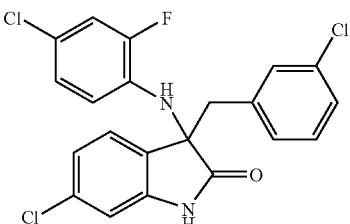

M. W. 435.72    $C_{21}H_{14}Cl_3FN_2O$

The title compound was prepared by the same procedure for rac-6-chloro-3-(3-chloro-benzyl)-3-(4-propoxy-phenylamino)-1,3-dihydro-indol-2-one. MS: 435 (M+H)$^+$.

EXAMPLE 11

Preparation of rac-3-(4-bromo-2-fluoro-phenylamino)-6-chloro-3-(3-chloro-benzyl)-1,3-dihydro-indol-2-one

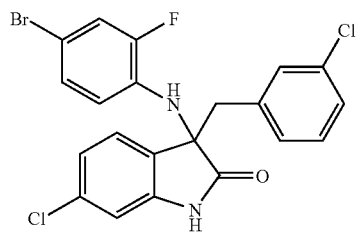

M. W. 480.17    $C_{21}H_{14}BrCl_2FN_2O$

The title compound was prepared by the same procedure for rac-6-chloro-3-(3-chloro-benzyl)-3-(4-propoxy-phenylamino)-1,3-dihydro-indol-2-one. MS: 480 (M+H)$^+$.

EXAMPLE 12

Preparation of rac-6-chloro-3-(3-chloro-benzyl)-3-(3-ethyl-phenylamino)-1,3-dihydro-indol-2-one

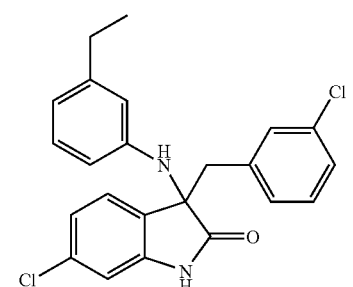

M. W. 411.33    $C_{33}H_{20}Cl_2N_2O$

The title compound was prepared by the same procedure for rac-6-chloro-3-(3-chloro-benzyl)-3-(4-propoxy-phenylamino)-1,3-dihydro-indol-2-one. MS: 411 (M+H)+.

EXAMPLE 13

Preparation of rac-6-chloro-3-(3-chloro-benzyl)-3-(4-isopropoxy-phenylamino)-1,3-dihydro-indol-2-one

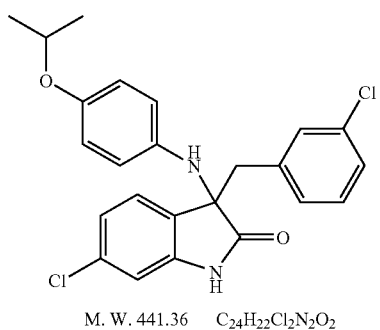

M. W. 441.36    C$_{24}$H$_{22}$Cl$_2$N$_2$O$_2$

The title compound was prepared by the same procedure for rac-6-chloro-3-(3-chloro-benzyl)-3-(4-propoxy-phenylamino)-1,3-dihydro-indol-2-one. MS: 441 (M+H)+.

H$^1$-NMR (400 MHz, DMSO-d$_6$) δ 10.54 (s, 1H), 7.22 (m, 1H), 7.15 (m, 2H), 7.02 (dd, 1H), 6.86 (t, 1H), 6.76 (d, 1H), 6.64 (d, 1H), 6.54 (m, 2H), 6.18 (m, 3H), 4.28 (m, 1H), 3.24 (dd, 2H), 1.13 (d, 6H).

EXAMPLE 14

Preparation of rac-6-chloro-3-(3-chloro-benzyl)-3-(2,6-dichloro-phenylamino)-1,3-dihydro-indol-2-one

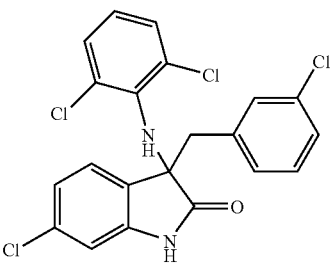

M. W. 452.17    C$_{21}$H$_{14}$Cl$_4$N$_2$O

The title compound was prepared by the same procedure for rac-6-chloro-3-(3-chloro-benzyl)-3-(4-propoxy-phenylamino)-1,3-dihydro-indol-2-one. MS: 452 (M+H)+.

EXAMPLE 15

Preparation of rac-6-chloro-3-(3-chloro-benzyl)-3-(3,4-difluoro-phenylamino)-1,3-dihydro-indol-2-one

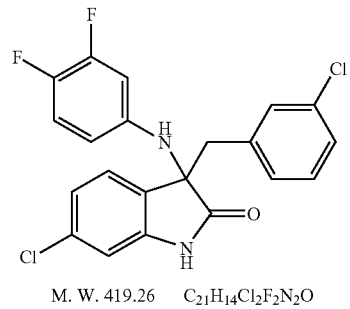

M. W. 419.26    C$_{21}$H$_{14}$Cl$_2$F$_2$N$_2$O

The title compound was prepared by the same procedure for rac-6-chloro-3-(3-chloro-benzyl)-3-(4-propoxy-phenylamino)-1,3-dihydro-indol-2-one. MS: 419 (M+H)+.

H$^1$-NMR (400 MHz, DMSO-d$_6$) δ 10.68 (s, 1H), 7.22 (m, 3H), 7.05 (m, 2H), 6.84 (m, 2H), 6.76 (d, 1H), 6.68 (d, 1H), 6.15 (m, 1H), 5.96 (m, 1H), 3.31 (d, 1H), 3.14 (d, 1H).

EXAMPLE 16

Preparation of rac-6-chloro-3-(3-chloro-benzyl)-3-(3-trifluoromethoxy-phenylamino)-1,3-dihydro-indol-2-one

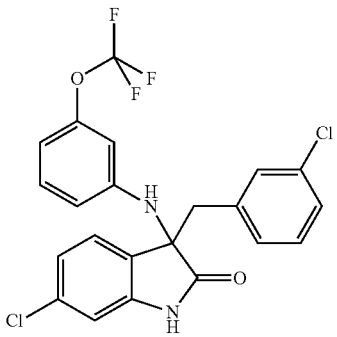

M. W. 467.28    C$_{22}$H$_{15}$Cl$_2$F$_3$N$_2$O$_2$

The title compound was prepared by the same procedure for rac-6-chloro-3-(3-chloro-benzyl)-3-(4-propoxy-phenylamino)-1,3-dihydro-indol-2-one. MS: 467 (M+H)+.

H¹-NMR (400 MHz, DMSO-d$_6$) δ 10.73 (s, 1H), 7.22 (m, 3H), 7.05 (m, 3H), 6.86 (t, 1H), 6.76 (d, 1H), 6.68 (d, 1H), 6.46 (m, 1H), 6.19 (dd, 1H), 6.12 (d, 1H), 3.29 (d, 1H), 3.15 (d, 1H).

EXAMPLE 17

Preparation of rac-6-chloro-3-(3-chloro-benzyl)-3-(3-hydroxymethyl-phenylamino)-1,3-dihydro-indol-2-one

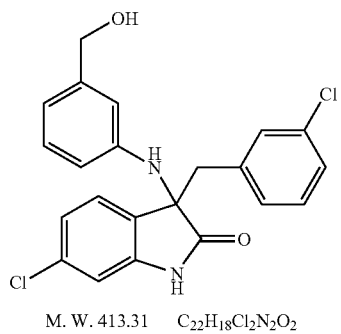

M. W. 413.31    $C_{22}H_{18}Cl_2N_2O_2$

The title compound was prepared by the same procedure for rac-6-chloro-3-(3-chloro-benzyl)-3-(4-propoxy-phenylamino)-1,3-dihydro-indol-2-one. MS: 413 (M+H)⁺.

EXAMPLE 18

Preparation of rac-6-chloro-3-(3-chloro-benzyl)-3-(4-difluoromethoxy-phenylamino)-1,3-dihydro-indol-2-one

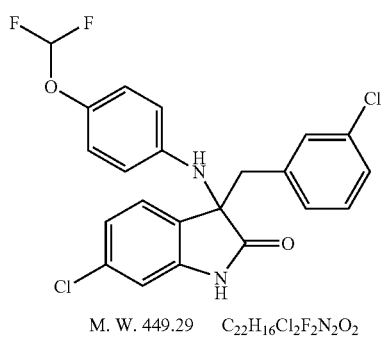

M. W. 449.29    $C_{22}H_{16}Cl_2F_2N_2O_2$

The title compound was prepared by the same procedure for rac-6-chloro-3-(3-chloro-benzyl)-3-(4-propoxy-phenylamino)-1,3-dihydro-indol-2-one. MS: 449 (M+H)⁺.

H¹-NMR (400 MHz, DMSO-d$_6$) δ 10.63 (s, 1H), 7.20 (m, 3H), 7.03 (dd, 1H), 6.85 (t, 1H), 6.80 (d, 2H), 6.76 (d, 1H), 6.70 (d, 1H), 6.66 (d, 1H), 6.22 (m, 2H), 3.29 (d, 1H), 3.15 (d, 1H).

EXAMPLE 19

Preparation of rac-6-chloro-3-(3-chloro-benzyl)-3-(3-difluoromethoxy-phenylamino)-1,3-dihydro-indol-2-one

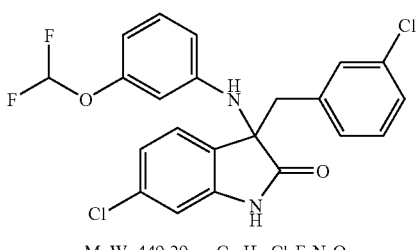

M. W. 449.29    $C_{22}H_{16}Cl_2F_2N_2O_2$

The title compound was prepared by the same procedure for rac-6-chloro-3-(3-chloro-benzyl)-3-(4-propoxy-phenylamino)-1,3-dihydro-indol-2-one. MS: 449 (M+H)⁺.

EXAMPLE 20

Preparation of rac-6-chloro-3-(3-chloro-benzyl)-3-(4-trifluoromethyl-phenylamino)-1,3-dihydro-indol-2-one

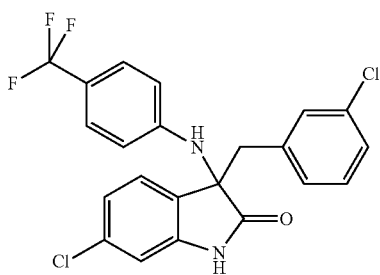

M. W. 451.28    $C_{22}H_{15}Cl_2F_3N_2O$

The title compound was prepared by the same procedure for rac-6-chloro-3-(3-chloro-benzyl)-3-(4-propoxy-phenylamino)-1,3-dihydro-indol-2-one. MS: 451 (M+H)⁺.

EXAMPLE 21

Preparation of rac-3-(4-butoxy-phenylamino)-6-chloro-3-(3-chloro-benzyl)-1,3-dihydro-indol-2-one

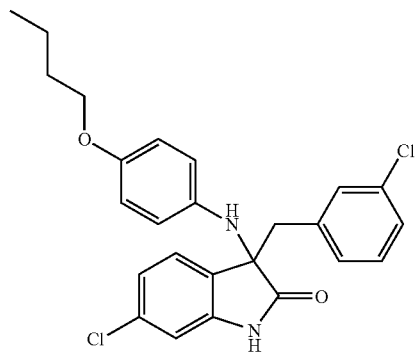

M. W. 455.39   C₂₅H₂₄Cl₂N₂O₂

The title compound was prepared by the same procedure for rac-6-chloro-3-(3-chloro-benzyl)-3-(4-propoxy-phenylamino)-1,3-dihydro-indol-2-one. MS: 455 (M+H)⁺.

EXAMPLE 22

Preparation of rac-3-(3-acetyl-phenylamino)-6-chloro-3-(3-chloro-benzyl)-1,3-dihydro-indol-2-one

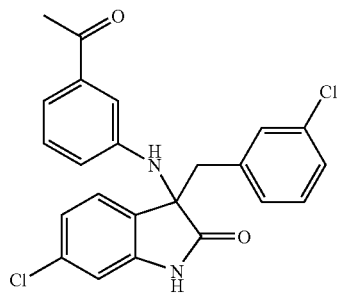

M. W. 425.32   C₂₃H₁₈Cl₂N₂O₂

The title compound was prepared by the same procedure for rac-6-chloro-3-(3-chloro-benzyl)-3-(4-propoxy-phenylamino)-1,3-dihydro-indol-2-one. MS: 425 (M+H)⁺.

EXAMPLE 23

Preparation of rac-6-chloro-3-(3-chloro-benzyl)-3-phenylamino-1,3-dihydro-indol-2-one

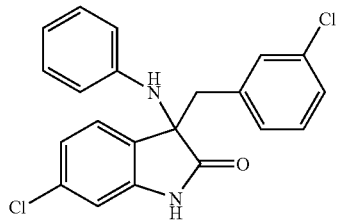

M. W. 383.28   C₂₁H₁₆Cl₂N₂O

The title compound was prepared by the same procedure for rac-6-chloro-3-(3-chloro-benzyl)-3-(4-propoxy-phenylamino)-1,3-dihydro-indol-2-one. MS: 383 (M+H)⁺.

EXAMPLE 24

Preparation of rac-6-chloro-3-(3-chloro-benzyl)-3-(4-methoxy-phenylamino)-1,3-dihydro-indol-2-one

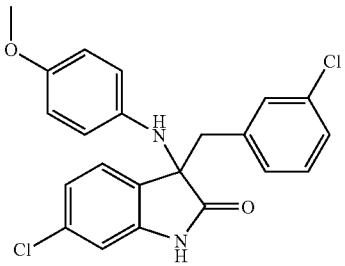

M. W. 413.31   C₂₂H₁₈Cl₂N₂O₂

The title compound was prepared by the same procedure for rac-6-chloro-3-(3-chloro-benzyl)-3-(4-propoxy-phenylamino)-1,3-dihydro-indol-2-one. MS: 413 (M+H)+.

EXAMPLE 25

Preparation of rac-6-chloro-3-(3-chloro-benzyl)-3-(3-trifluoromethyl-phenylamino)-1,3-dihydro-indol-2-one

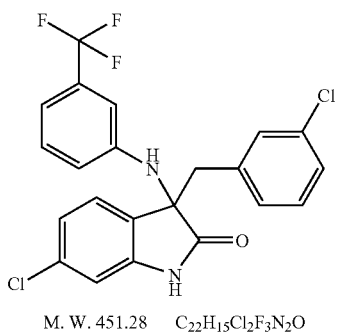

M. W. 451.28   $C_{22}H_{15}Cl_2F_3N_2O$

The title compound was prepared by the same procedure for rac-6-chloro-3-(3-chloro-benzyl)-3-(4-propoxy-phenylamino)-1,3-dihydro-indol-2-one. MS: 451 (M+H)+.

H$^1$-NMR (400 MHz, DMSO-d$_6$) δ 10.73 (s, 1H), 7.22 (m, 5H), 7.03 (d, 1H), 6.86 (t, 1H), 6.83 (d, 1H), 6.78 (d, 1H), 6.70 (d, 1H), 6.57 (s, 1H), 6.35 (dd, 1H), 3.31 (d, 1H), 3.17 (d, 1H).

EXAMPLE 26

Preparation of rac-3-[6-chloro-3-(3-chloro-benzyl)-2-oxo-2,3-dihydro-indol-3-ylamino]-benzonitrile

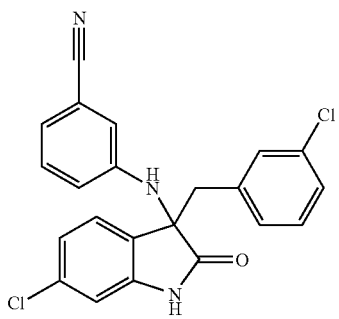

M. W. 408.29   $C_{22}H_{15}Cl_2N_3O$

The title compound was prepared by the same procedure for rac-6-chloro-3-(3-chloro-benzyl)-3-(4-propoxy-phenylamino)-1,3-dihydro-indol-2-one. MS: 408 (M+H)+.

EXAMPLE 27

Preparation of rac-6-chloro-3-(3-chloro-benzyl)-3-(4-ethoxy-phenylamino)-1,3-dihydro-indol-2-one

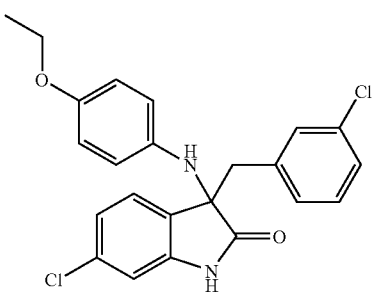

M. W. 427.33   $C_{23}H_{20}Cl_2N_2O_2$

The title compound was prepared by the same procedure for rac-6-chloro-3-(3-chloro-benzyl)-3-(4-propoxy-phenylamino)-1,3-dihydro-indol-2-one. MS: 427 (M+H)+.

EXAMPLE 28

Preparation of rac-6-chloro-3-(3-chloro-benzyl)-3-(3-chloro-phenylamino)-1,3-dihydro-indol-2-one

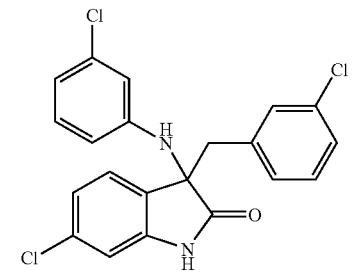

M. W. 417.73   $C_{21}H_{15}Cl_3N_2O$

The title compound was prepared by the same procedure for rac-6-chloro-3-(3-chloro-benzyl)-3-(4-propoxy-phenylamino)-1,3-dihydro-indol-2-one. MS: 417 (M+H)⁺.

EXAMPLE 29

Preparation of rac-3-(4-bromo-2-methyl-phenylamino)-6-chloro-3-(3-chloro-benzyl)-1,3-dihydroindol-2-one

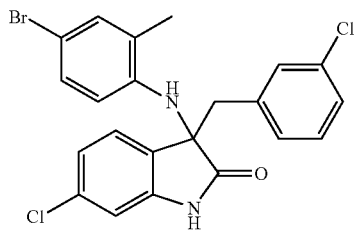

M. W. 476.20    $C_{22}H_{17}BrCl_2N_2O$

The title compound was prepared by the same procedure for rac-6-chloro-3-(3-chloro-benzyl)-3-(4-propoxy-phenylamino)-1,3-dihydro-indol-2-one. MS: 476 (M+H)⁺.

EXAMPLE 30

Preparation of rac-3-(4-bromo-3-methyl-phenylamino)-6-chloro-3-(3-chloro-benzyl)-1,3-dihydroindol-2-one

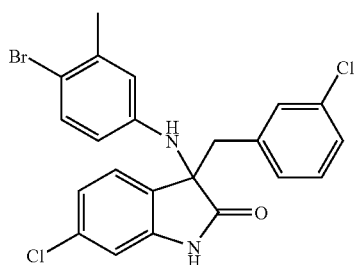

M. W. 476.20    $C_{22}H_{17}BrCl_2N_2O$

The title compound was prepared by the same procedure for rac-6-chloro-3-(3-chloro-benzyl)-3-(4-propoxy-phenylamino)-1,3-dihydro-indol-2-one. MS: 476 (M+H)⁺.

EXAMPLE 31

Preparation of rac-6-chloro-3-(3-chloro-benzyl)-3-(5-fluoro-2-methyl-phenylamino)-1,3-dihydro-indol-2-one

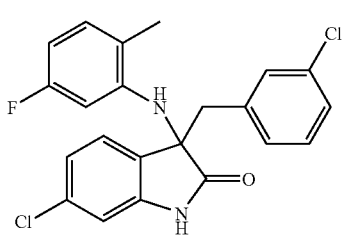

M. W. 415.30    $C_{22}H_{17}Cl_2FN_2O$

The title compound was prepared by the same procedure for rac-6-chloro-3-(3-chloro-benzyl)-3-(4-propoxy-phenylamino)-1,3-dihydro-indol-2-one. MS: 415 (M+H)⁺.

EXAMPLE 32

Preparation of rac-6-chloro-3-(3-chloro-benzyl)-3-(2,3-difluoro-phenylamino)-1,3-dihydro-indol-2-one

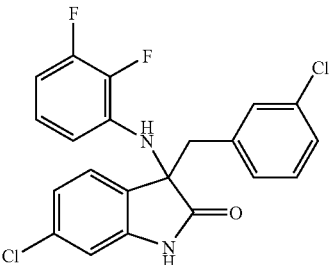

M. W. 419.26    $C_{21}H_{14}Cl_2F_2N_2O$

The title compound was prepared by the same procedure for rac-6-chloro-3-(3-chloro-benzyl)-3-(4-propoxy-phenylamino)-1,3-dihydro-indol-2-one. MS: 419 (M+H)⁺.

EXAMPLE 33

Preparation of rac-6-chloro-3-(3-chloro-benzyl)-3-(2-trifluoromethyl-phenylamino)-1,3-dihydro-indol-2-one

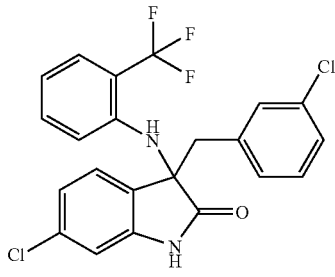

M. W. 451.28    C₂₂H₁₅Cl₂F₃N₂O

The title compound was prepared by the same procedure for rac-6-chloro-3-(3-chloro-benzyl)-3-(4-propoxy-phenylamino)-1,3-dihydro-indol-2-one. MS: 451 (M+H)⁺.

EXAMPLE 34

Preparation of rac-6-chloro-3-(3-chloro-benzyl)-3-(2-fluoro-phenylamino)-1,3-dihydro-indol-2-one

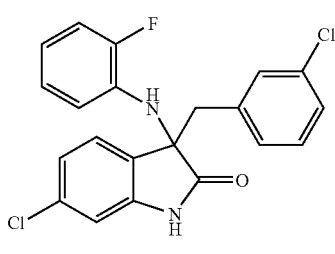

M. W. 401.27    C₂₁H₁₅Cl₂FN₂O

The title compound was prepared by the same procedure for rac-6-chloro-3-(3-chloro-benzyl)-3-(4-propoxy-phenylamino)-1,3-dihydro-indol-2-one. MS: 401 (M+H)⁺.

EXAMPLE 35

Preparation of rac-6-chloro-3-(3-chloro-benzyl)-3-(4-fluoro-2-methyl-phenylamino)-1,3-dihydro-indol-2-one

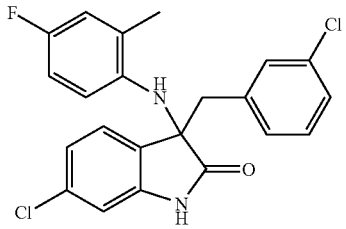

M. W. 415.30    C₂₂H₁₇Cl₂FN₂O

The title compound was prepared by the same procedure for rac-6-chloro-3-(3-chloro-benzyl)-3-(4-propoxy-phenylamino)-1,3-dihydro-indol-2-one. MS: 415 (M+H)⁺.

EXAMPLE 36

Preparation of rac-6-chloro-3-(3-chloro-benzyl)-3-(4-chloro-3-methyl-phenylamino)-1,3-dihydro-indol-2-one

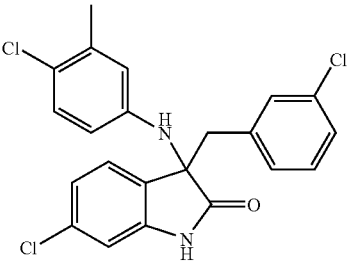

M. W. 431.75    C₂₂H₁₇Cl₃N₂O

The title compound was prepared by the same procedure for rac-6-chloro-3-(3-chloro-benzyl)-3-(4-propoxy-phenylamino)-1,3-dihydro-indol-2-one. MS: 431 (M+H)+.

EXAMPLE 37

Preparation of rac-6-chloro-3-(3-chloro-benzyl)-3-(3,4,5-trifluoro-phenylamino)-1,3-dihydro-indol-2-one

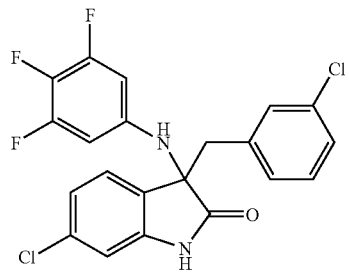

M. W. 437.25    $C_{21}H_{13}Cl_2F_3N_2O$

The title compound was prepared by the same procedure for rac-6-chloro-3-(3-chloro-benzyl)-3-(4-propoxy-phenylamino)-1,3-dihydro-indol-2-one. MS: 437 (M+H)+.

H$^1$-NMR (400 MHz, DMSO-d$_6$) δ 10.76 (s, 1H), 7.22 (m, 4H), 7.07 (dd, 2H), 6.84 (t, 1H), 6.76 (d, 1H), 6.71 (d, 1H), 5.96 (m, 2H), 3.31 (d, 1H), 3.14 (d, 1H).

EXAMPLE 38

Preparation of rac-6-chloro-3-(3-chloro-benzyl)-3-(2-chloro-phenylamino)-1,3-dihydro-indol-2-one

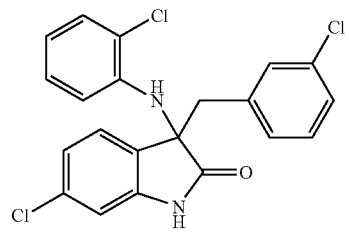

M. W. 417.73    $C_{21}H_{15}Cl_3N_2O$

The title compound was prepared by the same procedure for rac-6-chloro-3-(3-chloro-benzyl)-3-(4-propoxy-phenylamino)-1,3-dihydro-indol-2-one. MS: 417 (M+H)+.

EXAMPLE 39

Preparation of rac-6-chloro-3-(3-chloro-benzyl)-3-(5-chloro-2-methyl-phenylamino)-1,3-dihydro-indol-2-one

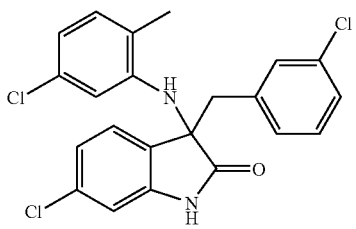

M. W. 431.75    $C_{22}H_{17}Cl_3N_2O$

The title compound was prepared by the same procedure for rac-6-chloro-3-(3-chloro-benzyl)-3-(4-propoxy-phenylamino)-1,3-dihydro-indol-2-one. MS: 431 (M+H)+.

EXAMPLE 40

Preparation of rac-6-chloro-3-(3-chloro-benzyl)-3-(3-hydroxy-phenylamino)-1,3-dihydro-indol-2-one

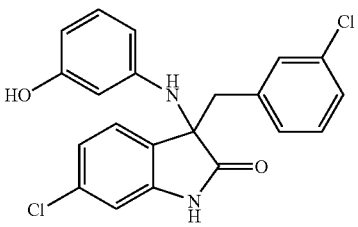

M. W. 399.28    $C_{21}H_{16}Cl_2N_2O_2$

The title compound was prepared by the same procedure for rac-6-chloro-3-(3-chloro-benzyl)-3-(4-propoxy-phenylamino)-1,3-dihydro-indol-2-one. MS: 399 (M+H)⁺.

EXAMPLE 41

Preparation of rac-6-chloro-3-(3-chloro-benzyl)-3-(3-methoxy-phenylamino)-1,3-dihydro-indol-2-one

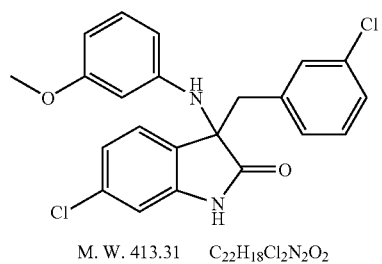

M. W. 413.31   $C_{22}H_{18}Cl_2N_2O_2$

The title compound was prepared by the same procedure for rac-6-chloro-3-(3-chloro-benzyl)-3-(4-propoxy-phenylamino)-1,3-dihydro-indol-2-one. MS: 413 (M+H)⁺.

EXAMPLE 42

Preparation of rac-6-chloro-3-(3-chloro-benzyl)-3-cyclohexylamino-1,3-dihydro-indol-2-one

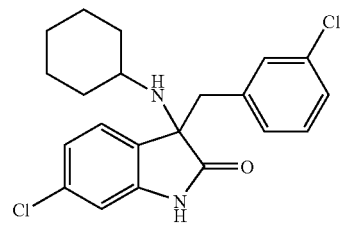

M. W. 389.33   $C_{21}H_{22}Cl_2N_2O$

The mixture of rac-3-bromo-6-chloro-3-(3-chloro-benzyl)-1,3-dihydro-indol-2-one (100 mg, 0.27 mmol) (from example 1c supra), cyclohexylamine (40 mg, 0.41 mmol) and DIPEA (104.5 mg, 0.81 mmol) in dimethyl formide (2 mL) was stirred at room temperature for 2 h. Then water (10 mL) was added and the aqueous layer was extracted with ethyl acetate (3×10 mL). The combined organic layer was concentrated and the residue was purified by preparative HPLC to give 51 mg of rac-6-chloro-3-(3-chloro-benzyl)-3-cyclohexylamino-1,3-dihydro-indol-2-one as a white solid. MS: 389 (M+H)⁺.

EXAMPLE 43

Preparation of rac-6-chloro-3-(3-chloro-benzyl)-3-(2-methyl-pyrrolidin-1-yl)-1,3-dihydro-indol-2-one

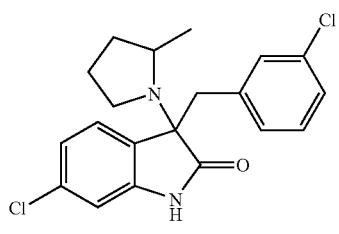

M. W. 375.30   $C_{20}H_{20}Cl_2N_2O$

The title compound was prepared by the same procedure for rac-6-chloro-3-(3-chloro-benzyl)-3-cyclohexylamino-1,3-dihydro-indol-2-one. MS: 375 (M+H)⁺.

EXAMPLE 44

Preparation of rac-6-chloro-3-(3-chloro-benzyl)-3-(4-methyl-cyclohexylamino)-1,3-dihydro-indol-2-one

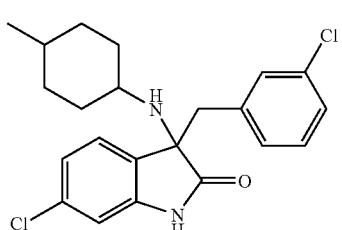

M. W. 403.36   $C_{22}H_{24}Cl_2N_2O$

The title compound was prepared by the same procedure for rac-6-chloro-3-(3-chloro-benzyl)-3-cyclohexylamino-1,3-dihydro-indol-2-one. MS: 403 (M+H)⁺.

EXAMPLE 45

Preparation of rac-3-azetidin-1-yl-6-chloro-3-(3-chloro-benzyl)-1,3-dihydro-indol-2-one

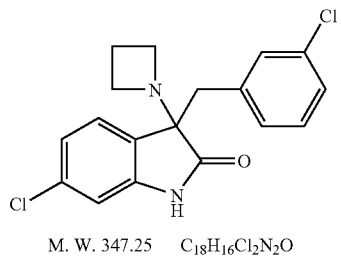

M. W. 347.25    $C_{18}H_{16}Cl_2N_2O$

The title compound was prepared by the same procedure for rac-6-chloro-3-(3-chloro-benzyl)-3-cyclohexylamino-1,3-dihydro-indol-2-one. MS: 347 (M+H)⁺.

EXAMPLE 46

Preparation of rac-(2R)-[6-chloro-3-(3-chloro-benzyl)-2-oxo-2,3-dihydro-indol-3-ylamino]3,3-dimethyl-butyric acid

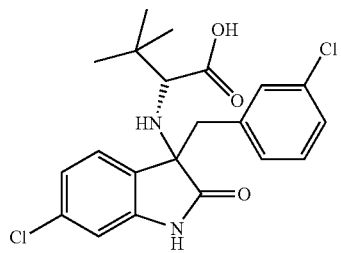

M. W. 421.33    $C_{21}H_{22}Cl_2N_2O_3$

The title compound was prepared by the same procedure for rac-6-chloro-3-(3-chloro-benzyl)-3-cyclohexylamino-1,3-dihydro-indol-2-one. MS: 421 (M+H)⁺.

EXAMPLE 47

Preparation of rac-6-chloro-3-(3-chloro-benzyl)-3-[(1S)-hydroxymethyl-2,2-dimethyl-propylamino]-1,3-dihydro-indol-2-one

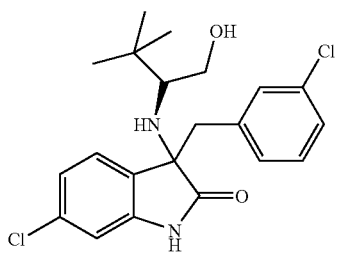

M. W. 407.34    $C_{21}H_{24}Cl_2N_2O_2$

The title compound was prepared by the same procedure for rac-6-chloro-3-(3-chloro-benzyl)-3-cyclohexylamino-1,3-dihydro-indol-2-one. MS: 407 (M+H)⁺.

EXAMPLE 48

Preparation of rac-6-chloro-3-(3-chloro-benzyl)-3-(4-hydroxy-cyclohexylamino)-1,3-dihydro-indol-2-one

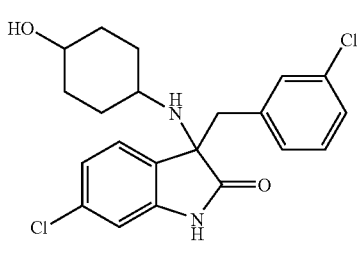

M. W. 405.33    $C_{21}H_{22}Cl_2N_2O_2$

The title compound was prepared by the same procedure for rac-6-chloro-3-(3-chloro-benzyl)-3-cyclohexylamino-1,3-dihydro-indol-2-one. MS: 405 (M+H)+.

EXAMPLE 49

Preparation of rac-6-chloro-3-(3-chloro-benzyl)-3-cyclobutylamino-1,3-dihydro-indol-2-one

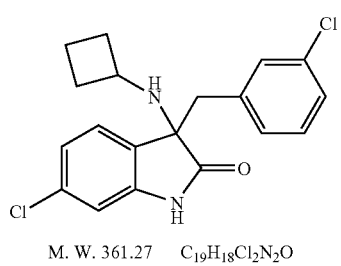

M. W. 361.27     $C_{19}H_{18}Cl_2N_2O$

The title compound was prepared by the same procedure for rac-6-chloro-3-(3-chloro-benzyl)-3-cyclohexylamino-1,3-dihydro-indol-2-one. MS: 361 (M+H)+.

EXAMPLE 50

Preparation of rac-1-[6-chloro-3-(3-chloro-benzyl)-2-oxo-2,3-dihydrol-indol-3-yl]-piperidine-3-carboxylic acid amide

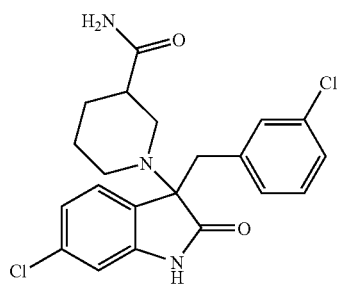

M. W. 418.33     $C_{21}H_{21}Cl_2N_3O_2$

The title compound was prepared by the same procedure for rac-6-chloro-3-(3-chloro-benzyl)-3-cyclohexylamino-1,3-dihydro-indol-2-one. MS: 418 (M+H)+.

EXAMPLE 51

Preparation of rac-6-chloro-3-(3-chloro-benzyl)-3-(4-hydroxy-piperidin-1-yl)-1,3-dihydro-indol-2-one

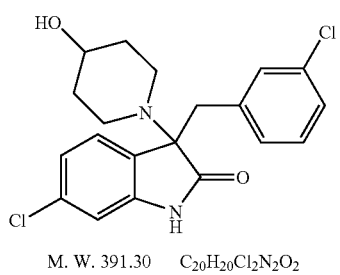

M. W. 391.30     $C_{20}H_{20}Cl_2N_2O_2$

The title compound was prepared by the same procedure for rac-6-chloro-3-(3-chloro-benzyl)-3-cyclohexylamino-1,3-dihydro-indol-2-one. MS: 391 (M+H)+.

EXAMPLE 52

Preparation of rac-6-chloro-3-(3-chloro-benzyl)-3-(3-hydroxy-pyrrolidin-1-yl)-1,3-dihydro-indol-2-one

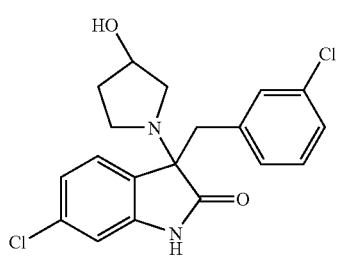

M. W. 377.27     $C_{19}H_{18}Cl_2N_2O_2$

The title compound was prepared by the same procedure for rac-6-chloro-3-(3-chloro-benzyl)-3-cyclohexylamino-1,3-dihydro-indol-2-one. MS: 377 (M+H)+.

EXAMPLE 53

Preparation of rac-6-chloro-3-(3-chloro-benzyl)-3-(isopropyl-methyl-amino)-1,3-dihydro-indol-2-one

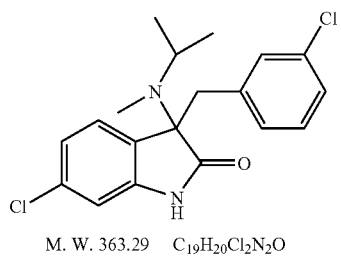

M. W. 363.29   $C_{19}H_{20}Cl_2N_2O$

The title compound was prepared by the same procedure for rac-6-chloro-3-(3-chloro-benzyl)-3-cyclohexylamino-1,3-dihydro-indol-2-one. MS: 363 (M+H)+.

EXAMPLE 54

Preparation of rac-6-chloro-3-(3-chloro-benzyl)-3-[(1R)-hydroxymethyl-2,2-dimethyl-propylamino]-1,3-dihydro-indol-2-one

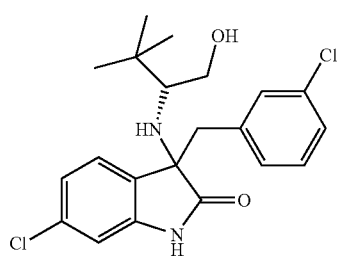

M. W. 407.34   $C_{21}H_{24}Cl_2N_2O_2$

The title compound was prepared by the same procedure for rac-6-chloro-3-(3-chloro-benzyl)-3-cyclohexylamino-1,3-dihydro-indol-2-one. MS: 407 (M+H)+.

EXAMPLE 55

Preparation of rac-1-[6-chloro-3-(3-chloro-benzyl)-2-oxo-2,3-dihydrol-1H-indol-3-yl]-piperidine-4-carboxylic acid amide

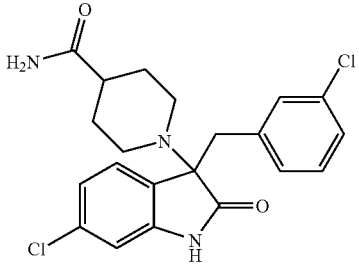

M. W. 418.33   $C_{21}H_{21}Cl_2N_3O_2$

The title compound was prepared by the same procedure for rac-6-chloro-3-(3-chloro-benzyl)-3-cyclohexylamino-1,3-dihydro-indol-2-one. MS: 418 (M+H)+.

EXAMPLE 56

Preparation of rac-6-chloro-3-(3-chloro-benzyl)-3-(4-methyl-piperazin-1-yl)-1,3-dihydro-indol-2-one

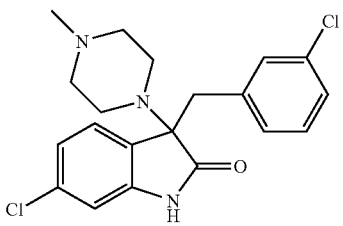

M. W. 390.32   $C_{20}H_{21}Cl_2N_3O$

The title compound was prepared by the same procedure for rac-6-chloro-3-(3-chloro-benzyl)-3-cyclohexylamino-1,3-dihydro-indol-2-one. MS: 390 (M+H)+.

EXAMPLE 57

Preparation of rac-6-chloro-3-(3-chloro-benzyl)-3-[4-(2-fluoro-phenyl)-piperazin-1-yl]-1,3-dihydro-indol-2-one

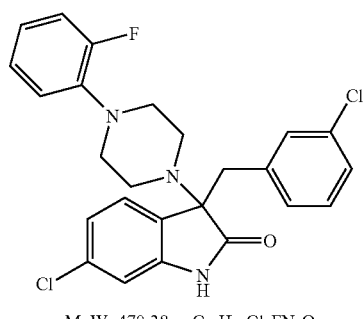

M. W. 470.38   $C_{25}H_{22}Cl_2FN_3O$

The title compound was prepared by the same procedure for rac-6-chloro-3-(3-chloro-benzyl)-3-cyclohexylamino-1,3-dihydro-indol-2-one. MS: 470 (M+H)+.

EXAMPLE 58

Preparation of rac-6-chloro-3-(3-chloro-benzyl)-3-[4-(3-trifluoromethyl-pyridin-2-yl)-piperazin-1-yl]-1,3-dihydro-indol-2-one

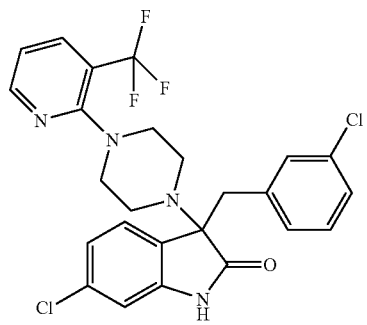

M. W. 521.37   $C_{25}H_{21}Cl_2F_3N_4O$

The title compound was prepared by the same procedure for rac-6-chloro-3-(3-chloro-benzyl)-3-cyclohexylamino-1,3-dihydro-indol-2-one. MS: 521 (M+H)+.

EXAMPLE 59

Preparation of rac-6-chloro-3-(3-chloro-benzyl)-3-[2-(2-hydroxy-ethoxy)-ethylamino]-1,3-dihydro-indol-2-one

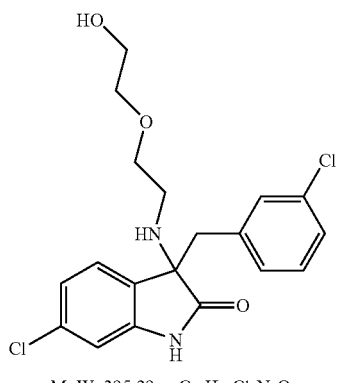

M. W. 395.29   $C_{19}H_{20}Cl_2N_2O_3$

The title compound was prepared by the same procedure for rac-6-chloro-3-(3-chloro-benzyl)-3-cyclohexylamino-1,3-dihydro-indol-2-one. MS: 395 (M+H)+.

EXAMPLE 60

Preparation of rac-6-chloro-3-(3-chloro-benzyl)-3-thiomorpholin-4-yl-1,3-dihydro-indol-2-one

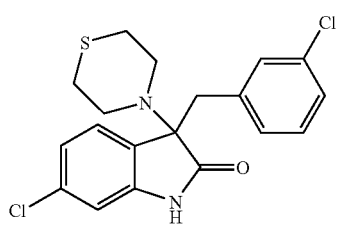

M. W. 393.34   $C_{19}H_{18}Cl_2N_4OS$

The title compound was prepared by the same procedure for rac-6-chloro-3-(3-chloro-benzyl)-3-cyclohexylamino-1,3-dihydro-indol-2-one. MS: 393 (M+H)⁺.

EXAMPLE 61

Preparation of rac-6-chloro-3-(3-chloro-benzyl)-3-cyclopropylamino-1,3-dihydro-indol-2-one

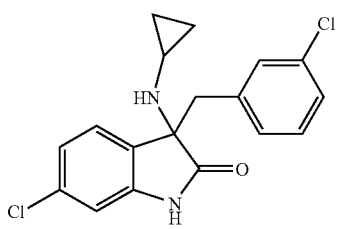

M. W. 347.25   C$_{18}$H$_{16}$Cl$_2$N$_2$O

The title compound was prepared by the same procedure for rac-6-chloro-3-(3-chloro-benzyl)-3-cyclohexylamino-1,3-dihydro-indol-2-one. MS: 347 (M+H)⁺.

EXAMPLE 62

Preparation of rac-6-chloro-3-(3-chloro-benzyl)-3-(3-hydroxy-piperidin-1-yl)-1,3-dihydro-indol-2-one

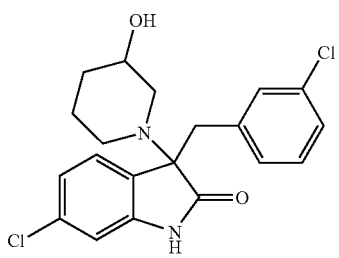

M. W. 391.30   C$_{20}$H$_{20}$Cl$_2$N$_2$O$_2$

The title compound was prepared by the same procedure for rac-6-chloro-3-(3-chloro-benzyl)-3-cyclohexylamino-1,3-dihydro-indol-2-one. MS: 391 (M+H)⁺.

EXAMPLE 63

Preparation of rac-6-chloro-3-(3-chloro-benzyl)-3-(4-oxo-piperidin-1-yl)-1,3-dihydro-indol-2-one

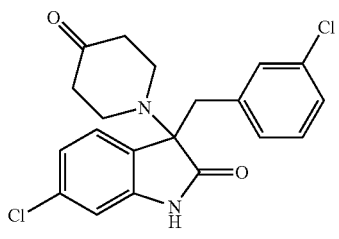

M. W. 389.28   C$_{20}$H$_{18}$Cl$_2$N$_2$O$_2$

The title compound was prepared by the same procedure for rac-6-chloro-3-(3-chloro-benzyl)-3-cyclohexylamino-1,3-dihydro-indol-2-one. MS: 390 (M+H)⁺. H$^1$-NMR (400 MHz, DMSO-d$_6$) δ 10.46 (s, 1H), 7.40 (d, 1H), 7.13 (m, 3H), 6.89 (s, 1H), 6.80 (d, 1H), 6.59 (s, 1H), 3.37 (dd, 2H), 2.88 (s, 4H), 2.33 (s, 4H).

EXAMPLE 64

Preparation of rac-6-chloro-3-(3-chloro-benzyl)-3-(2-hydroxy-cyclohexylamino)-1,3-dihydro-indol-2-one

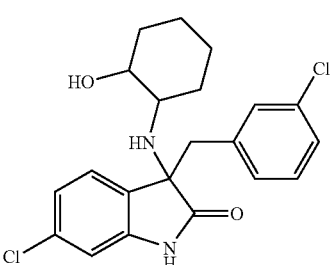

M. W. 405.33   C$_{21}$H$_{22}$Cl$_2$N$_2$O$_2$

The title compound was prepared by the same procedure for rac-6-chloro-3-(3-chloro-benzyl)-3-cyclohexylamino-1,3-dihydro-indol-2-one. MS: 405 (M+H)+.

EXAMPLE 65

Preparation of rac-6-chloro-3-(3-chloro-benzyl)-3-(1-hydroxymethyl-2-methyl-propylamino)-1,3-dihydro-indol-2-one

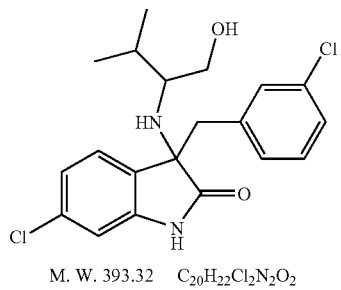

M. W. 393.32   $C_{20}H_{22}Cl_2N_2O_2$

The title compound was prepared by the same procedure for rac-6-chloro-3-(3-chloro-benzyl)-3-cyclohexylamino-1,3-dihydro-indol-2-one. MS: 393 (M+H)+. $H^1$-NMR (400 MHz, DMSO-$d_6$) δ 10.39 (s, 1H), 7.20 (m, 1H), 7.18 (t, 1H), 7.00 (m, 3H), 6.80 (m, 1H), 6.66 (t, 1H), 4.21 (t, 1H), 3.29 (m, 1H), 3.19 (m, 1H), 3.31 (d, 1H), 2.83 (d, 1H), 2.47 (m, 1H), 1.88 (m, 1H), 1.60 (m, 1H), 0.70 (dd, 6H).

EXAMPLE 66

Preparation of rac-6-chloro-3-(3-chloro-benzyl)-3-(1-cyclohexyl-ethylamino)-1,3-dihydro-indol-2-one

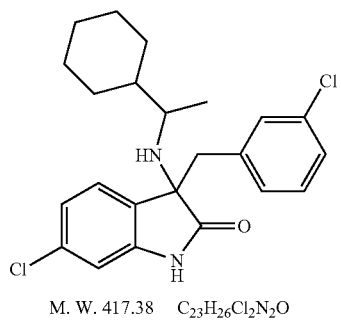

M. W. 417.38   $C_{23}H_{26}Cl_2N_2O$

The title compound was prepared by the same procedure for rac-6-chloro-3-(3-chloro-benzyl)-3-cyclohexylamino-1,3-dihydro-indol-2-one. MS: 417 (M+H)+.

EXAMPLE 67

Preparation of rac-6-chloro-3-(3-chloro-benzyl)-3-(2-hydroxy-1-hydroxymethyl-1-methyl-ethylamino)-1,3-dihydro-indol-2-one

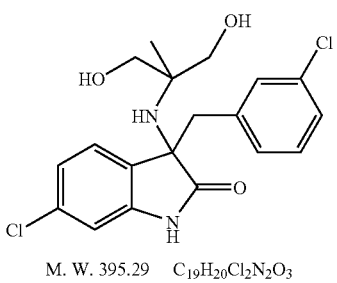

M. W. 395.29   $C_{19}H_{20}Cl_2N_2O_3$

The title compound was prepared by the same procedure for rac-6-chloro-3-(3-chloro-benzyl)-3-cyclohexylamino-1,3-dihydro-indol-2-one. MS: 395 (M+H)+.

EXAMPLE 68

Preparation of rac-(2S)-[6-chloro-3-(3-chloro-benzyl)-2-oxo-2,3-dihydro-indol-3-ylamino]-3-methyl-butyramide

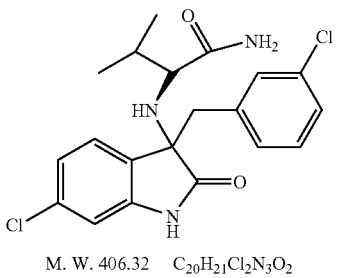

M. W. 406.32   $C_{20}H_{21}Cl_2N_3O_2$

The title compound was prepared by the same procedure for rac-6-chloro-3-(3-chloro-benzyl)-3-cyclohexylamino-1,3-dihydro-indol-2-one. MS: 406 (M+H)+. $H^1$-NMR (400 MHz, DMSO-$d_6$) δ 10.36 (s, 1H), 7.30 (d, 1H), 7.13 (m, 3H), 6.96 (t, 1H), 6.87 (t, 1H), 6.78 (m, 2H), 6.57 (s, 1H), 3.33 (m, 1H), 3.17 (dd, 2H), 2.84 (d, 1H), 1.72 (m, 1H), 0.80 (dd, 6H).

EXAMPLE 69

Preparation of rac-(2S)-[6-chloro-3-(3-chloro-benzyl)-2-oxo-2,3-dihydro-1H-indol-3-ylamino]-3-methyl-butyric acid methyl ester

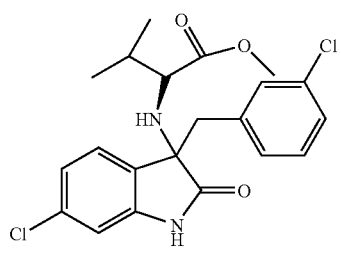

M.W. 421.33    C₂₁H₂₂Cl₂N₂O₃

The title compound was prepared by the same procedure for rac-6-chloro-3-(3-chloro-benzyl)-3-cyclohexylamino-1,3-dihydro-indol-2-one. MS: 421 (M+H)⁺.

EXAMPLE 70

Preparation of rac-(S)-1-[6-chloro-3-(3-chloro-benzyl)-2-oxo-2,3-dihydro-1H-indol-3-yl]-pyrrolidine-2-carboxylic acid amide

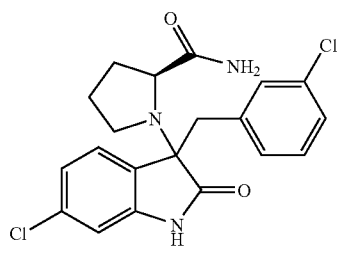

M.W. 404.30    C₂₀H₁₉Cl₂N₃O₂

The title compound was prepared by the same procedure for rac-6-chloro-3-(3-chloro-benzyl)-3-cyclohexylamino-1,3-dihydro-indol-2-one. MS: 404 (M+H)⁺. H¹-NMR (400 MHz, DMSO-d₆) δ 10.38 (s, 1H), 7.82 (d, 1H), 7.56 (s, 1H), 7.28 (s, 1H), 7.08 (m, 3H), 6.79 (s, 1H), 6.70 (d, 1H), 6.55 (s, 1H), 4.40 (d, 1H), 3.19 (dd, 2H), 2.75 (m, 1H), 2.21 (m, 1H), 1.90 (m, 2H), 1.60 (m, 2H).

EXAMPLE 71

Preparation of rac-6-chloro-3-(3-chloro-benzyl)-3-(2-hydroxy-1-hydroxymethyl-ethylamino)-1,3-dihydro-indol-2-one

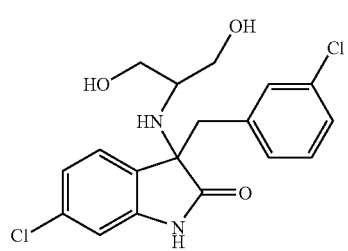

M.W. 381.26    C₁₈H₁₈Cl₂N₂O₃

The title compound was prepared by the same procedure for rac-6-chloro-3-(3-chloro-benzyl)-3-cyclohexylamino-1,3-dihydro-indol-2-one. MS: 381 (M+H)⁺.

EXAMPLE 72

Preparation of rac-(2S)-[6-chloro-3-(3-chloro-benzyl)-2-oxo-2,3-dihydro-1H-indol-3-ylamino]-4-methyl-pentanoic acid tert-butyl ester

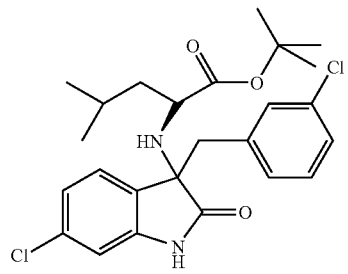

M.W. 477.44    C₂₅H₃₀Cl₂N₂O₃

The title compound was prepared by the same procedure for rac-6-chloro-3-(3-chloro-benzyl)-3-cyclohexylamino-1,3-dihydro-indol-2-one. MS: 477 (M+H)⁺.

EXAMPLE 73

Preparation of rac-6-chloro-3-(3-chloro-benzyl)-3-(cyclopropylmethyl-propyl-amino)-1,3-dihydro-indol-2-one

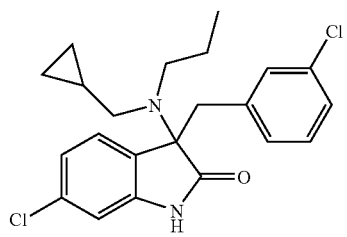

M. W. 403.36    $C_{22}H_{24}Cl_2N_2O$

The title compound was prepared by the same procedure for rac-6-chloro-3-(3-chloro-benzyl)-3-cyclohexylamino-1,3-dihydro-indol-2-one. MS: 403 (M+H)⁺.

EXAMPLE 74

Preparation of rac-6-chloro-3-(3-chloro-benzyl)-3-(2-hydroxy-1-methyl-ethylamino)-1,3-dihydro-indol-2-one

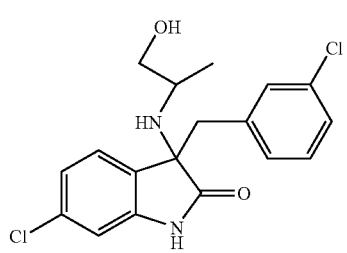

M. W. 365.26    $C_{18}H_{18}Cl_2N_2O_2$

The title compound was prepared by the same procedure for rac-6-chloro-3-(3-chloro-benzyl)-3-cyclohexylamino-1,3-dihydro-indol-2-one. MS: 365 (M+H)⁺.

EXAMPLE 75

Preparation of rac-{[6-chloro-3-(3-chloro-benzyl)-2-oxo-2,3-dihydro-1H-indol-3-yl]-phenyl-amino}-acetic acid

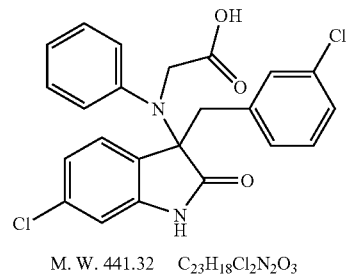

M. W. 441.32    $C_{23}H_{18}Cl_2N_2O_3$

The title compound was prepared by the same procedure for rac-6-chloro-3-(3-chloro-benzyl)-3-cyclohexylamino-1,3-dihydro-indol-2-one. MS: 441 (M+H)⁺. H¹-NMR (400 MHz, DMSO-d₆) δ12.45 (s, 1H), 10.42 (s, 1H), 7.44 (d, 1H), 7.16 (m, 4H), 6.96 (m, 1H), 6.93 (m, 3H), 6.76 (m, 1H), 6.67 (d, 1H), 6.64 (d, 1H), 4.00 (dd, 2H), 3.31 (dd, 2H).

EXAMPLE 76a

Preparation of Intermediate E/Z-6-chloro-3-(4-chloro-benzylidene)-1,3-dihydro-indol-2-one

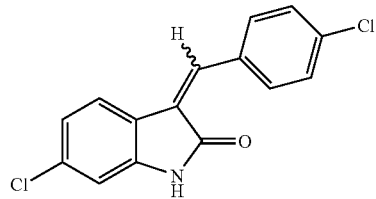

M. W. 290.15    $C_{15}H_9Cl_2NO$

To the mixture of 6-chlorooxindole (16.2 g, 92 mmol) (Crescent) and 4-chlorobenzaldehyde (12.9 g, 92 mmol) (Aldrich) in methanol (100 mL) was added pyrrolidine (6.55 g, 92 mol) (Aldrich) dropwisely. The mixture was then heated at 70° C. for 3 h. After cooling to 4° C., the resulting precipitate was collected and dried to give 21 g of E/Z-6-chloro-3-(4-chloro-benzylidene)-1,3-dihydro-indol-2-one as a bright yellow solid. MS: 291 (M+H)+.

EXAMPLE 76b

Preparation of Intermediate rac-6-chloro-3-(4-chloro-benzyl)-1,3-dihydro-indol-2-one

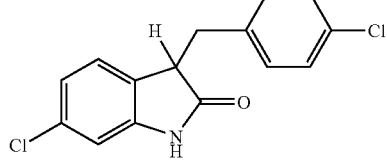

M. W. 292.17    $C_{15}H_{11}Cl_2NO$

Sodium borohydride (3.0 g, 79 mmol) (Aldrich) was added in small portions to a suspension of 6-chloro-3-(4-chloro-benzylidene)-1,3-dihydro-indol-2-one (19 g, 66 mmol) (from example 76a supra) in methanol (200 mL) and DMSO (50 mL) at such a rate that gas evolution was not too vigorous. When the addition was complete, mixture was stirred at room temperature for 0.5 h-1 h. After water (200 mL) was added, the resulting precipitate was collected and dried to give 18.3 g of rac-6-chloro-3-(4-chloro-benzyl)-1,3-dihydro-indol-2-one as a light yellow solid. MS: 293 (M+H)+.

EXAMPLE 76c

Preparation of Intermediate rac-3-bromo-6-chloro-3-(4-chloro-benzyl)-1,3-dihydro-indol-2-one

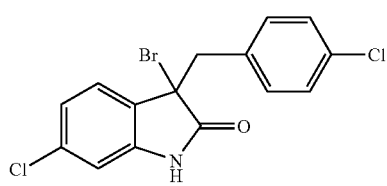

M. W. 371.06    $C_{15}H_{10}BrCl_2NO$

The title compound was prepared by the same procedure for rac-3-bromo-6-chloro-3-(3-chloro-benzyl)-1,3-dihydro-indol-2-one. MS: 371 (M+H)+.

EXAMPLE 76d

Preparation of Intermediate rac-3,5-dibromo-6-chloro-3-(4-chloro-benzyl)-1,3-dihydro-indol-2-one

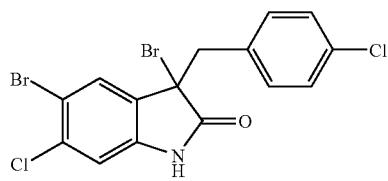

M. W. 449.96    $C_{15}H_9Br_2Cl_2NO$

The solution of bromine (2.2 g, 14.4 mmol) in dichloromethane (10 mL) was added dropwisely to the solution of rac-6-chloro-3-(4-chloro-benzyl)-1,3-dihydro-indol-2-one (2.0 g, 6.85 mmol) in dichloromethane (50 mL). The reaction mixture was stirred at room temperature for 1 h and then washed with water (3×50 mL), dried over $Na_2SO_4$ and concentrated in vacuo to give 2.2 g of rac-3,5-dibromo-6-chloro-3-(4-chloro-benzyl)-1,3-dihydro-indol-2-one as a solid. MS: 451 (M+H)+.

EXAMPLE 76e

Preparation of rac-6-chloro-3-(4-chloro-benzyl)-3-cyclohexylamino-1,3-dihydro-indol-2-one

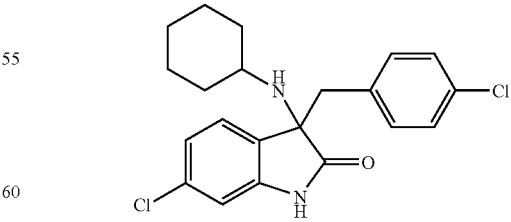

M. W. 389.33    $C_{21}H_{22}Cl_2N_2O$

The title compound was prepared by the same procedure for rac-6-chloro-3-(3-chloro-benzyl)-3-cyclohexylamino-1,3-dihydro-indol-2-one. MS: 389 (M+H)+. $H^1$-NMR (400

MHz, Acetone-$d_6$) δ 7.30 (d, 1H), 7.10 (d, 2H), 7.05 (dd, 1H), 6.80 (d, 2H), 6.72 (d, 1H), 3.00 (dd, 2H), 2.20 (m, 1H), 1.15 (m, 5H), 1.00 (m, 5H).

EXAMPLE 77

Preparation of rac-5-bromo-6-chloro-3-(4-chloro-benzyl)-3-cyclohexylamino-1,3-dihydro-indol-2-one

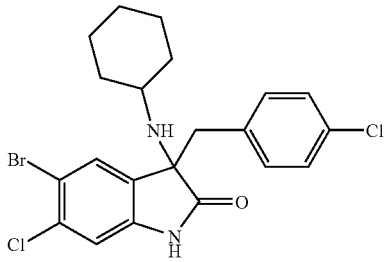

M. W. 468.22   $C_{21}H_{21}BrCl_2N_2O$

The title compound was prepared by the same procedure for rac-6-chloro-3-(3-chloro-benzyl)-3-cyclohexylamino-1,3-dihydro-indol-2-one. MS: 469 (M+H)$^+$.

EXAMPLE 78

Preparation of rac-6-chloro-3-(4-chloro-benzyl)-3-cyclohexylamino-1-(2-oxo-2-piperidin-yl-ethyl)-1,3-dihydro-indol-2-one

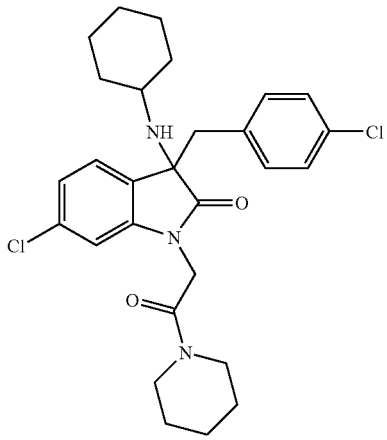

M. W. 514.50   $C_{28}H_{33}Cl_2N_3O_2$

To the mixture of 2-chloro-1-piperidin-1-yl-ethanone (41 mg, 31 mmol) and KI (43 mg, 0.26 mmol) in dimethylformide (5 mL) was added rac-3-bromo-6-chloro-3-(4-chloro-benzyl)-1,3-dihydro-indol-2-one (100 mg, 0.26 mmol) prepared in example 76c. After stirring at room temperature for 2 h, water (10 mL) was added and the crude was extracted with ethyl acetate (3×20 mL). The combined organic solution was concentrated in vacuo. The residue was purified with preparative HPLC to give rac-6-chloro-3-(4-chloro-benzyl)-3-cyclo-hexylamino-1-(2-oxo-2-piperidin-1-yl-ethyl)-1,3-dihydro-indol-2-one as a white solid. MS: 514 (M+H)$^+$.

EXAMPLE 79

Preparation of rac-5-bromo-6-chloro-3-(4-chloro-benzyl)-3-cyclohexylamino-1-(2-oxo-2-piperidin-1-yl-ethyl)-1,3-dihydro-indol-2-one

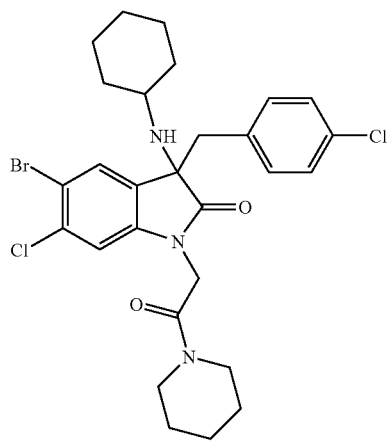

M. W. 593.40   $C_{28}H_{32}BrCl_2N_3O_2$

The title compound was prepared by the same procedure for rac-6-chloro-3-(4-chloro-benzyl)-3-cyclohexylamino-1-(2-oxo-2-piperidin-1-yl-ethyl)-1,3-dihydro-indol-2-one MS: 594 (M+H)$^+$; H$^1$-NMR (400 MHz, DMSO-$d_6$) δ 7.42 (s, 1H), 7.19 (m, 2H), 7.09 (s, 1H), 6.84 (d, 2H), 4.33 (dd, 2H), 3.40 (m, 4H), 3.00 (dd, 2H), 2.62 (d, 1H), 2.20 (m, 1H), 1.57 (m, 10H), 0.90 (m, 6H).

EXAMPLE 80a

Preparation of Intermediate cyclohexylamino-acetic acid ethyl ester

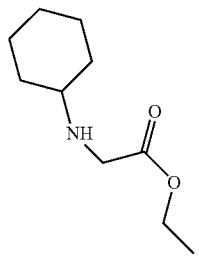

M. W. 185.27   $C_{10}H_{19}NO_2$

To a solution of cyclohexylamine (45 g, 0.45 mol) in dichloromethane (100 mL) was slowly added bromo-acetic acid ethyl ester (15 g, 0.09 mol) in dichloromethane (150 mL) at 0° C. After the addition, the mixture was stirred at room temperature for 1 h and then washed with water (3×200 mL). The organic solution was dried with Na$_2$SO$_4$ and concentrated in vacuo. The residue was purified with chromatography (DCM: MeOH=30:1) to give cyclohexylamino-acetic acid ethyl ester as an oil. MS: 186 (M+H)+.

EXAMPLE 80b

Preparation of rac-{[6-chloro-3-(3-chloro-benzyl)-2-oxo-2,3-dihydro-1H-indol-3-yl]-cyclohexyl-amino}-acetic acid ethyl ester

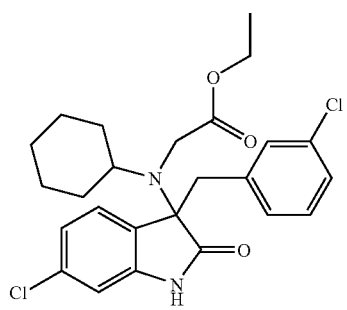

M. W. 475.42  $C_{25}H_{28}Cl_2N_2O_3$

The title compound was prepared by the same procedure for rac-6-chloro-3-(3-chloro-benzyl)-3-cyclohexylamino-1,3-dihydro-1H-indol-2-one. MS: 476 (M+H)+; H¹-NMR (400 MHz, CDCl₃) δ 7.75 (s, 1H), 7.50 (d, 1H), 7.11 (dd, 1H), 7.04 (m, 1H), 6.93 (t, 1H), 1H), 6.78 (t, 1H), 6.66 (d, 2H), 4.35 (d, 1H), 4.18 (q, 2H), 3.59 (d, 1H), 3.31 (d, 1H), 3.17 (d, 1H), 2.66 (m, 1H), 1.66 (m, 6H), 1.30 (t, 3H), 1.00 (m, 4H).

EXAMPLE 81

Preparation of rac-{[6-chloro-3-(3-chloro-benzyl)-2-oxo-2,3-dihydro-1H-indol-3-yl]-cyclohexyl-amino}-acetic acid

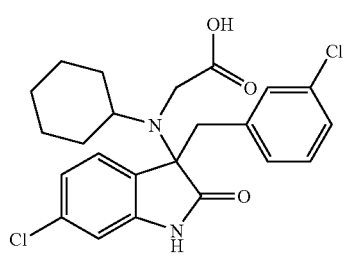

M. W. 447.37  $C_{23}H_{24}Cl_2N_2O_3$

To the mixture of methanol (120 mL) and water (30 mL) were added rac-{[6-chloro-3-(3-chloro-benzyl)-2-oxo-2,3-dihydro-indol-3-yl]-cyclohexyl-amino}-acetic acid ethyl ester (5 g, 105 mmol) and KOH (0.8 g, 210 mmol). After the reaction mixture was heated at reflux for overnight, the crude was concentrated. Then water (100 mL) was added. The mixture was acidified with HCl to PH=4 and extracted with ethyl acetate (100 mL×3). The combined organic layer was dried over Na₂SO₄ and concentrated in vacuo to give 4.7 g of rac-{[6-chloro-3-(3-chloro-benzyl)-2-oxo-2,3-dihydro-1H-indol-3-yl]-cyclohexyl-amino}-acetic acid as a light yellow solid. MS: 447 (M+H)+.

EXAMPLE 82

Preparation of rac-3-{[2-(4-acetyl-piperazin-1-yl)-2-oxo-ethyl]-cyclohexyl-amino}-6-chloro-3-(3-chloro-benzyl)-1,3-dihydro-indol-2-one

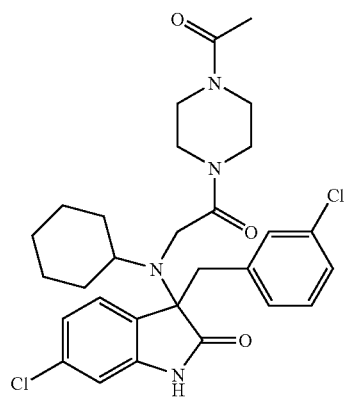

M. W. 557.53  $C_{29}H_{34}Cl_2N_4O_3$

To the mixture of DIPEA (43 mg, 0.33 mmol), HATU (64 mg, 0.17 mmol) and 1-piperazin-1-yl-ethanone (22 mg, 0.17 mmol) in dichloromethane (3 mL) was added rac-{[6-chloro-3-(3-chloro-benzyl)-2-oxo-2,3-dihydro-indol-3-yl]-cyclohexyl-amino}-acetic acid (50 mg, 0.11 mmol). After the mixture was stirred at room temperature for 3 h, the crude was washed with water (3×10 mL). The organic solution was concentrated in vacuo and the residue was puritificated by preparative HPLC to give 24 mg of rac-3-{[2-(4-acetyl-piperazin-1-yl)-2-oxo-ethyl]-cyclohexyl-amino}-6-chloro-3-(3-chloro-benzyl)-1,3-dihydro-indol-2-one as a white solid. MS: 557 (M+H)+.

EXAMPLE 83

Preparation of rac-1-(2-{[6-chloro-3-(3-chloro-benzyl)-2-oxo-2,3-dihydro-1H-indol-3-yl]-cyclohexyl-amino}-acetyl)-1,3-diisopropyl-urea

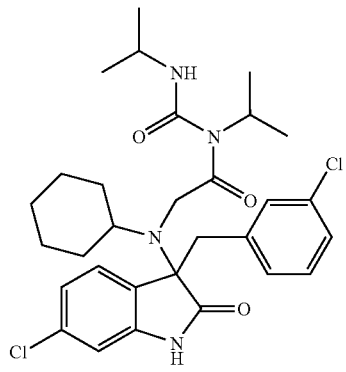

M. W. 573.57   $C_{30}H_{38}Cl_2N_4O_3$

To a solution of DIC (21 mg, 0.17 mmol) in dichloromethane (3 mL) was added rac-{[6-chloro-3-(3-chloro-benzyl)-2-oxo-2,3-dihydro-indol-3-yl]-cyclohexyl-amino}-acetic acid (50 mg, 0.11 mmol). After the mixture was stirred at room temperature for 3 h, the crude was washed with water (3×10 mL). The organic solution was concentrated in vacuo and the residue was purified by preparative HPLC to give 21 mg of rac-1-(2-{[6-chloro-3-(3-chloro-benzyl)-2-oxo-2,3-dihydro-1H-indol-3-yl]-cyclohexyl-amino}-acetyl)-1,3-diisopropyl-urea as a white solid. MS: 573 (M+H)+

$H^1$-NMR (400 MHz, CDCl$_3$) δ 7.45 (d, 1H), 7.26 (s, 2H), 7.00 (dd, 1H), 6.96 (t, 1H), 6.83 (t, 1H), 6.67 (s, 1H), 6.55 (d, 1H), 6.47 (d, 1H), 4.42 (d, 1H), 4.28 (m, 1H), 3.92 (m, 1H), 3.59 (d, 1H), 3.17 (dd, 2H), 2.64 (m, 1H), 1.57 (m, 6H), 1.35 (dd, 6H), 1.15 (dd, 6H), 0.90 (m, 4H).

EXAMPLE 84

Preparation of rac-4-(2-{[6-Chloro-3-(3-chloro-benzyl)-2-oxo-2,3-dihydro-1H-indol-3-yl]-cyclohexyl-amino}-acetyl)-piperazine-1-carboxylic acid tert-butyl ester

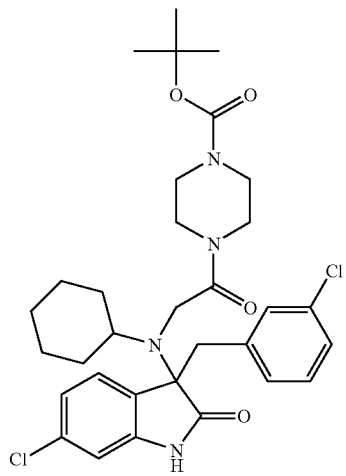

M. W. 615.61   $C_{32}H_{40}Cl_2N_4O_4$

The title compound was prepared by the same procedure for rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 616 (M+H)+.

EXAMPLE 85

Preparation of rac-6-chloro-3-(3-chloro-benzyl)-3-{cyclohexyl-[2-oxo-2-(3-oxo-piperazin-yl)-ethyl]-amino}-1,3-dihydro-indol-2-one

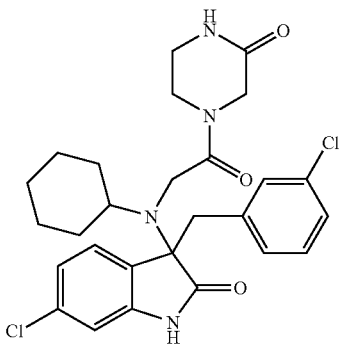

M. W. 529.47   $C_{27}H_{30}Cl_2N_4O_3$

The title compound was prepared by the same procedure for rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 529 (M+H)+.

EXAMPLE 86

Preparation of rac-6-chloro-3-(3-chloro-benzyl)-3-{cyclohexyl-[2-(4-isopropyl-piperazin-yl)-2-oxo-ethyl]-amino}-1,3-dihydro-indol-2-one

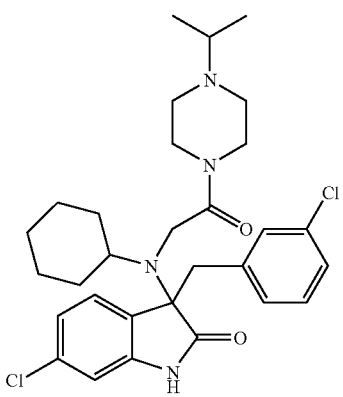

M. W. 557.57   $C_{30}H_{38}Cl_2N_4O_2$

The title compound was prepared by the same procedure for rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 557 (M+H)+.

EXAMPLE 87

Preparation of rac-6-chloro-3-(3-chloro-benzyl)-3-(cyclohexyl-{2-[4-(3-hydroxy-propyl)-piperazin-1-yl]-2-oxo-ethyl}-amino)-1,3-dihydro-indol-2-one

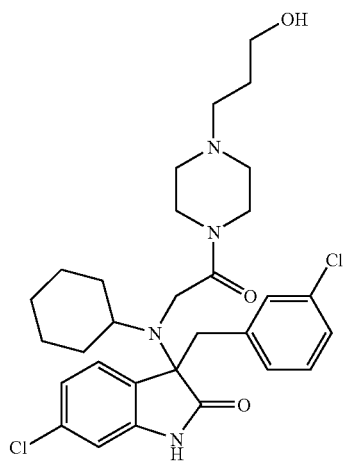

M. W. 573.57    $C_{30}H_{38}Cl_2N_4O_3$

The title compound was prepared by the same procedure for rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 574 (M+H)+.

EXAMPLE 88

Preparation of rac-2-{[6-chloro-3-(3-chloro-benzyl)-2-oxo-2,3-dihydro-1H-indol-3-yl]-cyclohexyl-amino}-N-(2-morpholin-4-yl-ethyl)-acetamide

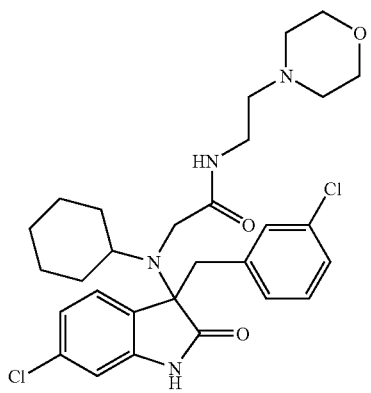

M. W. 559.54    $C_{29}H_{36}Cl_2N_4O_3$

The title compound was prepared by the same procedure for rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 559 (M+H)+.

EXAMPLE 89

Preparation of rac-2-{[6-chloro-3-(3-chloro-benzyl)-2-oxo-2,3-dihydro-1H-indol-3-yl]-cyclohexyl-amino}-N-[2-(3H-imidazol-4-yl)-ethyl]-acetamide

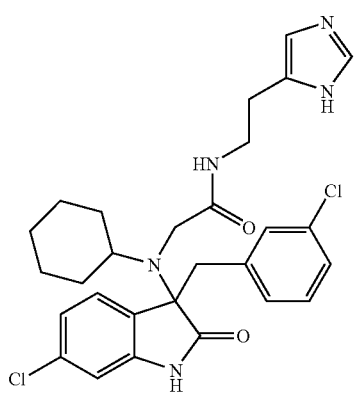

M. W. 540.50    $C_{28}H_{31}Cl_2N_5O_2$

The title compound was prepared by the same procedure for rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 540 (M+H)+.

EXAMPLE 90

Preparation of rac-2-{[6-chloro-3-(3-chloro-benzyl)-2-oxo-2,3-dihydro-1H-indol-3-yl]-cyclohexyl-amino}-N-cyclobutyl-acetamide

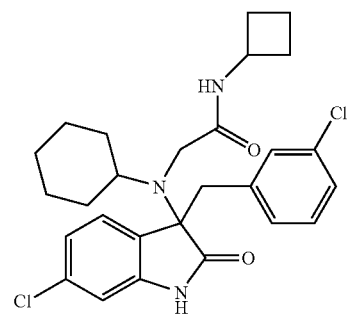

M. W. 500.47    $C_{27}H_{31}Cl_2N_3O_2$

The title compound was prepared by the same procedure for rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 500 (M+H)+. H$^1$-NMR (400 MHz, DMSO-d$_6$) δ 10.36 (s, 1H), 8.12 (d, 1H), 7.78 (d, 1H), 7.12 (m, 3H), 6.70 (s, 1H), 6.66 (d, 1H), 6.50 (s, 1H), 4.32 (m, 1H), 3.91 (d, 1H), 3.48 (d, 1H), 3.21 (dd, 2H), 2.47 (m, 1H), 2.12 (m, 4H), 1.38 (m, 12H).

EXAMPLE 91

Preparation of rac-2-{[6-chloro-3-(3-chloro-benzyl)-2-oxo-2,3-dihydro!-1H-indol-3-yl]-cyclohexyl-amino}-N-(1,1-dimethyl-propyl)-acetamide

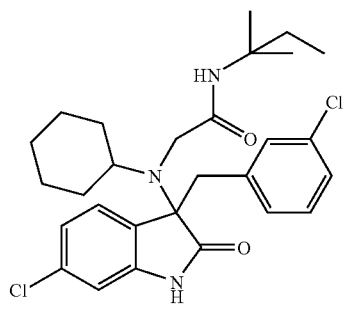

M. W. 516.52   $C_{28}H_{35}Cl_2N_3O_2$

The title compound was prepared by the same procedure for rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 516 (M+H)$^+$.

EXAMPLE 92

Preparation of rac-2-{[6-chloro-3-(3-chloro-benzyl)-2-oxo-2,3-dihydro-1H-indol-3-yl]-cyclohexyl-amino}-N-(2-dimethylamino-1-methyl-ethyl)-acetamide

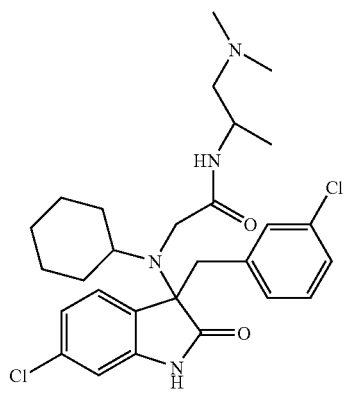

M. W. 531.53   $C_{28}H_{36}Cl_2N_4O_2$

The title compound was prepared by the same procedure for rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 531 (M+H)$^+$.

EXAMPLE 93

Preparation of rac-2-{[6-chloro-3-(3-chloro-benzyl)-2-oxo-2,3-dihydro-1H-indol-3-yl]-cyclohexyl-amino}-N-(1,1,3,3-tetramethyl-butyl)-acetamide

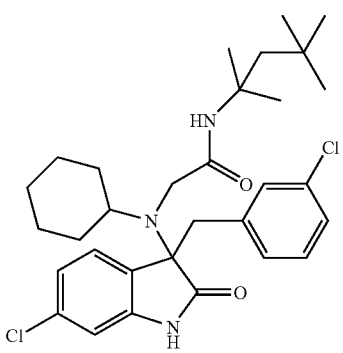

M. W. 558.60   $C_{31}H_{41}Cl_2N_3O_2$

The title compound was prepared by the same procedure for rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 558 (M+H)$^+$.

EXAMPLE 94

Preparation of rac-2-{[6-chloro-3-(3-chloro-benzyl)-2-oxo-2,3-dihydro-1H-indol-3-yl]-cyclohexyl-amino}-N-[(1S)-cyclohexyl-ethyl]-acetamide

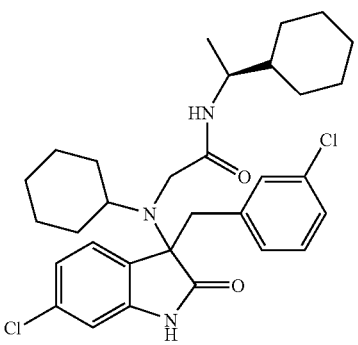

M. W. 556.58   $C_{31}H_{39}Cl_2N_3O_2$

The title compound was prepared by the same procedure for rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 556 (M+H)⁺.

EXAMPLE 95

Preparation of rac-2-{[6-chloro-3-(3-chloro-benzyl)-2-oxo-2,3-dihydro-1H-indol-3-yl]-cyclohexyl-amino}-N-piperidin-1-yl-acetamide

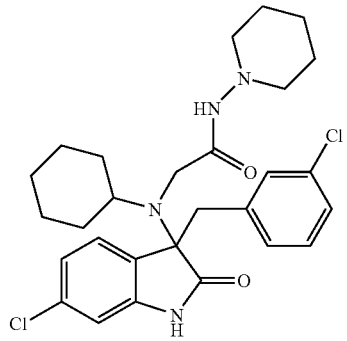

M. W. 529.51    $C_{28}H_{34}Cl_2N_4O_2$

The title compound was prepared by the same procedure for rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 529 (M+H)⁺.

EXAMPLE 96

Preparation of rac-2-{[6-chloro-3-(3-chloro-benzyl)-2-oxo-2,3-dihydro-1H-indol-3-yl]-cyclohexyl-amino}-N-furan-2-ylmethyl-acetamide

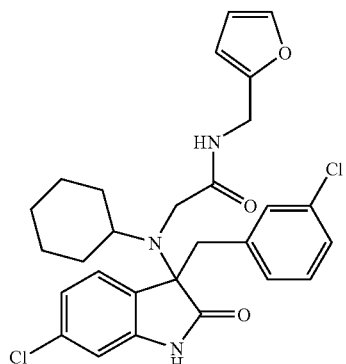

M. W. 526.47    $C_{28}H_{29}Cl_2N_3O_3$

The title compound was prepared by the same procedure for rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 526 (M+H)⁺. H¹-NMR (400 MHz, DMSO-d₆) δ10.30 (s, 1H), 8.40 (t, 1H), 7.80 (d, 1H), 7.52 (q, 1H), 7.13 (m, 2H), 7.03 (t, 1H), 6.67 (t, 1H), 6.58 (d, 1H), 6.52 (d, 1H), 6.38 (m, 2H), 4.44 (m, 2H), 4.13 (d, 1H), 3.50 (d, 1H), 3.17 (dd, 2H), 2.42 (m, 1H), 1.12 (m, 10H).

EXAMPLE 97

Preparation of rac-2-{[6-chloro-3-(3-chloro-benzyl)-2-oxo-2,3-dihydro-1H-indol-3-yl]-cyclohexyl-amino}-N-(2-hydroxy-1,1-dimethyl-ethyl)-acetamide

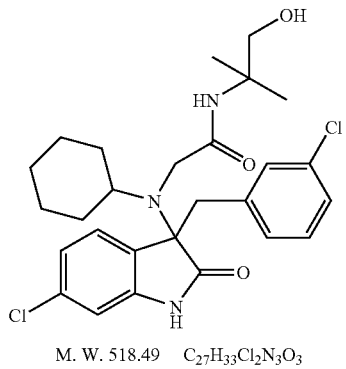

M. W. 518.49    $C_{27}H_{33}Cl_2N_3O_3$

The title compound was prepared by the same procedure for rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 518 (M+H)⁺.

EXAMPLE 98

Preparation of rac-6-chloro-3-(3-chloro-benzyl)-3-[cyclohexyl-(2-oxo-2-piperazin-1-yl-ethyl)-amino]-1,3-dihydro-indol-2-one

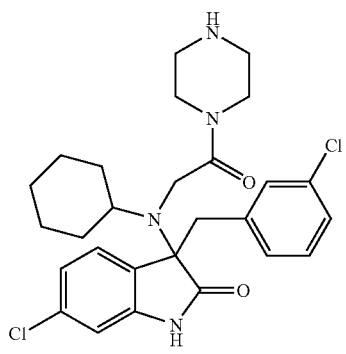

M. W. 515.49    $C_{27}H_{32}Cl_2N_4O_2$

To trifluoroacetic acid (1 mL) was added rac-4-(2-{[6-chloro-3-(3-chloro-benzyl)-2-oxo-2,3-dihydro!-indol-3-yl]-cyclohexyl-amino}-acetyl)-piperazine-1-carboxylic acid-butyl ester (100 mg, 0.163 mmol). After the mixture was stirred at room temperature for 1 h, the crude was concentrated in vacuo to give 68 mg of rac-6-chloro-3-(3-chloro-benzyl)-3-[cyclohexyl-(2-oxo-2-piperazin-1-yl-ethyl)-amino]-1,3-dihydro-indol-2-one as a solid.

MS: 515 (M+H)⁺; H¹-NMR (400 MHz, CDCl₃) δ 9.86 (s, 1H), 8.82 (s, 1H), 7.52 (d, 1H), 7.09 (d, 1H), 6.96 (d, 1H), 6.87

(t, 1H), 6.75 (s, 1H), 6.62 (s, 1H), 6.51 (d, 1H), 3.99 (m, 6H), 3.30 (m, 6H), 2.82 (m, 1H), 1.22 (m, 10H).

EXAMPLE 99

Preparation of rac-(2S)-[6-chloro-3-(3-chloro-benzyl)-2-oxo-2,3-dihydro-1H-indol-3-ylamino]-4-methyl-pentanoic acid

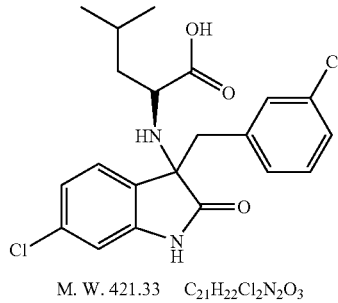

M. W. 421.33  C$_{21}$H$_{22}$Cl$_2$N$_2$O$_3$

To the aqueous solution K$_2$CO$_3$ (1.6 µL, 1N) was added (2S)-amino-4-methyl-pentanoic (106 mg, 0.81 mmol), then followed by the addition of rac-3-bromo-6-chloro-3-(3-chloro-benzyl)-1,3-dihydro-indol-2-one (200 mg, 0.54 mmol) in dioxane (5 mL). After the mixture was stirred at room temperature for 4 h, the reaction mixture was concentrated in vacuo. Water (10 mL) was added and the crude was acidified with HCl to PH=4. The mixture was extracted with ethyl acetate (3×10 mL). The combined organic layer was concentrated in vacuo. The residue was purified by chromatography (DCM: MeOH=80:1) to give 184 mg of rac-(2S)-[6-chloro-3-(3-chloro-benzyl)-2-oxo-2,3-dihydro-1H-indol-3-ylamino]-4-methyl-pentanoic acid as a white solid. MS: 421 (M+H)$^+$. H$^1$-NMR (400 MHz, CDCl$_3$) δ 10.04 (s, 1H), 7.12 (m, 5H), 6.93 (t, 1H), 6.76 (m, 2H), 3.32 (m, 1H), 3.16 (dd, 2H), 1.89 (m, 1H), 1.50 (m, 2H), 0.90 (dd, 6H).

EXAMPLE 100

Preparation of rac-(2R)-[6-chloro-3-(3-chloro-benzyl)-2-oxo-2,3-dihydro-1H-indol-3-ylamino]-3-methyl-butyric acid

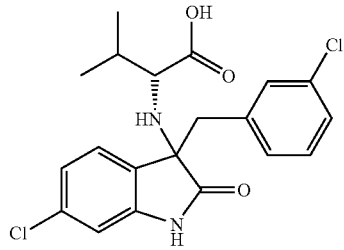

M. W. 407.30  C$_{20}$H$_{20}$Cl$_2$N$_2$O$_3$

The title compound was prepared by the same procedure for rac-(2S)-[6-chloro-3-(3-chloro-benzyl)-2-oxo-2,3-dihydro-indol-3-ylamino]-4-methyl-pentanoic acid. MS: 407 (M+H)$^+$.

EXAMPLE 101

Preparation of rac-1-(2-{[6-chloro-3-(3-chloro-benzyl)-2-oxo-2,3-dihydro-1H-indol-3-yl]-phenyl-amino}-acetyl)-piperidine-4-carboxylic acid amide

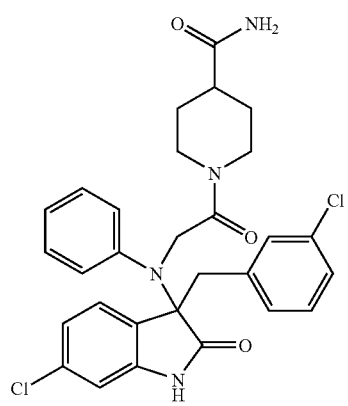

M. W. 551.48  C$_{29}$H$_{28}$Cl$_2$N$_4$O$_3$

The title compound was prepared by the same procedure for rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 551 (M+H)$^+$.

EXAMPLE 102

Preparation of rac-6-chloro-3-(3-chloro-benzyl)-3-{[2-(4-hydroxy-piperidin-1-yl)-2-oxo-ethyl]-phenyl-amino}-1,3-dihydro-indol-2-one

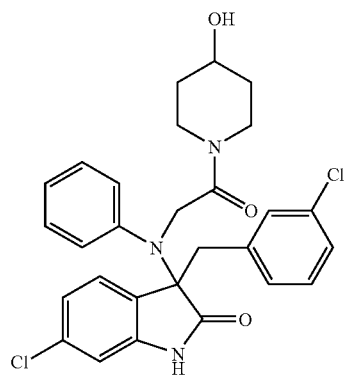

M. W. 524.45  C$_{28}$H$_{27}$Cl$_2$N$_3$O$_3$

The title compound was prepared by the same procedure for rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 524 (M+H)⁺.

EXAMPLE 103

Preparation of rac-2-{[6-chloro-3-(3-chloro-benzyl)-2-oxo-2,3-dihydro-1H-indol-3-yl]-phenyl-amino}-N-(4-hydroxy-cyclohexyl)-acetamide

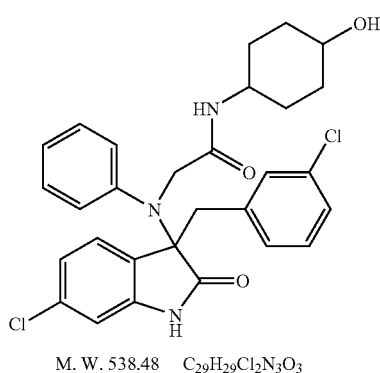

M. W. 538.48    C₂₉H₂₉Cl₂N₃O₃

The title compound was prepared by the same procedure for rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 538 (M+H)⁺.

EXAMPLE 104

Preparation of rac-6-chloro-3-(3-chloro-benzyl)-3-({2-[4-(2-hydroxy-ethyl)-piperazin-1-yl]-oxo-ethyl}-phenyl-amino)-1,3-dihydro-indol-2-one

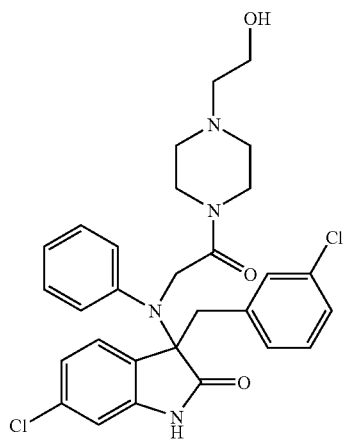

M. W. 553.49    C₂₉H₃₀Cl₂N₄O₃

The title compound was prepared by the same procedure for rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 553 (M+H)⁺.

EXAMPLE 105

Preparation of rac-6-chloro-3-(3-chloro-benzyl)-3-{[2-(3-hydroxy-pyrrolidin-1-yl)-2-oxo-ethyl]-phenyl-amino}-1,3-dihydro-indol-2-one

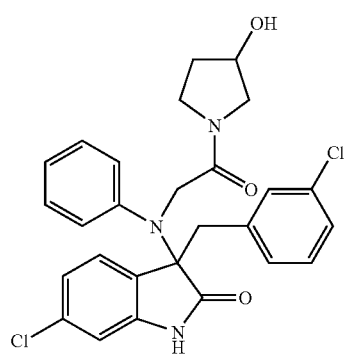

M. W. 510.42    C₂₇H₂₅Cl₂N₃O₃

The title compound was prepared by the same procedure for rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 510 (M+H)⁺.

EXAMPLE 106

Preparation of rac-2-{[6-chloro-3-(3-chloro-benzyl)-2-oxo-2,3-dihydro-1H-indol-3-yl]-phenyl-amino}-N-(2-hydroxy-ethyl)-acetamide

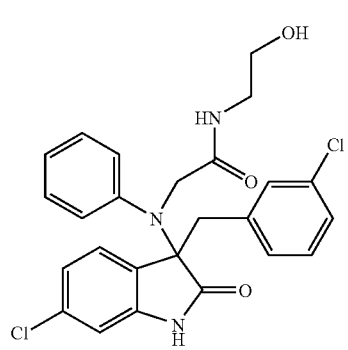

M. W. 484.39    C₂₅H₂₃Cl₂N₃O₃

The title compound was prepared by the same procedure for rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 484 (M+H)⁺.

EXAMPLE 107

Preparation of rac-{(2S)-[6-chloro-3-(3-chloro-benzyl)-2-oxo-2,3-dihydro-1H-indol-3-ylamino]-4-methyl-pentanoyl}-piperidine-4-carboxylic acid amide

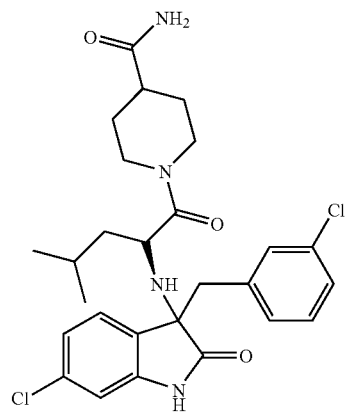

M. W. 531.49  $C_{27}H_{32}Cl_2N_4O_3$

The title compound was prepared by the same procedure for rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 531 (M+H)⁺.

EXAMPLE 108

Preparation of rac-6-chloro-3-(3-chloro-benzyl)-3-[(1S)-(3-hydroxy-pyrrolidine-1-carbonyl)-3-methyl-butylamino]-1,3-dihydro-indol-2-one

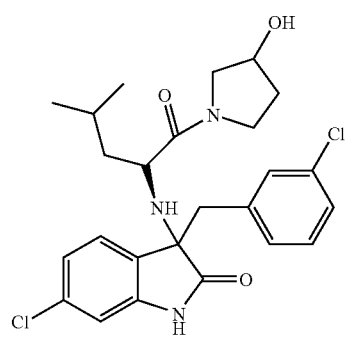

M. W. 490.43  $C_{25}H_{29}Cl_2N_3O_3$

The title compound was prepared by the same procedure for rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 490 (M+H)⁺.

EXAMPLE 109

Preparation of rac-6-chloro-3-(3-chloro-benzyl)-3-{(1S)-[4-(2-hydroxy-ethyl)-piperazine-carbonyl]-3-methyl-butylamino}-1,3-dihydro-indol-2-one

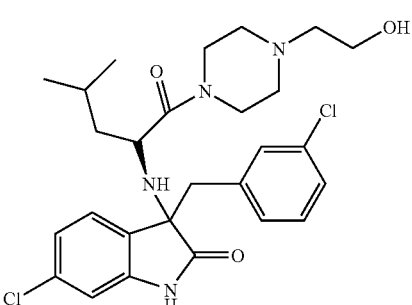

M. W. 533.50  $C_{27}H_{34}Cl_2N_4O_3$

The title compound was prepared by the same procedure for rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 532 (M+H)⁺.

EXAMPLE 110

Preparation of rac-(2S)-[6-chloro-3-(3-chloro-benzyl)-2-oxo-2,3-dihydro-1H-indol-3-ylamino]-4-methyl-pentanoic acid (2-hydroxy-ethyl)-amide

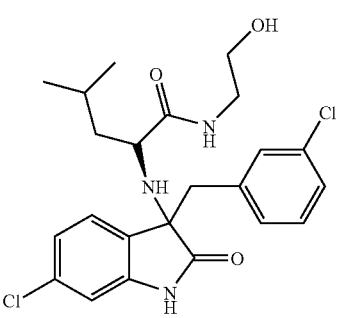

M. W. 464.40  $C_{23}H_{27}Cl_2N_3O_3$

85

The title compound was prepared by the same procedure for rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 464 (M+H)⁺.

EXAMPLE 111

Preparation of rac-6-chloro-3-(3-chloro-benzyl)-3-[(1S)-(4-hydroxy-piperidine-1-carbonyl)-3-methyl-butylamino]-1,3-dihydro-indol-2-one

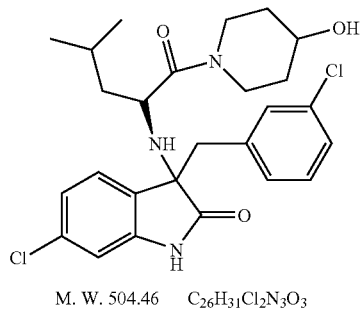

M. W. 504.46    $C_{26}H_{31}Cl_2N_3O_3$

The title compound was prepared by the same procedure for rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 504 (M+H)⁺.

EXAMPLE 112

Preparation of rac-2-{[6-chloro-3-(3-chloro-benzyl)-2-oxo-2,3-dihydro-1H-indol-3-yl]-cyclohexyl-amino}-N-cyclohexyl-acetamide

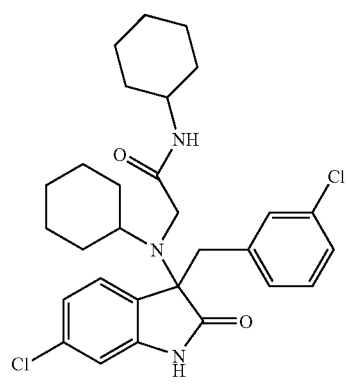

M. W. 528.53    $C_{29}H_{35}Cl_2N_3O_2$

86

The title compound was prepared by the same procedure for rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 528 (M+H)⁺.

EXAMPLE 113

Preparation of rac-2-{[6-chloro-3-(3-chloro-benzyl)-2-oxo-2,3-dihydro-1H-indol-3-yl]-cyclohexyl-amino}-N-phenyl-acetamide

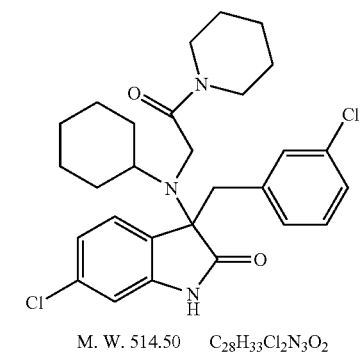

M. W. 514.50    $C_{28}H_{33}Cl_2N_3O_2$

The title compound was prepared by the same procedure for rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 514 (M+H)⁺.

EXAMPLE 114

Preparation of rac-2-{[6-chloro-3-(3-chloro-benzyl)-2-oxo-2,3-dihydro-1H-indol-3-yl]-cyclohexyl-amino}-N-phenyl-acetamide

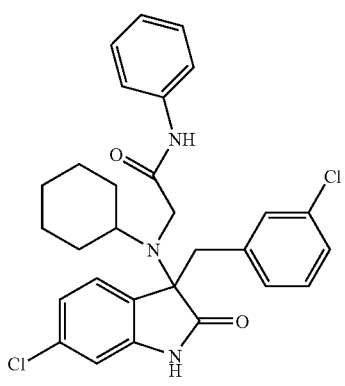

M. W. 522.48    $C_{29}H_{29}Cl_2N_3O_2$

The title compound was prepared by the same procedure for rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 522 (M+H)⁺.

EXAMPLE 115

Preparation of rac-2-{[6-chloro-3-(3-chloro-benzyl)-2-oxo-2,3-dihydro-1H-indol-3-yl]-cyclohexyl-amino}-N-phenyl-acetamide

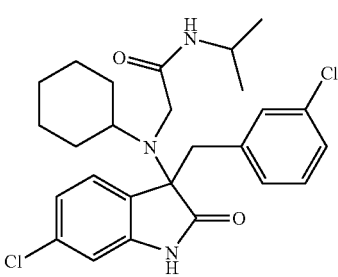

M. W. 488.46   C₂₆H₃₁Cl₂N₃O₂

The title compound was prepared by the same procedure for rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 488 (M+H)⁺.

EXAMPLE 116

Preparation of rac-N-tert-butyl-2-{[6-chloro-3-(3-chloro-benzyl)-2-oxo-2,3-dihydro-1H-indol-3-yl]-cyclohexyl-amino}-acetamide

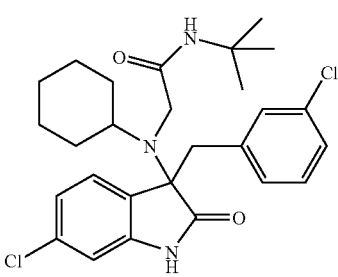

M. W. 502.49   C₂₇H₃₃Cl₂N₃O₂

The title compound was prepared by the same procedure for rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 502 (M+H)⁺.

EXAMPLE 117

Preparation of rac-2-{[6-chloro-3-(3-chloro-benzyl)-2-oxo-2,3-dihydro-1H-indol-3-yl]-cyclohexyl-amino}-N-cyclopropyl-acetamide

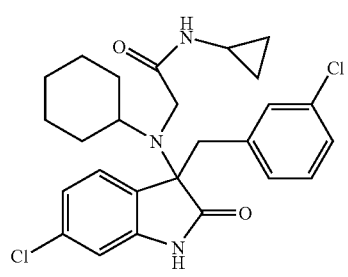

M. W. 486.45   C₂₆H₂₉Cl₂N₃O₂

The title compound was prepared by the same procedure for rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 486 (M+H)⁺.

EXAMPLE 118

Preparation of rac-(2S)-[6-chloro-3-(3-chloro-benzyl)-2-oxo-2,3-dihydro-1H-indol-3-ylamino]-4-methyl-pentanoic acid methyl ester

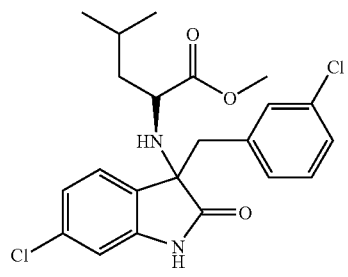

M. W. 435.35   C₂₂H₂₄Cl₂N₂O₃

The title compound was prepared by the same procedure for rac-6-chloro-3-(3-chloro-benzyl)-3-cyclohexylamino-1,3-dihydro-indol-2-one. MS: 435 (M+H)+

EXAMPLE 119

Preparation of rac-6-chloro-3-(3-chloro-benzyl)-3-[4-(4-trifluoromethyl-phenyl)-piperazin-yl]-1,3-dihydro-indol-2-one

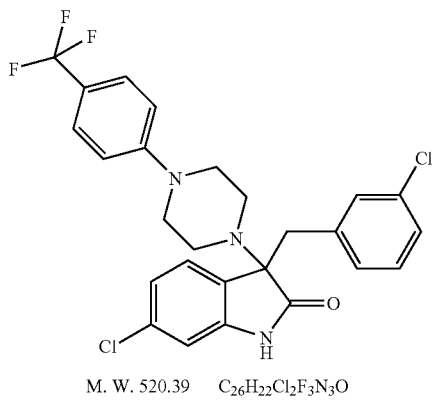

M. W. 520.39   $C_{26}H_{22}Cl_2F_3N_3O$

The mixture of rac-3-bromo-6-chloro-3-(3-chloro-benzyl)-1,3-dihydro-indol-2-one (100 mg, 0.270 mmol), 1-(4-trifluoromethyl-phenyl)-piperazine (75 mg, 0.324 mmol) and DIPEA (42 mg, 0.324 mmol) In acetonitrile (3 mL) was stirred at room temperature for overnight. The crude was concentrated and the residue was purified with preparative HPLC to give 76 mg of rac-6-chloro-3-(3-chloro-benzyl)-3-[4-(4-trifluoromethyl-phenyl)-piperazin-1-yl]-1,3-dihydro-indol-2-one as a white solid. MS: 520 (M+H)+. $H^1$-NMR (400 MHz, CDCl$_3$) δ 7.584 (s, 1H), 7.493 (d, 2H), 7.240 (d, 1H), 7.081 (t, 2H), 7.011 (t, 1H), 6.908 (d, 3H), 6.766 (d, 1H), 6.684 (d, 1H), 3.431 (d, 1H), 3.329-3.206 (m, 5H), 2.947 (t, 4H).

EXAMPLE 120

Preparation of rac-6-chloro-3-(3-chloro-benzyl)-3-[4-(3-chloro-phenyl)-piperazin-1-yl]-1,3-dihydro-indol-2-one

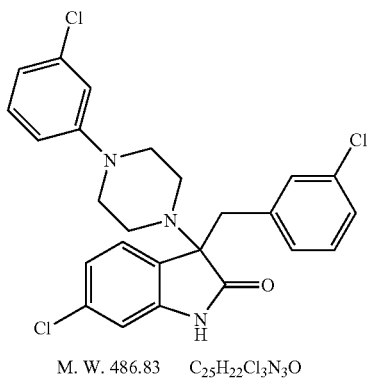

M. W. 486.83   $C_{25}H_{22}Cl_3N_3O$

The title compound was prepared by the same procedure for rac-6-chloro-3-(3-chloro-benzyl)-3-[4-(4-trifluoromethyl-phenyl)-piperazin-1-yl]-1,3-dihydro-indol-2-one. MS m/z 486 (M+H)+.

EXAMPLE 121

Preparation of rac-6-chloro-3-(3-chloro-benzyl)-3-(4-phenyl-piperazin-1-yl)-1,3-dihydro-indol-2-one

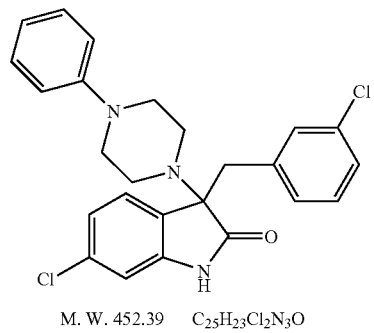

M. W. 452.39   $C_{25}H_{23}Cl_2N_3O$

The title compound was prepared by the same procedure for rac-6-chloro-3-(3-chloro-benzyl)-3-[4-(4-trifluoromethyl-phenyl)-piperazin-1-yl]-1,3-dihydro-indol-2-one. MS m/z 452 (M+H)+.

EXAMPLE 122

Preparation of rac-2-{[6-chloro-3-(3-chloro-benzyl)-2-oxo-2,3-dihydro-1H-indol-3-yl]-phenyl-amino}-N-cyclohexy-acetamide

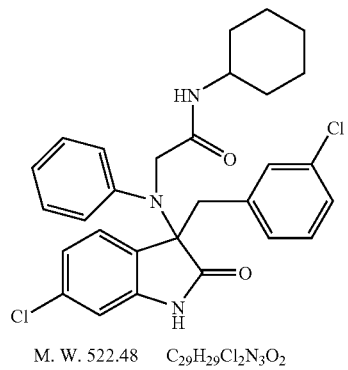

M. W. 522.48   $C_{29}H_{29}Cl_2N_3O_2$

The mixture of rac-{[6-chloro-3-(3-chloro-benzyl)-2-oxo-2,3-dihydro-1H-indol-3-yl]-phenyl-amino}-acetic acid (70 mg, 0.159 mmol), cyclohexylamine (19 mg, 0.191 mmol) EDC.HCl (36 mg, 0.191 mmol), HOBt (26 mmg, 0.191 mmol) and DIPEA (25 mg, 0.191 mmol) in acetonitrile (3 mL) was stirred at room temperature for overnight. The reaction mixture was concentrated and the residue was purified with chromatography to give 45 mg of rac-2-{[6-chloro-3-(3- chloro-benzyl)-2-oxo-2,3-dihydro-1H-indol-3-yl]-phenyl-amino}-N-cyclohexy-acetamide as a yellow solid. MS m/z 522 (M+H)⁺.

EXAMPLE 123

Preparation of rac-2-{[6-chloro-3-(3-chloro-benzyl)-2-oxo-2,3-dihydro-1H-indol-3-yl]-phenyl-amino}-N-isopropoyl-acetamide

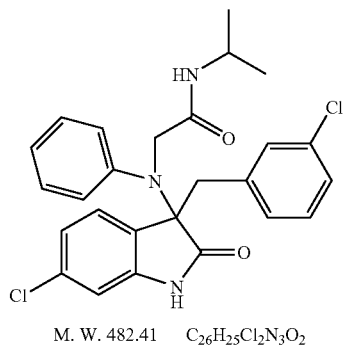

M. W. 482.41    C<sub>26</sub>H<sub>25</sub>Cl<sub>2</sub>N<sub>3</sub>O<sub>2</sub>

The title compound was prepared by the same procedure for rac-2-{[6-chloro-3-(3-chloro-benzyl)-2-oxo-2,3-dihydro-1H-indol-3-yl]-phenyl-amino}-N-cyclohexy-acetamide MS m/z 482 (M+H)⁺.

EXAMPLE 124

Preparation of rac-2-{[6-chloro-3-(3-chloro-benzyl)-2-oxo-2,3-dihydro-1H-indol-3-yl]-phenyl-amino}-N-cyclopentyl-acetamide

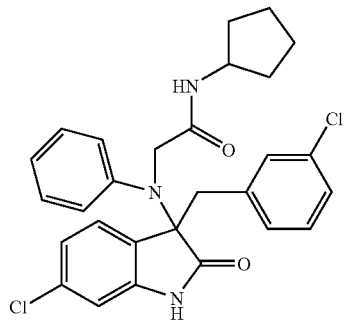

M. W. 508.45    C<sub>28</sub>H<sub>27</sub>Cl<sub>2</sub>N<sub>3</sub>O<sub>2</sub>

The title compound was prepared by the same procedure for rac-2-{[6-chloro-3-(3-chloro-benzyl)-2-oxo-2,3-dihydro-1H-indol-3-yl]-phenyl-amino}-N-cyclohexy-acetamide MS m/z 508 (M+H)⁺.

EXAMPLE 125

Preparation of rac-2-{[6-chloro-3-(3-chloro-benzyl)-2-oxo-2,3-dihydro-1H-indol-3-yl]-phenyl-amino}-N-cyclopropyl-acetamide

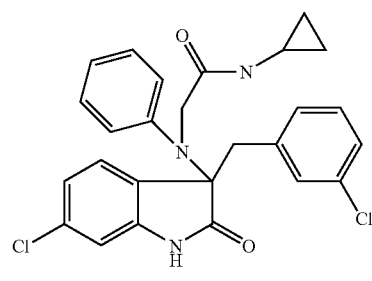

M. W. 480.40    C<sub>26</sub>H<sub>23</sub>Cl<sub>2</sub>N<sub>3</sub>O<sub>2</sub>

The title compound was prepared by the same procedure for rac-2-{[6-chloro-3-(3-chloro-benzyl)-2-oxo-2,3-dihydro-1H-indol-3-yl]-phenyl-amino}-N-cyclohexy-acetamide MS m/z 480 (M+H)⁺.

EXAMPLE 126

Preparation of rac-2-{[6-chloro-3-(3-chloro-benzyl)-2-oxo-2,3-dihydro-1H-indol-3-yl]-phenyl-amino}-N-phenyl-acetamide

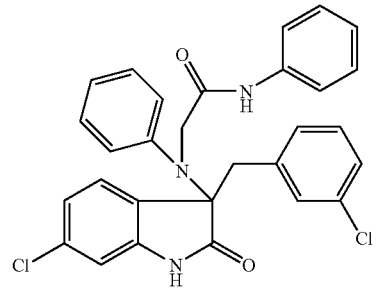

M. W. 516.43    C<sub>29</sub>H<sub>23</sub>Cl<sub>2</sub>N<sub>3</sub>O<sub>2</sub>

The title compound was prepared by the same procedure for rac-2-{[6-chloro-3-(3-chloro-benzyl)-2-oxo-2,3-dihydro-1H-indol-3-yl]-phenyl-amino}-N-cyclohexy-acetamide MS m/z 516 (M+H)⁺.

EXAMPLE 127

Preparation of rac-6-chloro-3-(3-chloro-benzyl)-3-({2-[4-(3-hydroxy-propyl)-piperazin-1-yl]-2-oxo-ethyl}-phenyl-amino)-1,3-dihydro-indol-2-one

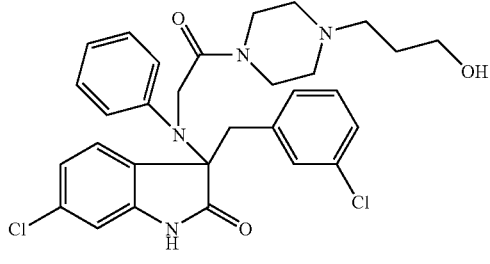

M. W. 567.52   $C_{30}H_{32}Cl_2N_4O_3$

The title compound was prepared by the same procedure for rac-2-{[6-chloro-3-(3-chloro-benzyl)-2-oxo-2,3-dihydro-1H-indol-3-yl]-phenyl-amino}-N-cyclohexy-acetamide MS m/z 567 (M+H)⁺.

EXAMPLE 128

Preparation of rac-2-{[6-chloro-3-(3-chloro-benzyl)-2-oxo-2,3-dihydro-1H-indol-3-yl]-phenyl-amino}-N-cyclobutyl-acetamide

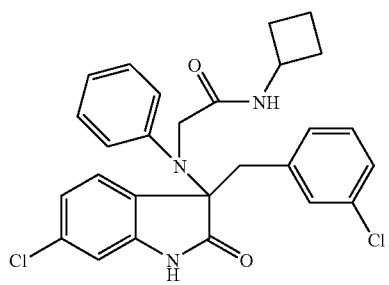

M. W. 494.43   $C_{27}H_{25}Cl_2N_3O_2$

The title compound was prepared by the same procedure for rac-2-{[6-chloro-3-(3-chloro-benzyl)-2-oxo-2,3-dihydro-1H-indol-3-yl]-phenyl-amino}-N-cyclohexy-acetamide MS m/z 494 (M+H)⁺.

EXAMPLE 129

Preparation of rac-2-{[6-chloro-3-(3-chloro-benzyl)-2-oxo-2,3-dihydro-1H-indol-3-yl]-phenyl-amino}-N-[2-(3H-imidazol-4-yl)-ethyl]-acetamide

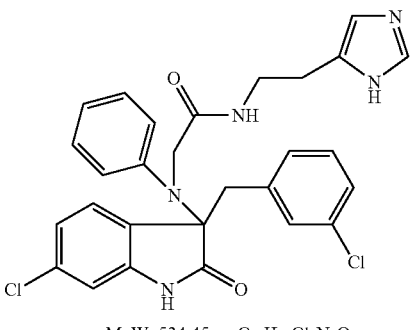

M. W. 534.45   $C_{28}H_{25}Cl_2N_5O_2$

The title compound was prepared by the same procedure for rac-2-{[6-chloro-3-(3-chloro-benzyl)-2-oxo-2,3-dihydro-1H-indol-3-yl]-phenyl-amino}-N-cyclohexy-acetamide MS m/z 535 (M+H)⁺.

EXAMPLE 130

Preparation of rac-4-(2-{[6-chloro-3-(3-chloro-benzyl)-2-oxo-2,3-dihydro-1H-indol-3-yl]-phenyl-amino}-acetyl)-piperazine-1-carboxylic acid tert-butyl ester

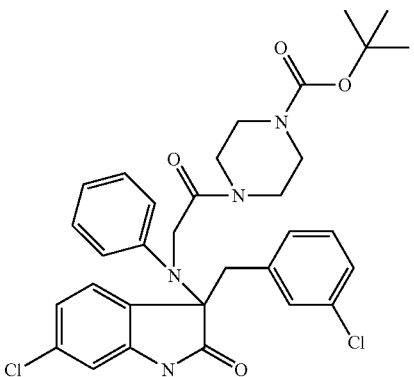

M. W. 609.56   $C_{32}H_{34}Cl_2N_4O_4$

The title compound was prepared by the same procedure for rac-2-{[6-chloro-3-(3-chloro-benzyl)-2-oxo-2,3-dihydro-1H-indol-3-yl]-phenyl-amino}-N-cyclohexy-acetamide MS m/z 609 (M+H)⁺.

EXAMPLE 131

Preparation of rac-2-{[6-chloro-3-(3-chloro-benzyl)-2-oxo-2,3-dihydro-1H-indol-3-yl]-phenyl-amino}-N-piperidin-1-yl-acetamide

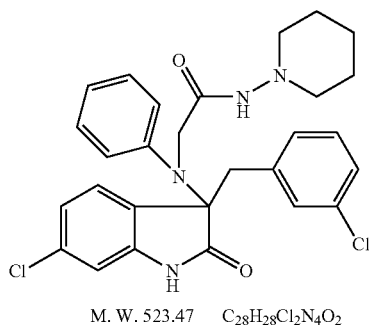

M. W. 523.47    C₂₈H₂₈Cl₂N₄O₂

The title compound was prepared by the same procedure for rac-2-{[6-chloro-3-(3-chloro-benzyl)-2-oxo-2,3-dihydro-1H-indol-3-yl]-phenyl-amino}-N-cyclohexy-acetamide MS m/z 523 (M+H)⁺.

EXAMPLE 132

Preparation of rac-(2S)-[6-chloro-3-(3-chloro-benzyl)-2-oxo-2,3-dihydro-1H-indol-3-ylamino]-3-phenyl-propionic acid

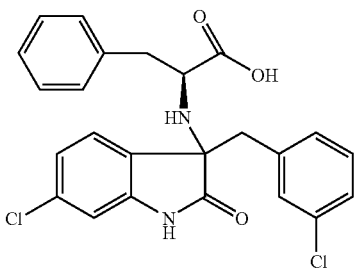

M. W. 455.34    C₂₄H₂₀Cl₂N₂O₃

To an aqueous solution of NaOH (1N, 10 mL) at 0° C. was added L-2-amino-3-phenyl-propionic acid (1.47 g, 8.92 mmol), followed by the addition of solution of 3,6-dichloro-3-(3-chloro-benzyl)-1,3-dihydro-indol-2-one (3 g, 8.1 mmol) in 1,4-dioxane (3 mL). After the reaction mixture was stirred at 0° C. for 4 h, the solution was concentrated and extracted with diethyl ether. The organic layer was dried over Na₂SO₄, filtered and concentrated.

The residue was purified with preparative HPLC to give rac-(2S)-[6-chloro-3-(3-chloro-benzyl)-2-oxo-2,3-dihydro-1H-indol-3-lamino]-3-phenyl-propionic acid. ???? MS m/z 455 (M+H)⁺.

EXAMPLE 133

Preparation of rac-(2S)-[6-chloro-3-(3-chloro-benzyl)-2-oxo-2,3-dihydro-1H-indol-3-ylamino]-N-(4-hydroxy-cyclohexyl)-3-phenyl-propionamide

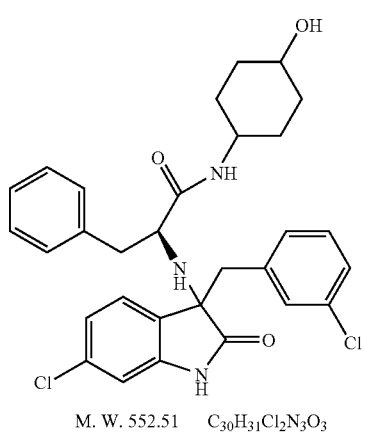

M. W. 552.51    C₃₀H₃₁Cl₂N₃O₃

The title compound was prepared by the same procedure for rac-2-{[6-chloro-3-(3-chloro-benzyl)-2-oxo-2,3-dihydro-1H-indol-3-yl]-phenyl-amino}-N-cyclohexy-acetamide MS m/z 552 (M+H)⁺.

EXAMPLE 134

Preparation of rac-3-[(1S)-benzyl-2-(4-hydroxy-piperidin-1-yl)-2-oxo-ethylamino]-6-chloro-3-(3-chloro-benzyl)-1,3-dihydro-indol-2-one

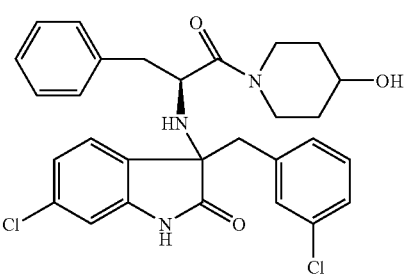

M. W. 538.48    C₂₉H₂₉Cl₂N₃O₃

The title compound was prepared by the same procedure for rac-2-{[6-chloro-3-(3-chloro-benzyl)-2-oxo-2,3-dihydro-1H-indol-3-yl]-phenyl-amino}-N-cyclohexy-acetamide MS m/z 538 (M+H)$^+$.

EXAMPLE 135

Preparation of rac-(2S)-[6-chloro-3-(3-chloro-benzyl)-2-oxo-2,3-dihydro-1H-indol-3-ylamino]-N-(2-hydroxy-ethyl)-3-phenyl-propionamide

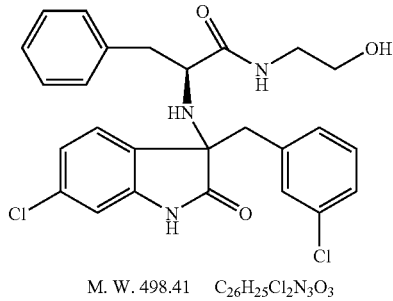

M. W. 498.41    $C_{26}H_{25}Cl_2N_3O_3$

The title compound was prepared by the same procedure for rac-2-{[6-chloro-3-(3-chloro-benzyl)-2-oxo-2,3-dihydro-1H-indol-3-yl]-phenyl-amino}-N-cyclohexy-acetamide MS m/z 498 (M+H)$^+$.

EXAMPLE 136

Preparation of rac-3-{(1S)-benzyl-2-[4-(2-hydroxy-ethyl)-piperazin-1-yl]-2-oxo-ethylamino}-6-chloro-3-(3-chloro-benzyl)-1,3-dihydro-indol-2-one

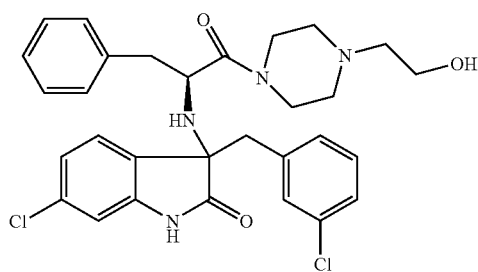

M. W. 567.52    $C_{30}H_{32}Cl_2N_4O_3$

The title compound was prepared by the same procedure for rac-2-{[6-chloro-3-(3-chloro-benzyl)-2-oxo-2,3-dihydro-1H-indol-3-yl]-phenyl-amino}-N-cyclohexy-acetamide MS m/z 567 (M+H)$^+$.

EXAMPLE 137

Preparation of rac-1-{(2S)-[6-chloro-3-(3-chloro-benzyl)-2-oxo-2,3-dihydro-1H-indol-3-ylamino]-3-phenyl-propionyl}-piperidine-4-carboxylic acid amide

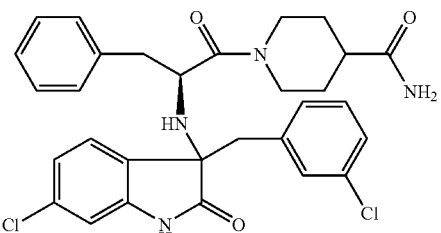

M. W. 565.50    $C_{30}H_{30}Cl_2N_4O_3$

The title compound was prepared by the same procedure for rac-2-{[6-chloro-3-(3-chloro-benzyl)-2-oxo-2,3-dihydro-1H-indol-3-yl]-phenyl-amino}-N-cyclohexy-acetamide MS m/z 565 (M+H)$^+$.

EXAMPLE 138

Preparation of rac-6-chloro-3-(3-chloro-benzyl)-3-[(2-oxo-2-piperazin-1-yl-ethyl)-phenyl-amino]-1,3-dihydro-indol-2-one

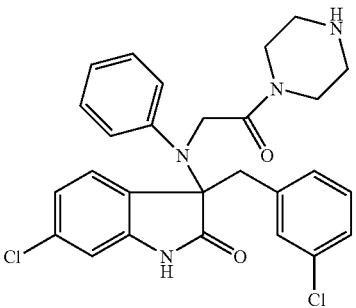

M. W. 509.44    $C_{27}H_{26}Cl_2N_4O_2$

The mixture of rac-{[6-chloro-3-(3-chloro-benzyl)-2-oxo-2,3-dihydro-1H-indol-3-yl]-phenyl-amino}-acetic acid (70 mg, 0.159 mmol), piperazine-1-carboxylic acid tert-butyl ester (36 mg, 0.191 mmol), EDC.HCl (36 mg, 0.191 mmol), HOBt (26 mmg, 0.191 mmol) and DIPEA (42 mg, 0.191 mmol) in acetonitrile (3 mL) was stirred at room temperature for overnight. The reaction mixture was concentrated and extracted with dichloromethane. The organic layer was dried over Na$_2$SO$_4$, filtered and concentrated.

The residue was dissolved in trifluoroacetic acid (5 mL) and stirred at room temperature for 0.5 h. Then the solution was concentrated and the residue was purified by preparative HPLC to give 5.8 mg of rac-6-chloro-3-(3-chloro-benzyl)-3-

[(2-oxo-2-piperazin-1-yl-ethyl)-phenyl-amino]-1,3-dihydro-indol-2-one as a yellow solid. MS m/z 509 (M+H)+

EXAMPLE 139

Preparation of rac-4-[6-chloro-3-(3-chloro-benzyl)-2-oxo-2,3-dihydro-1H-indol-3-yl]-piperazine-1-carboxylic acid tert-butyl ester

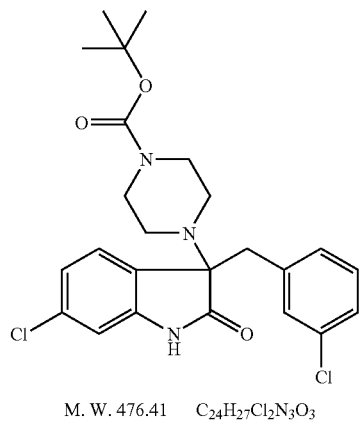

M. W. 476.41   $C_{24}H_{27}Cl_2N_3O_3$

The mixture of rac-3-bromo-6-chloro-3-(3-chloro-benzyl)-1,3-dihydro-indol-2-one (1 g, 2.703 mmol), piperazine-1-carboxylic acid tert-butyl ester (0.604 g, 3.24 mmol) and DIPEA (0.419 g, 3.24 mmol) in acetonitrile (20 mL) was stirred at room temperature for overnight. The reaction mixture was concentrated and extracted with dichloromethane. The organic layer was dried over Na$_2$SO$_4$, filtered and concentrated to give 1.1 g of rac-4-[6-chloro-3-(3-chloro-benzyl)-2-oxo-2,3-dihydro-1H-indol-3-yl]-piperazine-1-carboxylic acid tert-butyl ester. MS m/z 476 (M+H)+.

EXAMPLE 140

Preparation of rac-6-chloro-3-(3-chloro-benzyl)-3-piperazin-1-yl-1,3-dihydro-indol-2-one

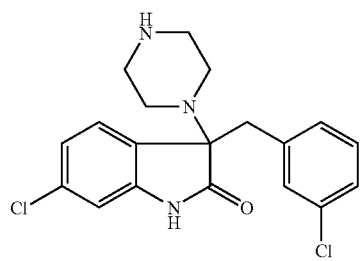

M. W. 376.29   $C_{19}H_{19}Cl_2N_3O$

The mixture of rac-4-[6-chloro-3-(3-chloro-benzyl)-2-oxo-2,3-dihydro-1H-indol-3-yl]-piperazine-1-carboxylic acid tert-butyl ester (900 mg, 1.89 mmol) in trifluoroacetic acid (10 mL) was stirred at room temperature for 0.5 h. Then the solution was concentrated and extracted with dichloromethane. The organic layer was dried over Na$_2$SO$_4$, filtered and concentrated to give 0.6 g of rac-6-chloro-3-(3-chloro-benzyl)-3-piperazin-1-yl-1,3-dihydro-indol-2-one as a yellow solid. MS m/z 376 (M+H)+.

EXAMPLE 141

Preparation of rac-3-(4-benzoyl-piperazin-1-yl)-6-chloro-3-(3-chloro-benzyl)-1,3-dihydro-indol-2-one

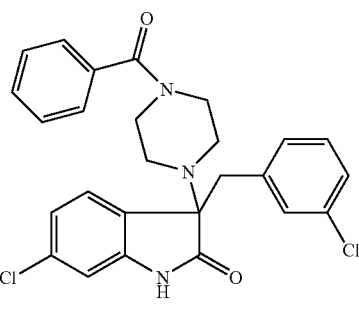

M. W. 480.40   $C_{26}H_{23}Cl_2N_3O_2$

The mixture of rac-6-chloro-3-(3-chloro-benzyl)-3-piperazin-1-yl-1,3-dihydro-indol-2-one (100 mg, 0.266 mmol), benzoyl chloride (37 mg, 0.266 mmol) and DIPEA (34 mg, 0.266 mmol) in acetonitrile (3 mL) was stirred at room temperature for overnight. Then the mixture was concentrated and the residue was purified with preparative HPLC to give 29 mg of rac-3-(4-benzoyl-piperazin-1-yl)-6-chloro-3-(3-chloro-benzyl)-1,3-dihydro-indol-2-one as a light orange solid. MS m/z 480 (M+H)+.

EXAMPLE 142

Preparation of rac-3-(4-benzenesulfonyl-piperazin-1-yl)-6-chloro-3-(3-chloro-benzyl)-1,3-dihydro-indol-2-one

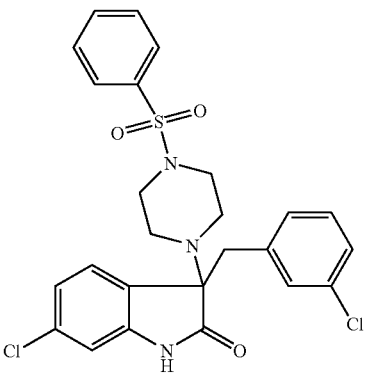

M. W. 516.45   $C_{25}H_{23}Cl_2N_3O_3S$

101

The title compound was prepared following the same procedure for rac-3-(4-benzoyl-piperazin-1-yl)-6-chloro-3-(3-chloro-benzyl)-1,3-dihydro-indol-2-one. MS m/z 516 (M+H)⁺

EXAMPLE 143

Preparation of rac-6-chloro-3-(3-chloro-benzyl)-3-[4-(thiophene-2-sulfonyl)-piperazin-1-yl]-1,3-dihydro-indol-2-one

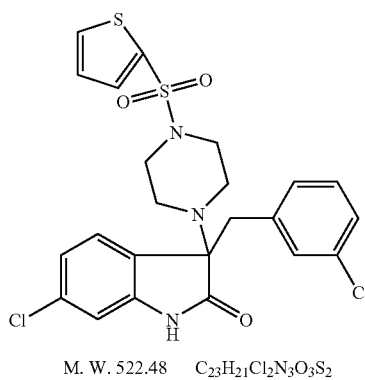

M. W. 522.48    $C_{23}H_{21}Cl_2N_3O_3S_2$

The title compound was prepared following the same procedure for rac-3-(4-benzoyl-piperazin-1-yl)-6-chloro-3-(3-chloro-benzyl)-1,3-dihydro-indol-2-one. MS m/z 522 (M+H)⁺.

EXAMPLE 144

Preparation of rac-3-[6-chloro-3-(3-chloro-benzyl)-2-oxo-2,3-dihydro-1H-indol-3-ylamino]-benzoic acid

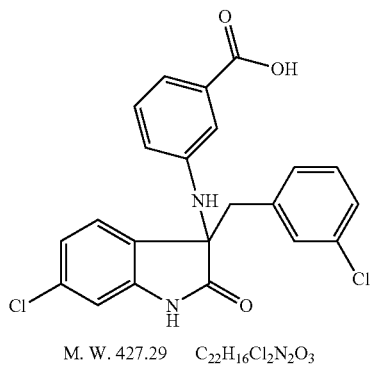

M. W. 427.29    $C_{22}H_{16}Cl_2N_2O_3$

The mixture of rac-3-bromo-6-chloro-3-(3-chloro-benzyl)-1,3-dihydro-indol-2-one (740 mg, 2 mmol), 3-aminobenzoic acid (301 mg, 2.2 mmol) and K₂CO₃ (552 mg, 4 mmol) in DMF (5 mL) was stirred for 0.5 h and then poured into water (100 mL). The resulting solution was acidified by acetic acid and filtered. The filter cake was washed by water and dried to give rac-3-[6-chloro-3-(3-chloro-benzyl)-2-oxo-2,3-dihydro-1H-indol-3-ylamino]-benzoic acid as a pale yellow solid. MS m/z 425 (M–H)⁻.

EXAMPLE 145

Preparation of rac-2-[6-chloro-3-(3-chloro-benzyl)-2-oxo-2,3-dihydro-1H-indol-3-ylamino]-benzoic acid

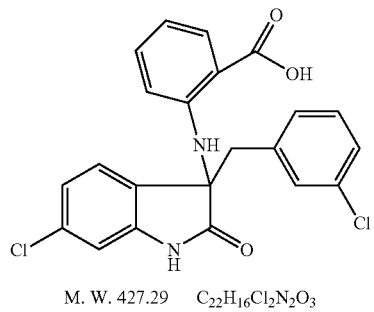

M. W. 427.29    $C_{22}H_{16}Cl_2N_2O_3$

The title compound was prepared by the same procedure for rac-3-[6-chloro-3-(3-chloro-benzyl)-2-oxo-2,3-dihydro-1H-indol-3-ylamino]-benzoic acid. MS m/z 425 (M–H)⁻.

EXAMPLE 146

Preparation of rac-1-[6-chloro-3-(3-chloro-benzyl)-2-oxo-2,3-dihydro-1H-indol-3-yl]-piperidine-3-carboxylic acid

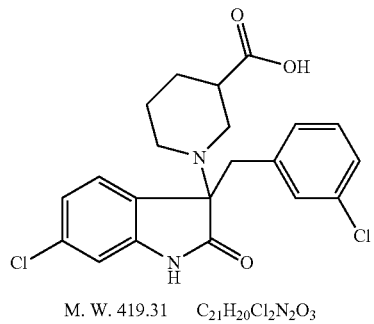

M. W. 419.31    $C_{21}H_{20}Cl_2N_2O_3$

To the mixture of piperidine-3-carboxylic acid (600 mg, 4.5 mmol) and NaOH (360 mg, 9 mmol) in water (5 mL) and dioxane (5 mL) was added rac-3-bromo-6-chloro-3-(3-chloro-benzyl)-1,3-dihydro-indol-2-one (1.1 g, 3 mmol). The mixture was stirred at room temperature for 1 h and then diluted by water (30 mL). The resulting solution was neutralized to pH=7 with hydrochloride acid and extracted by dichloromethane. The organic phase was dried over Na₂SO₄, filtered and concentrated to give rac-1-[6-chloro-3-(3-chlorobenzyl)-2-oxo-2,3-dihydro-1H-indol-3-yl]-piperidine-3-carboxylic acid yield: (0.9 g, 71%). MS: [M−H]⁻=417.

EXAMPLE 147

Preparation of rac-6-chloro-3-(3-chloro-benzyl)-3-[3-(4-methyl-piperazine-1-carbonyl)-phenylamino]-1,3-dihydro-indol-2-one

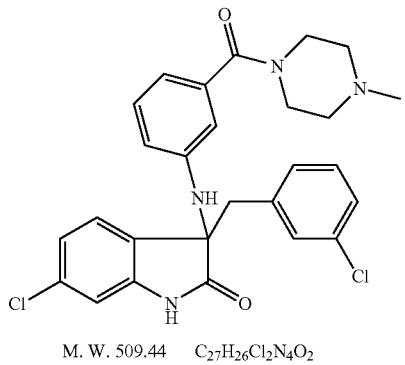

M. W. 509.44    $C_{27}H_{26}Cl_2N_4O_2$

The mixture of rac-3-[6-chloro-3-(3-chloro-benzyl)-2-oxo-2,3-dihydro-1H-indol-3-ylamino]-benzoic acid (60 mg, 0.14 mmol), 1-methyl-piperazine (56 mg, 0.56 mmol) and EDCl (54 mg, 0.28 mmol) in dichlorometahne (2 mL) was stirred at room temperature for overnight. The reaction mixture was purified by preparative HPLC to give rac-6-chloro-3-(3-chloro-benzyl)-3-[3-(4-methyl-piperazine-1-carbonyl)-phenylamino]-1,3-dihydro-indol-2-one as a powder. ¹H NMR (CDCl₃, 400 MHz): δ 7.21-6.74 (m, 9H), 6.49 (d, 1H), 6.17 (s, 1H), 4.70 (s, 1H), 3.80-3.45 (br, 8H), 3.28-3.15 (q, 2H), 2.66 (s, 3H). MS: [M+H]⁺=509

EXAMPLE 148

Preparation of rac-3-[3-(4-acetyl-piperazine-1-carbonyl)-phenylamino]-6-chloro-3-(3-chloro-benzyl)-1,3-dihydro-indol-2-one

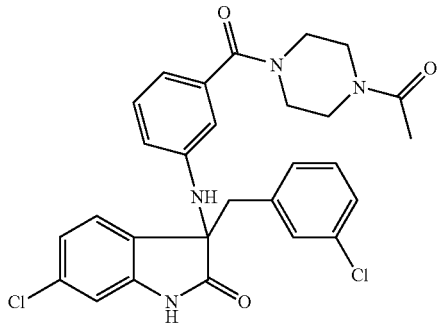

M. W. 537.45    $C_{28}H_{26}Cl_2N_4O_3$

The title compound was prepared following the similar procedure as rac-6-chloro-3-(3-chloro-benzyl)-3-{3-[4-(2-hydroxy-ethyl)-piperazine-1-carbonyl]-phenylamino}-1,3-dihydro-indol-2-one. MS: [M+H]⁺=537

EXAMPLE 149

Preparation of rac-6-chloro-3-(3-chloro-benzyl)-3-{2-[4-(2-methoxy-ethyl)-piperazine-1-carbonyl]-phenylamino}-1,3-dihydro-indol-2-one

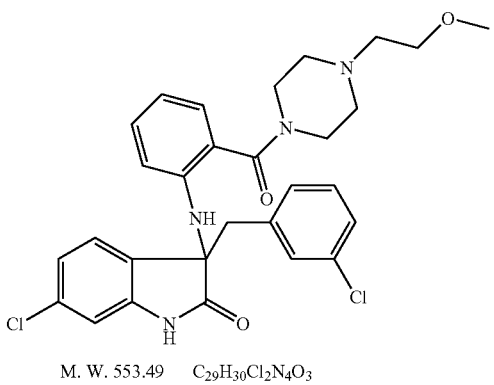

M. W. 553.49    $C_{29}H_{30}Cl_2N_4O_3$

The title compound was prepared following the similar procedure as rac-6-chloro-3-(3-chloro-benzyl)-3-{3-[4-(2-hydroxy-ethyl)-piperazine-1-carbonyl]-phenylamino}-1,3-dihydro-indol-2-one. MS: [M+H]⁺=553

EXAMPLE 150

Preparation of rac-6-chloro-3-(3-chloro-benzyl)-3-{2-[4-(2-hydroxy-ethyl)-piperazine-1-carbonyl]-phenylamino}-1,3-dihydro-indol-2-one

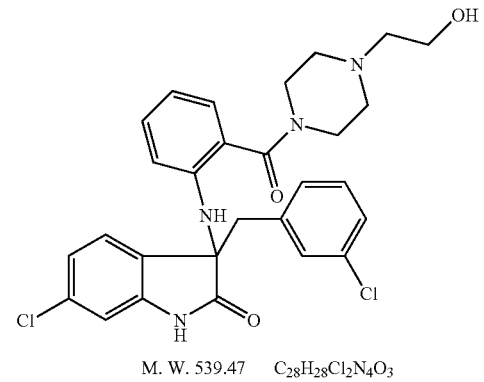

M. W. 539.47    $C_{28}H_{28}Cl_2N_4O_3$

The title compound was prepared following the similar procedure as rac-6-chloro-3-(3-chloro-benzyl)-3-{3-[4-(2- hydroxy-ethyl)-piperazine-1-carbonyl]-phenylamino}-1,3-dihydro-indol-2-one. MS: [M+H]$^+$=539

EXAMPLE 151

Preparation of rac-3-[2-(4-acetyl-piperazine-1-carbonyl)-phenylamino]-6-chloro-3-(3-chloro-benzyl)-1,3-dihydro-indol-2-one

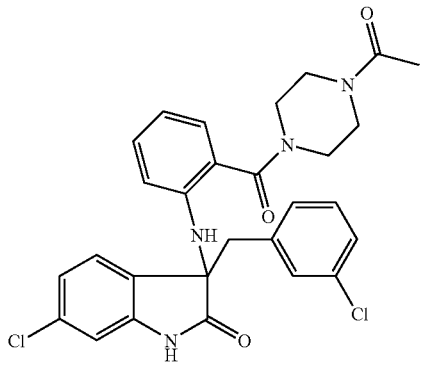

M. W. 537.45    $C_{28}H_{26}Cl_2N_4O_3$

The title compound was prepared following the similar procedure as rac-6-chloro-3-(3-chloro-benzyl)-3-{3-[4-(2-hydroxy-ethyl)-piperazine-1-carbonyl]-phenylamino}-1,3-dihydro-indol-2-one. MS: [M+H]$^+$=537

EXAMPLE 152

Preparation of rac-1-{1-[6-Chloro-3-(3-chloro-benzyl)-2-oxo-2,3-dihydro-1H-indol-3-yl]-piperidine-3-carbonyl}-piperidine-4-carboxylic acid amide

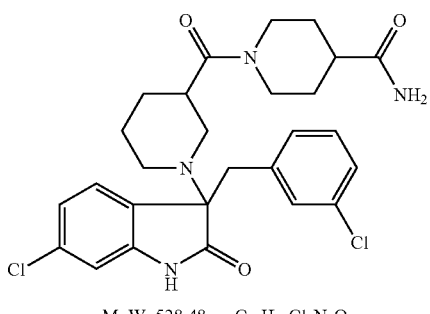

M. W. 528.48    $C_{28}H_{31}Cl_2N_3O_3$

The title compound was prepared following the similar procedure as rac-6-chloro-3-(3-chloro-benzyl)-3-{3-[4-(2-hydroxy-ethyl)-piperazine-1-carbonyl]-phenylamino}-1,3-dihydro-indol-2-one. MS: [M+H]$^+$=529

EXAMPLE 153

Preparation of rac-3-[3-(4-acetyl-piperazine-1-carbonyl)-piperidin-1-yl]-6-chloro-3-(3-chloro-benzyl)-1,3-dihydro-indol-2-one

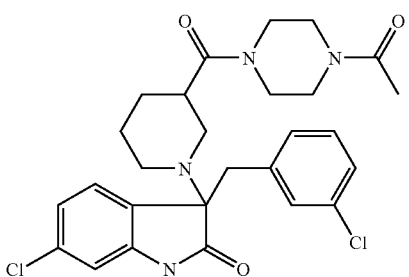

M. W. 529.47    $C_{27}H_{30}Cl_2N_4O_3$

The title compound was prepared following the similar procedure as rac-6-chloro-3-(3-chloro-benzyl)-3-{3-[4-(2-hydroxy-ethyl)-piperazine-1-carbonyl]-phenylamino}-1,3-dihydro-indol-2-one. MS: [M+H]$^+$=529

EXAMPLE 154

Preparation of rac-6-chloro-3-(3-chloro-benzyl)-3-[3-(morpholine-4-carbonyl)-piperidin-1-yl]-1,3-dihydro-indol-2-one

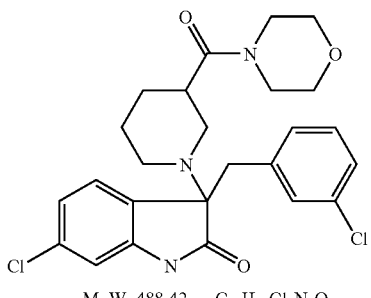

M. W. 488.42    $C_{25}H_{27}Cl_2N_3O_3$

The title compound was prepared following the similar procedure as rac-6-chloro-3-(3-chloro-benzyl)-3-{3-[4-(2- hydroxy-ethyl)-piperazine-1-carbonyl]-phenylamino}-1,3-dihydro-indol-2-one. MS: [M+H]$^+$=488

EXAMPLE 155

Preparation of rac-6-chloro-3-(3-chloro-benzyl)-3-{3-[4-(2-hydroxy-ethyl)-piperazine-1-carbonyl]-phenylamino}-1,3-dihydro-indol-2-one

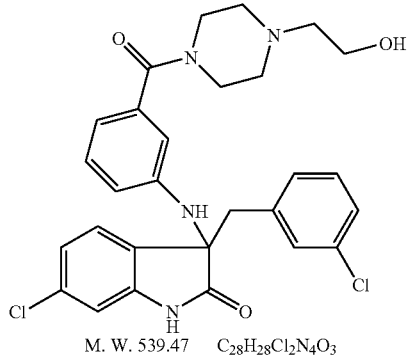

M. W. 539.47   $C_{28}H_{28}Cl_2N_4O_3$

The title compound was prepared following the similar procedure as rac-6-chloro-3-(3-chloro-benzyl)-3-{3-[4-(2-hydroxy-ethyl)-piperazine-1-carbonyl]-phenylamino}-1,3-dihydro-indol-2-one. MS: [M+H]$^+$=539

EXAMPLE 156

Preparation of rac-6-chloro-3-(3-chloro-benzyl)-3-[3-(4-methyl-piperazine-1-carbonyl)-piperidin-1-yl]-1,3-dihydro-indol-2-one

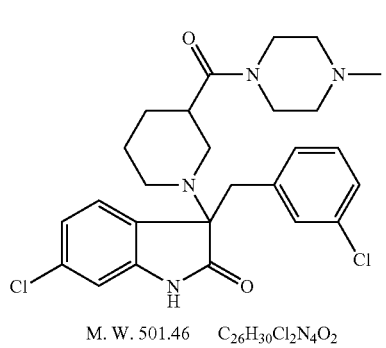

M. W. 501.46   $C_{26}H_{30}Cl_2N_4O_2$

The title compound was prepared following the similar procedure as rac-6-chloro-3-(3-chloro-benzyl)-3-{3-[4-(2- hydroxy-ethyl)-piperazine-1-carbonyl]-phenylamino}-1,3-dihydro-indol-2-one. MS: [M+H]$^+$=501

EXAMPLE 157

Preparation of rac-6-chloro-3-(3-chloro-benzyl)-3-{3-[4-(2-hydroxy-ethyl)-piperazine-1-carbonyl]-piperidin-1-yl}-1,3-dihydro-indol-2-one

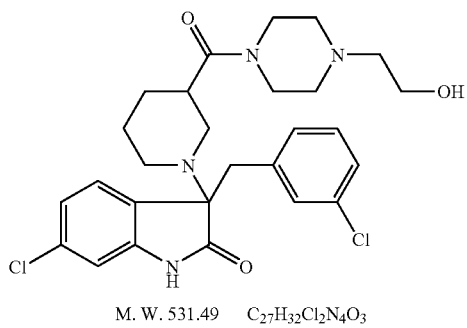

M. W. 531.49   $C_{27}H_{32}Cl_2N_4O_3$

The title compound was prepared following the similar procedure as rac-6-chloro-3-(3-chloro-benzyl)-3-{3-[4-(2-hydroxy-ethyl)-piperazine-1-carbonyl]-phenylamino}-1,3-dihydro-indol-2-one. MS: [M+H]$^+$=531

EXAMPLE 158

Preparation of rac-6-chloro-3-(3-chloro-benzyl)-3-{3-[4-(2-methoxy-ethyl)-piperazine-1-carbonyl]-piperidin-1-yl}-1,3-dihydro-indol-2-one

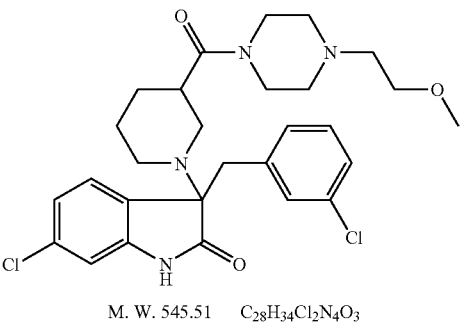

M. W. 545.51   $C_{28}H_{34}Cl_2N_4O_3$

The title compound was prepared following the similar procedure as rac-6-chloro-3-(3-chloro-benzyl)-3-{3-[4-(2- hydroxy-ethyl)-piperazine-1-carbonyl]-phenylamino}-1,3-dihydro-indol-2-one. MS: [M+H]⁺=545.

EXAMPLE 159

Preparation of rac-6-chloro-3-(3-chloro-benzyl)-3-[2-(morpholine-4-carbonyl)-phenylamino]-1,3-dihydro-indol-2-one

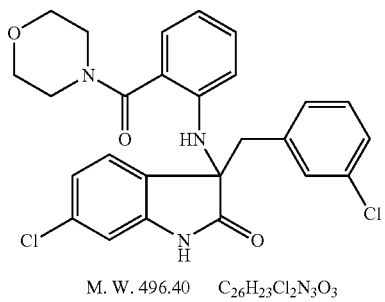

M. W. 496.40   C₂₆H₂₃Cl₂N₃O₃

The title compound was prepared following the similar procedure as rac-6-chloro-3-(3-chloro-benzyl)-3-{3-[4-(2-hydroxy-ethyl)-piperazine-1-carbonyl]-phenylamino}-1,3-dihydro-indol-2-one. MS: [M+H]⁺=496.

EXAMPLE 160

Preparation of rac-6-(4-{1-[6-chloro-3-(3-chloro-benzyl)-2-oxo-2,3-dihydro-1H-indol-3-yl]-piperidine-3-carbonyl}-piperazin-1-yl)-nicotinonitrile

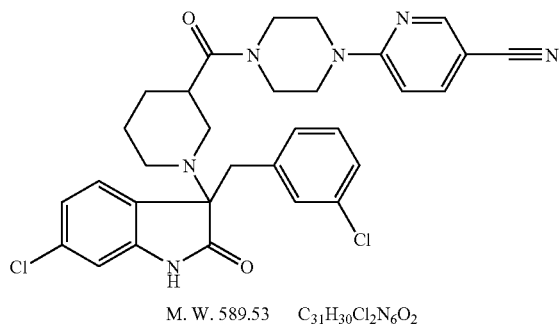

M. W. 589.53   C₃₁H₃₀Cl₂N₆O₂

The title compound was prepared following the similar procedure as rac-6-chloro-3-(3-chloro-benzyl)-3-{3-[4-(2- hydroxy-ethyl)-piperazine-1-carbonyl]-phenylamino}-1,3-dihydro-indol-2-one. MS: [M+H]⁺=589.

EXAMPLE 161

Preparation of rac-6-chloro-3-(3-chloro-benzyl)-3-[3-(4-pyridin-2-yl-piperazine-1-carbonyl)-piperidin-1-yl]-1,3-dihydro-indol-2-one

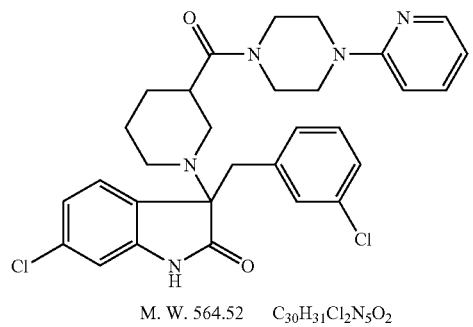

M. W. 564.52   C₃₀H₃₁Cl₂N₅O₂

The title compound was prepared following the similar procedure as rac-6-chloro-3-(3-chloro-benzyl)-3-{3-[4-(2-hydroxy-ethyl)-piperazine-1-carbonyl]-phenylamino}-1,3-dihydro-indol-2-one. MS: [M+H]⁺=564

EXAMPLE 162

Preparation of rac-3-{3-[4-(4-acetyl-phenyl)-piperazine-1-carbonyl]-piperidin-1-yl}-6-chloro-3-(3-chloro-benzyl)-1,3-dihydro-indol-2-one

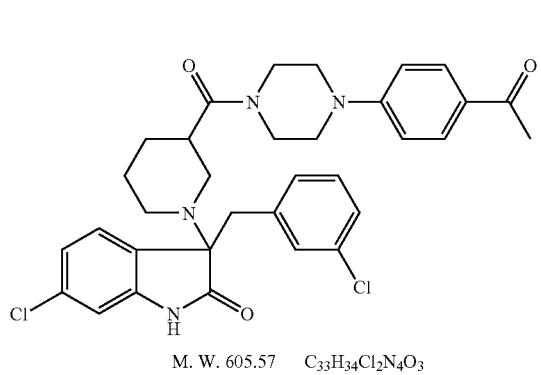

M. W. 605.57   C₃₃H₃₄Cl₂N₄O₃

The title compound was prepared following the similar procedure as rac-6-chloro-3-(3-chloro-benzyl)-3-{3-[4-(2- hydroxy-ethyl)-piperazine-1-carbonyl]-phenylamino}-1,3-dihydro-indol-2-one. MS: [M+H]$^+$=605.

EXAMPLE 163

Preparation of rac-6-chloro-3-(3-chloro-benzyl)-3-[3-(4-pyrimidin-2-yl-piperazine-1-carbonyl)-piperidin-1-yl]-1,3-dihydro-indol-2-one

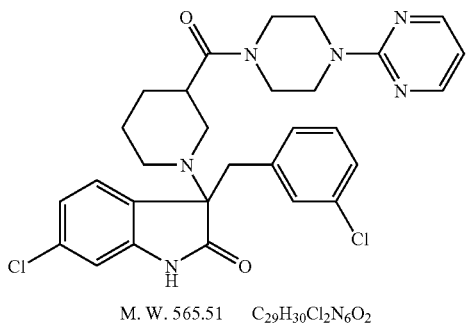

M. W. 565.51    $C_{29}H_{30}Cl_2N_6O_2$

The title compound was prepared following the similar procedure as rac-6-chloro-3-(3-chloro-benzyl)-3-{3-[4-(2-hydroxy-ethyl)-piperazine-1-carbonyl]-phenylamino}-1,3-dihydro-indol-2-one. MS: [M+H]$^+$=565.

EXAMPLE 164

Preparation of rac-6-chloro-3-(3-chloro-benzyl)-3-{3-[4-(3,4-dichloro-phenyl)-piperazine-carbonyl]-piperidin-1-yl}-1,3-dihydro-indol-2-one

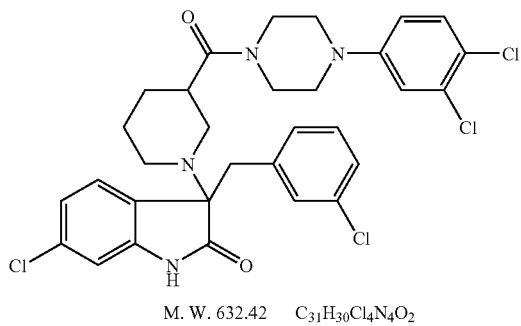

M. W. 632.42    $C_{31}H_{30}Cl_4N_4O_2$

The title compound was prepared following the similar procedure as rac-6-chloro-3-(3-chloro-benzyl)-3-{3-[4-(2- hydroxy-ethyl)-piperazine-1-carbonyl]-phenylamino}-1,3-dihydro-indol-2-one. MS: [M+H]$^+$=631.

EXAMPLE 165

Preparation of rac-6-chloro-3-(3-chloro-benzyl)-3-{3-[4-(3-hydroxy-propyl)-piperazine-1-carbonyl]-piperidin-1-yl}-1,3-dihydro-indol-2-one

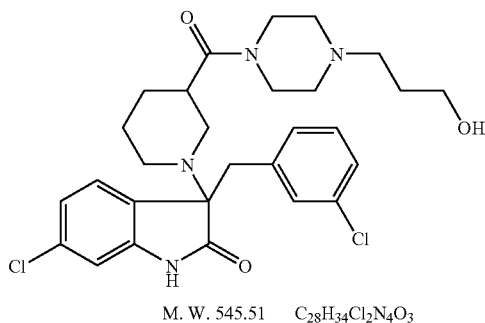

M. W. 545.51    $C_{28}H_{34}Cl_2N_4O_3$

The title compound was prepared following the similar procedure as rac-6-chloro-3-(3-chloro-benzyl)-3-{3-[4-(2-hydroxy-ethyl)-piperazine-1-carbonyl]-phenylamino}-1,3-dihydro-indol-2-one. MS: [M+H]$^+$=545.

EXAMPLE 166

Preparation of rac-1-[6-chloro-3-(3-chloro-benzyl)-2-oxo-2,3-dihydro-1H-indol-3-yl]-piperidine-3-carboxylic acid (2-hydroxy-ethyl)-amide

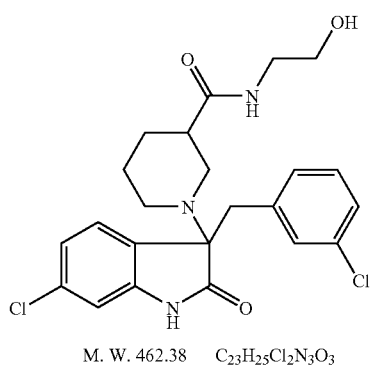

M. W. 462.38    $C_{23}H_{25}Cl_2N_3O_3$

The title compound was prepared following the similar procedure as rac-6-chloro-3-(3-chloro-benzyl)-3-{3-[4-(2- hydroxy-ethyl)-piperazine-1-carbonyl]-phenylamino}-1,3-dihydro-indol-2-one. MS: [M+H]⁺=462.

EXAMPLE 167

Preparation of rac-1-[6-chloro-3-(3-chloro-benzyl)-2-oxo-2,3-dihydro-1H-indol-3-yl]-piperidine-3-carboxylic acid (2-hydroxy-1-hydroxymethyl-ethyl)-amide

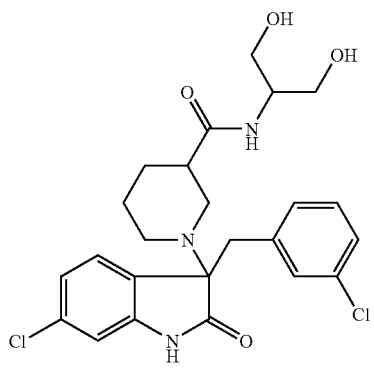

M. W. 492.41   C₂₄H₂₇Cl₂N₃O₄

The title compound was prepared following the similar procedure as rac-6-chloro-3-(3-chloro-benzyl)-3-{3-[4-(2-hydroxy-ethyl)-piperazine-1-carbonyl]-phenylamino}-1,3-dihydro-indol-2-one. MS: [M+H]⁺=492.

EXAMPLE 168

Preparation of rac-1-[6-chloro-3-(3-chloro-benzyl)-2-oxo-2,3-dihydro-1H-indol-3-yl]-piperidine-3-carboxylic acid (2-morpholin-4-yl-ethyl)-amide

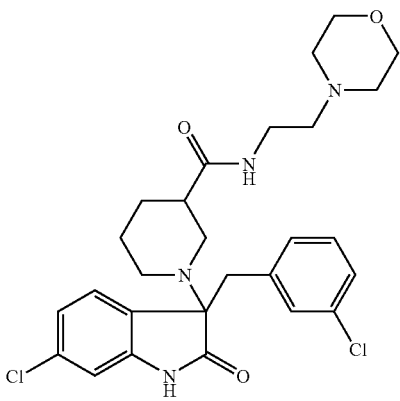

M. W. 531.49   C₂₇H₃₂Cl₂N₄O₃

The title compound was prepared following the similar procedure as rac-6-chloro-3-(3-chloro-benzyl)-3-{3-[4-(2- hydroxy-ethyl)-piperazine-1-carbonyl]-phenylamino}-1,3-dihydro-indol-2-one. MS: [M+H]⁺=531.

EXAMPLE 169

Preparation of rac-({1-[6-chloro-3-(3-chloro-benzyl)-2-oxo-2,3-dihydro-1H-indol-3-yl]-piperidine-3-carbonyl}-amino)-acetic acid ethyl ester

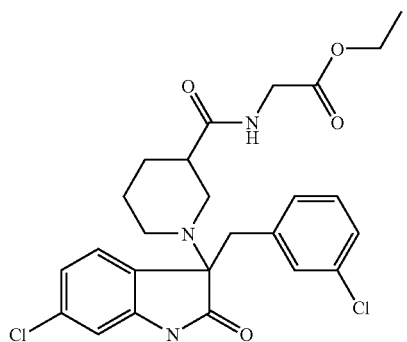

M. W. 504.42   C₂₅H₂₇Cl₂N₃O₄

The title compound was prepared following the similar procedure as rac-6-chloro-3-(3-chloro-benzyl)-3-{3-[4-(2-hydroxy-ethyl)-piperazine-1-carbonyl]-phenylamino}-1,3-dihydro-indol-2-one. MS: [M+H]⁺=504.

EXAMPLE 170

Preparation of rac-1-{2-[6-chloro-3-(3-chloro-benzyl)-2-oxo-2,3-dihydro-1H-indol-3-ylamino]-benzoyl}-piperidine-4-carboxylic acid amide

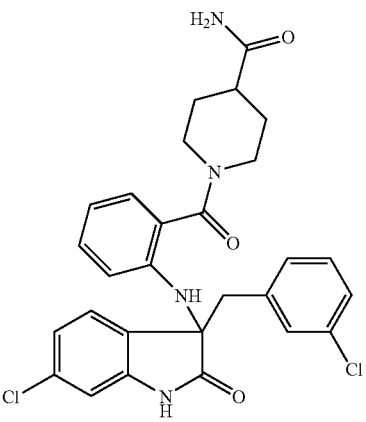

M. W. 537.45   C₂₈H₂₆Cl₂N₄O₃

The title compound was prepared following the similar procedure as rac-6-chloro-3-(3-chloro-benzyl)-3-{3-[4-(2- hydroxy-ethyl)-piperazine-1-carbonyl]-phenylamino}-1,3-dihydro-indol-2-one. MS: [M+H]$^+$=537.

EXAMPLE 171

Preparation of rac-1-{3-[6-chloro-3-(3-chloro-benzyl)-2-oxo-2,3-dihydro-1H-indol-3-ylamino]-benzoyl}-piperidine-4-carboxylic acid amide

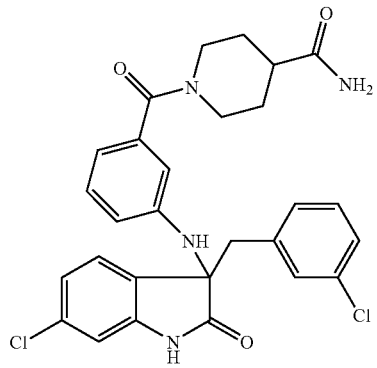

M. W. 537.45   $C_{28}H_{26}Cl_2N_4O_3$

The title compound was prepared following the similar procedure as rac-6-chloro-3-(3-chloro-benzyl)-3-{3-[4-(2-hydroxy-ethyl)-piperazine-1-carbonyl]-phenylamino}-1,3-dihydro-indol-2-one. MS: [M+H]$^+$=537.

EXAMPLE 172

Preparation of rac-6-chloro-3-(3-chloro-benzyl)-3-{3-[4-(2-methoxy-ethyl)-piperazine-1-carbonyl]-phenylamino}-1,3-dihydro-indol-2-one

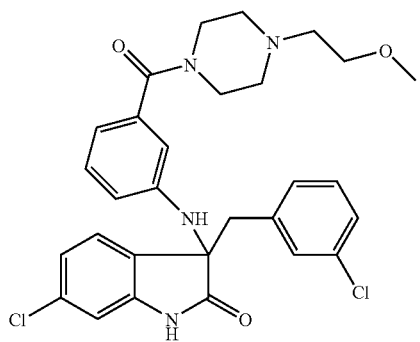

M. W. 553.49   $C_{29}H_{30}Cl_2N_4O_3$

The title compound was prepared following the similar procedure as rac-6-chloro-3-(3-chloro-benzyl)-3-{3-[4-(2-hydroxy-ethyl)-piperazine-1-carbonyl]-phenylamino}-1,3-dihydro-indol-2-one. MS: [M+H]$^+$=553.

EXAMPLE 173

Preparation of rac-6-chloro-3-(3-chloro-benzyl)-3-[3-(morpholine-4-carbonyl)-phenylamino]-1,3-dihydro-indol-2-one

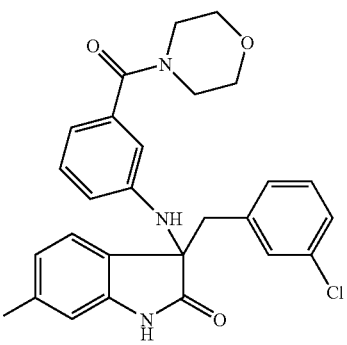

M. W. 496.40   $C_{26}H_{23}Cl_2N_3O_3$

The title compound was prepared following the similar procedure as rac-6-chloro-3-(3-chloro-benzyl)-3-{3-[4-(2-hydroxy-ethyl)-piperazine-1-carbonyl]-phenylamino}-1,3-dihydro-indol-2-one. MS: [M+H]$^+$=496.

EXAMPLE 174a

Preparation of Intermediate (3S)-(chloro-carbonyl-amino)-piperidine-1-carboxylic acid tert-butyl ester

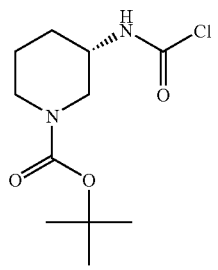

M. W. 262.74   $C_{11}H_{19}ClN_2O_3$

To a solution of triphosgene (3 g, 10 mmol) in dichloromethane (150 mL) at −10° C. was added pyridine (1.6 mL, 20 mmol), followed by the addition of a solution of (S)-3-amino-piperidine-1-carboxylic acid tert-butyl ester (4 g, 20 mmol) in dichloromethane (5 mL). The mixture was allowed to warm up to room temperature and stirred at room temperature for 4 h. Then the mixture was cooled to −10° C. again and HCl (1N, 20 mL) was added. After the mixture was stirred at −10° C. for 0.5 h, the mixture was partitioned. The organic layer was washed with saturated NaHCO$_3$, dried over Na$_2$SO$_4$, concentrated in vacuo. The residue was purified by

117 chromatography to give 2 g of (3S)-(chloro-carbonyl-amino)-piperidine-1-carboxylic acid tert-butyl ester as a brown oil.

EXAMPLE 174b

Preparation of Intermediate (3S)-[(4-methyl-piperazine-1-carbonyl)-amino]-piperidine-1-carboxylic acid tert-butyl ester

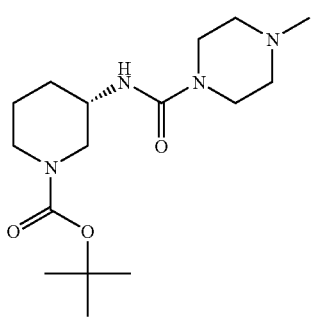

M. W. 326.44   $C_{16}H_{30}N_4O_3$

The mixture of (3S)-(chloro-carbonyl-amino)-piperidine-1-carboxylic acid tert-butyl ester (300 mg, 1.14 mmol), 1-methyl-piperazine (100 mg, 1 mmol) and $Na_2CO_3$ (1 g, 9.4 mmol) in dichloromethane (5 mL)) was stirred at room temperature for 4 h. Then the mixture was diluted with dichloromethane (10 mL), washed with water, dried over $Na_2SO_4$ and concentrated to give 300 mg of (3S)-[(4-methyl-piperazine-1-carbonyl)-amino]-piperidine-1-carboxylic acid tert-butyl ester as a yellow oil.

EXAMPLE 174c

Preparation of rac-(4-methyl-piperazine-1-carboxylic acid{1-[6-chloro-3-(3-chloro-benzyl)-2-oxo-2,3-dihydro-1H-indol-3-yl]-piperidin-(3S)-yl}-amide

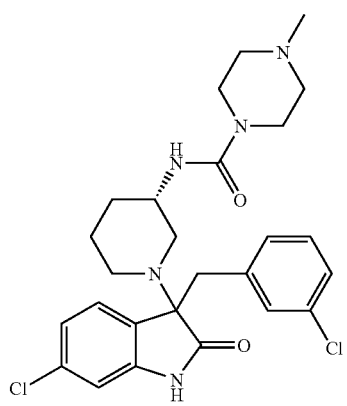

M. W. 516.48   $C_{26}H_{31}Cl_2N_5O_2$ (3S)-[(4-methyl-piperazine-1-carbonyl)-amino]-piperidine-1-carboxylic acid tert-butyl ester (50 mg, 0.15 mmol) was dissolved in TFA (2 mL) and stirred for 0.5 h. The mixture was concentrated in vacuo and the residue was dissolved in dioxane (2 mL) and DMF (0.5 mL). To the above solution were added rac-3-bromo-6-chloro-3-(3-chloro-ben-

118 zyl)-1,3-dihydro-indol-2-one (40 mg, 0.11 mmol) and DIPEA (220 mg, 1.7 mmol). The resulting mixture was stirred for 1 h, concentrated in vacuo. The residue was purified by preparative HPLC to give 29 mg of rac-(4-methyl-piperazine-1-carboxylic acid{1-[6-chloro-3-(3-chloro-benzyl)-2-oxo-2,3-dihydro-1H-indol-3-yl]-piperidin-(3S)-yl}-amide. MS: [M+H]$^+$=516

EXAMPLE 175

Preparation of rac-4-(2-hydroxy-ethyl)-piperazine-1-carboxylic acid{1-[6-chloro-3-(3-chloro-benzyl)-2-oxo-2,3-dihydro-1H-indol-3-yl]-piperidin-(3S)-yl}-amide

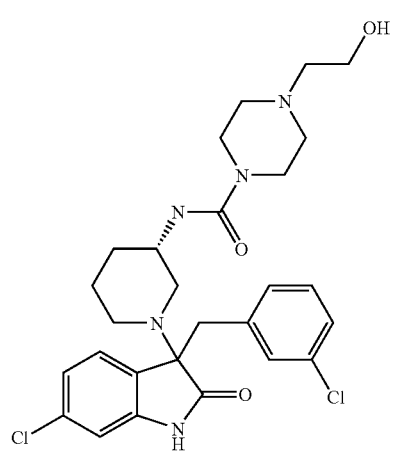

M. W. 546.50   $C_{27}H_{33}Cl_2N_5O_3$

The title compound was prepared following the similar procedure as rac-4-methyl-piperazine-1-carboxylic acid{1-[6-chloro-3-(3-chloro-benzyl)-2-oxo-2,3-dihydro-1H-indol-3-yl]-piperidin-(3S)-yl}-amide. MS: [M+H]$^+$=546

EXAMPLE 176

Preparation of rac-morpholine-4-carboxylic acid{1-[6-chloro-3-(3-chloro-benzyl)-2-oxo-2,3-dihydro-1H-indol-3-yl]-piperidin-(3S)-yl}-amide

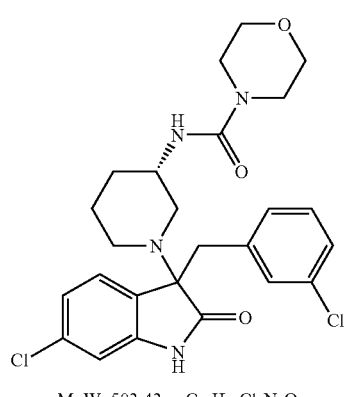

M. W. 503.43   $C_{25}H_{28}Cl_2N_4O_3$

The title compound was prepared following the similar procedure as rac-4-methyl-piperazine-1-carboxylic acid{1-[6-chloro-3-(3-chloro-benzyl)-2-oxo-2,3-dihydro-1H-indol-3-yl]-piperidin-(3S)-yl}-amide. MS: [M+H]$^+$=503.

EXAMPLE 177

Preparation of rac-4-(2-methoxy-ethyl)-piperazine-1-carboxylic acid{1-[6-chloro-3-(3-chloro-benzyl)-2-oxo-2,3-dihydro-1H-indol-3-yl]-piperidin-(3S)-yl}-amide

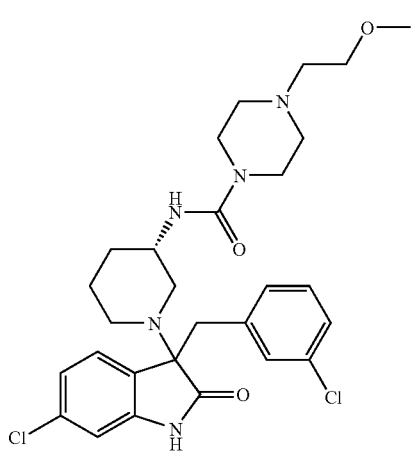

M. W. 560.53   $C_{28}H_{35}Cl_2N_5O_3$

The title compound was prepared following the similar procedure as rac-4-methyl-piperazine-1-carboxylic acid{1-[6-chloro-3-(3-chloro-benzyl)-2-oxo-2,3-dihydro-1H-indol-3-yl]-piperidin-(3S)-yl}-amide. MS: [M+H]$^+$=560.

EXAMPLE 178

Preparation of rac-4-acetyl-piperazine-1-carboxylic acid{1-[6-chloro-3-(3-chloro-benzyl)-2-oxo-2,3-dihydro-1H-indol-3-yl]-piperidin-(3S)-yl}-amide

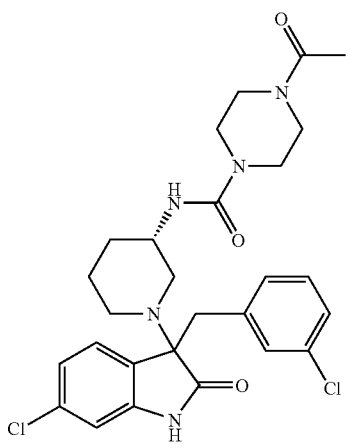

M. W. 544.49   $C_{27}H_{31}Cl_2N_5O_3$

The title compound was prepared following the similar procedure as rac-4-methyl-piperazine-1-carboxylic acid{1-[6-chloro-3-(3-chloro-benzyl)-2-oxo-2,3-dihydro-1H-indol-3-yl]-piperidin-(3S)-yl}-amide. MS: [M+H]$^+$=544.

EXAMPLE 179

Preparation of rac-6-chloro-3-(3-chloro-benzyl)-3-(cyclopropylmethyl-amino)-1,3-dihydro-indol-2-one

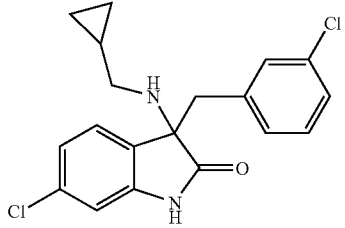

M. W. 361.27   $C_{19}H_{18}Cl_2N_2O$

To a solution of cyclopropanemethylamine (142 mg, 2.0 mmol) in dichloromethane (20 mL) was added rac-3-bromo-6-chloro-3-(3-chloro-benzyl)-1,3-dihydro-indol-2-one (0.37 g, 0.99 mmol). After the mixture was stirred at room temperature for 1 h, another portion of dichloromethane (20 mL) was added. The mixture was washed with water (20 mL×2). The organic layer was separated, dried over Na$_2$SO$_4$ and concentrated to give 0.34 g of rac-6-chloro-3-(3-chloro-benzyl)-3-(cyclopropylmethyl-amino)-1,3-dihydro-indol-2-one as a white solid. MS: [M+H]$^+$=361

EXAMPLE 180

Preparation of rac-6-chloro-3-(3-chloro-benzyl)-3-[cyclohexyl-(2-morpholin-4-yl-2-oxo-ethyl)-amino]-1,3-dihydro-indol-2-one

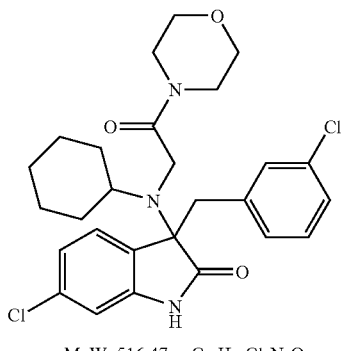

M. W. 516.47   $C_{27}H_{31}Cl_2N_3O_3$

To the mixture of rac-{[6-chloro-3-(3-chloro-benzyl)-2-oxo-2,3-dihydro-1H-indol-3-yl]-cyclohexyl-amino}-acetic acid (22 mg) and morpholine (6 mg) in dichloromethane (2 mL) was added N-(3-dimethylaminopropyl)-N'-ethylcarbodiimide hydrochloride (19 mg) and 4-dimethylaminopyrimidine (12 mg). After stirred for 3 h at room temperature, the mixture was purified with chromatograghy to give 20 mg of rac-6-chloro-3-(3-chloro-benzyl)-3-[cyclohexyl-(2-morpholin-4-yl-2-oxo-ethyl)-amin-1,3-dihydro-indol-2-one as a white solid MS: [M+H]$^+$=516.

EXAMPLE 181

Preparation of rac-6-chloro-3-(3-chloro-benzyl)-3-{cyclohexyl-[2-(4-methyl-piperazin-1-yl)-2-oxo-ethyl]-amino}-1,3-dihydro-indol-2-one

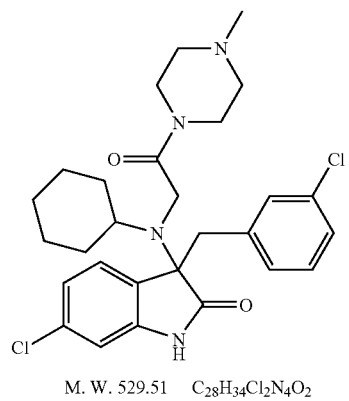

M. W. 529.51    $C_{28}H_{34}Cl_2N_4O_2$

The title compound was prepared following the similar procedure as rac-6-chloro-3-(3-chloro-benzyl)-3-[cyclohexyl-(2-morpholin-4-yl-2-oxo-ethyl)-amino]-1,3-dihydro-indol-2-one. MS: [M+H]$^+$=529.

EXAMPLE 182

Preparation of rac-1-(2-{[6-chloro-3-(3-chloro-benzyl)-2-oxo-2,3-dihydro-1H-indol-3-yl]-cyclohexyl-amino}-acetyl)-piperidine-4-carboxylic acid amide

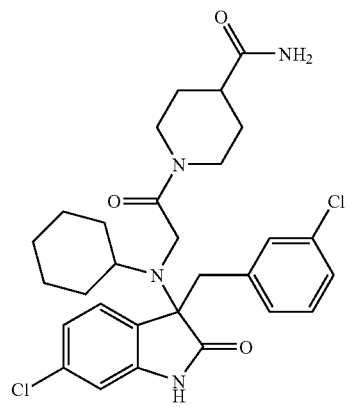

M. W. 557.53    $C_{29}H_{34}Cl_2N_4O_3$

The title compound was prepared following the similar procedure as rac-6-chloro-3-(3-chloro-benzyl)-3-[cyclohexyl-(2-morpholin-4-yl-2-oxo-ethyl)-amino]-1,3-dihydro-indol-2-one. MS: [M+H]$^+$=557.

EXAMPLE 183

Preparation of rac-6-chloro-3-(3-chloro-benzyl)-3-(cyclohexyl-{2-[4-(2-hydroxy-ethyl)-piperazin-1-yl]-2-oxo-ethyl}-amino)-1,3-dihydro-indol-2-one

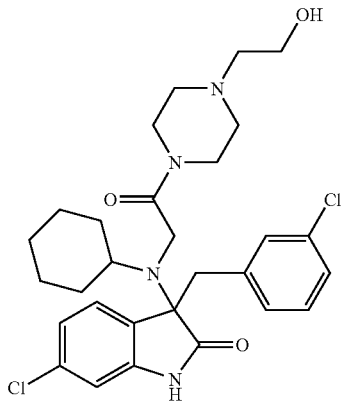

M. W. 559.54    $C_{29}H_{36}Cl_2N_4O_3$

The title compound was prepared following the similar procedure as rac-6-chloro-3-(3-chloro-benzyl)-3-[cyclohexyl-(2-morpholin-4-yl-2-oxo-ethyl)-amino]-1,3-dihydro-indol-2-one. MS: [M+H]$^+$=559.

EXAMPLE 184

Preparation of rac-6-chloro-3-(3-chloro-benzyl)-3-(cyclohexyl-{2-[4-(2-methoxy-ethyl)-piperazin-1-yl]-2-oxo-ethyl}-amino)-1,3-dihydro-indol-2-one

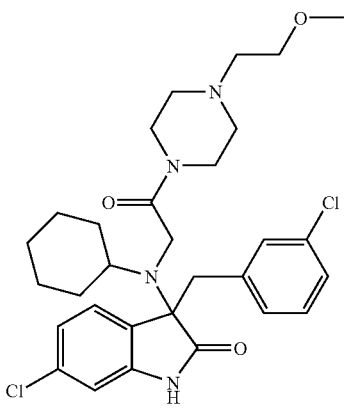

M. W. 573.57    $C_{30}H_{38}Cl_2N_4O_3$

The title compound was prepared following the similar procedure as rac-6-chloro-3-(3-chloro-benzyl)-3-[cyclohexyl-(2-morpholin-4-yl-2-oxo-ethyl)-amino]-1,3-dihydro-indol-2-one. MS: [M+H]⁺=573.

EXAMPLE 185

Preparation of rac-4-chloro-2-[6-chloro-3-(3-chloro-benzyl)-2-oxo-2,3-dihydro-1H-indol-ylamino]-benzoic acid

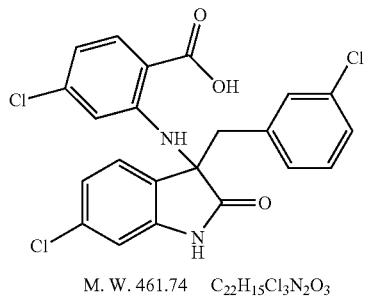

M. W. 461.74   $C_{22}H_{15}Cl_3N_2O_3$

The mixture of 2-amino-4-chloro benzoic acid (171 mg, 1 mmol) and K₂CO₃ (200 mg, 1.4 mmol) in DMF (2 mL) was stirred at room temperature for overnight. The mixture was then poured into ice water, followed by the addition of HCl (1N) until pH ~7. The mixture was extracted with dichloromethane (50 mL×3). The organic phase was separated, dried over Na₂SO₄ and concentrated. The residue was purified with chromatography to give 320 mg of rac-4-chloro-2-[6-chloro-3-(3-chloro-benzyl)-2-oxo-2,3-dihydro-1H-indol-3-ylamino]-benzoic acid as a white solid. MS: [M+H]⁺=461.

EXAMPLE 186

Preparation of rac-6-chloro-3-(3-chloro-benzyl)-3-[5-chloro-2-(morpholine-4-carbonyl)-phenylamino]-1,3-dihydro-indol-2-one

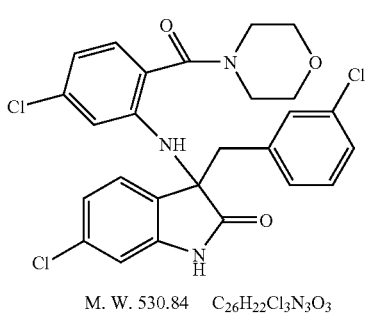

M. W. 530.84   $C_{26}H_{22}Cl_3N_3O_3$

The mixture of 4-chloro-2-[6-chloro-3-(3-chloro-benzyl)-2-oxo-2,3-dihydro-1H-indol-3-ylamino]-benzoic acid (23 mg, 0.05 mmol), morpholine (26 mg, 0.3 mmol) and EDCl (15 mg, 0.08 mmol) in dichloromethane (1 mL) was stirred at room temperature for overnight. The crude was then purified with chromatography to give 22 mg of rac-6-chloro-3-(3-chloro-benzyl)-3-[5-chloro-2-(morpholine-4-carbonyl)-phenylamino]-1,3-dihydro-indol-2-one as a white solid. MS: [M+H]⁺=530.

EXAMPLE 187

Preparation of rac-1-{4-chloro-2-[6-chloro-3-(3-chloro-benzyl)-2-oxo-2,3-dihydro-1H-indol-3-ylamino]-benzoyl}-piperidine-4-carboxylic acid amide

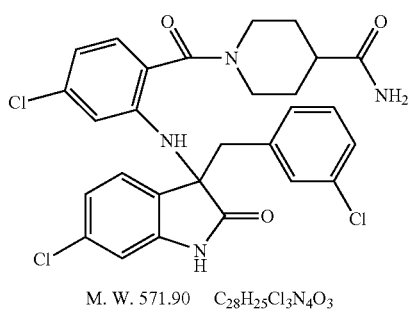

M. W. 571.90   $C_{28}H_{25}Cl_3N_4O_3$

The title compound was prepared following the similar procedure as rac-6-chloro-3-(3-chloro-benzyl)-3-[5-chloro-2-(morpholine-4-carbonyl)-phenylamino]-1,3-dihydro-indol-2-one. MS: [M+H]⁺=570.9.

EXAMPLE 188

Preparation of rac-6-chloro-3-(3-chloro-benzyl)-3-[5-chloro-2-(4-methyl-piperazine-1-carbonyl)-phenylamino]-1,3-dihydro-indol-2-one

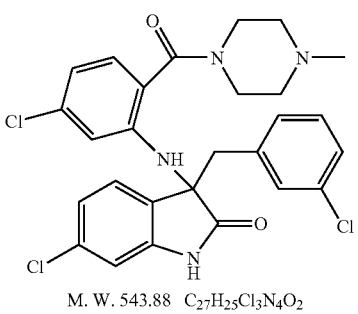

M. W. 543.88   $C_{27}H_{25}Cl_3N_4O_2$

The title compound was prepared following the similar procedure as rac-6-chloro-3-(3-chloro-benzyl)-3-[5-chloro- 2-(morpholine-4-carbonyl)-phenylamino]-1,3-dihydro-indol-2-one. MS: [M+H]⁺=542.9.

EXAMPLE 189

Preparation of rac-6-chloro-3-(3-chloro-benzyl)-3-{5-chloro-2-[4-(2-hydroxy-ethyl)-piperazine-1-carbonyl]-phenylamino}-1,3-dihydro-indol-2-one

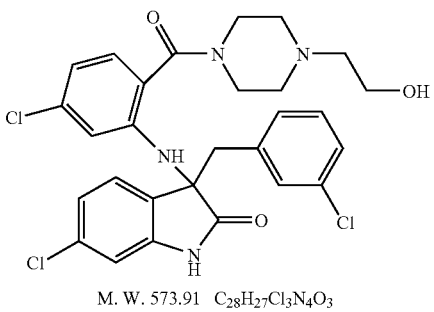

M. W. 573.91  C₂₈H₂₇Cl₃N₄O₃

The title compound was prepared following the similar procedure as rac-6-chloro-3-(3-chloro-benzyl)-3-[5-chloro-2-(morpholine-4-carbonyl)-phenylamino]-1,3-dihydro-indol-2-one. MS: [M+H]⁺=573.

EXAMPLE 190

Preparation of rac-6-chloro-3-(3-chloro-benzyl)-3-{5-chloro-2-[4-(2-methoxy-ethyl)-piperazine-1-carbonyl]-phenylamino}-1,3-dihydro-indol-2-one

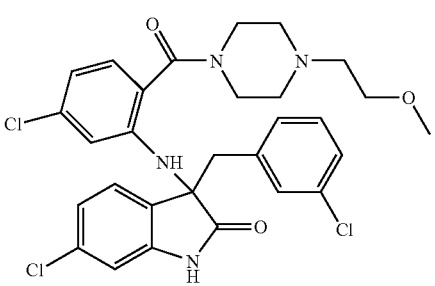

M. W. 587.94  C₂₉H₂₉Cl₃N₄O₃

The title compound was prepared following the similar procedure as rac-6-chloro-3-(3-chloro-benzyl)-3-[5-chloro-2-(morpholine-4-carbonyl)-phenylamino]-1,3-dihydro-indol-2-one. MS: [M+H]⁺=587.

EXAMPLE 191

Preparation of rac-3-[2-(4-acetyl-piperazine-1-carbonyl)-5-chloro-phenylamino]-6-chloro-3-(3-chloro-benzyl)-1,3-dihydro-indol-2-one

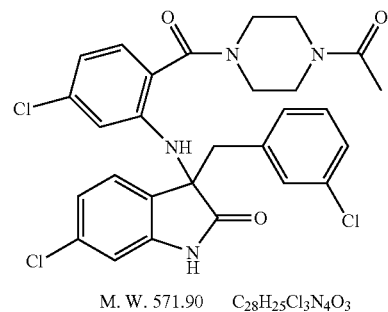

M. W. 571.90  C₂₈H₂₅Cl₃N₄O₃

The title compound was prepared following the similar procedure as rac-6-chloro-3-(3-chloro-benzyl)-3-[5-chloro-2-(morpholine-4-carbonyl)-phenylamino]-1,3-dihydro-indol-2-one. MS: [M+H]⁺=571.

EXAMPLE 192

Preparation of rac-6-chloro-3-(3-chloro-benzyl)-3-[(2-hydroxy-ethyl)-phenyl-amino]-1,3-dihydro-indol-2-one

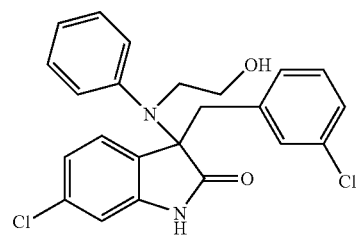

M. W. 427.33  C₂₃H₂₀Cl₂N₂O₂

The mixture of rac-3-bromo-6-chloro-3-(3-chloro-benzyl)-1,3-dihydro-indol-2-one (370 mg, 1 mmol), N-phenylethanolamine (165 mg, 1.2 mmol) and K₂CO₃ (276 mg, 2 mmol) in DMF (2 mL) was stirred at room temperature for 3 h. The mixture was poured into water (30 mL), extracted with ethyl acetate (10 mL×3). The organic layer was separated, dried over Na₂SO₄ and concentrated. The residue was purified with chromatography to give 51 mg of rac-6-chloro-3-

(3-chloro-benzyl)-3-[(2-hydroxy-ethyl)-phenyl-amino]-1,3-dihydro-indol-2-one as a white solid. MS: [M+H]$^+$=427.

EXAMPLE 193a

Preparation of Intermediate
2-phenylamino-acetamide

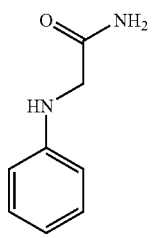

M. W. 150.18 C$_8$H$_{10}$N$_2$O

The mixture of 2-chloroacetamide (3.1 g), aniline (3.1 g), K$_2$CO$_3$ (4.5 g) and KI (1 g) in acetonitrile (50 mL) and water (10 mL) was stirred at room temperature for overnight. The solvent was evaporated to about 20 ml under vacuum and the residue was poured into water (40 mL). The solution was extracted with ethyl acetate (3×20 mL), dried over Na$_2$SO$_4$ and concentrated. The residue was purified with chromatography to give 0.48 g of 2-phenylamino-acetamide.

EXAMPLE 193b

Preparation of rac-2-{[6-chloro-3-(3-chloro-benzyl)-2-oxo-2,3-dihydro-1H-indol-3-yl]-phenyl-amino}-acetamide

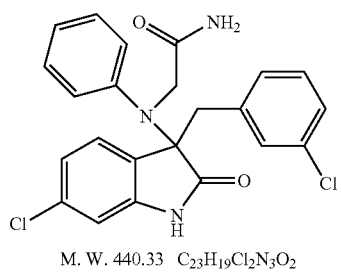

M. W. 440.33 C$_{23}$H$_{19}$Cl$_2$N$_3$O$_2$

The mixture of rac-3-bromo-6-chloro-3-(3-chloro-benzyl)-1,3-dihydro-indol-2-one (370 mg, 1 mmol), 2-phenylamino-acetamide (200 mg, 1.33 mmol) and K$_2$CO$_3$ (300 mg, 2.2 mmol) in DMF (2 mL) was stirred at room temperature for 1 h. The mixture was poured into water (30 ml), extracted with ethyl acetate (10 mL×3). The organic phase was separated, dried over Na$_2$SO$_4$ and concentrated. The residue was purified with chromatography to give 60 mg of rac-2-{[6-chloro-3-(3-chloro-benzyl)-2-oxo-2,3-dihydro-1H-indol-3-yl]-phenyl-amino}-acetamide. MS: [M+H]$^+$=439.8.

EXAMPLE 194a

Preparation of Intermediate
(3-methoxy-phenylamino)-acetic acid ethyl ester

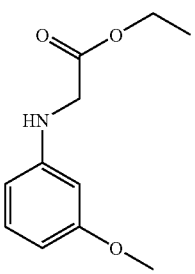

M. W. 209.25 C$_{11}$H$_{15}$N$_3$O

The mixture of 3-methoxyaniline (3.7 g), ethyl bromoacetate (5 g) and triethylamine (4 g) in dichloromethane (30 mL) was stirred at room temperature for overnight. The mixture was washed with water (50 ml), dried over Na$_2$SO$_4$ and concentrated. The residue was purified with chromatography to give 1.7 g of (3-methoxy-phenylamino)-acetic acid ethyl ester. $^1$HNMR: δ 1.33 (3H), 3.796 (3H), 3.92 (2H), 4.26 (2H), 6.21 (1H), 6.29 (1H), 6.36 (1H), 7.13 (1H).

EXAMPLE 194b

Preparation of rac-[[6-chloro-3-(3-chloro-benzyl)-2-oxo-2,3-dihydro-1-H-indol-3-yl]-(3-methoxy-phenyl)-amino]-acetic acid ethyl ester

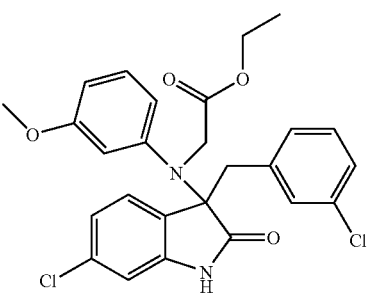

M. W. 499.40 C$_{26}$H$_{24}$Cl$_2$N$_2$O$_4$

The title compound was prepared following the similar procedure as rac-2-{[6-chloro-3-(3-chloro-benzyl)-2-oxo-2,3-dihydro-1H-indol-3-yl]-phenyl-amino}-acetamide. MS: [M+H]⁺=499.

EXAMPLE 195

Preparation of rac-6-Chloro-3-(3-chloro-benzyl)-3-[4-(2-ethoxy-phenyl)-piperazin-1-yl]-1,3-dihydro-indol-2-one

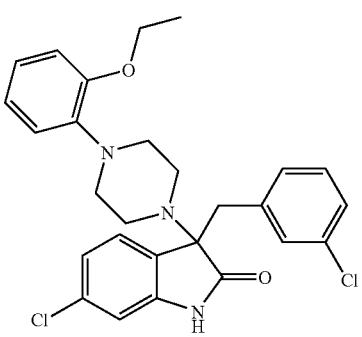

M. W. 496.4  $C_{27}H_{27}Cl_2N_3O_4$

The title compound was prepared by the same procedure for rac-6-chloro-3-(3-chloro-benzyl)-3-[4-(4-trifluoromethyl-phenyl)-piperazin-1-yl]-1,3-dihydro-indol-2-one. MS m/z 496 (M+H)⁺.

EXAMPLE 196

Preparation of rac-2-[6-Chloro-3-(3-chloro-benzyl)-2-oxo-2,3-dihydro-1H-indol-3-ylamino]-4,5-difluoro-benzoic acid

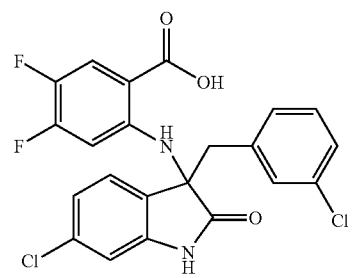

M. W. 463.27  $C_{22}H_{14}Cl_2F_2N_2O_3$

The title compound was prepared by the same procedure for rac-3-[6-chloro-3-(3-chloro-benzyl)-2-oxo-2,3-dihydro-1H-indol-3-ylamino]-benzoic acid. MS m/z 461 (M−H)⁻.

EXAMPLE 197

Preparation of rac-2-[6-Chloro-3-(3-chloro-benzyl)-2-oxo-2,3-dihydro-1H-indol-3-ylamino]-4,5-dimethoxyl-benzoic acid

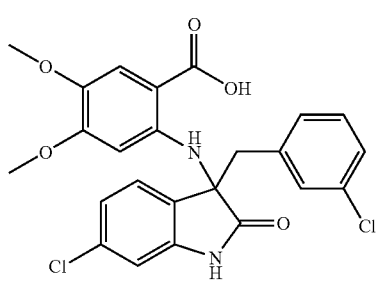

M. W. 487.34  $C_{24}H_{20}Cl_2N_2O_5$

The title compound was prepared by the same procedure for rac-3-[6-chloro-3-(3-chloro-benzyl)-2-oxo-2,3-dihydro-1H-indol-3-ylamino]-benzoic acid. MS m/z 487 (M+H)⁺.

EXAMPLE 198

Preparation of rac-2-[6-Chloro-3-(3-chloro-benzyl)-2-oxo-2,3-dihydro-1H-indol-3-ylamino]-4-methoxyl-benzoic acid

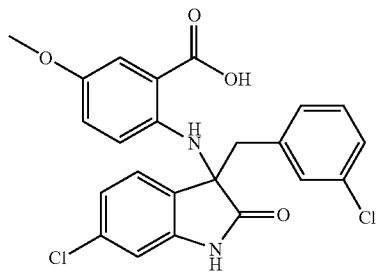

M. W. 457.32  $C_{23}H_{18}Cl_2N_2O_4$

131

The title compound was prepared by the same procedure for rac-3-[6-chloro-3-(3-chloro-benzyl)-2-oxo-2,3-dihydro-1H-indol-3-ylamino]-benzoic acid. MS m/z 457 (M+H)+.

EXAMPLE 199

Preparation of rac-6-Chloro-3-(3-chloro-benzyl)-3-[4,5-difluoro-2-(morpholine-4-carbonyl)-phenylamino]-1,3-dihydro-indol-2-one

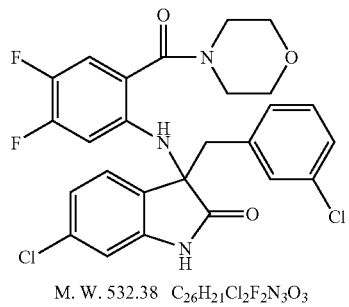

M. W. 532.38   $C_{26}H_{21}Cl_2F_2N_3O_3$

The title compound was prepared following the similar procedure as rac-6-chloro-3-(3-chloro-benzyl)-3-[5-chloro-2-(morpholine-4-carbonyl)-phenylamino]-1,3-dihydro-indol-2-one. MS m/z 532 (M+H)+.

EXAMPLE 200

Preparation of rac-6-Chloro-3-(3-chloro-benzyl)-3-[4,5-dimethoxy-2-(morpholine-4-carbonyl)-phenylamino]-1,3-dihydro-indol-2-one

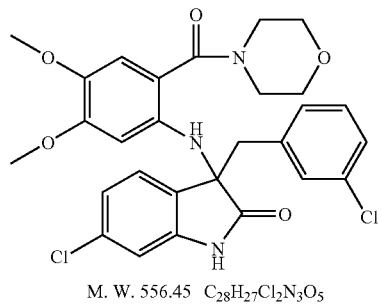

M. W. 556.45   $C_{28}H_{27}Cl_2N_3O_5$

The title compound was prepared following the similar procedure as rac-6-chloro-3-(3-chloro-benzyl)-3-[5-chloro-

132

2-(morpholine-4-carbonyl)-phenylamino]-1,3-dihydro-indol-2-one. MS m/z 556 (M+H)+.

EXAMPLE 201

Preparation of rac-6-Chloro-3-(3-chloro-benzyl)-3-[4-methoxy-2-(morpholine-4-carbonyl)-phenylamino]-1,3-dihydro-indol-2-one

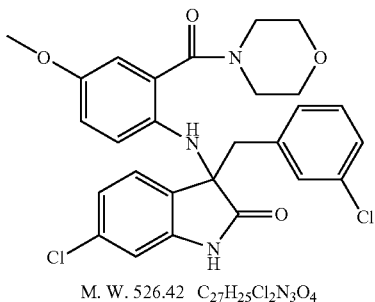

M. W. 526.42   $C_{27}H_{25}Cl_2N_3O_4$

The title compound was prepared following the similar procedure as rac-6-chloro-3-(3-chloro-benzyl)-3-[5-chloro-2-(morpholine-4-carbonyl)-phenylamino]-1,3-dihydro-indol-2-one. MS m/z 526 (M+H)+.

EXAMPLE 202

Preparation of rac-2-[6-Chloro-3-(3-chloro-benzyl)-2-oxo-2,3-dihydro-1H-indol-3-ylamino]-4,5-difluoro-N,N!-dimethyl-benzamide

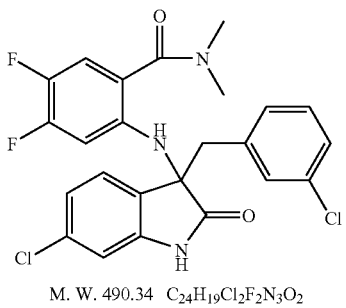

M. W. 490.34   $C_{24}H_{19}Cl_2F_2N_3O_2$

The title compound was prepared following the similar procedure as rac-6-chloro-3-(3-chloro-benzyl)-3-[5-chloro- 2-(morpholine-4-carbonyl)-phenylamino]-1,3-dihydro-indol-2-one. MS m/z 490 (M+H)⁺.

EXAMPLE 203

Preparation of rac-2-[6-Chloro-3-(3-chloro-benzyl)-2-oxo-2,3-dihydro-1H-indol-3-ylamino]-4,5-difluoro-N!-methyl-benzamide

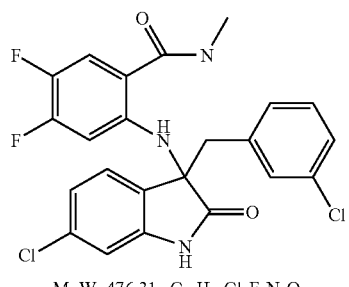

M. W. 476.31  $C_{23}H_{17}Cl_2F_2N_3O_2$

The title compound was prepared following the similar procedure as rac-6-chloro-3-(3-chloro-benzyl)-3-[5-chloro-2-(morpholine-4-carbonyl)-phenylamino]-1,3-dihydro-indol-2-one. MS m/z 476 (M+H)⁺.

EXAMPLE 204

Preparation of rac-2-[6-Chloro-3-(3-chloro-benzyl)-2-oxo-2,3-dihydro-1H-indol-3-ylamino]-4,5-difluoro-N-(2-morpholin-4-yl-ethyl)-benzamide

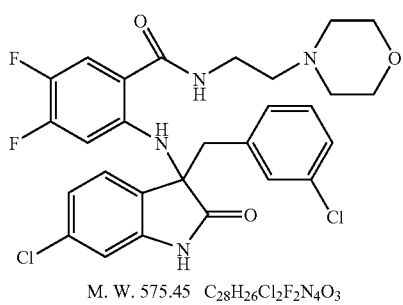

M. W. 575.45  $C_{28}H_{26}Cl_2F_2N_4O_3$

The title compound was prepared following the similar procedure as rac-6-chloro-3-(3-chloro-benzyl)-3-[5-chloro- 2-(morpholine-4-carbonyl)-phenylamino]-1,3-dihydro-indol-2-one. MS m/z 575 (M+H)⁺.

EXAMPLE 205

Preparation of rac-2-[6-Chloro-3-(3-chloro-benzyl)-2-oxo-2,3-dihydro-1H-indol-3-ylamino]-4,5-difluoro-N-(2-morpholin-4-yl-propyl)-benzamide

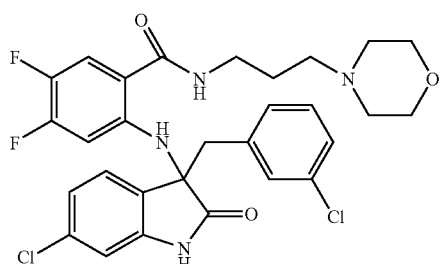

M. W. 589.47  $C_{29}H_{28}Cl_2F_2N_4O_3$

The title compound was prepared following the similar procedure as rac-6-chloro-3-(3-chloro-benzyl)-3-[5-chloro-2-(morpholine-4-carbonyl)-phenylamino]-1,3-dihydro-indol-2-one. MS m/z 589 (M+H)⁺.

EXAMPLE 206

Preparation of rac-4-Chloro-2-[6-chloro-3-(3-chloro-benzyl)-2-oxo-2,3-dihydro-1H-indol-3-ylamino]-N-cyclobutyl-benzamide

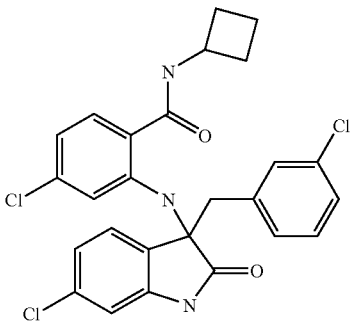

M. W. 514.84  $C_{26}H_{22}Cl_3N_3O_2$

The title compound was prepared following the similar procedure as rac-6-chloro-3-(3-chloro-benzyl)-3-[5-chloro-2-(morpholine-4-carbonyl)-phenylamino]-1,3-dihydro-indol-2-one. MS: [M+H]⁺=514.

EXAMPLE 207

Preparation of rac-1-[6-Chloro-3-(3-chloro-benzyl)-2-oxo-2,3-dihydro-1H-indol-3-yl]-piperidine-3-carboxylic acid cyclobutylamide

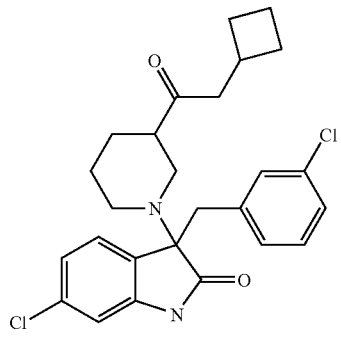

M. W. 472.42  $C_{25}H_{27}Cl_2N_3O_2$

The title compound was prepared following the similar procedure as rac-6-chloro-3-(3-chloro-benzyl)-3-{3-[4-(2-hydroxy-ethyl)-piperazine-1-carbonyl]-phenylamino}-1,3-dihydro-indol-2-one. MS: [M+H]⁺=529

EXAMPLE 208a

Preparation of Intermediate
6-Chloro-2,3-dihydro-1H-indole

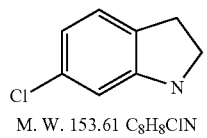

M. W. 153.61 $C_8H_8ClN$

Sodium borohydride (2.0 g, 53 mmol) (Aldrich) was added in small portions to a mixture of 6-Chloro-1H-indole (1.0 g, 6.6 mmol) (Aldrich) in TFA (10 mL), which was cooled in ice-water bath, at such a rate that gas evolution was not too vigorous. When the addition was complete, the mixture was allowed to warm to room temperature and stirred overnight. The resulting mixture was concentrated in vacuo and the residue was dissolved in DCM. The organic layer was washed with Na₂CO₃ solution, dried with Na₂SO₄, and concentrated to give 0.6 g crude 6-Chloro-2,3-dihydro-1H-indole. MS: [M+H]⁺=154

EXAMPLE 208b

Preparation of rac-6,6'-Dichloro-3'-(3-chloro-benzyl)-2,3,1',3'-tetrahydro-[1,3']biindolyl-2'-one

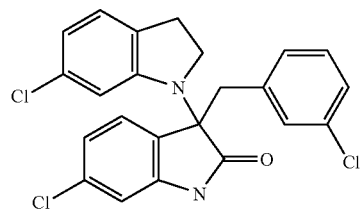

M. W. 443.76  $C_{23}H_{17}Cl_3N_2O$

The mixture of rac-3-bromo-6-chloro-3-(3-chloro-benzyl)-1,3-dihydro-indol-2-one (100 mg, 0.27 mmol) (from example 1c supra), 6-Chloro-2,3-dihydro-1H-indole (62 mg, 0.45 mmol) and K₂CO₃ (110 mg, 0.80 mmol) in DMF (1 mL) was stirred at room temperature overnight. Then water (10 mL) was added and the desired product was precipitated out. The crude product was purified by prep-HPLC to give 55 mg rac-6,6'-Dichloro-3'-(3-chloro-benzyl)-2,3,1',3'-tetrahydro-[1,3']biindolyl-2'-one. MS: [M+H]⁺=443

EXAMPLE 209

Preparation of rac-7,6'-Dichloro-3'-(3-chloro-benzyl)-2,3,1',3'-tetrahydro-[1,3']biindolyl-2'-one

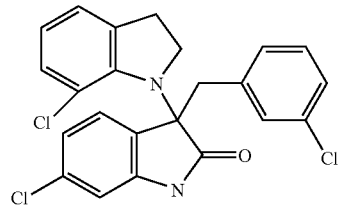

M. W. 443.76,  $C_{23}H_{17}Cl_3N_2O$

The title compound was prepared following the similar procedure as rac-6,6'-Dichloro-3'-(3-chloro-benzyl)-2,3,1',3'-tetrahydro-[1,3']biindolyl-2'-one. MS: [M+H]$^+$=443

EXAMPLE 210

Preparation of rac-6'-Chloro-3'-(3-chloro-benzyl)-2,3,1',3'-tetrahydro-[1,3']biindolyl-2'-one

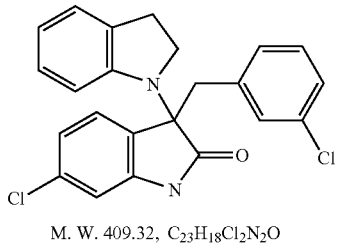

M. W. 409.32, $C_{23}H_{18}Cl_2N_2O$

The title compound was prepared following the similar procedure as rac-6,6'-Dichloro-3'-(3-chloro-benzyl)-2,3,1',3'-tetrahydro-[1,3']biindolyl-2'-one. MS: [M+H]$^+$=409

EXAMPLE 211a

Preparation of Intermediate rac-6-Methoxy-2,3-dihydro-1H-indole-2-carboxylic acid ethyl ester

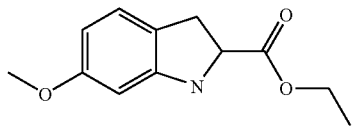

M. W. 221.26, $C_{12}H_{15}NO_3$

Sodium cyanoborohydride (750 mg, 12 mmol) (Aldrich) was added in small portions to a mixture of 6-Methoxy-1H-indole-2-carboxylic acid ethyl ester (500 mg, 2.4 mmol) (Aldrich) in TFA (10 mL), which was cooled in ice-water bath, at such a rate that gas evolution was not too vigorous. When the addition was complete, the mixture was allowed to warm to room temperature and stirred for 2.5 hr. The resulting mixture was concentrated in vacuo and the residue was dissolved in DCM. The organic layer was washed with Na$_2$CO$_3$ solution, dried with Na$_2$SO$_4$, and concentrated to give 400 mg rac-6-Methoxy-2,3-dihydro-1H-indole-2-carboxylic acid ethyl ester. MS: [M+H]$^+$=222

EXAMPLE 211b

Preparation of Intermediate rac-6'-Chloro-3'-(3-chloro-benzyl)-6-methoxy-2'-oxo-2,3,2',3'-tetrahydro-1'H-[1,3']biindolyl-2-carboxylic acid ethyl ester

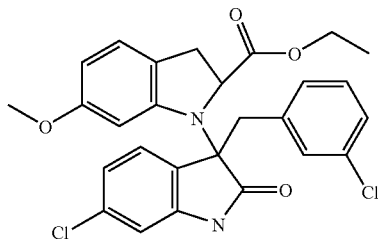

M. W. 511.41, $C_{27}H_{24}Cl_2N_2O_4$

The title compound was prepared following the similar procedure as rac-6,6'-Dichloro-3'-(3-chloro-benzyl)-2,3,1',3'-tetrahydro-[1,3']biindolyl-2'-one. MS: [M+H]+=511

EXAMPLE 211c

Preparation of Intermediate rac-6'-Chloro-3'-(3-chloro-benzyl)-6-methoxy-2'-oxo-2,3,2',3'-tetrahydro-1'H-[1,3']biindolyl-2-carboxylic acid

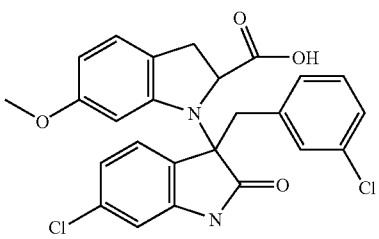

M. W. 483.36, $C_{25}H_{20}Cl_2N_2O_4$

A mixture of rac-6'-Chloro-3'-(3-chloro-benzyl)-6-methoxy-2'-oxo-2,3,2',3'-tetrahydro-1'H-[1,3']biindolyl-2-carboxylic acid methyl ester (250 mg, 0.5 mmol), NaOH (40 mg, 1.0 mmol) in methanol (4 mL) and water (2 mL) was heated to reflux for 3 hr. Then the mixture was concentrated in vacuo to remove methanol. Water (10 mL) was added to the residue. The resulting mixture was acidified with acetic acid, extracted with ethyl acetate. The organic layer was washed with water, dried with Na$_2$SO$_4$, concentrated in vacuo to give 250 mg rac-6'-Chloro-3'-(3-chloro-benzyl)-6-methoxy-2'-oxo-2,3,2',3'-tetrahydro-1'H-[1,3']biindolyl-2-carboxylic acid. MS: [M−H]−=481

EXAMPLE 211d

Preparation of rac-6'-Chloro-3'-(3-chloro-benzyl)-6-methoxy-2'-oxo-2,3,2',3'-tetrahydro-1'H-[1,3']biindolyl-2-carboxylic acid cyclobutylamide

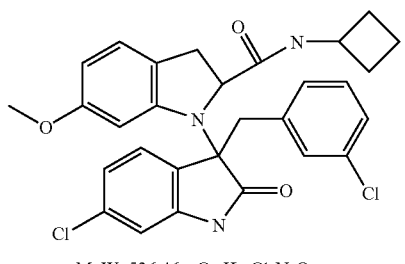

M. W. 536.46, $C_{29}H_{27}Cl_2N_3O_3$

The title compound was prepared following the similar procedure as rac-6-chloro-3-(3-chloro-benzyl)-3-[5-chloro-2-(morpholine-4-carbonyl)-phenylamino]-1,3-dihydro-indol-2-one. MS: [M+H]+=536

EXAMPLE 212

Preparation of rac-6'-Chloro-3'-(3-chloro-benzyl)-6-methoxy-2'-oxo-2,3,2',3'-tetrahydro-1'H-[1,3']biindolyl-2-carboxylic acid cyclohexylamide

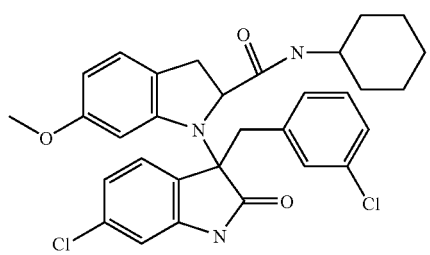

M. W. 564.52, $C_{31}H_{31}Cl_2N_3O_3$

The title compound was prepared following the similar procedure as rac-6-chloro-3-(3-chloro-benzyl)-3-[5-chloro-2-(morpholine-4-carbonyl)-phenylamino]-1,3-dihydro-indol-2-one. MS: [M+H]+=564

EXAMPLE 213

Preparation of rac-6'-Chloro-3'-(3-chloro-benzyl)-2-[4-(2-hydroxy-ethyl)-piperazine-1-carbonyl]-6-methoxy-2,3,1',3'-tetrahydro-[1,3']biindolyl-2'-one

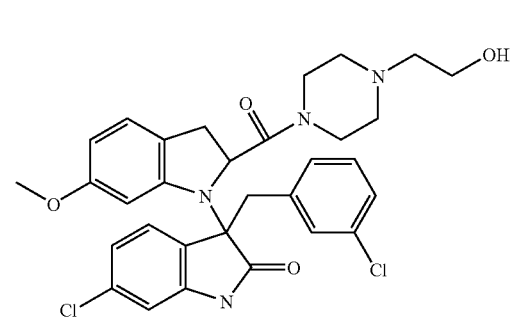

M. W. 595.53, $C_{31}H_{32}Cl_2N_4O_4$

The title compound was prepared following the similar procedure as rac-6-chloro-3-(3-chloro-benzyl)-3-[5-chloro-2-(morpholine-4-carbonyl)-phenylamino]-1,3-dihydro-indol-2-one. MS: [M+H]+=595

EXAMPLE 214

Preparation of rac-6'-Chloro-3'-(3-chloro-benzyl)-6-methoxy-2-(morpholine-4-carbonyl)-2,3,1',3'-tetrahydro-[1,3']biindolyl-2'-one

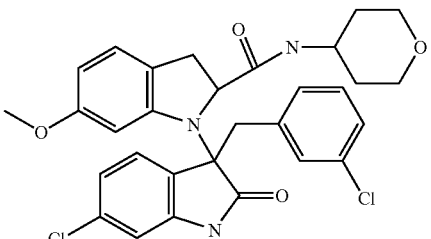

M. W. 566.49, $C_{30}H_{29}Cl_2N_3O_4$

The title compound was prepared following the similar procedure as rac-6-chloro-3-(3-chloro-benzyl)-3-[5-chloro-2-(morpholine-4-carbonyl)-phenylamino]-1,3-dihydro-indol-2-one. MS: [M+H]⁺=566

EXAMPLE 215

Preparation of rac-6,6'-Dichloro-3'-(3-chloro-benzyl)-2-(morpholine-4-carbonyl)-2,3,1',3'-tetrahydro-[1,3']biindolyl-2'-one

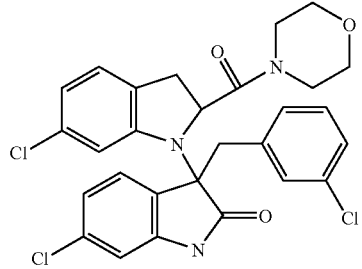

M. W. 556.88, $C_{28}H_{24}Cl_3N_3O_3$

The title compound was prepared following the similar procedure as rac-6-chloro-3-(3-chloro-benzyl)-3-[5-chloro-2-(morpholine-4-carbonyl)-phenylamino]-1,3-dihydro-indol-2-one. MS: [M+H]⁺=556

EXAMPLE 216

Preparation of rac-6,6'-Dichloro-3'-(3-chloro-benzyl)-2'-oxo-2,3,2',3'-tetrahydro-1'H-[1,3']biindolyl-2-carboxylic acid cyclobutylamide

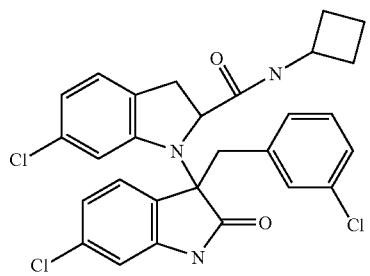

M. W. 540.88    $C_{28}H_{24}Cl_3N_3O_2$

The title compound was prepared following the similar procedure as rac-6-chloro-3-(3-chloro-benzyl)-3-[5-chloro-2-(morpholine-4-carbonyl)-phenylamino]-1,3-dihydro-indol-2-one. MS: [M+H]⁺=542

EXAMPLE 217

Preparation of rac-2-(4-Acetyl-piperazine-1-carbonyl)-6,6'-dichloro-3'-(3-chloro-benzyl)-2,3,1',3'-tetrahydro-[1,3']biindolyl-2'-one

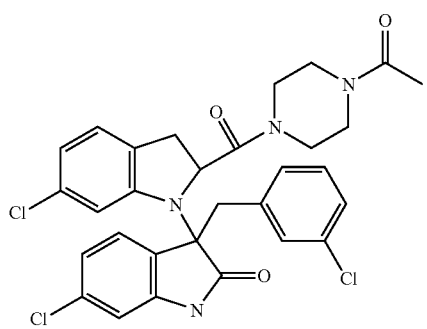

M. W. 597.93, $C_{30}H_{27}Cl_3N_4O_3$

The title compound was prepared following the similar procedure as rac-6-chloro-3-(3-chloro-benzyl)-3-[5-chloro-2-(morpholine-4-carbonyl)-phenylamino]-1,3-dihydro-indol-2-one. MS: [M+H]⁺=597

EXAMPLE 218a

Preparation of Intermediate rac-6,6'-Dichloro-3'-(3-chloro-benzyl)-2'-oxo-2',3'-dihydro-1'H-[1,3']biindolyl-2-carboxylic acid ethyl ester

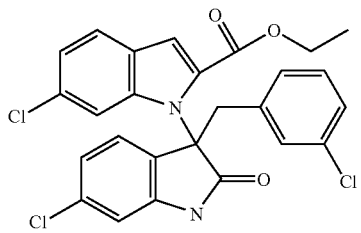

M. W. 513.81,  $C_{26}H_{19}Cl_3N_2O_3$

The solution of rac-6'-Chloro-3'-(3-chloro-benzyl)-6-methoxy-2'-oxo-2,3,2',3'-tetrahydro-1'H-[1,3']biindolyl-2-carboxylic acid ethyl ester (1.0 g, 1.9 mmol) and DDQ (0.73 g, 3.2 mmol) in toluene (50 mL) was heated to 90° C. for 4 h. Then the mixture was cooled to room temperature and washed with NaOH solution (10%) and water. The organic layer was dried with $Na_2SO_4$, concentrated in vacuo to give 0.9 g rac-6,6'-Dichloro-3'-(3-chloro-benzyl)-2'-oxo-2',3'-dihydro-1'H-[1,3']biindolyl-2-carboxylic acid ethyl ester as yellow solid. MS: [M+H]+=513

EXAMPLE 218b

Preparation of Intermediate rac-6,6'-Dichloro-3'-(3-chloro-benzyl)-2'-oxo-2',3'-dihydro-1'H-[1,3']biindolyl-2-carboxylic acid

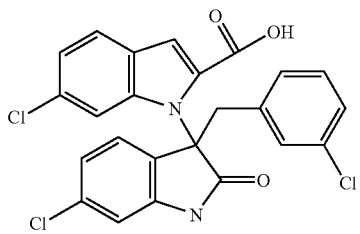

M. W. 485.76, $C_{24}H_{15}Cl_3N_2O_3$

The title compound was prepared following the similar procedure as rac-6'-Chloro-3'-(3-chloro-benzyl)-6-methoxy-2'-oxo-2,3,2',3'-tetrahydro-1'H-[1,3']biindolyl-2-carboxylic acid. MS: [M−H]−=483

EXAMPLE 218c

Preparation of rac-6,6'-Dichloro-3'-(3-chloro-benzyl)-2'-oxo-2',3'-dihydro-1'H-[1,3']biindolyl-2-carboxylic acid cyclobutylamide

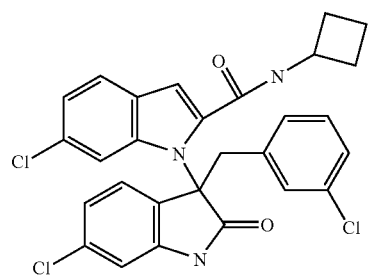

M. W. 538.87, $C_{28}H_{22}Cl_3N_3O_2$

The title compound was prepared following the similar procedure as rac-6-chloro-3-(3-chloro-benzyl)-3-[5-chloro-2-(morpholine-4-carbonyl)-phenylamino]-1,3-dihydro-indol-2-one. MS: [M+H]+=538

EXAMPLE 219

Preparation of rac-2-(4-Acetyl-piperazine-1-carbonyl)-6,6'-dichloro-3'-(3-chloro-benzyl)-1',3'-dihydro-[1,3']biindolyl-2'-one

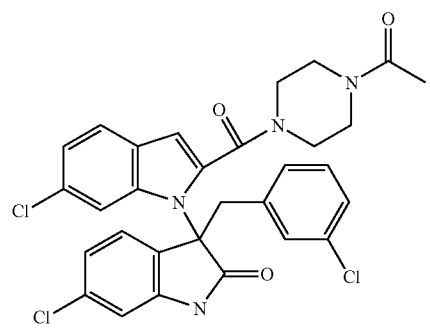

M. W. 595.92, $C_{30}H_{25}Cl_3N_4O_3$

The title compound was prepared following the similar procedure as rac-6-chloro-3-(3-chloro-benzyl)-3-[5-chloro-2-(morpholine-4-carbonyl)-phenylamino]-1,3-dihydro-indol-2-one. MS: [M+H]+=595

EXAMPLE 220

Preparation of rac-2-[6-Chloro-3-(3-chloro-benzyl)-2-oxo-2,3-dihydro-1H-indol-3-ylamino]-4-ethynyl-benzoic acid

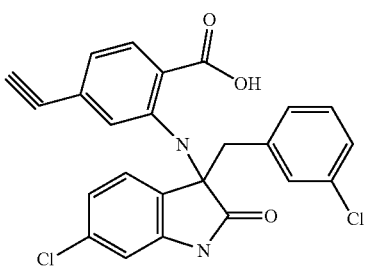

M. W. 451.31, $C_{24}H_{16}Cl_2N_2O_3$

The title compound was prepared following the similar procedure as rac-3-[6-chloro-3-(3-chloro-benzyl)-2-oxo-2,3-dihydro-1H-indol-3-ylamino]-benzoic acid. MS: [M−H]−= 449

EXAMPLE 221

Preparation of rac-4-Bromo-2-[6-chloro-3-(3-chloro-benzyl)-2-oxo-2,3-dihydro-1H-indol-3-ylamino]-benzoic acid

M. W. 506.19, C₂₂H₁₅BrCl₂N₂O₃

The title compound was prepared following the similar procedure as rac-3-[6-chloro-3-(3-chloro-benzyl)-2-oxo-2,3-dihydro-1H-indol-3-ylamino]-benzoic acid. MS: [M−H]−= 503

EXAMPLE 222

Preparation of rac-3-[5-Bromo-2-(morpholine-4-carbonyl)-phenylamino]-6-chloro-3-(3-chloro-benzyl)-1,3-dihydro-indol-2-one

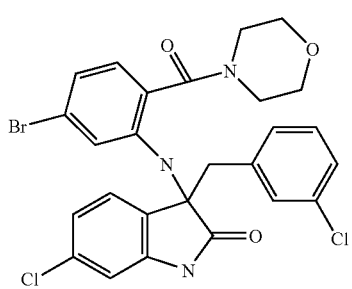

M.W. 575.29, C₂₆H₂₂BrCl₂N₃O₃

The title compound was prepared following the similar procedure as rac-6-chloro-3-(3-chloro-benzyl)-3-[5-chloro-2-(morpholine-4-carbonyl)-phenylamino]-1,3-dihydro-indol-2-one. MS: [M+H]+=574

EXAMPLE 223

Preparation of rac-6-Chloro-3-(3-chloro-benzyl)-3-[5-ethynyl-2-(morpholine-4-carbonyl)-phenylamino]-1,3-dihydro-indol-2-one

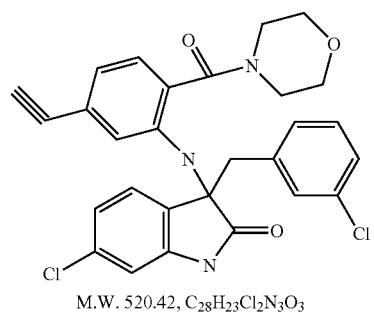

M.W. 520.42, C₂₈H₂₃Cl₂N₃O₃

The title compound was prepared following the similar procedure as rac-6-chloro-3-(3-chloro-benzyl)-3-[5-chloro-2-(morpholine-4-carbonyl)-phenylamino]-1,3-dihydro-indol-2-one. MS: [M+H]+=520

EXAMPLE 224

Preparation of rac-2-[6-Chloro-3-(3-chloro-benzyl)-2-oxo-2,3-dihydro-1H-indol-3-yloxy]-3-isopropyl-benzoic acid

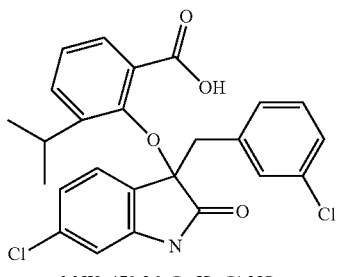

M.W. 470.36, C₂₅H₂₁Cl₂NO₄

From 2-hydroxyl-3-isopropyl benzoic acid and rac-3-bromo-6-chloro-3-(3-chloro-benzyl)-1,3-dihydro-indol-2-one, the title compound was prepared following the similar procedure as rac-3-[6-chloro-3-(3-chloro-benzyl)-2-oxo-2,3-dihydro-1H-indol-3-ylamino]-benzoic acid. MS: [M−H]−= 468

EXAMPLE 225

Preparation of rac-6-Chloro-3-(3-chloro-benzyl)-3-[2-methyl-5-(morpholine-4-sulfonyl)-phenylamino]-1,3-dihydro-indol-2-one

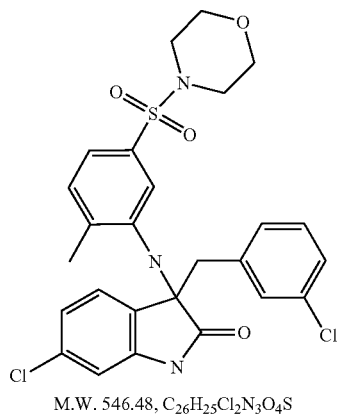

M.W. 546.48, $C_{26}H_{25}Cl_2N_3O_4S$

The title compound was prepared following the similar procedure as rac-6,6'-Dichloro-3'-(3-chloro-benzyl)-2,3,1',3'-tetrahydro-[1,3']biindolyl-2'-one. MS: [M+H]+=546

EXAMPLE 226

Preparation of rac-3-[5-(4-Acetyl-piperazine-1-sulfonyl)-2-methyl-phenylamino]-6-chloro-3-(3-chloro-benzyl)-1,3-dihydro-indol-2-one

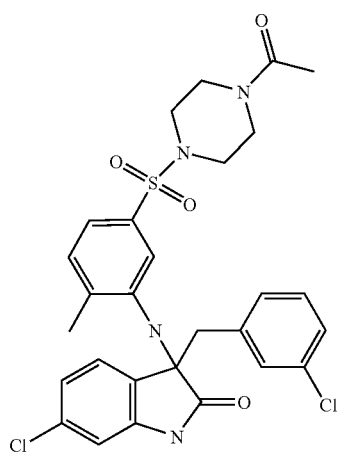

M.W. 587.53, $C_{28}H_{28}Cl_2N_4O_4S$

The title compound was prepared following the similar procedure as rac-6,6'-Dichloro-3'-(3-chloro-benzyl)-2,3,1',3'-tetrahydro-[1,3']biindolyl-2'-one. MS: [M+H]+=587

EXAMPLE 227

Preparation of rac-3-[2-(4-Acetyl-piperazine-1-carbonyl)-5-ethynyl-phenylamino]-6-chloro-3-(3-chloro-benzyl)-1,3-dihydro-indol-2-one

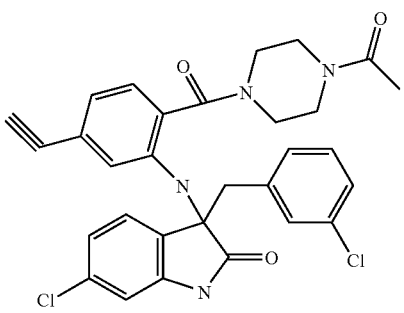

M.W. 561.47, $C_{30}H_{26}Cl_2N_4O_3$

The title compound was prepared following the similar procedure as rac-6-chloro-3-(3-chloro-benzyl)-3-[5-chloro-2-(morpholine-4-carbonyl)-phenylamino]-1,3-dihydro-indol-2-one. MS: [M+H]+=561

EXAMPLE 228

Preparation of rac-3-[2-(4-Acetyl-piperazine-1-carbonyl)-5-bromo-phenylamino]-6-chloro-3-(3-chloro-benzyl)-1,3-dihydro-indol-2-one

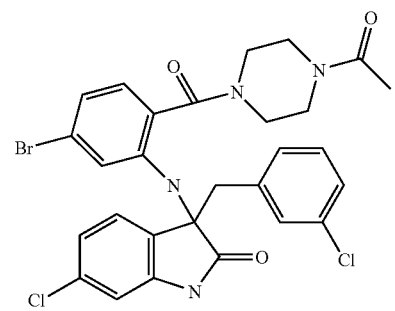

M.W. 616.35, $C_{28}H_{25}BrCl_2N_4O_3$

The title compound was prepared following the similar procedure as rac-6-chloro-3-(3-chloro-benzyl)-3-[5-chloro-2-(morpholine-4-carbonyl)-phenylamino]-1,3-dihydro-indol-2-one. MS: [M+H]+=615

EXAMPLE 229

Preparation of rac-6-Chloro-3-(3-chloro-benzyl)-3-[2-isopropyl-6-(morpholine-4-carbonyl)-phenoxy]-1,3-dihydro-indol-2-one

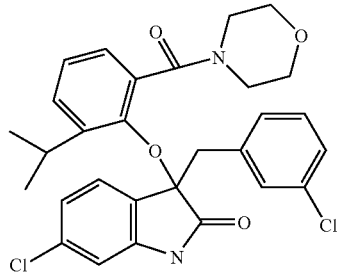

M.W. 539.46, C29H28Cl2N2O4

The title compound was prepared following the similar procedure as rac-6-chloro-3-(3-chloro-benzyl)-3-[5-chloro-2-(morpholine-4-carbonyl)-phenylamino]-1,3-dihydro-indol-2-one. MS: [M+H]+=539

EXAMPLE 230

Preparation of rac-3-[2-(4-Acetyl-piperazine-1-carbonyl)-6-isopropyl-phenoxy]-6-chloro-3-(3-chloro-benzyl)-1,3-dihydro-indol-2-one

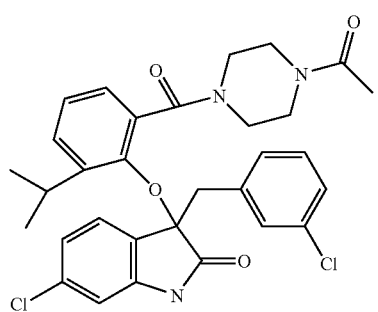

M.W. 580.52, C31H31Cl2N3O4

The title compound was prepared following the similar procedure as rac-6-chloro-3-(3-chloro-benzyl)-3-[5-chloro-2-(morpholine-4-carbonyl)-phenylamino]-1,3-dihydro-indol-2-one. MS: [M+H]+=580

EXAMPLE 231

Preparation of rac-6-Chloro-3-(3-chloro-benzyl)-3-[3-(morpholine-4-sulfonyl)-phenylamino]-1,3-dihydro-indol-2-one

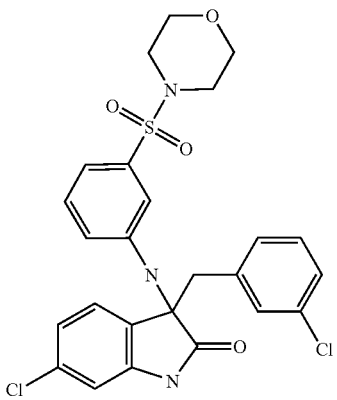

M.W. 532.45, C25H23Cl2N3O4S

The title compound was prepared following the similar procedure as rac-6,6'-Dichloro-3'-(3-chloro-benzyl)-2,3,1',3'-tetrahydro-[1,3']biindolyl-2'-one. MS: [M+H]+=532

EXAMPLE 232a

Preparation of Intermediate 4-Chloro-2-nitro-benzenesulfonyl chloride

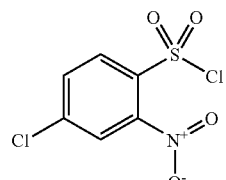

M.W. 256.07, C6H3Cl2NO4S

The mixture of 4-Chloro-2-nitro-phenylamine (2.0 g, 11.6 mmol) (Aldrich) in TFA (30 mL) and conc. hydrochloric acid (3 mL) was cooled to −5° C., then a solution of NaNO2 in water (5 mL) was dropped into at such a rate that the temperature did not above 5° C. When the addition was complete, the mixture was stirred at 0° C. for additional 5 min, then poured into a mixture of acetic acid (40 mL), sulfurous acid (40 mL), CuCl2 (824 mg, 6.1 mmol) and CuCl (50 mg, 0.5 mmol), which was cooled to 0° C. in advance. The whole was stirred at room temperature for 40 min, diluted with water (100 mL), filtered. The filter cake was washed with water, dried in vacuo to give 1.5 g 4-Chloro-2-nitro-benzenesulfonyl chloride. MS: [M+H]+=256

EXAMPLE 232b

Preparation of Intermediate 4-(2-Amino-4-chloro-benzenesulfonylamino)-piperidine-1-carboxylic acid tert-butyl ester

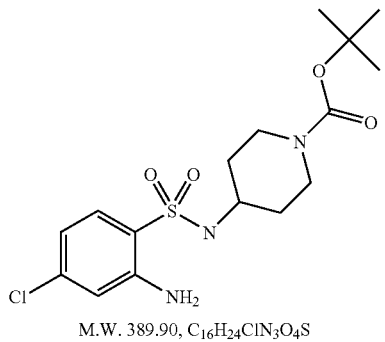

M.W. 389.90, $C_{16}H_{24}ClN_3O_4S$

The mixture of 4-Chloro-2-nitro-benzenesulfonyl chloride (255 mg, 1 mmol), 4-Amino-piperidine-1-carboxylic acid tert-butyl ester (200 mg, 1 mmol) and $K_2CO_3$ (276 mg, 2 mmol) in DCM (3 mL) was stirred at room temperature for 1 hr. The mixture was concentrated in vacuo, the residue was dissolved in methanol, and then Ra—Ni (0.5 g) and hydrazine (1 mL, 17 mmol) was added. The resulting mixture was stirred at room temperature for 2 hr, filtered concentrated in vacuo. The residue was purified by column chromatography to give 380 mg 4-(2-Amino-4-chloro-benzenesulfonylamino)-piperidine-1-carboxylic acid tert-butyl ester as pale white solid. MS: [M+H]+=390

EXAMPLE 232c

Preparation of rac-4-{4-Chloro-2-[6-chloro-3-(3-chloro-benzyl)-2-oxo-2,3-dihydro-1H-indol-3-ylamino]-benzenesulfonylamino}-piperidine-1-carboxylic acid tert-butyl ester

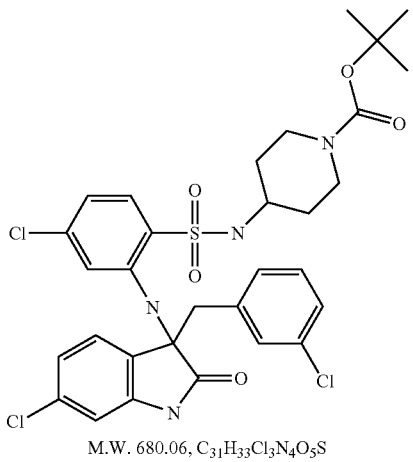

M.W. 680.06, $C_{31}H_{33}Cl_3N_4O_5S$

The mixture of 4-(2-Amino-4-chloro-benzenesulfonylamino)-piperidine-1-carboxylic acid tert-butyl ester (20 mg, 0.051 mmol), rac-3-bromo-6-chloro-3-(3-chloro-benzyl)-1,3-dihydro-indol-2-one (30 mg, 0.081 mmol) and $K_2CO_3$ (30 mg, 0.22 mmol) in DCM (1 mL) was stirred at room temperature overnight. The mixture was purified by column chromatography to give 22 mg rac-4-{4-Chloro-2-[6-chloro-3-(3-chloro-benzyl)-2-oxo-2,3-dihydro-1H-indol-3-ylamino]-benzenesulfonylamino}-piperidine-1-carboxylic acid tert-butyl ester. MS: [M+H]+=679

EXAMPLE 233

Preparation of rac-4-Chloro-2-[6-chloro-3-(3-chloro-benzyl)-2-oxo-2,3-dihydro-1#H!-indol-3-yloxy]-benzoic acid

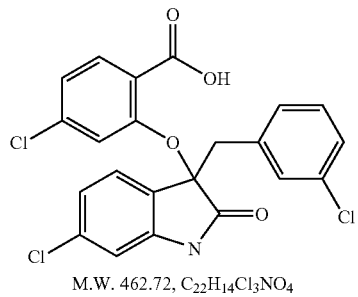

M.W. 462.72, $C_{22}H_{14}Cl_3NO_4$

The title compound was prepared following the similar procedure as rac-3-[6-chloro-3-(3-chloro-benzyl)-2-oxo-2,3-dihydro-1H-indol-3-ylamino]-benzoic acid. MS: [M−H]−= 460

EXAMPLE 234

Preparation of rac-4-{4-Bromo-2-[6-chloro-3-(3-chloro-benzyl)-2-oxo-2,3-dihydro-1H-indol-3-ylamino]-benzoylamino}-piperidine-1-carboxylic acid tert-butyl ester

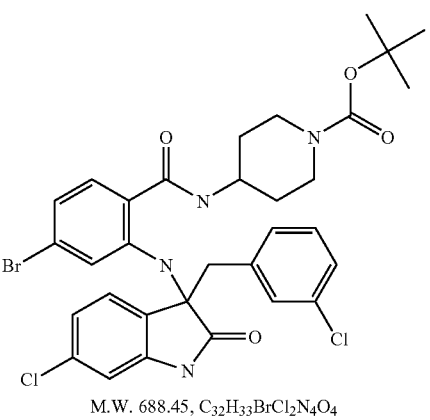

M.W. 688.45, $C_{32}H_{33}BrCl_2N_4O_4$

The title compound was prepared following the similar procedure as rac-6-chloro-3-(3-chloro-benzyl)-3-[5-chloro-2-(morpholine-4-carbonyl)-phenylamino]-1,3-dihydro-indol-2-one. MS: [M+H]$^+$=687

EXAMPLE 235

Preparation of rac-6-Chloro-3-(3-chloro-benzyl)-3-[5-chloro-2-(morpholine-4-carbonyl)-phenoxy]-1,3-dihydro-indol-2-one

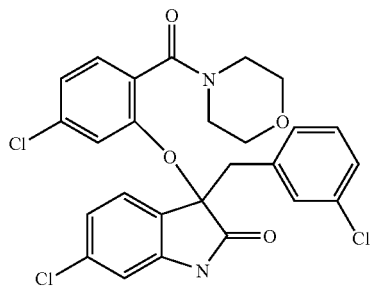

M.W. 531.83, C$_{26}$H$_{21}$Cl$_3$N$_2$O$_4$

The title compound was prepared following the similar procedure as rac-6-chloro-3-(3-chloro-benzyl)-3-[5-chloro-2-(morpholine-4-carbonyl)-phenylamino]-1,3-dihydro-indol-2-one. MS: [M+H]$^+$=531

EXAMPLE 236

Preparation of rac-3-[2-(4-Acetyl-piperazine-1-carbonyl)-5-chloro-phenoxy]-6-chloro-3-(3-chloro-benzyl)-1,3-dihydro-indol-2-one

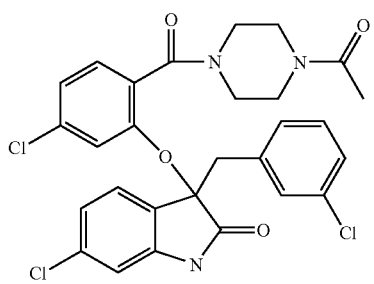

M.W. 572.88, C$_{28}$H$_{24}$Cl$_3$N$_3$O$_4$

The title compound was prepared following the similar procedure as rac-6-chloro-3-(3-chloro-benzyl)-3-[5-chloro-2-(morpholine-4-carbonyl)-phenylamino]-1,3-dihydro-indol-2-one. MS: [M+H]$^+$=572

EXAMPLE 237

Preparation of rac-4-Bromo-2-[6-chloro-3-(3-chloro-benzyl)-2-oxo-2,3-dihydro-1H-indol-3-ylamino]-N-piperidin-4-yl-benzamide

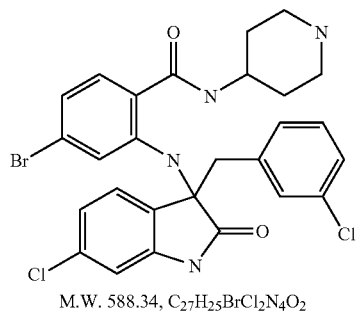

M.W. 588.34, C$_{27}$H$_{25}$BrCl$_2$N$_4$O$_2$

To a solution of rac-4-{4-Bromo-2-[6-chloro-3-(3-chloro-benzyl)-2-oxo-2,3-dihydro-1H-indol-3-ylamino]-benzoylamino}-piperidine-1-carboxylic acid tert-butyl ester (30 mg, 0.044 mmol) in DCM (2 mL) was added TFA (0.5 mL). The mixture was stirred for 3 h, concentrated. The residue was dissolved in DCM, the resulting solution was washed with Na$_2$CO$_3$ solution, dried with Na$_2$SO$_4$, concentrated to give 22 mg rac-4-Bromo-2-[6-chloro-3-(3-chloro-benzyl)-2-oxo-2,3-dihydro-1H-indol-3-ylamino]-N-piperidin-4-yl-benzamide. MS: [M+H]$^+$=587

EXAMPLE 238

Preparation of rac-4-Bromo-2-[6-chloro-3-(3-chloro-benzyl)-2-oxo-2,3-dihydro-1H-indol-3-ylamino]-N-(3-morpholin-4-yl-propyl)-benzamide

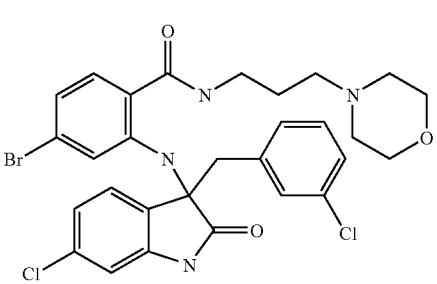

M.W. 632.39, C$_{29}$H$_{29}$BrCl$_2$N$_4$O$_3$

The title compound was prepared following the similar procedure as rac-6-chloro-3-(3-chloro-benzyl)-3-[5-chloro-2-(morpholine-4-carbonyl)-phenylamino]-1,3-dihydro-indol-2-one. MS: [M+H]⁺=631

EXAMPLE 239

Preparation of rac-2-{[6-Chloro-3-(3-chloro-benzyl)-2-oxo-2,3-dihydro-1H-indol-3-yl]-isopropyl-amino}-acetamide

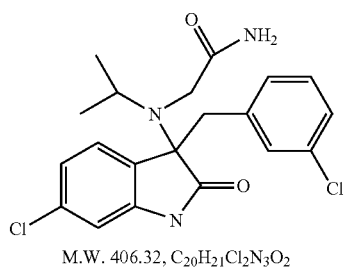

M.W. 406.32, C₂₀H₂₁Cl₂N₃O₂

The title compound was prepared following the similar procedure as rac-6,6'-Dichloro-3'-(3-chloro-benzyl)-2,3,1',3'-tetrahydro-[1,3']biindolyl-2'-one. MS: [M+H]+=406

EXAMPLE 240a

Preparation of Intermediate (2-Isopropylamino-ethyl)-carbamic acid tert-butyl ester

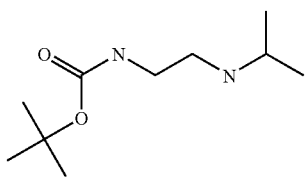

M.W. 202.30, C₁₀H₂₂N₂O₂

To a mixture of Isopropylamine (7 mL, 75 mmol), K2CO3 (2.7 g, 20 mmol) in acetonitrile (20 mL) was added dropwise a solution of (2-Bromo-ethyl)-carbamic acid tert-butyl ester (3.4 g, 15 mmol) in acetonitrile (10 mL). The resulting mixture was heated to 60° C. for 1.5 hr, concentrated in vacuo. The residue was dissolved in DCM, filtered and concentrated to give 3 g 2-Isopropylamino-ethyl)-carbamic acid tert-butyl ester as light yellow oil. MS: [M+H]+=203

EXAMPLE 240b

Preparation of Intermediate rac-(2-{[6-Chloro-3-(3-chloro-benzyl)-2-oxo-2,3-dihydro-1H-indol-3-yl]-isopropyl-amino}-ethyl)-carbamic acid tert-butyl ester

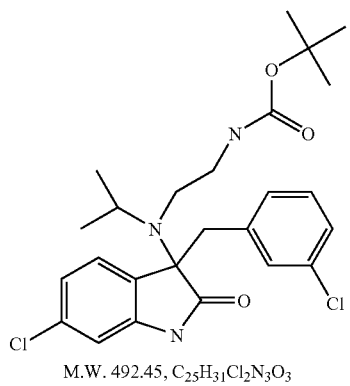

M.W. 492.45, C₂₅H₃₁Cl₂N₃O₃

A mixture of (2-Isopropylamino-ethyl)-carbamic acid tert-butyl ester (100 mg, 0.5 mmol), rac-3-bromo-6-chloro-3-(3-chloro-benzyl)-1,3-dihydro-indol-2-one (185 mg, 0.5 mmol) and K₂CO₃ (138 mg, 1 mmol) in DCM (1 mL) and acetonitrile (2 mL) was stirred at room temperature overnight. The mixture was concentrated and purified by column chromatography to give 180 mg rac-(2-{[6-Chloro-3-(3-chloro-benzyl)-2-oxo-2,3-dihydro-1H-indol-3-yl]-isopropyl-amino}-ethyl)-carbamic acid tert-butyl ester. MS: [M+H]+=492

EXAMPLE 240c

Preparation of rac-3-[(2-Amino-ethyl)-isopropyl-amino]-6-chloro-3-(3-chloro-benzyl)-1,3-dihydro-indol-2-one

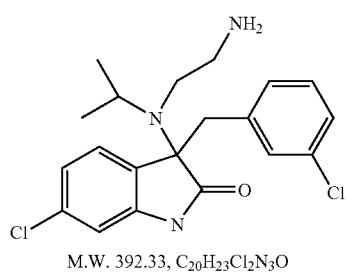

M.W. 392.33, C₂₀H₂₃Cl₂N₃O

To the solution of rac-(2-{[6-Chloro-3-(3-chloro-benzyl)-2-oxo-2,3-dihydro-1H-indol-3-yl]-isopropyl-amino}-ethyl)-carbamic acid tert-butyl ester (100 mg, 0.2 mmol) in DCM (10 mL) was added TFA (0.3 mL). The mixture was stirred at room temperature for 2 hr, then washed with NaOH solution (5%) and water. The organic layer was dried over Na₂SO₄, concentrated in vacuo to give 60 mg rac-3-[(2-Amino-ethyl)- isopropyl-amino]-6-chloro-3-(3-chloro-benzyl)-1,3-dihydro-indol-2-one. MS: [M+H]+=392

EXAMPLE 241

Preparation of rac-N-(2-{[6-Chloro-3-(3-chloro-benzyl)-2-oxo-2,3-dihydro-1H-indol-3-yl]-isopropyl-amino}-ethyl)-methanesulfonamide

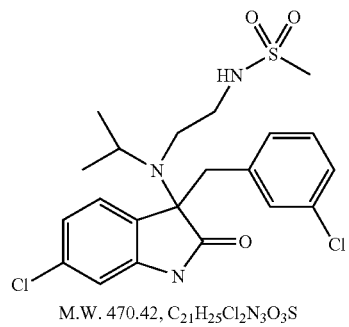

M.W. 470.42, $C_{21}H_{25}Cl_2N_3O_3S$

To a mixture of rac-3-[(2-Amino-ethyl)-isopropyl-amino]-6-chloro-3-(3-chloro-benzyl)-1,3-dihydro-indol-2-one (50 mg, 0.13 mmol) and $K_2CO_3$ (35 mg, 0.25 mmol) in DCM (2 mL) was added methylsulfonyl chloride (16 mg, 0.14 mmol). The resulting solution was stirred at room temperature for 2 hr, then purified by flash column chromatography to give 65 mg rac-N-(2-{[6-Chloro-3-(3-chloro-benzyl)-2-oxo-2,3-dihydro-1H-indol-3-yl]-isopropyl-amino}-ethyl)-methanesulfonamide. MS: [M+H]+=470

EXAMPLE 242

Preparation of rac-N-(2-{[6-Chloro-3-(3-chloro-benzyl)-2-oxo-2,3-dihydro-1H-indol-3-yl]-isopropyl-amino}-ethyl)-acetamide

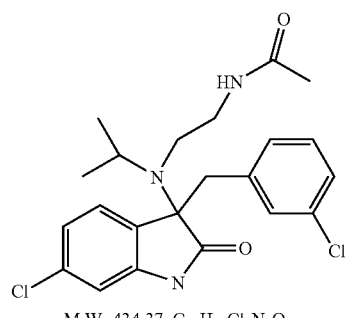

M.W. 434.37, $C_{22}H_{25}Cl_2N_3O_2$

The title compound was prepared following the similar procedure as rac-N-(2-{[6-Chloro-3-(3-chloro-benzyl)-2-oxo-2,3-dihydro-1H-indol-3-yl]-isopropyl-amino}-ethyl)-methanesulfonamide. MS: [M+H]+=434

EXAMPLE 243

Preparation of rac-3-(2-{[6-Chloro-3-(3-chloro-benzyl)-2-oxo-2,3-dihydro-1H-indol-3-yl]-isopropyl-amino}-ethyl)-1,1-dimethyl-urea

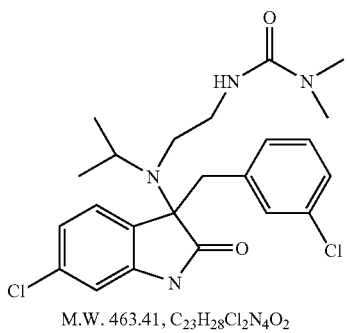

M.W. 463.41, $C_{23}H_{28}Cl_2N_4O_2$

The title compound was prepared following the similar procedure as rac-N-(2-{[6-Chloro-3-(3-chloro-benzyl)-2-oxo-2,3-dihydro-1H-indol-3-yl]-isopropyl-amino}-ethyl)-methanesulfonamide. MS: [M+H]+=463

EXAMPLE 244

Preparation of rac-4-Acetyl-piperazine-1-carboxylic acid (2-{[6-chloro-3-(3-chloro-benzyl)-2-oxo-2,3-dihydro-1H-indol-3-yl]-isopropyl-amino}-ethyl)-amide

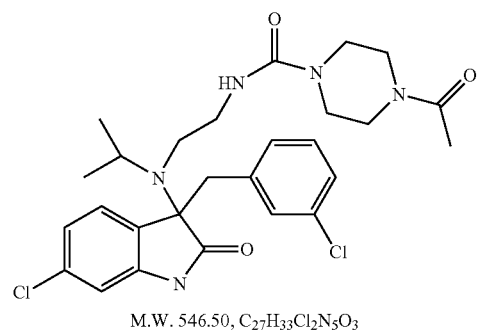

M.W. 546.50, $C_{27}H_{33}Cl_2N_5O_3$

The title compound was prepared following the similar procedure as rac-N-(2-{[6-Chloro-3-(3-chloro-benzyl)-2- oxo-2,3-dihydro-1H-indol-3-yl]-isopropyl-amino}-ethyl)-methanesulfonamide. MS: [M+H]+=546

EXAMPLE 245

Preparation of rac-Morpholine-4-carboxylic acid (2-{[6-chloro-3-(3-chloro-benzyl)-2-oxo-2,3-dihydro-1H-indol-3-yl]-isopropyl-amino}-ethyl)-amide

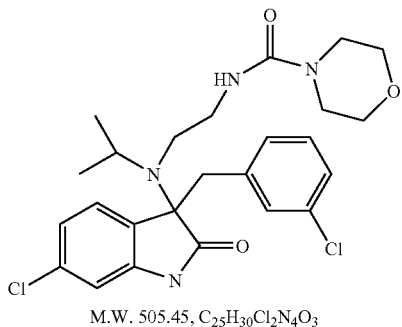

M.W. 505.45, $C_{25}H_{30}Cl_2N_4O_3$

The title compound was prepared following the similar procedure as rac-N-(2-{[6-Chloro-3-(3-chloro-benzyl)-2-oxo-2,3-dihydro-1H-indol-3-yl]-isopropyl-amino}-ethyl)-methanesulfonamide. MS: [M+H]+=505

EXAMPLE 246

Preparation of rac-Cyclobutanecarboxylic acid (2-{[6-chloro-3-(3-chloro-benzyl)-2-oxo-2,3-dihydro-1H-indol-3-yl]-isopropyl-amino}-ethyl)-amide

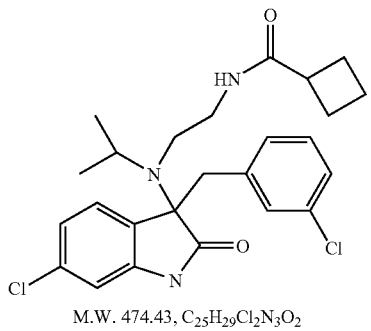

M.W. 474.43, $C_{25}H_{29}Cl_2N_3O_2$

The mixture of rac-3-[(2-Amino-ethyl)-isopropyl-amino]-6-chloro-3-(3-chloro-benzyl)-1,3-dihydro-indol-2-one (60 mg, 0.15 mmol), cyclobutanecarboxylic acid (18.4 mg, 0.18 mmol), EDCl (37 mg, 0.19 mmol), HOBt (30 mg, 0.19 mmol) and DIPEA (40 uL, 0.225) in DCM (2 mL) was stirred at root temperature for 2 hr. The mixture was purified by flash column chromatography to give 60 mg rac-Cyclobutanecarboxylic acid (2-{[6-chloro-3-(3-chloro-benzyl)-2-oxo-2,3-dihydro-1H-indol-3-yl]-isopropyl-amino}-ethyl)-amide. MS: [M+H]+=474

EXAMPLE 247

Preparation of rac-1-Acetyl-piperidine-4-carboxylic acid (2-{[6-chloro-3-(3-chloro-benzyl)-2-oxo-2,3-dihydro-1H-indol-3-yl]-isopropyl-amino}-ethyl)-amide

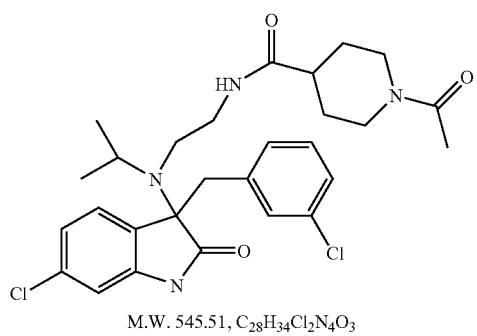

M.W. 545.51, $C_{28}H_{34}Cl_2N_4O_3$

The title compound was prepared following the similar procedure as rac-Cyclobutanecarboxylic acid (2-{[6-chloro-3-(3-chloro-benzyl)-2-oxo-2,3-dihydro-1H-indol-3-yl]-isopropyl-amino}-ethyl)-amide. MS: [M+H]+=545

EXAMPLE 248

Preparation of rac-N-(2-Acetylamino-ethyl)-2-[6-chloro-3-(3-chloro-benzyl)-2-oxo-2,3-dihydro-1H-indol-3-ylamino]-4-methoxy-benzamide

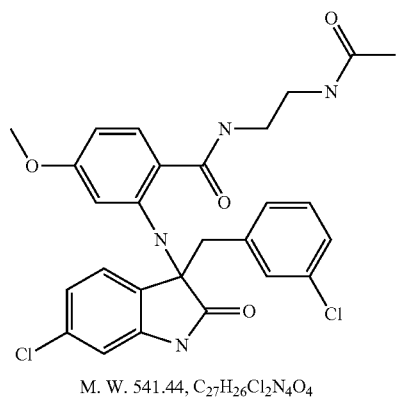

M. W. 541.44, $C_{27}H_{26}Cl_2N_4O_4$

The title compound was prepared following the similar procedure as rac-Cyclobutanecarboxylic acid (2-{[6-chloro- 3-(3-chloro-benzyl)-2-oxo-2,3-dihydro-1H-indol-3-yl]-iso-propyl-amino}-ethyl)-amide. MS: [M+H]+=541

EXAMPLE 249

Preparation of rac-2-[6-Chloro-3-(3-chloro-benzyl)-2-oxo-2,3-dihydro-1H-indol-3-ylamino]-N-(3-dimethylamino-propyl)-4-methoxy-benzamide

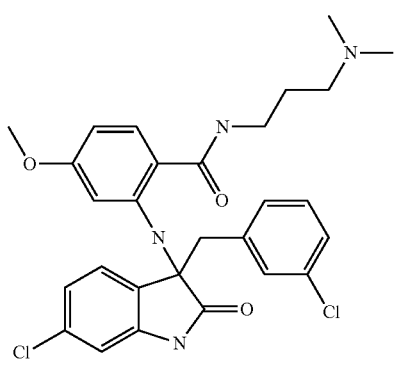

M. W. 541.48, C$_{28}$H$_{30}$Cl$_2$N$_4$O$_3$

The title compound was prepared following the similar procedure as rac-Cyclobutanecarboxylic acid (2-{[6-chloro-3-(3-chloro-benzyl)-2-oxo-2,3-dihydro-1H-indol-3-yl]-iso-propyl-amino}-ethyl)-amide. MS: [M+H]+=541

EXAMPLE 250

Preparation of rac-6-Chloro-3-(3-chloro-benzyl)-3-[5-methoxy-2-(morpholine-4-carbonyl)-phenylamino]-1,3-dihydro-indol-2-one

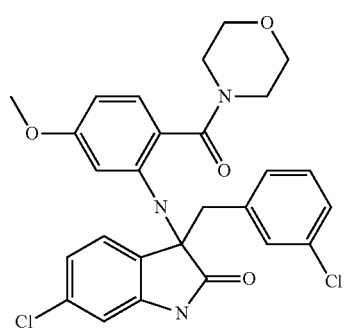

M. W. 526.42, C$_{27}$H$_{25}$Cl$_2$N$_3$O$_4$

The title compound was prepared following the similar procedure as rac-Cyclobutanecarboxylic acid (2-{[6-chloro- 3-(3-chloro-benzyl)-2-oxo-2,3-dihydro-1H-indol-3-yl]-iso-propyl-amino}-ethyl)-amide. MS: [M+H]+=526

EXAMPLE 251

Preparation of rac-N-(2-Acetylamino-ethyl)-2,4-dichloro-6-[6-chloro-3-(3-chloro-benzyl)-2-oxo-2,3-dihydro-1H-indol-3-ylamino]-benzamide

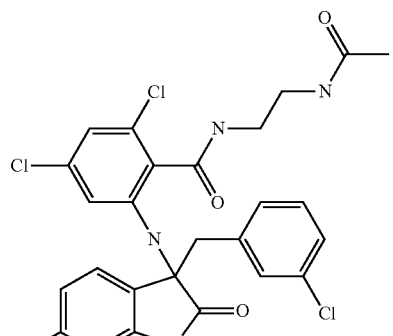

M. W. 580.30, C$_{26}$H$_{22}$Cl$_4$N$_4$O$_3$

The title compound was prepared following the similar procedure as rac-Cyclobutanecarboxylic acid (2-{[6-chloro-3-(3-chloro-benzyl)-2-oxo-2,3-dihydro-1H-indol-3-yl]-iso-propyl-amino}-ethyl)-amide. MS: [M+H]+=579

EXAMPLE 252

Preparation of rac-2,4-Dichloro-6-[6-chloro-3-(3-chloro-benzyl)-2-oxo-2,3-dihydro-1H-indol-3-ylamino]-N-(3-dimethylamino-propyl)-benzamide

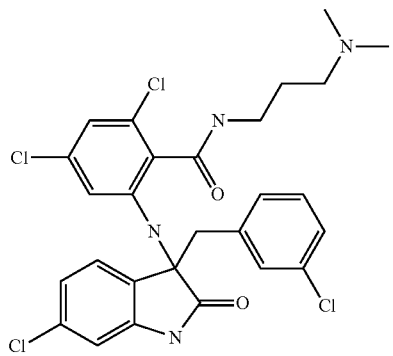

M. W. 580.35, C$_{27}$H$_{26}$Cl$_4$N$_4$O$_2$

The title compound was prepared following the similar procedure as rac-Cyclobutanecarboxylic acid (2-{[6-chloro- 3-(3-chloro-benzyl)-2-oxo-2,3-dihydro-1H-indol-3-yl]-isopropyl-amino}-ethyl)-amide. MS: [M+H]+=579

EXAMPLE 253

Preparation of rac-6-Chloro-3-(3-chloro-benzyl)-3-[3,5-dichloro-2-(morpholine-4-carbonyl)-phenylamino]-1,3-dihydro-indol-2-one

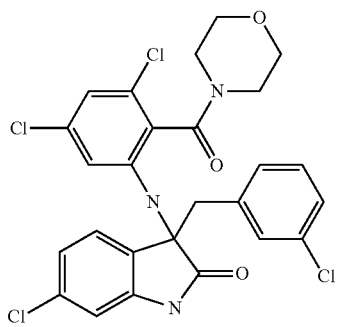

M. W. 565.29, $C_{26}H_{21}Cl_4N_3O_3$

The title compound was prepared following the similar procedure as rac-Cyclobutanecarboxylic acid (2-{[6-chloro-3-(3-chloro-benzyl)-2-oxo-2,3-dihydro-1H-indol-3-yl]-isopropyl-amino}-ethyl)-amide. MS: [M+H]+=564

EXAMPLE 254

Preparation of rac-3-Chloro-2-[6-chloro-3-(3-chloro-benzyl)-2-oxo-2,3-dihydro-1H-indol-3-ylamino]-N-cyclohexyl-benzamide

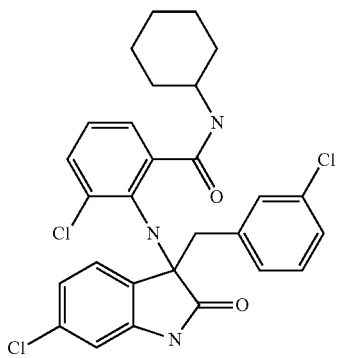

M. W. 542.90, $C_{28}H_{26}Cl_3N_3O_2$

The title compound was prepared following the similar procedure as rac-Cyclobutanecarboxylic acid (2-{[6-chloro- 3-(3-chloro-benzyl)-2-oxo-2,3-dihydro-1H-indol-3-yl]-isopropyl-amino}-ethyl)-amide. MS: [M+H]+=542

EXAMPLE 255

Preparation of rac-3-Chloro-2-[6-chloro-3-(3-chloro-benzyl)-2-oxo-2,3-dihydro-1H-indol-3-ylamino]-N-cyclobutyl-benzamide

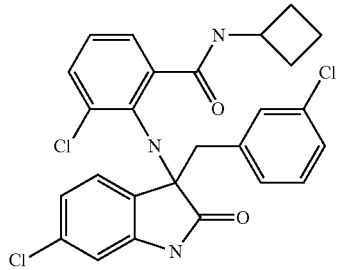

M. W. 514.84, $C_{26}H_{22}Cl_3N_3O_2$

The title compound was prepared following the similar procedure as rac-Cyclobutanecarboxylic acid (2-{[6-chloro-3-(3-chloro-benzyl)-2-oxo-2,3-dihydro-1H-indol-3-yl]-isopropyl-amino}-ethyl)-amide. MS: [M+H]+=514

EXAMPLE 256

Preparation of rac-6-Chloro-3-(3-chloro-benzyl)-3-{2-chloro-6-[4-(2-hydroxy-ethyl)-piperazine-1-carbonyl]-phenylamino}-1,3-dihydro-indol-2-one

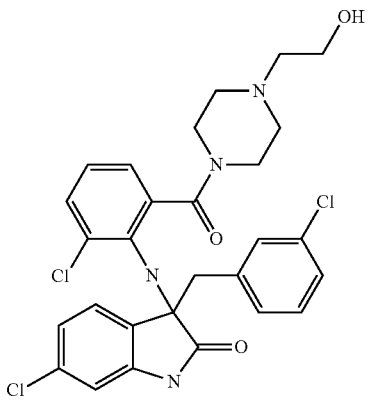

M. W. 573.91, $C_{28}H_{27}Cl_3N_4O_3$

The title compound was prepared following the similar procedure as rac-Cyclobutanecarboxylic acid (2-{[6-chloro- 3-(3-chloro-benzyl)-2-oxo-2,3-dihydro-1H-indol-3-yl]-isopropyl-amino}-ethyl)-amide. MS: [M+H]+=573

EXAMPLE 257

Preparation of rac-2-[6-Chloro-3-(3-chloro-benzyl)-2-oxo-2,3-dihydro-1H-indol-3-ylamino]-N-cyclohexyl-3-methoxy-benzamide

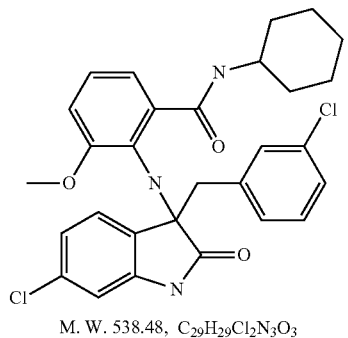

M. W. 538.48, C$_{29}$H$_{29}$Cl$_2$N$_3$O$_3$

The title compound was prepared following the similar procedure as rac-Cyclobutanecarboxylic acid (2-{[6-chloro-3-(3-chloro-benzyl)-2-oxo-2,3-dihydro-1H-indol-3-yl]-isopropyl-amino}-ethyl)-amide. MS: [M+H]+=538

EXAMPLE 258

Preparation of rac-2-[6-Chloro-3-(3-chloro-benzyl)-2-oxo-2,3-dihydro-1H-indol-3-ylamino]-N-cyclobutyl-3-methoxy-benzamide

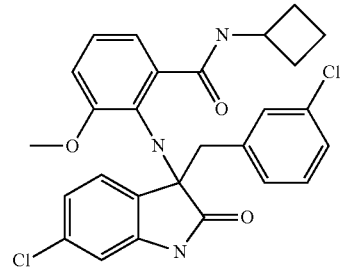

M. W. 510.42, C$_{27}$H$_{25}$Cl$_2$N$_3$O$_3$

The title compound was prepared following the similar procedure as rac-Cyclobutanecarboxylic acid (2-{[6-chloro-3-(3-chloro-benzyl)-2-oxo-2,3-dihydro-1H-indol-3-yl]-isopropyl-amino}-ethyl)-amide. MS: [M+H]+=510

EXAMPLE 259

Preparation of rac-6-Chloro-3-(3-chloro-benzyl)-3-{2-[4-(2-hydroxy-ethyl)-piperazine-1-carbonyl]-6-methoxy-phenylamino}-1,3-dihydro-indol-2-one

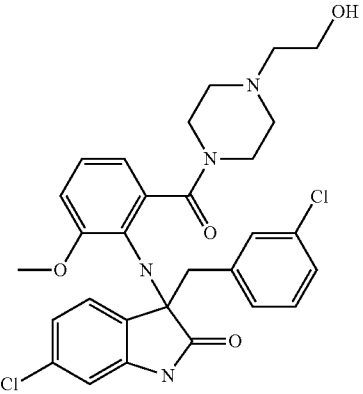

M. W. 569.49, C$_{29}$H$_{30}$Cl$_2$N$_4$O$_4$

The title compound was prepared following the similar procedure as rac-Cyclobutanecarboxylic acid (2-{[6-chloro-3-(3-chloro-benzyl)-2-oxo-2,3-dihydro-1H-indol-3-yl]-isopropyl-amino}-ethyl)-amide. MS: [M+H]+=569

EXAMPLE 260

Preparation of rac-1-{2-[6-Chloro-3-(3-chloro-benzyl)-2-oxo-2,3-dihydro-1H-indol-3-ylamino]-3-methoxy-benzoyl}-piperidine-4-carboxylic acid amide

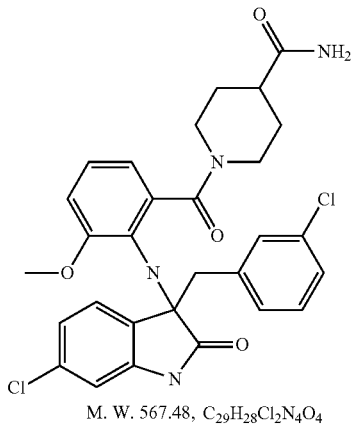

M. W. 567.48, C$_{29}$H$_{28}$Cl$_2$N$_4$O$_4$

The title compound was prepared following the similar procedure as rac-Cyclobutanecarboxylic acid (2-{[6-chloro- 3-(3-chloro-benzyl)-2-oxo-2,3-dihydro-1H-indol-3-yl]-isopropyl-amino}-ethyl)-amide. MS: [M+H]+=567

EXAMPLE 261

Preparation of rac-2-[[6-Chloro-3-(3-chloro-benzyl)-2-oxo-2,3-dihydro-1H-indol-3-yl]-(3-chloro-phenyl)-amino]-N-cyclohexyl-acetamide

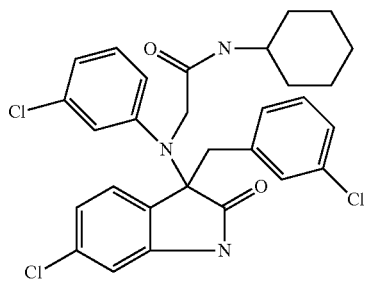

M. W. 556.918  $C_{29}H_{28}Cl_3N_3O_2$

The mixture of [[6-Chloro-3-(3-chloro-benzyl)-2-oxo-2,3-dihydro-1H-indol-3-yl]-(3-chloro-phenyl)-amino]-acetic acid 100 mg, 0.211 mmol), Cyclohexylamine (25 mg, 0.253 mmol), EDC.HCl (48 mmg, 0.253 mmol), HOBt (34 mmg, 0.253 mmol) and DIPEA (82 mmg, 0.633 mmol) in acetonitrile (2 mL) was stirred at room temperature for overnight. The crude was then purified with Prep-HPLC to give 48 mg of rac-2-[[6-Chloro-3-(3-chloro-benzyl)-2-oxo-2,3-dihydro-1H-indol-3-yl]-(3-chloro-phenyl)-amino]-N-cyclohexyl-acetamide as a yellow solid. MS: [M+H]+=556.

EXAMPLE 262

Preparation of rac-2-[[6-Chloro-3-(3-chloro-benzyl)-2-oxo-2,3-dihydro-1H-indol-3-yl]-(3-chloro-phenyl)-amino]-N-cyclobutyl-acetamide

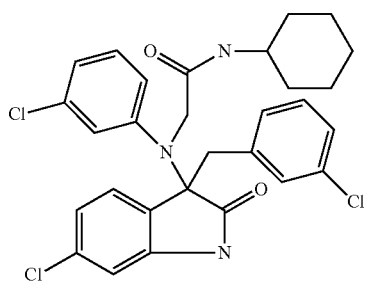

M. W. 528.865  $C_{27}H_{24}Cl_3N_3O_2$

The title compound was prepared by the same procedure for rac-2-[[6-Chloro-3-(3-chloro-benzyl)-2-oxo-2,3-dihydro-1H-indol-3-yl]-(3-chloro-phenyl)-amino]-N-cyclohexyl-acetamide MS: 528 (M+H)+.

EXAMPLE 263

Preparation of rac-1-{2-[[6-Chloro-3-(3-chloro-benzyl)-2-oxo-2,3-dihydro-1H-indol-3-yl]-(3-chloro-phenyl)-amino]-acetyl}-piperidine-4-carboxylic acid amide

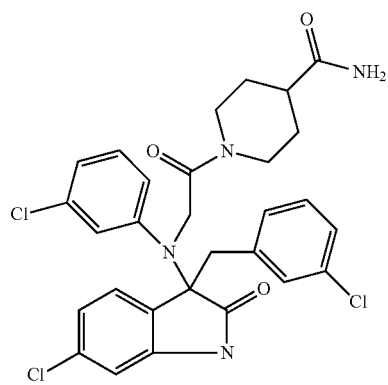

M. W. 585.916  $C_{29}H_{27}Cl_3N_4O_3$

The title compound was prepared by the same procedure for rac-2-[[6-Chloro-3-(3-chloro-benzyl)-2-oxo-2,3-dihydro-1H-indol-3-yl]-(3-chloro-phenyl)-amino]-N-cyclohexyl-acetamide MS: 585 (M+H)+.

EXAMPLE 264

Preparation of rac-6-Chloro-3-(3-chloro-benzyl)-3-((3-chloro-phenyl)-{2-[4-(2-hydroxy-ethyl)-piperazin-1-yl]-2-oxo-ethyl}-amino)-1,3-dihydro-indol-2-one

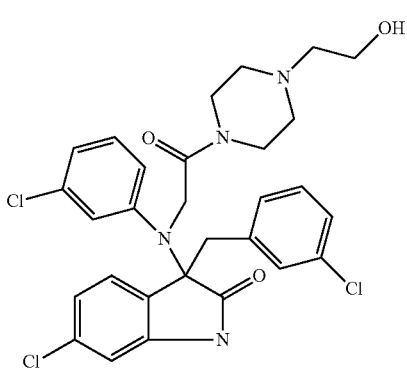

M. W. 587.932  $C_{29}H_{29}Cl_3N_4O_3$

The title compound was prepared by the same procedure for rac-2-[[6-Chloro-3-(3-chloro-benzyl)-2-oxo-2,3-dihydro-1H-indol-3-yl]-(3-chloro-phenyl)-amino]-N-cyclohexyl-acetamide MS: 587 (M+H)⁺.

EXAMPLE 265

Preparation of rac-1-{2-[[6-Chloro-3-(3-chloro-benzyl)-2-oxo-2,3-dihydro-1H-indol-3-yl]-(1-ethyl-propyl)-amino]-acetyl}-piperidine-4-carboxylic acid amide

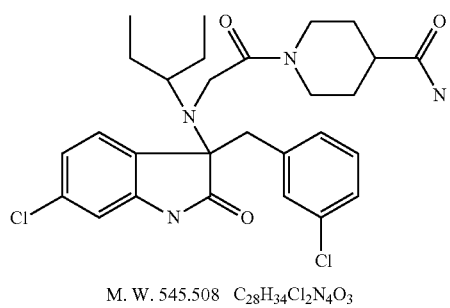

M. W. 545.508  $C_{28}H_{34}Cl_2N_4O_3$

The title compound was prepared by the same procedure for rac-2-[[6-Chloro-3-(3-chloro-benzyl)-2-oxo-2,3-dihydro-1H-indol-3-yl]-(3-chloro-phenyl)-amino]-N-cyclohexyl-acetamide MS: 545 (M+H)⁺.

EXAMPLE 266

Preparation of rac-1-(2-{[6-Chloro-3-(3-chloro-benzyl)-2-oxo-2,3-dihydro-1H-indol-3-yl]-isopropyl-amino}-acetyl)-piperidine-4-carboxylic acid amide

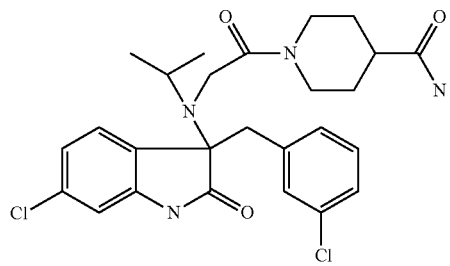

M. W. 517.454  $C_{26}H_{30}Cl_2N_4O_3$

The title compound was prepared by the same procedure for rac-2-[[6-Chloro-3-(3-chloro-benzyl)-2-oxo-2,3-dihy-dro-1H-indol-3-yl]-(3-chloro-phenyl)-amino]-N-cyclohexyl-acetamide MS: 517 (M+H)⁺.

EXAMPLE 267

Preparation of rac-2-[[6-Chloro-3-(3-chloro-benzyl)-2-oxo-2,3-dihydro-1H-indol-3-yl]-(1-ethyl-propyl)-amino]-N-cyclobutyl-acetamide

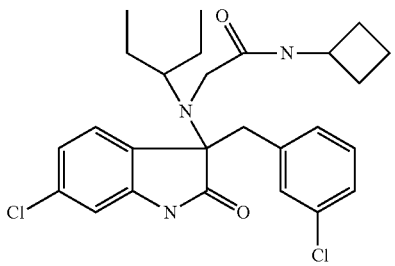

M. W. 488.456  $C_{26}H_{31}Cl_2N_3O_2$

The title compound was prepared by the same procedure for rac-2-[[6-Chloro-3-(3-chloro-benzyl)-2-oxo-2,3-dihydro-1H-indol-3-yl]-(3-chloro-phenyl)-amino]-N-cyclohexyl-acetamide MS: 488 (M+H)⁺.

EXAMPLE 268

Preparation of rac-6-Chloro-3-(3-chloro-benzyl)-3-({2-[4-(2-hydroxy-ethyl)-piperazin-1-yl]-2-oxo-ethyl}-isopropyl-amino)-1,3-dihydro-indol-2-one

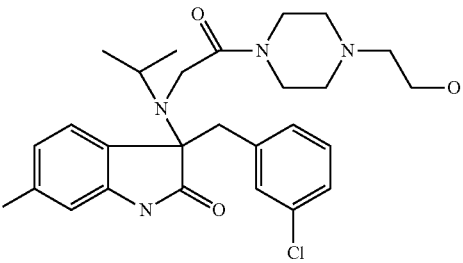

M. W. 519.47  $C_{26}H_{32}Cl_2N_4O_3$

The title compound was prepared by the same procedure for rac-2-[[6-Chloro-3-(3-chloro-benzyl)-2-oxo-2,3-dihydro-1H-indol-3-yl]-(3-chloro-phenyl)-amino]-N-cyclohexyl-acetamide MS: 519 (M+H)+.

EXAMPLE 269

Preparation of rac-2-{[6-Chloro-3-(3-chloro-benzyl)-2-oxo-2,3-dihydro-1H-indol-3-yl]-isopropyl-amino}-N-cyclohexyl-acetamide

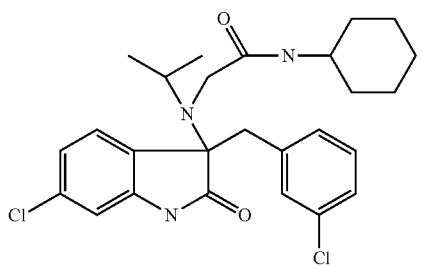

M. W. 488.456   $C_{26}H_{31}Cl_2N_3O_2$

The title compound was prepared by the same procedure for rac-2-[[6-Chloro-3-(3-chloro-benzyl)-2-oxo-2,3-dihydro-1H-indol-3-yl]-(3-chloro-phenyl)-amino]-N-cyclohexyl-acetamide MS: 488 (M+H)+.

EXAMPLE 270

Preparation of rac-[[6-Chloro-3-(3-chloro-benzyl)-2-oxo-2,3-dihydro-1H-indol-3-yl]-(1-ethyl-propyl)-amino]-acetic acid ethyl ester

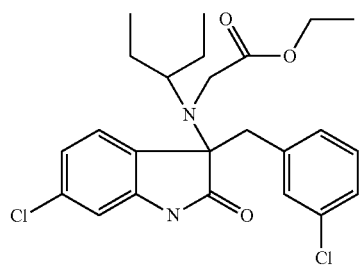

M. W. 463.402   $C_{24}H_{28}Cl_2N_2O_3$

The title compound was prepared by the same procedure for rac-2-[[6-Chloro-3-(3-chloro-benzyl)-2-oxo-2,3-dihydro-1H-indol-3-yl]-(3-chloro-phenyl)-amino]-N-cyclohexyl-acetamide MS: 463 (M+H)+.

EXAMPLE 271

Preparation of rac-2-{[6-Chloro-3-(3-chloro-benzyl)-2-oxo-2,3-dihydro-1H-indol-3-yl]-isopropyl-amino}-N-cyclobutyl-acetamide

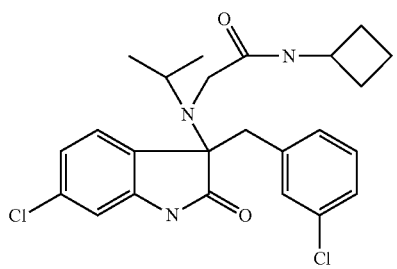

M. W. 460.402   $C_{24}H_{27}Cl_2N_3O_2$

The title compound was prepared by the same procedure for rac-2-[[6-Chloro-3-(3-chloro-benzyl)-2-oxo-2,3-dihydro-1H-indol-3-yl]-(3-chloro-phenyl)-amino]-N-cyclohexyl-acetamide MS: 460 (M+H)+.

EXAMPLE 272

Preparation of rac-2-[[6-Chloro-3-(3-chloro-benzyl)-2-oxo-2,3-dihydro-1H-indol-3-yl]-(1-ethyl-propyl)-amino]-N-cyclohexyl-acetamide

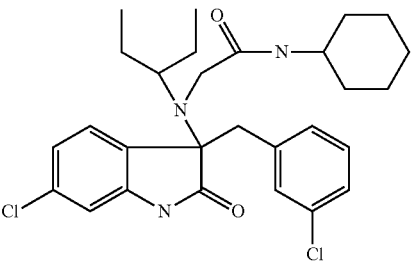

M. W. 516.509   $C_{24}H_{27}Cl_2N_3O_2$

The title compound was prepared by the same procedure for rac-2-[[6-Chloro-3-(3-chloro-benzyl)-2-oxo-2,3-dihydro-1H-indol-3-yl]-(3-chloro-phenyl)-amino]-N-cyclo-hexyl-acetamide MS: 516 (M+H)+.

EXAMPLE 273

Preparation of rac-[[6-Chloro-3-(3-chloro-benzyl)-2-oxo-2,3-dihydro-1H-indol-3-yl]-(3-chloro-phenyl)-amino]-acetic acid

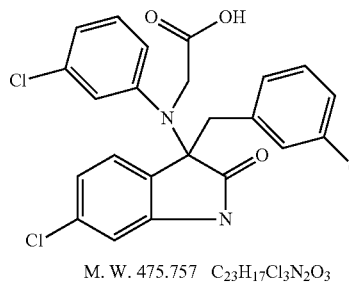

M. W. 475.757   $C_{23}H_{17}Cl_3N_2O_3$

At room temperature, (3-Chloro-phenylamino)-acetic acid (1.25 g, 6.8 mmol) was dissolved in 10 ml 1N $K_2CO_3$ aqueous solution, then 3-Bromo-6-chloro-3-(3-chloro-benzyl)-1,3-dihydro-indol-2-one (2.5 g, 6.8 mmol) and 10 ml 1,4-dioxane were added slowly. After stirred for about 3 h, the solution was concentrated and the water layer was extracted with $CH_2Cl_2$. The organic layer was dried, concentrated to obtain the crude product and the crude product was purified by chromatography to obtain 1.2 g yellow solid rac-[[6-Chloro-3-(3-chloro-benzyl)-2-oxo-2,3-dihydro-1H-indol-3-yl]-(3-chloro-phenyl)-amino]-acetic acid.

MS: 475 (M+H)+.

EXAMPLE 274

Preparation of rac-{[6-Chloro-3-(3-chloro-benzyl)-2-oxo-2,3-dihydro-1H-indol-3-yl]-isopropyl-amino}-acetic acid ethyl ester

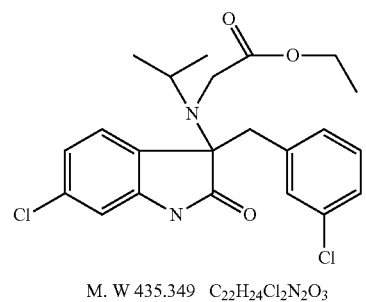

M. W 435.349   $C_{22}H_{24}Cl_2N_2O_3$

At room temperature, 3-Bromo-6-chloro-3-(3-chloro-benzyl)-1,3-dihydro-indol-2-one (4.57 g, 12.3 mmol) and Isopropylamino-acetic acid ethyl ester (2.15 g, 14.8 mmol), DIPEA (2.14 ml) were mixed in about 40 ml dichloromethane. After stirred for about 3 h, the solution was concentrated and the crude product was purified by chromatography to obtain 4.7 g solid rac-{[6-Chloro-3-(3-chloro-benzyl)-2-oxo-2,3-dihydro-1H-indol-3-yl]-isopropyl-amino}-acetic acid ethyl ester. MS: 435 (M+H)+.

EXAMPLE 275

Preparation of rac-{[6-Chloro-3-(3-chloro-benzyl)-2-oxo-2,3-dihydro-1H-indol-3-yl]-isopropyl-amino}-acetic acid

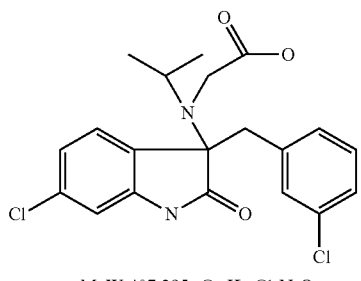

M. W 407.295   $C_{20}H_{20}Cl_2N_2O_3$ rac-{[6-Chloro-3-(3-chloro-benzyl)-2-oxo-2,3-dihydro-1H-indol-3-yl]-isopropyl-amino}-acetic acid ethyl ester (4.5 g, 10.4 mmol) was dissolved in a mixture of MeOH and KOH aqueous solution. This mixed solution was refluxed overnight and then the solution was concentrated. The PH of water layer was adjusted to 5-6 and then the water layer was extracted with dichloromethane. The organic layer was dried, concentrated and purified by chromatography to obtain 3.2 g solid rac-{[6-Chloro-3-(3-chloro-benzyl)-2-oxo-2,3-dihydro-1H-indol-3-yl]-isopropyl-amino}-acetic acid.

MS: 407 (M+H)+.

EXAMPLE 276

Preparation of rac-[[6-Chloro-3-(3-chloro-benzyl)-2-oxo-2,3-dihydro-1H-indol-3-yl]-(1-ethyl-propyl)-amino]-acetic acid

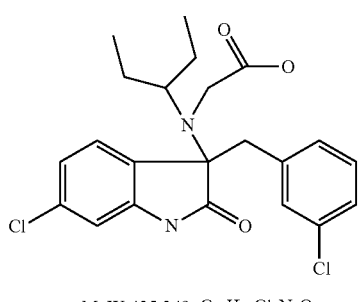

M. W 435.349   $C_{22}H_{24}Cl_2N_2O_3$

The title compound was prepared by the same procedure for rac-{[6-Chloro-3-(3-chloro-benzyl)-2-oxo-2,3-dihydro-1H-indol-3-yl]-isopropyl-amino}-acetic acid MS: 435 (M+H)+.

EXAMPLE 277

Preparation of rac-6'-Chloro-3'-(3-chloro-benzyl)-2-(morpholine-4-carbonyl)-1',3'-dihydro-[1,3']biindolyl-2'-one

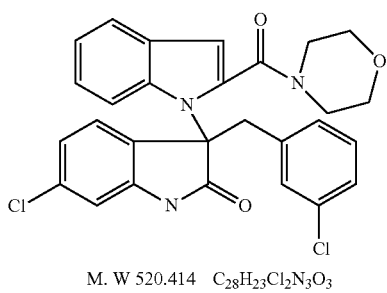

M. W 520.414  C28H23Cl2N3O3

At room temperature, 6'-Chloro-3'-(3-chloro-benzyl)-2-(morpholine-4-carbonyl)-2,3,1',3'-tetrahydro-[1,3']biindolyl-2'-one (60 mg, 0.115 mmol) and DDQ (47 mg, 0.207 mmol) were dissolved in 5 ml toluene. After stirred overnight, the solution was concentrated and then the residue was dissolved in EtOAc. The organic layer was washed with 10% NaOH aqueous solution and dried, concentrated to obtain crude product. The crude product was purified by chromatography to obtain 20 mg yellow solid rac-6'-Chloro-3'-(3-chloro-benzyl)-2-(morpholine-4-carbonyl)-1',3'-dihydro-[1,3']biindolyl-2'-one. MS: 520 (M+H)+.

EXAMPLE 278

Preparation of rac-2-(4-Acetyl-piperazine-1-carbonyl)-6'-chloro-3'-(3-chloro-benzyl)-1',3'-dihydro-[1,3']biindolyl-2'-one

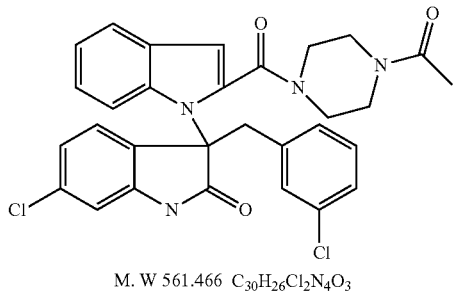

M. W 561.466  C30H26Cl2N4O3

The title compound was prepared by the same procedure rac-6'-Chloro-3'-(3-chloro-benzyl)-2-(morpholine-4-carbonyl)-1',3'-dihydro-[1,3']biindolyl-2'-one

MS: 561 (M+H)+.

EXAMPLE 279

Preparation of rac-6'-Chloro-3'-(3-chloro-benzyl)-2'-oxo-2',3'-dihydro-1'H-[1,3']biindolyl-2-carboxylic acid cyclobutylamide

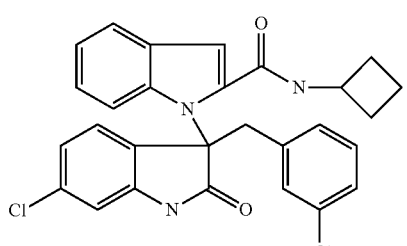

M. W 504.415  C28H23Cl2N3O2

The title compound was prepared by the same procedure rac-6'-Chloro-3'-(3-chloro-benzyl)-2-(morpholine-4-carbonyl)-1',3'-dihydro-[1,3']biindolyl-2'-one

MS: 504 (M+H)+.

EXAMPLE 280

Preparation of rac-2-(4-Acetyl-piperazine-1-carbonyl)-6'-chloro-3'-(3-chloro-benzyl)-2,3,1',3'-tetrahydro-[1,3']biindolyl-2'-one

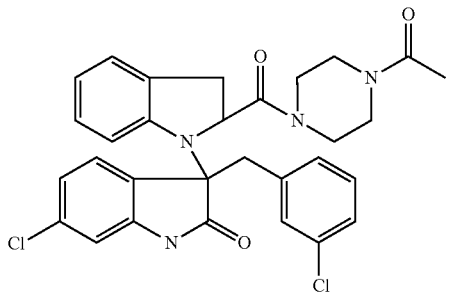

M. W 563.482  C30H28Cl2N4O3

The title compound was prepared by the same procedure for rac-2-[[6-Chloro-3-(3-chloro-benzyl)-2-oxo-2,3-dihydro-1H-indol-3-yl]-(3-chloro-phenyl)-amino]-N-cyclohexyl-acetamide MS: 563 (M+H)⁺.

EXAMPLE 281

Preparation of rac-2-(4-Acetyl-piperazine-1-carbonyl)-6'-chloro-3'-(3-chloro-benzyl)-2,3,1',3'-tetrahydro-[1,3']biindolyl-2'-one

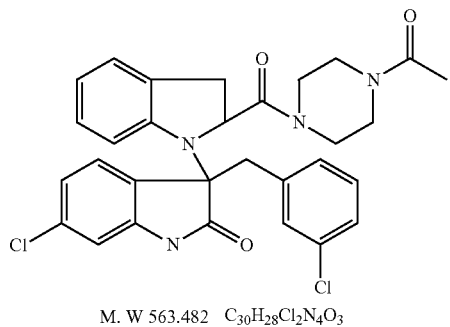

M. W 563.482  $C_{30}H_{28}Cl_2N_4O_3$

The title compound was prepared by the same procedure for rac-2-[[6-Chloro-3-(3-chloro-benzyl)-2-oxo-2,3-dihydro-1H-indol-3-yl]-(3-chloro-phenyl)-amino]-N-cyclohexyl-acetamide MS: 563 (M+H)⁺.

EXAMPLE 282

Preparation of rac-6'-Chloro-3'-(3-chloro-benzyl)-2-(morpholine-4-carbonyl)-2,3,1',3'-tetrahydro-[1,3']biindolyl-2'-one

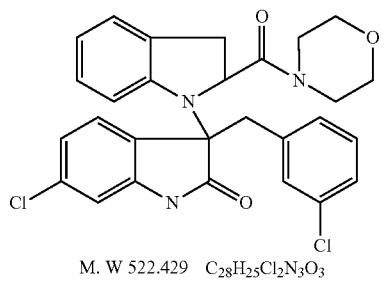

M. W 522.429  $C_{28}H_{25}Cl_2N_3O_3$

The title compound was prepared by the same procedure for rac-2-[[6-Chloro-3-(3-chloro-benzyl)-2-oxo-2,3-dihy-dro-1H-indol-3-yl]-(3-chloro-phenyl)-amino]-N-cyclohexyl-acetamide MS: 522 (M+H)⁺.

EXAMPLE 283

Preparation of rac-6'-Chloro-3'-(3-chloro-benzyl)-2-(morpholine-4-carbonyl)-2,3,1',3'-tetrahydro-[1,3']biindolyl-2'-one

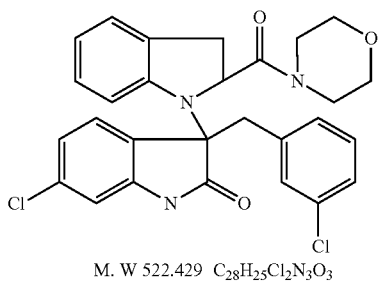

M. W 522.429  $C_{28}H_{25}Cl_2N_3O_3$

The title compound was prepared by the same procedure for rac-2-[[6-Chloro-3-(3-chloro-benzyl)-2-oxo-2,3-dihydro-1H-indol-3-yl]-(3-chloro-phenyl)-amino]-N-cyclohexyl-acetamide MS: 522 (M+H)⁺.

EXAMPLE 284

Preparation of rac-6'-Chloro-3'-(3-chloro-benzyl)-2'-oxo-2,3,2',3'-tetrahydro-1'H-[1,3']biindolyl-2-carboxylic acid cyclobutylamide

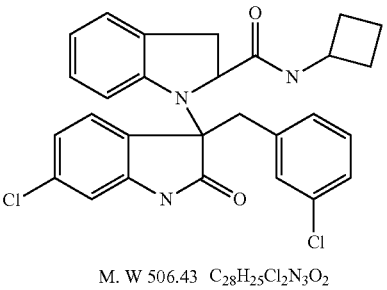

M. W 506.43  $C_{28}H_{25}Cl_2N_3O_2$

The title compound was prepared by the same procedure for rac-2-[[6-Chloro-3-(3-chloro-benzyl)-2-oxo-2,3-dihydro-1H-indol-3-yl]-(3-chloro-phenyl)-amino]-N-cyclohexyl-acetamide MS: 506 (M+H)⁺.

EXAMPLE 285

Preparation of rac-3-[2-(4-Acetyl-piperazine-1-carbonyl)-6-ethoxy-phenylamino]-6-chloro-3-(3-chlorobenzyl)-1,3-dihydro-indol-2-one

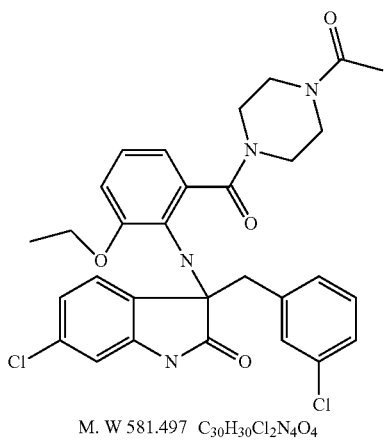

M. W 581.497   $C_{30}H_{30}Cl_2N_4O_4$

The title compound was prepared by the same procedure for rac-2-[[6-Chloro-3-(3-chloro-benzyl)-2-oxo-2,3-dihydro-1H-indol-3-yl]-(3-chloro-phenyl)-amino]-N-cyclohexyl-acetamide MS: 581 (M+H)⁺.

EXAMPLE 286

Preparation of rac-6-Chloro-3-(3-chloro-benzyl)-3-[2-ethoxy-6-(morpholine-4-carbonyl)-phenylamino]-1,3-dihydro-indol-2-one

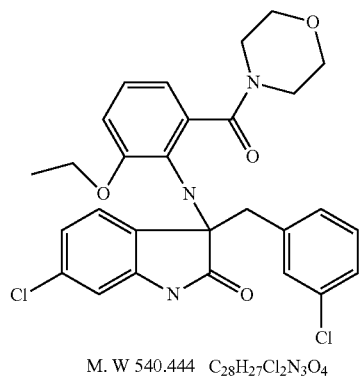

M. W 540.444   $C_{28}H_{27}Cl_2N_3O_4$

The title compound was prepared by the same procedure for rac-2-[[6-Chloro-3-(3-chloro-benzyl)-2-oxo-2,3-dihydro-1H-indol-3-yl]-(3-chloro-phenyl)-amino]-N-cyclohexyl-acetamide MS: 540 (M+H)⁺.

EXAMPLE 287

Preparation of rac-2-[6-Chloro-3-(3-chloro-benzyl)-2-oxo-2,3-dihydro-1H-indol-3-ylamino]-3-ethoxy-benzoic acid

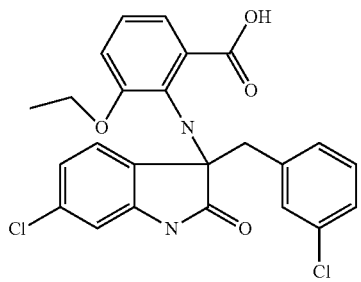

M. W 471.338   $C_{24}H_{20}Cl_2N_2O_4$

At room temperature, 2-Amino-3-ethoxy-benzoic acid (0.59 g, 3.26 mmol), 3-Bromo-6-chloro-3-(3-chloro-benzyl)-1,3-dihydro-indol-2-one (1.21 g, 3.26 mmol) and DIPEA (0.68 ml) were mixed in about 6 ml $CH_2Cl_2$. After stirred overnight, the solution was concentrated and the crude product was purified by chromatography to obtain 400 mg solid rac-2-[6-Chloro-3-(3-chloro-benzyl)-2-oxo-2,3-dihydro-1H-indol-3-ylamino]-3-ethoxy-benzoic acid. MS: 471 (M+H)⁺.

EXAMPLE 288

Preparation of rac-5-Chloro-2-[6-chloro-3-(3-chloro-benzyl)-2-oxo-2,3-dihydro-1H-indol-3-ylamino]-benzoic acid

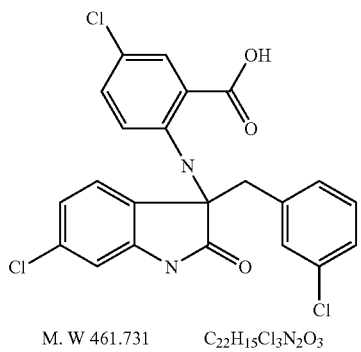

M. W 461.731   $C_{22}H_{15}Cl_3N_2O_3$

The title compound was prepared by the same procedure for rac-2-[6-Chloro-3-(3-chloro-benzyl)-2-oxo-2,3-dihydro-1H-indol-3-ylamino]-3-ethoxy-benzoic acid.

MS: 461 (M+H)⁺.

EXAMPLE 289

Preparation of rac-2-[6-Chloro-3-(3-chloro-benzyl)-2-oxo-2,3-dihydro-1H-indol-3-ylamino]-5-methyl-benzoic acid

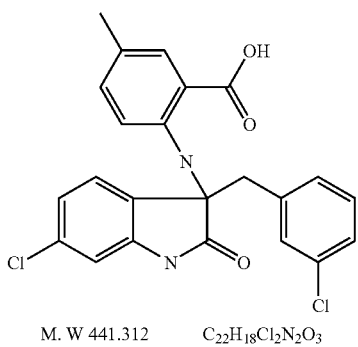

M. W 441.312    C22H18Cl2N2O3

The title compound was prepared by the same procedure for rac-2-[6-Chloro-3-(3-chloro-benzyl)-2-oxo-2,3-dihydro-1H-indol-3-ylamino]-3-ethoxy-benzoic acid.
MS: 441 (M+H)$^+$.

EXAMPLE 290

Preparation of rac-2-[6-Chloro-3-(3-chloro-benzyl)-2-oxo-2,3-dihydro-1H-indol-3-ylamino]-3,5-dimethyl-benzoic acid

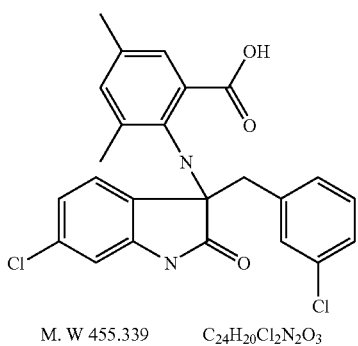

M. W 455.339    C24H20Cl2N2O3

The title compound was prepared by the same procedure for rac-2-[6-Chloro-3-(3-chloro-benzyl)-2-oxo-2,3-dihydro-1H-indol-3-ylamino]-3-ethoxy-benzoic acid. MS: 455 (M+H)$^+$.

EXAMPLE 291

Preparation of rac-6'-Chloro-3'-(3-chloro-benzyl)-2'-oxo-2,3,2',3'-tetrahydro-1'H-[1,3']biindolyl-2-carboxylic acid

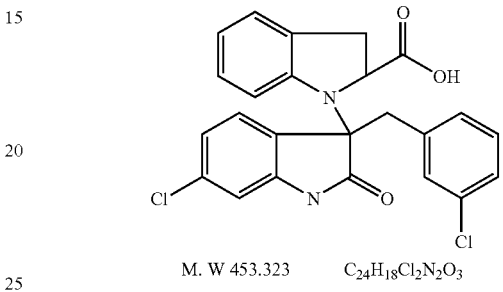

M. W 453.323    C24H18Cl2N2O3

The title compound was prepared by the same procedure for rac-2-[6-Chloro-3-(3-chloro-benzyl)-2-oxo-2,3-dihydro-1H-indol-3-ylamino]-3-ethoxy-benzoic acid.
MS: 453 (M+H)$^+$.

EXAMPLE 292

Preparation of rac-2-{[6-Chloro-3-(3-chloro-benzyl)-2-oxo-2,3-dihydro-1H-indol-3-yl]-piperidin-4-yl-amino}-N-cyclobutyl-acetamide

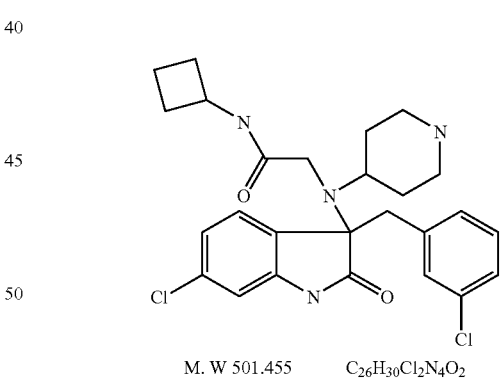

M. W 501.455    C26H30Cl2N4O2

At room temperature, 4-{[6-Chloro-3-(3-chloro-benzyl)-2-oxo-2,3-dihydro-1H-indol-3-yl]-cyclobutylcarbamoylmethyl-amino}-piperidine-1-carboxylic acid tert-butyl ester (700 mg, 1.17 mmol) was dissolved a mixture solution of CF$_3$COOH and CH$_2$Cl$_2$. After stirred 0.5 h, the solution was concentrated and the organic layer was washed with NaOH aqueous solution. The organic layer was dried, concentrated to obtain crude product. The crude product was purified by chromatography to obtain 200 mg rac-2-{[6-Chloro-3-(3-chloro-benzyl)-2-oxo-2,3-dihydro-1H-indol-3-yl]-piperidin-4-yl-amino}-N-cyclobutyl-acetamide.
MS: 501 (M+H)$^+$.

EXAMPLE 293

Preparation of rac-4-{[6-Chloro-3-(3-chloro-benzyl)-2-oxo-2,3-dihydro-1H-indol-3-yl]-cyclobutylcarbamoylmethyl-amino}-piperidine-1-carboxylic acid dimethylamide

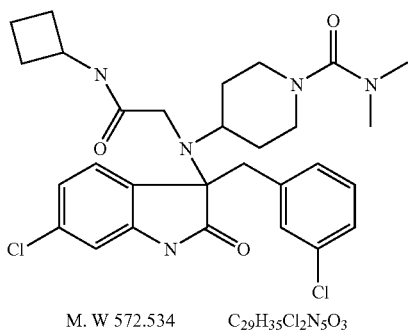

M. W 572.534    $C_{29}H_{35}Cl_2N_5O_3$

At room temperature, rac-2-{[6-Chloro-3-(3-chloro-benzyl)-2-oxo-2,3-dihydro-1H-indol-3-yl]-piperidin-4-yl-amino}-N-cyclobutyl-acetamide (77 mg, 0.154 mmol) and dimethylcarbamyl chloride (14 mg, 0.185 mmol) and $K_2CO_3$ were mixed in about 2 ml $CH_2Cl_2$. After stirred for about 1 h, the solution was concentrated and the crude product was purified by chromatography to obtain 20 mg solid rac-4-{[6-Chloro-3-(3-chloro-benzyl)-2-oxo-2,3-dihydro-1H-indol-3-yl]-cyclobutylcarbamoylmethyl-amino}-piperidine-1-carboxylic acid dimethylamide.

MS: 572 (M+H)$^+$.

EXAMPLE 294

Preparation of rac-2-{(1-Acetyl-piperidin-4-yl)-[6-chloro-3-(3-chloro-benzyl)-2-oxo-2,3-dihydro-1H-indol-3-yl]-amino}-N-cyclobutyl-acetamide

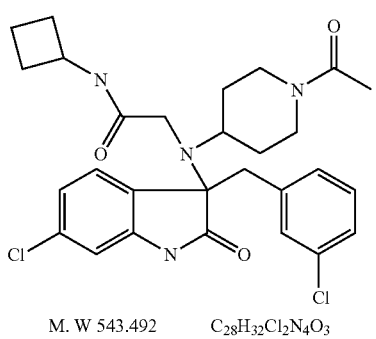

M. W 543.492    $C_{28}H_{32}Cl_2N_4O_3$

The title compound was prepared by the same procedure for rac-4-{[6-Chloro-3-(3-chloro-benzyl)-2-oxo-2,3-dihydro-1H-indol-3-yl]-cyclobutylcarbamoylmethyl-amino}-piperidine-1-carboxylic acid dimethylamide MS: 543 (M+H)$^+$.

EXAMPLE 295

Preparation of rac-4-{[6-Chloro-3-(3-chloro-benzyl)-2-oxo-2,3-dihydro-1H-indol-3-yl]-cyclobutylcarbamoylmethyl-amino}-piperidine-1-carboxylic acid tert-butyl ester

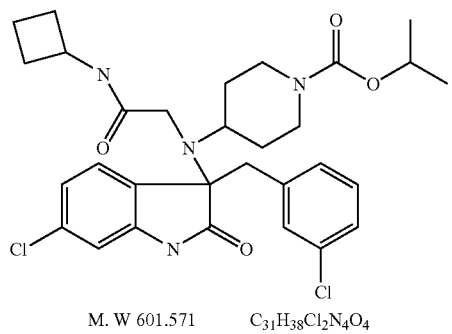

M. W 601.571    $C_{31}H_{38}Cl_2N_4O_4$

The title compound was prepared by the same procedure for rac-2-[6-Chloro-3-(3-chloro-benzyl)-2-oxo-2,3-dihydro-1H-indol-3-ylamino]-3-ethoxy-benzoic acid.

MS: 601 (M+H)$^+$.

EXAMPLE 296

Preparation of rac-3-[2-(4-Acetyl-piperazine-1-carbonyl)-6-isopropyl-phenylamino]-6-chloro-3-(3-chloro-benzyl)-1,3-dihydro-indol-2-one

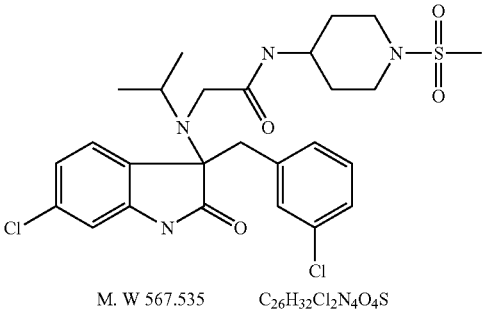

M. W 567.535    $C_{26}H_{32}Cl_2N_4O_4S$

The title compound was prepared by the same procedure for rac-2-[[6-Chloro-3-(3-chloro-benzyl)-2-oxo-2,3-dihydro-1H-indol-3-yl]-(3-chloro-phenyl)-amino]-N-cyclo-hexyl-acetamide MS: 579 (M+H)⁺.

EXAMPLE 297

Preparation of rac-2-{[6-Chloro-3-(3-chloro-benzyl)-2-oxo-2,3-dihydro-1H-indol-3-yl]-isopropyl-amino}-N-(1-methanesulfonyl-piperidin-4-yl)-acetamide

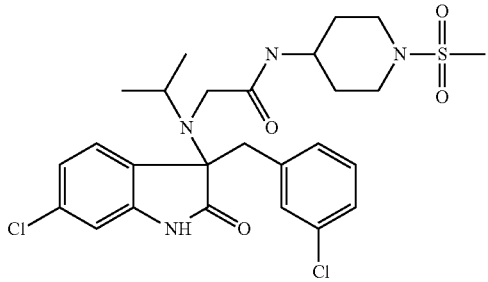

M.W 567.535    $C_{26}H_{32}Cl_2N_4O_4S$

The title compound was prepared by the same procedure for rac-4-{[6-Chloro-3-(3-chloro-benzyl)-2-oxo-2,3-dihydro-1H-indol-3-yl]-cyclobutylcarbamoylmethyl-amino}-piperidine-1-carboxylic acid dimethylamide
MS: 567 (M+H)⁺.

EXAMPLE 298

Preparation of rac-N-(1-Acetyl-piperidin-4-yl)-2-{[6-chloro-3-(3-chloro-benzyl)-2-oxo-2,3-dihydro-1H-indol-3-yl]-isopropyl-amino}-acetamide

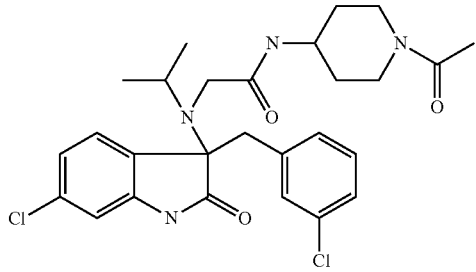

M. W 531.481    $C_{27}H_{32}Cl_2N_4O_3$

The title compound was prepared by the same procedure for rac-4-{[6-Chloro-3-(3-chloro-benzyl)-2-oxo-2,3-dihydro-1H-indol-3-yl]-cyclobutylcarbamoylmethyl-amino}-piperidine-1-carboxylic acid dimethylamide
MS: 531 (M+H)⁺.

EXAMPLE 299

Preparation of rac-2-{[6-Chloro-3-(3-chloro-benzyl)-2-oxo-2,3-dihydro-1H-indol-3-yl]-isopropyl-amino}-N-piperidin-4-yl-acetamide

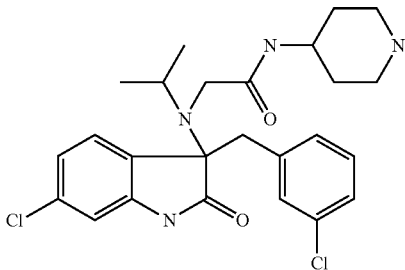

M. W 489.444    $C_{25}H_{30}Cl_2N_4O_2$

The title compound was prepared by the same procedure for rac-2-{[6-Chloro-3-(3-chloro-benzyl)-2-oxo-2,3-dihydro-1H-indol-3-yl]-piperidin-4-yl-amino}-N-cyclobutyl-acetamide MS: 489 (M+H)⁺.

EXAMPLE 300

Preparation of rac-4-(2-{[6-Chloro-3-(3-chloro-benzyl)-2-oxo-2,3-dihydro-1H-indol-3-yl]-isopropyl-amino}-acetylamino)-piperidine-1-carboxylic acid tert-butyl ester

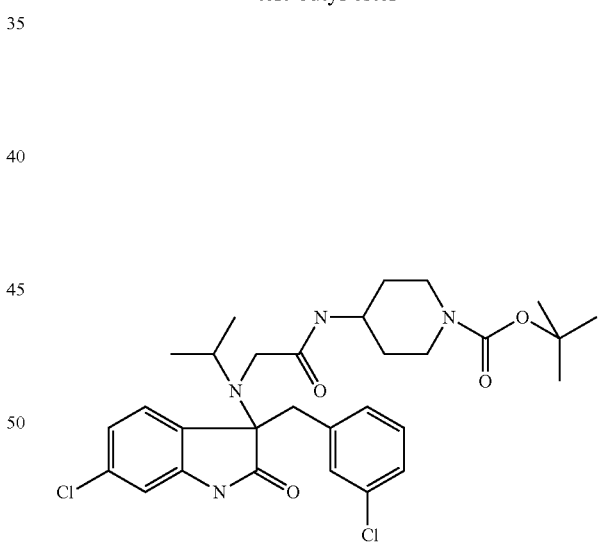

M. W 589.56    $C_{30}H_{38}Cl_2N_4O_4$

The title compound was prepared by the same procedure for rac-2-[[6-Chloro-3-(3-chloro-benzyl)-2-oxo-2,3-dihydro-1H-indol-3-yl]-(3-chloro-phenyl)-amino]-N-cyclo-hexyl-acetamide MS: 589 (M+H)+.

EXAMPLE 301

Preparation of rac-3-{2-[(1-Acetyl-piperidin-4-ylamino)-methyl]-5-bromo-phenylamino}-6-chloro-3-(3-chloro-benzyl)-1,3-dihydro-indol-2-one

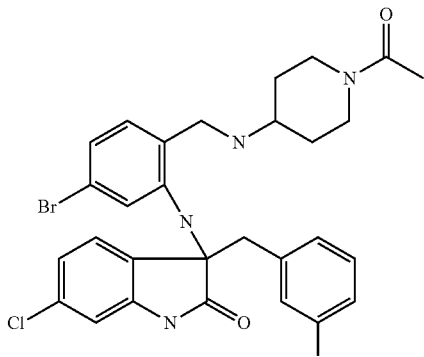

M. W 616.384  $C_{29}H_{29}BrCl_2N_4O_2$

The title compound was prepared by the same procedure for rac-4-{[6-Chloro-3-(3-chloro-benzyl)-2-oxo-2,3-dihydro-1H-indol-3-yl]-cyclobutylcarbamoylmethyl-amino}-piperidine-1-carboxylic acid dimethylamide
MS: 615 (M+H)+.

EXAMPLE 302

Preparation of rac-3-[2-(4-Acetyl-piperazin-1-ylmethyl)-5-bromo-phenylamino]-6-chloro-3-(3-chloro-benzyl)-1,3-dihydro-indol-2-one

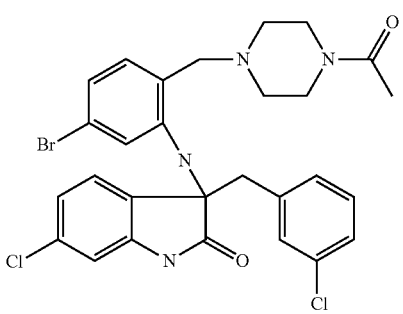

M. W 602.357  $C_{28}H_{27}BrCl_2N_4O_2$

At room temperature, 3-(5-Bromo-2-hydroxymethyl-phenylamino)-6-chloro-3-(3-chloro-benzyl)-1,3-dihydro-indol-2-one (100 mg, 0.137 mmol) was dissolved in 2 ml dried $CH_2Cl_2$. Then $SOCl_2$ (49 mg, 0.333 mmol) was added slowly. After stirred for about half an hour, K2CO3 (84 mg, 0.612 mmol) and 1-piperazin-1-yl-ethanone (32 mg, 0.245 mmol) were added. This solution was stirred for about 2 h, then the solution was concentrated and the crude product was purified by Prep-HPLC to obtain 7 mg white solid rac-3-[2-(4-Acetyl-piperazin-1-ylmethyl)-5-bromo-phenylamino]-6-chloro-3-(3-chloro-benzyl)-1,3-dihydro-indol-2-one.
MS: 601 (M+H)+.

EXAMPLE 303

Preparation of rac-3-{5-Bromo-2-[(1-methanesulfo-nyl-piperidin-4-ylamino)-methyl]-phenylamino}-6-chloro-3-(3-chloro-benzyl)-1,3-dihydro-indol-2-one

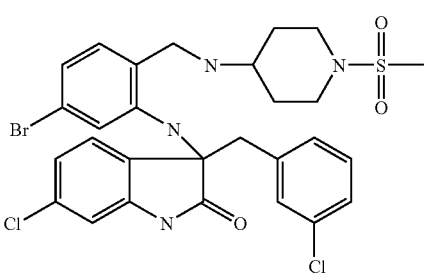

M. W. 652.438  $C_{28}H_{29}BrCl_2N_4O_3S$

The title compound was prepared by the same procedure for rac-4-{[6-Chloro-3-(3-chloro-benzyl)-2-oxo-2,3-dihydro-1H-indol-3-yl]-cyclobutylcarbamoylmethyl-amino}-piperidine-1-carboxylic acid dimethylamide
MS: 651 (M+H)+.

EXAMPLE 304

Preparation of rac-4-{4-Bromo-2-[6-chloro-3-(3-chloro-benzyl)-2-oxo-2,3-dihydro-1H-indol-3-ylamino]-benzylamino}-piperidine-1-carboxylic acid tert-butyl ester

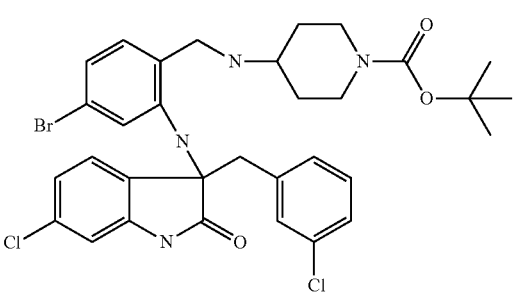

M. W 674.464  $C_{32}H_{35}BrCl_2N_4O_3$

The title compound was prepared by the same procedure for rac-3-[2-(4-Acetyl-piperazin-1-ylmethyl)-5-bromo-phenylamino]-6-chloro-3-(3-chloro-benzyl)-1,3-dihydro-indol-2-one MS: 673 (M+H)⁺.

EXAMPLE 305

Preparation of rac-3-(5-Bromo-2-cyclobutylaminomethyl-phenylamino)-6-chloro-3-(3-chloro-benzyl)-1,3-dihydro-indol-2-one

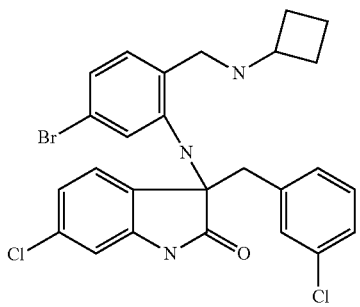

M. W 545.306  $C_{26}H_{24}BrCl_2N_3O$

The title compound was prepared by the same procedure for rac-3-[2-(4-Acetyl-piperazin-1-ylmethyl)-5-bromo-phenylamino]-6-chloro-3-(3-chloro-benzyl)-1,3-dihydro-indol-2-one MS: 544 (M+H)⁺.

EXAMPLE 306

Preparation of rac-3-(5-Bromo-2-morpholin-4-ylmethyl-phenylamino)-6-chloro-3-(3-chloro-benzyl)-1,3-dihydro-indol-2-one

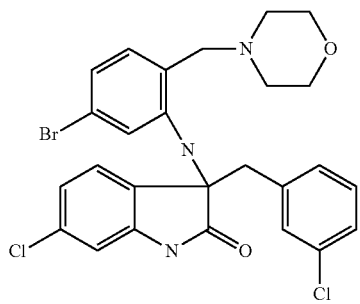

M. W 561.305  $C_{26}H_{24}BrCl_2N_3O_2$

The title compound was prepared by the same procedure for rac-3-[2-(4-Acetyl-piperazin-1-ylmethyl)-5-bromo-phenylamino]-6-chloro-3-(3-chloro-benzyl)-1,3-dihydro-indol-2-one MS: 560 (M+H)⁺.

EXAMPLE 307

Preparation of rac-3-(5-Bromo-2-hydroxymethyl-phenylamino)-6-chloro-3-(3-chloro-benzyl)-1,3-dihydro-indol-2-one

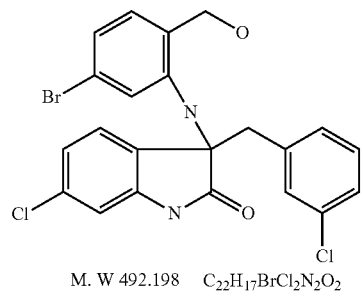

M. W 492.198  $C_{22}H_{17}BrCl_2N_2O_2$

The title compound was prepared by the same procedure for solid rac-{[6-Chloro-3-(3-chloro-benzyl)-2-oxo-2,3-dihydro-1H-indol-3-yl]-isopropyl-amino}-acetic acid ethyl ester.

MS: 491 (M+H)⁺.

EXAMPLE 308

Preparation of rac-4-Bromo-2-[6-chloro-3-(3-chloro-benzyl)-2-oxo-2,3-dihydro-1H-indol-3-ylamino]-N-(2-morpholin-4-yl-ethyl)-benzamide

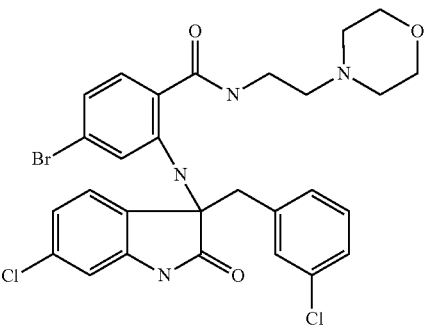

M. W 618.356  $C_{28}H_{27}BrCl_2N_4O_3$

The title compound was prepared by the same procedure for rac-2-[[6-Chloro-3-(3-chloro-benzyl)-2-oxo-2,3-dihydro-1H-indol-3-yl]-(3-chloro-phenyl)-amino]-N-cyclo-hexyl-acetamide MS: 617 (M+H)⁺.

EXAMPLE 309

Preparation of rac-N-(2-{4-Bromo-2-[6-chloro-3-(3-chloro-benzyl)-2-oxo-2,3-dihydro-1H-indol-3-ylamino]-benzylamino}-ethyl)-acetamide

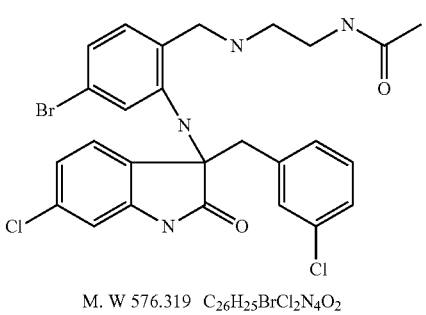

M. W 576.319   C$_{26}$H$_{25}$BrCl$_2$N$_4$O$_2$

The title compound was prepared by the same procedure for rac-3-[2-(4-Acetyl-piperazin-1-ylmethyl)-5-bromo-phenylamino]-6-chloro-3-(3-chloro-benzyl)-1,3-dihydro-indol-2-one. MS: 575 (M+H)⁺.

EXAMPLE 310

Preparation of rac-3-{5-Bromo-2-[(2,2-difluoro-ethylamino)-methyl]-phenylamino}-6-chloro-3-(3-chloro-benzyl)-1,3-dihydro-indol-2-one

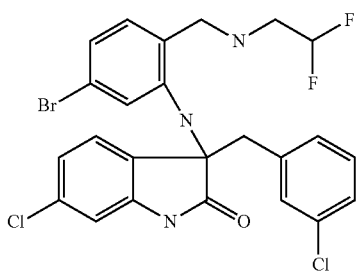

M. W 555.248   C$_{24}$H$_{20}$BrCl$_2$F$_2$N$_3$O

The title compound was prepared by the same procedure for rac-3-[2-(4-Acetyl-piperazin-1-ylmethyl)-5-bromo-phenylamino]-6-chloro-3-(3-chloro-benzyl)-1,3-dihydro-indol-2-one.

MS: 554 (M+H)⁺.

EXAMPLE 311

Preparation of rac-3-{5-Bromo-2-[(3-imidazol-1-yl-propylamino)-methyl]-phenylamino}-6-chloro-3-(3-chloro-benzyl)-1,3-dihydro-indol-2-one

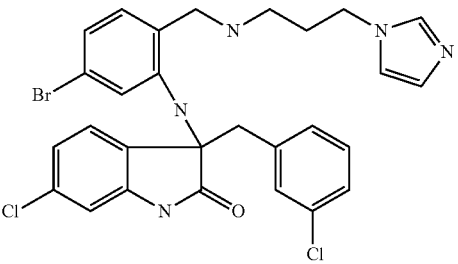

M. W 599.357   C$_{28}$H$_{26}$BrCl$_2$N$_5$O

The title compound was prepared by the same procedure for rac-3-[2-(4-Acetyl-piperazin-1-ylmethyl)-5-bromo-phenylamino]-6-chloro-3-(3-chloro-benzyl)-1,3-dihydro-indol-2-one.

MS: 598 (M+H)⁺

EXAMPLE 312

Preparation of rac-3-{5-Bromo-2-[(2,2,2-trifluoro-ethylamino)-methyl]-phenylamino}-6-chloro-3-(3-chloro-benzyl)-1,3-dihydro-indol-2-one

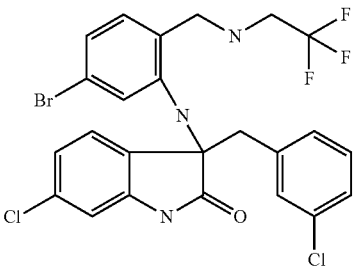

M. W 573.238   C$_{24}$H$_{19}$BrCl$_2$F$_3$N$_3$O

The title compound was prepared by the same procedure for rac-3-[2-(4-Acetyl-piperazin-1-ylmethyl)-5-bromo-phenylamino]-6-chloro-3-(3-chloro-benzyl)-1,3-dihydro-indol-2-one.

MS: 572 (M+H)⁺.

EXAMPLE 313

Preparation of rac-N-(2-Acetylamino-ethyl)-4-bromo-2-[6-chloro-3-(3-chloro-benzyl)-2-oxo-2,3-dihydro-1H-indol-3-ylamino]-benzamide

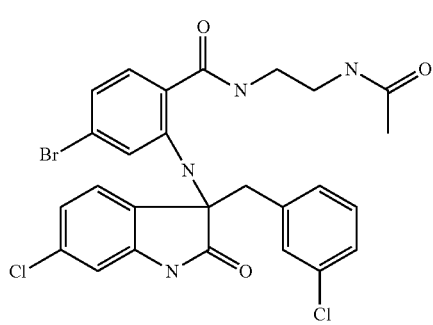

M. W 590.303    $C_{26}H_{23}BrCl_2N_4O_3$

The title compound was prepared by the same procedure for rac-2-[[6-Chloro-3-(3-chloro-benzyl)-2-oxo-2,3-dihydro-1H-indol-3-yl]-(3-chloro-phenyl)-amino]-N-cyclohexyl-acetamide MS: 589 (M+H)+.

EXAMPLE 314

Preparation of rac-4-Bromo-2-[6-chloro-3-(3-chlorobenzyl)-2-oxo-2,3-dihydro-1H-indol-3-ylamino]-N-(2,2-difluoro-ethyl)-benzamide

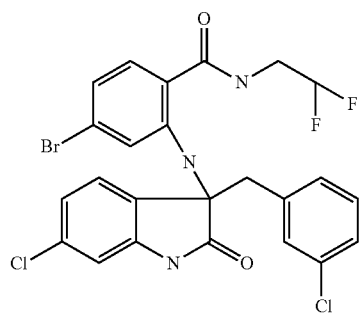

M. W 569.231    $C_{24}H_{18}BrCl_2F_2N_3O_2$

The title compound was prepared by the same procedure for rac-2-[[6-Chloro-3-(3-chloro-benzyl)-2-oxo-2,3-dihydro-1H-indol-3-yl]-(3-chloro-phenyl)-amino]-N-cyclohexyl-acetamide MS: 568 (M+H)+.

EXAMPLE 315

Preparation of rac-4-Bromo-2-[6-chloro-3-(3-chlorobenzyl)-2-oxo-2,3-dihydro-1H-indol-3-ylamino]-N-(3-imidazol-1-yl-propyl)-benzamide

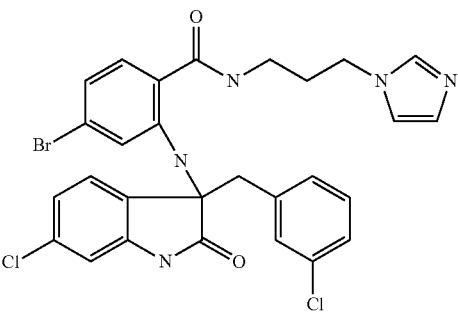

M. W 613.341    $C_{28}H_{24}BrCl_2N_5O_2$

The title compound was prepared by the same procedure for rac-2-[[6-Chloro-3-(3-chloro-benzyl)-2-oxo-2,3-dihydro-1H-indol-3-yl]-(3-chloro-phenyl)-amino]-N-cyclohexyl-acetamide MS: 612 (M+H)+.

EXAMPLE 316

Preparation of rac-4-Bromo-2-[6-chloro-3-(3-chlorobenzyl)-2-oxo-2,3-dihydro-1H-indol-3-ylamino]-N-(3-dimethylamino-propyl)-benzamide

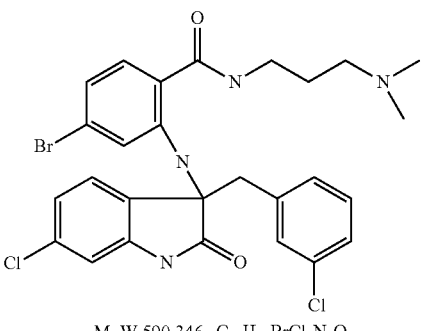

M. W 590.346    $C_{27}H_{27}BrCl_2N_4O_2$

The title compound was prepared by the same procedure for rac-2-[[6-Chloro-3-(3-chloro-benzyl)-2-oxo-2,3-dihydro-1H-indol-3-yl]-(3-chloro-phenyl)-amino]-N-cyclohexyl-acetamide MS: 589 (M+H)+.

EXAMPLE 317

Preparation of rac-4-Bromo-2-[6-chloro-3-(3-chlorobenzyl)-2-oxo-2,3-dihydro-1H-indol-3-ylamino]-N-(2,2,2-trifluoro-ethyl)-benzamide

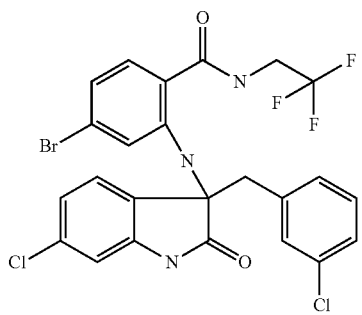

M. W 587.221  $C_{24}H_{17}BrCl_2F_3N_3O_2$

The title compound was prepared by the same procedure for rac-2-[[6-Chloro-3-(3-chloro-benzyl)-2-oxo-2,3-dihydro-1H-indol-3-yl]-(3-chloro-phenyl)-amino]-N-cyclohexyl-acetamide MS: 586 (M+H)+.

EXAMPLE 318

Preparation of rac-3-{5-Bromo-2-[(3-morpholin-4-yl-propylamino)-methyl]-phenylamino}-6-chloro-3-(3-chloro-benzyl)-1,3-dihydro-indol-2-one

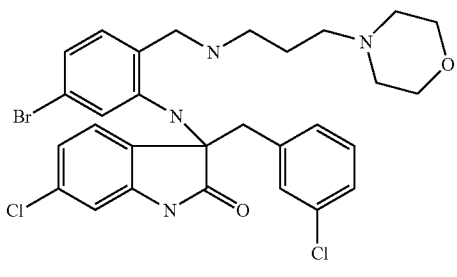

M. W. 618.4  $C_{29}H_{31}BrCl_2N_4O_2$

The title compound was prepared by the same procedure for rac-3-[2-(4-Acetyl-piperazin-1-ylmethyl)-5-bromo-phenylamino]-6-chloro-3-(3-chloro-benzyl)-1,3-dihydro-indol-2-one
MS: 617 (M+H)+.

EXAMPLE 319

Preparation of rac-3-{5-Bromo-2-[(2-morpholin-4-yl-ethylamino)-methyl]-phenylamino}-6-chloro-3-(3-chloro-benzyl)-1,3-dihydro-indol-2-one

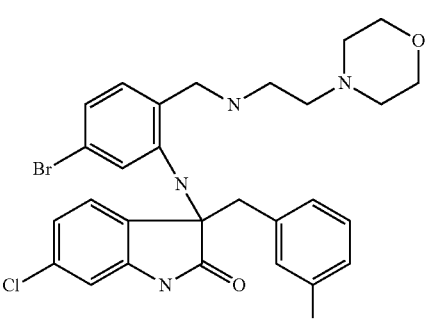

M. W 604.373  $C_{28}H_{29}BrCl_2N_4O_2$

The title compound was prepared by the same procedure for rac-3-[2-(4-Acetyl-piperazin-1-ylmethyl)-5-bromo-phenylamino]-6-chloro-3-(3-chloro-benzyl)-1,3-dihydro-indol-2-one MS: 603 (M+H)+.

EXAMPLE 320

Preparation of rac-3-{5-Bromo-2-[4-(2-methanesulfonyl-ethyl)-piperazine-1-carbonyl]-phenylamino}-6-chloro-3-(3-chloro-benzyl)-1,3-dihydro-indol-2-one

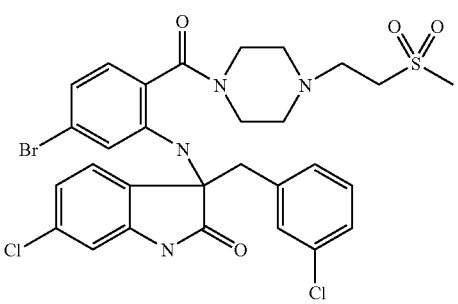

M. W 680.448  $C_{29}H_{29}BrCl_2N_4O_4S$

The title compound was prepared by the same procedure for rac-2-[[6-Chloro-3-(3-chloro-benzyl)-2-oxo-2,3-dihydro-1H-indol-3-yl]-(3-chloro-phenyl)-amino]-N-cyclohexyl-acetamide MS: 679 (M+H)⁺.

EXAMPLE 321

Preparation of rac-4-Chloro-2-{[6-chloro-3-(3-chloro-benzyl)-2-oxo-2,3-dihydro-1H-indol-3-yl]-methyl-amino}-benzoic acid

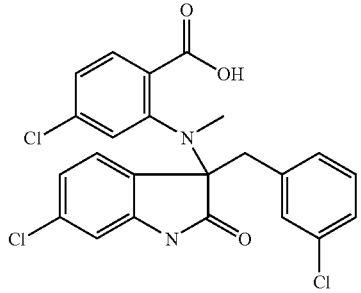

M. W 475.757    $C_{23}H_{17}Cl_3N_2O_3$

At room temperature, 3-Bromo-6-chloro-3-(3-chloro-benzyl)-1,3-dihydro-indol-2-one (800 mg, 2.16 mmol), 4-Chloro-2-methylamino-benzoic acid (400 mg, 2.16 mmol) and K2CO3 (298 mg, 2.16 mmol) were dissolved in about 8 ml DMSO. After stirred for about 2 h, the solution was poured into water to obtain the crude product. The crude product was purified by chromatography to obtain 600 mg solid rac-4-Chloro-2-{[6-chloro-3-(3-chloro-benzyl)-2-oxo-2,3-dihydro-1H-indol-3-yl]-methyl-amino}-benzoic acid

MS: 475 (M+H)⁺.

EXAMPLE 322

Preparation of rac-6-Chloro-3-(3-chloro-benzyl)-3-{[5-chloro-2-(morpholine-4-carbonyl)-phenyl]-methyl-amino}-1,3-dihydro-indol-2-one

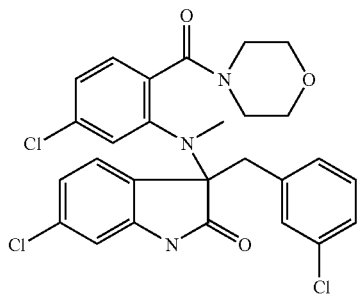

M. W 544.864    $C_{27}H_{24}Cl_3N_3O_3$

The title compound was prepared by the same procedure for rac-2-[[6-Chloro-3-(3-chloro-benzyl)-2-oxo-2,3-dihy-dro-1H-indol-3-yl]-(3-chloro-phenyl)-amino]-N-cyclohexyl-acetamide MS: 544 (M+H)⁺.

EXAMPLE 323

Preparation of rac-4-Chloro-2-{[6-chloro-3-(3-chloro-benzyl)-2-oxo-2,3-dihydro-1H-indol-3-yl]-methyl-amino}-N-(3-imidazol-1-yl-propyl)-benzamide

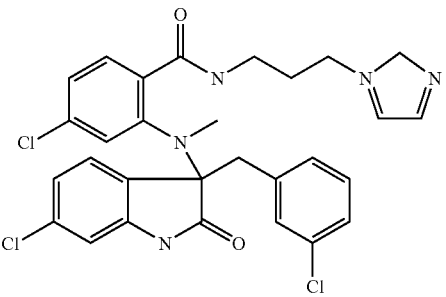

M. W 582.916    $C_{29}H_{28}Cl_3N_5O_2$

The title compound was prepared by the same procedure for rac-2-[[6-Chloro-3-(3-chloro-benzyl)-2-oxo-2,3-dihydro-1H-indol-3-yl]-(3-chloro-phenyl)-amino]-N-cyclohexyl-acetamide MS: 582 (M+H)⁺.

EXAMPLE 324

Preparation of rac-N-(2-Acetylamino-ethyl)-4-chloro-2-{[6-chloro-3-(3-chloro-benzyl)-2-oxo-2,3-dihydro-1H-indol-3-yl]-methyl-amino}-benzamide

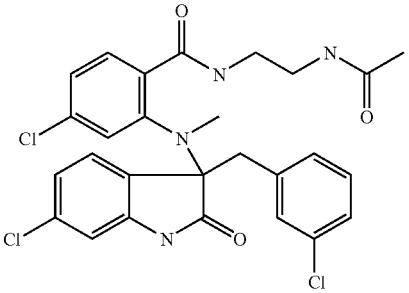

M. W 559.879    $C_{27}H_{25}Cl_3N_4O_3$

The title compound was prepared by the same procedure for rac-2-[[6-Chloro-3-(3-chloro-benzyl)-2-oxo-2,3-dihydro-1H-indol-3-yl]-(3-chloro-phenyl)-amino]-N-cyclohexyl-acetamide MS: 559 (M+H)⁺.

EXAMPLE 325

Preparation of rac-4-Chloro-2-{[6-chloro-3-(3-chloro-benzyl)-2-oxo-2,3-dihydro-1H-indol-3-yl]-methyl-amino}-N-(3-dimethylamino-propyl)-benzamide

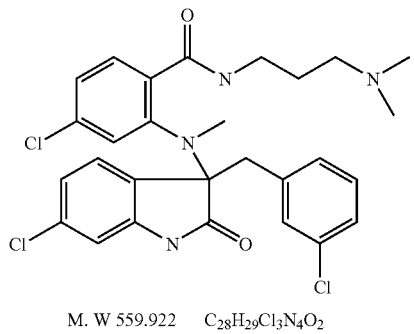

M. W 559.922   $C_{28}H_{29}Cl_3N_4O_2$

The title compound was prepared by the same procedure for rac-2-[[6-Chloro-3-(3-chloro-benzyl)-2-oxo-2,3-dihydro-1H-indol-3-yl]-(3-chloro-phenyl)-amino]-N-cyclohexyl-acetamide MS: 559 (M+H)⁺.

EXAMPLE 326

Preparation of rac-2-{[6-Chloro-3-(3-chloro-benzyl)-2-oxo-2,3-dihydro-1H-indol-3-yl]-cyclohexyl-amino}-N-cyclopentyl-acetamide

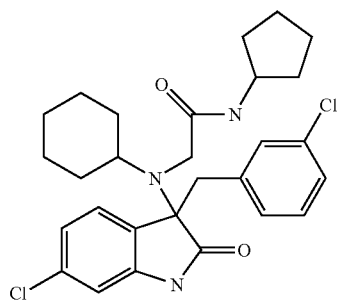

M. W. 514.50   $C_{28}H_{33}Cl_2N_3O_2$

The title compound was prepared by the same procedure for rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 514 (M+H)⁺.

EXAMPLE 327

Preparation of rac-{[6-Chloro-3-(3-chloro-benzyl)-2-oxo-2,3-dihydro-1H-indol-3-yl]-cyclopentyl-amino}-acetic acid ethyl ester

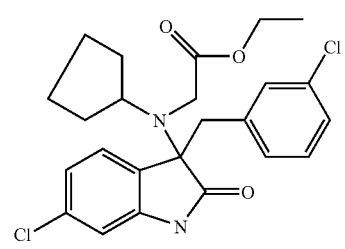

M. W. 461.39   $C_{24}H_{26}Cl_2N_2O_3$

The title compound was prepared by the same procedure for rac-{[6-chloro-3-(3-chloro-benzyl)-2-oxo-2,3-dihydro-1H-indol-3-yl]-cyclohexyl-amino}-acetic acid ethyl ester. MS: 461 (M+H)⁺.

EXAMPLE 328

Preparation of rac-{[6-Chloro-3-(3-chloro-benzyl)-2-oxo-2,3-dihydro-1H-indol-3-yl]-cycloheptyl-amino}-acetic acid ethyl ester

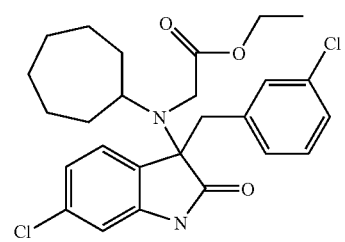

M. W. 489.45   $C_{26}H_{30}Cl_2N_2O_3$

The title compound was prepared by the same procedure for rac-{[6-chloro-3-(3-chloro-benzyl)-2-oxo-2,3-dihydro-1H-indol-3-yl]-cyclohexyl-amino}-acetic acid ethyl ester. MS: 489 (M+H)⁺.

EXAMPLE 329

Preparation of rac-{[6-Chloro-3-(3-chloro-benzyl)-2-oxo-2,3-dihydro-1H-indol-3-yl]-cyclobutyl-amino}-acetic acid ethyl ester

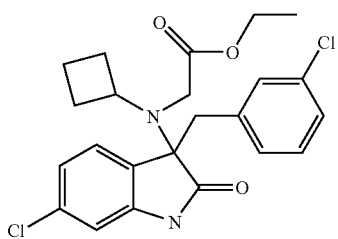

M. W. 447.37   $C_{23}H_{24}Cl_2N_2O_3$

The title compound was prepared by the same procedure for rac-{[6-chloro-3-(3-chloro-benzyl)-2-oxo-2,3-dihydro-1H-indol-3-yl]-cyclohexyl-amino}-acetic acid ethyl ester. MS: 447 (M+H)⁺.

EXAMPLE 330

Preparation of rac-{[6-Chloro-3-(3-chloro-benzyl)-2-oxo-2,3-dihydro-1H-indol-3-yl]-cyclopentyl-amino}-acetic acid

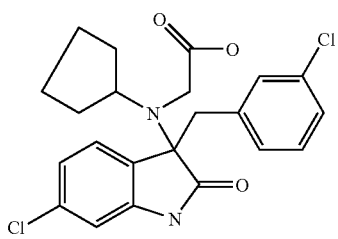

M. W. 433.34   $C_{22}H_{22}Cl_2N_2O_3$

The title compound was prepared by the same procedure rac-{[6-chloro-3-(3-chloro-benzyl)-2-oxo-2,3-dihydro-1H-indol-3-yl]-cyclohexyl-amino}-acetic acid. MS: 433 (M+H)⁺.

EXAMPLE 331

Preparation of rac-{[6-Chloro-3-(3-chloro-benzyl)-2-oxo-2,3-dihydro-1H-indol-3-yl]-cyclobutyl-amino}-acetic acid

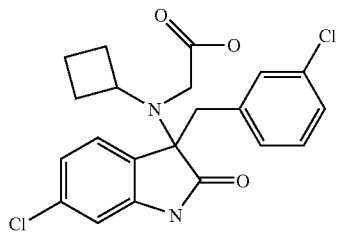

M. W. 461.39   $C_{24}H_{26}Cl_2N_2O_3$

The title compound was prepared by the same procedure for rac-{[6-chloro-3-(3-chloro-benzyl)-2-oxo-2,3-dihydro-1H-indol-3-yl]-cyclohexyl-amino}-acetic acid. MS: 461 (M+H)⁺.

EXAMPLE 332

Preparation of rac-2-{[6-Chloro-3-(3-chloro-benzyl)-2-oxo-2,3-dihydro-1H-indol-3-yl]-cyclobutyl-amino}-N-cyclobutyl-acetamide

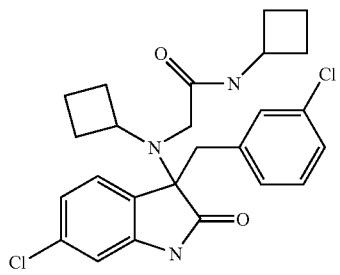

M. W. 472.42   $C_{25}H_{27}Cl_2N_3O_2$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 472 (M+H)$^+$.

EXAMPLE 333

Preparation of rac-2-{[6-Chloro-3-(3-chloro-benzyl)-2-oxo-2,3-dihydro-1H-indol-3-yl]-cyclobutyl-amino}-N-cyclopentyl-acetamide

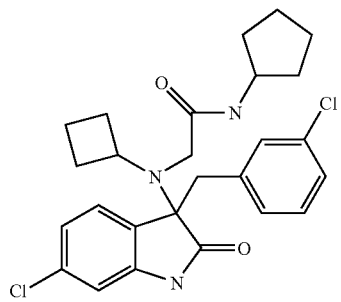

M. W. 486.45   $C_{26}H_{29}Cl_2N_3O_2$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 486 (M+H)$^+$.

EXAMPLE 334

Preparation of rac-2-{[6-Chloro-3-(3-chloro-benzyl)-2-oxo-2,3-dihydro-1H-indol-3-yl]-cyclobutyl-amino}-N-cyclohexyl-acetamide

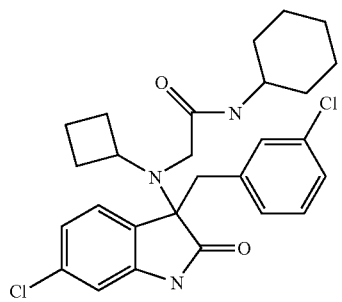

M. W. 500.47   $C_{27}H_{31}Cl_2N_3O_2$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 500 (M+H)$^+$.

EXAMPLE 335

Preparation of rac-2-{[6-Chloro-3-(3-chloro-benzyl)-2-oxo-2,3-dihydro-1H-indol-3-yl]-cyclobutyl-amino}-N-cyclopropyl-acetamide

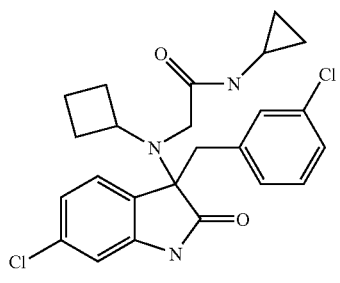

M. W. 458.39   $C_{24}H_{25}Cl_2N_3O_2$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 458 (M+H)$^+$.

EXAMPLE 336

Preparation of rac-6-Chloro-3-(3-chloro-benzyl)-3-(cyclobutyl-{2-[4-(2-hydroxy-ethyl)-piperazin-1-yl]-2-oxo-ethyl}-amino)-1,3-dihydro-indol-2-one

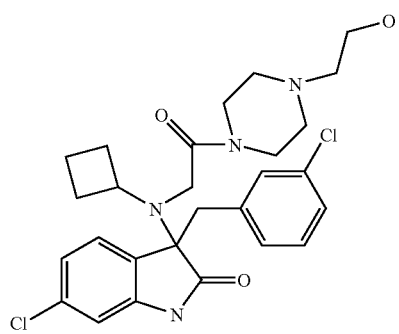

M. W. 531.49   $C_{27}H_{32}Cl_2N_4O_3$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 531 (M+H)⁺.

EXAMPLE 337

Preparation of rac-1-(2-{[6-Chloro-3-(3-chloro-benzyl)-2-oxo-2,3-dihydro-1H-indol-3-yl]-cyclobutyl-amino}-acetyl)-piperidine-4-carboxylic acid amide

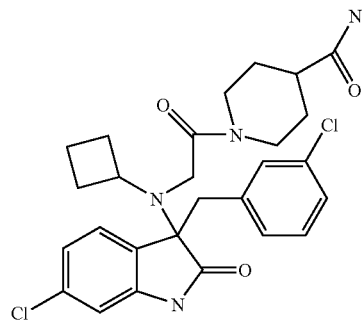

M. W. 529.47   $C_{27}H_{30}Cl_2N_4O_3$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 529 (M+H)⁺.

EXAMPLE 338

Preparation of rac-2-{[6-Chloro-3-(3-chloro-benzyl)-2-oxo-2,3-dihydro-1H-indol-3-yl]-cyclopentyl-amino}-N-cyclopropyl-acetamide

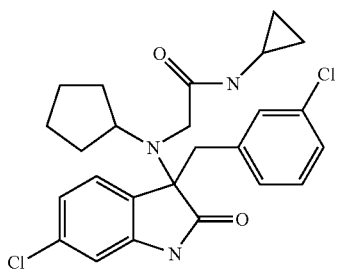

M. W. 472.42   $C_{25}H_{27}Cl_2N_3O_2$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 472 (M+H)⁺.

EXAMPLE 339

Preparation of rac-2-{[6-Chloro-3-(3-chloro-benzyl)-2-oxo-2,3-dihydro-1H-indol-3-yl]-cyclopentyl-amino}-N-cyclobutyl-acetamide

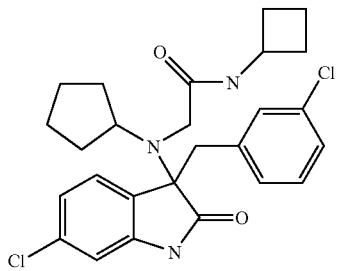

M. W. 486.45   $C_{26}H_{29}Cl_2N_3O_2$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 486 (M+H)⁺.

EXAMPLE 340

Preparation of rac-2-{[6-Chloro-3-(3-chloro-benzyl)-2-oxo-2,3-dihydro-1H-indol-3-yl]-cyclopentyl-amino}-N-cyclopentyl-acetamide

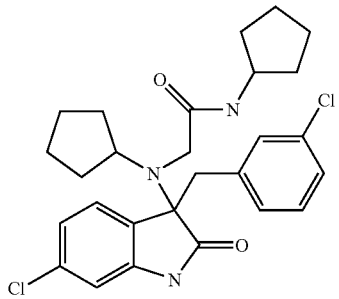

M. W. 500.47   $C_{27}H_{31}Cl_2N_3O_2$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 500 (M+H)$^+$.

EXAMPLE 341

Preparation of rac-2-{[6-Chloro-3-(3-chloro-benzyl)-2-oxo-2,3-dihydro-1H-indol-3-yl]-cyclopentyl-amino}-N-cyclohexyl-acetamide

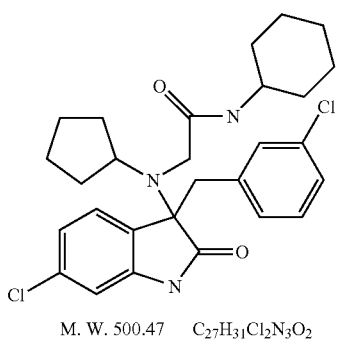

M. W. 500.47    $C_{27}H_{31}Cl_2N_3O_2$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 500 (M+H)$^+$.

EXAMPLE 342

Preparation of rac-6-Chloro-3-(3-chloro-benzyl)-3-(cyclopentyl-{2-[4-(2-hydroxy-ethyl)-piperazin-1-yl]-2-oxo-ethyl}-amino)-1,3-dihydro-indol-2-one

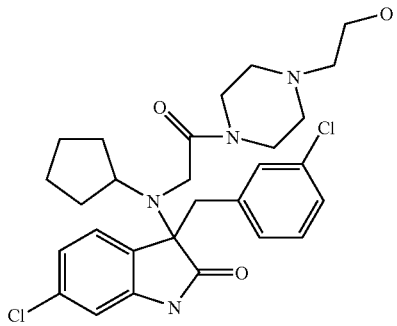

M. W. 545.51    $C_{28}H_{34}Cl_2N_4O_3$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 545 (M+H)$^+$.

EXAMPLE 343

Preparation of rac-1-(2-{[6-Chloro-3-(3-chloro-benzyl)-2-oxo-2,3-dihydro-1H-indol-3-yl]-cyclopentyl-amino}-acetyl)-piperidine-4-carboxylic acid amide

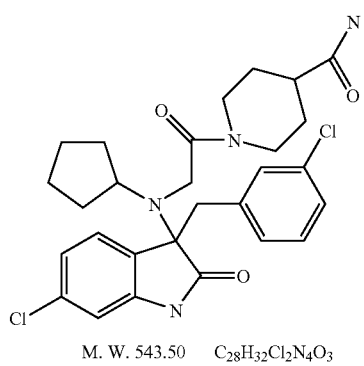

M. W. 543.50    $C_{28}H_{32}Cl_2N_4O_3$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 543 (M+H)$^+$.

EXAMPLE 344

Preparation of rac-2-{[6-Chloro-3-(3-chloro-benzyl)-2-oxo-2,3-dihydro-1H-indol-3-yl]-cycloheptyl-amino}-N-cyclopropyl-acetamide

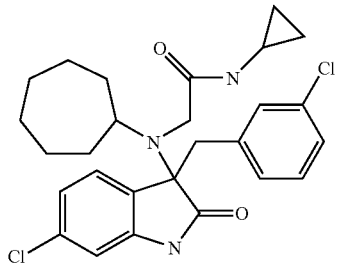

M. W. 500.47    $C_{27}H_{31}Cl_2N_3O_2$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 500 (M+H)+.

EXAMPLE 345

Preparation of rac-2-{[6-Chloro-3-(3-chloro-benzyl)-2-oxo-2,3-dihydro-1H-indol-3-yl]-cycloheptyl-amino}-N-cyclobutyl-acetamide

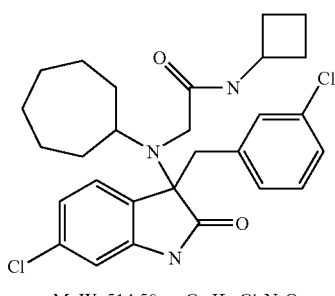

M. W. 514.50    $C_{28}H_{33}Cl_2N_3O_2$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 514 (M+H)+.

EXAMPLE 346

Preparation of rac-2-{[6-Chloro-3-(3-chloro-benzyl)-2-oxo-2,3-dihydro-1H-indol-3-yl]-cycloheptyl-amino}-N-cyclopentyl-acetamide

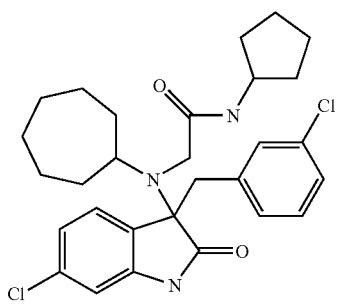

M. W. 528.53    $C_{29}H_{35}Cl_2N_3O_2$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 528 (M+H)+.

EXAMPLE 347

Preparation of rac-2-{[6-Chloro-3-(3-chloro-benzyl)-2-oxo-2,3-dihydro-1H-indol-3-yl]-cycloheptyl-amino}-N-cyclohexyl-acetamide

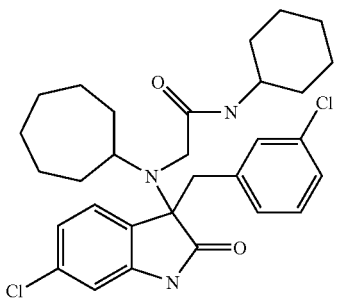

M. W. 542.55    $C_{30}H_{37}Cl_2N_3O_2$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 542 (M+H)+.

EXAMPLE 348

Preparation of rac-6-Chloro-3-(3-chloro-benzyl)-3-(cycloheptyl-{2-[4-(2-hydroxy-ethyl)-piperazin-1-yl]-2-oxo-ethyl}-amino)-1,3-dihydro-indol-2-one

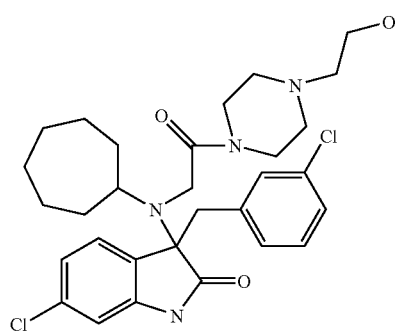

M. W. 573.57    $C_{30}H_{38}Cl_2N_4O_3$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 573 (M+H)+.

EXAMPLE 349

Preparation of rac-1-(2-{[6-Chloro-3-(3-chloro-benzyl)-2-oxo-2,3-dihydro-1H-indol-3-yl]-cycloheptyl-amino}-acetyl)-piperidine-4-carboxylic acid amide

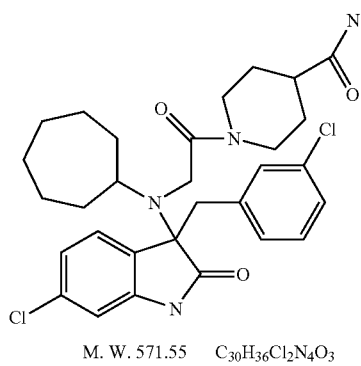

M. W. 571.55    $C_{30}H_{36}Cl_2N_4O_3$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 571 (M+H)+.

EXAMPLE 350

Preparation of rac-(S)-2-[6-Chloro-3-(3-chloro-benzyl)-2-oxo-2,3-dihydro-1H-indol-3-ylamino]-2,4-dimethyl-pentanoic acid cyclopropylamide

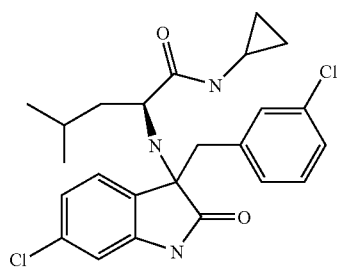

M. W. 474.43    $C_{25}H_{29}Cl_2N_3O_2$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 474 (M+H)+.

EXAMPLE 351

Preparation of rac-(S)-2-[6-Chloro-3-(3-chloro-benzyl)-2-oxo-2,3-dihydro-1H-indol-3-ylamino]-4-methyl-pentanoic acid cyclobutylamide

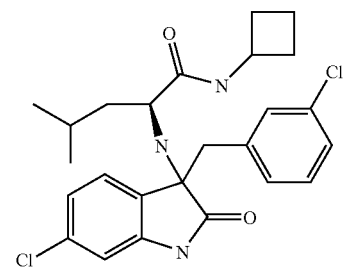

M. W. 488.46    $C_{26}H_{31}Cl_2N_3O_2$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 488 (M+H)+.

EXAMPLE 352

Preparation of rac-(S)-2-[6-Chloro-3-(3-chloro-benzyl)-2-oxo-2,3-dihydro-1H-indol-3-ylamino]-4-methyl-pentanoic acid cyclopentylamide

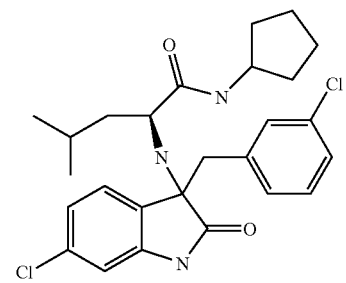

M. W. 502.49    $C_{27}H_{33}Cl_2N_3O_2$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 502 (M+H)+.

EXAMPLE 353

Preparation of rac-(S)-2-[6-Chloro-3-(3-chloro-benzyl)-2-oxo-2,3-dihydro-1H-indol-3-ylamino]-4-methyl-pentanoic acid cyclohexylamide

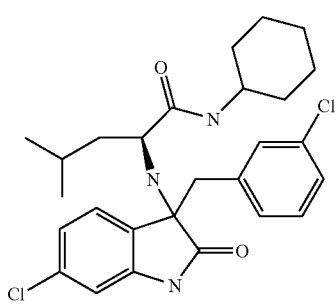

M. W. 516.52    C$_{28}$H$_{35}$Cl$_2$N$_3$O$_2$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 516 (M+H)+.

EXAMPLE 354

Preparation of rac-2-{[6-Chloro-3-(3-chloro-benzyl)-2-oxo-2,3-dihydro-1H-indol-3-yl]-cyclohexyl-amino}-acetamide

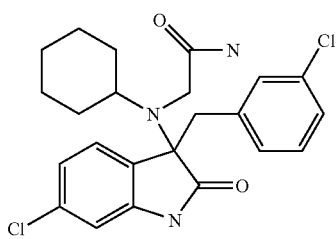

M. W. 446.38    C$_{23}$H$_{25}$Cl$_2$N$_3$O$_2$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 446 (M+H)+.

EXAMPLE 355

Preparation of rac-6'-Chloro-3'-(3-chloro-benzyl)-6-methoxy-2'-oxo-2',3'-dihydro-1'H-[1,3']biindolyl-2-carboxylic acid methyl ester

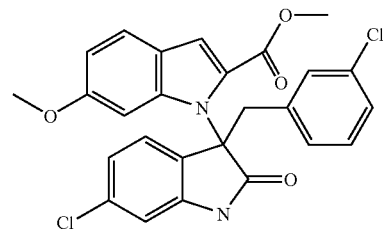

M. W. 495.37    C$_{26}$H$_{20}$Cl$_2$N$_2$O$_4$

To the solution of rac-6'-Chloro-3'-(3-chloro-benzyl)-6-methoxy-2'-oxo-2,3,2',3'-tetrahydro-1'H-[1,3']biindolyl-2-carboxylic acid methyl ester (0.65 g, 1.31 mmol) in 10 mL toluene was added DDQ (0.51 g, 2.23 mmol). The reaction mixture was stirred at room temperature for 6 hour. And the mixture was washed with water (3×10 mL). The organic solution was dried with Na$_2$SO$_4$ and concentrated in vacuo. The residue was purified with chromatography to give white solid. MS: 495 (M+H)+.

EXAMPLE 356

Preparation of rac-{[6-Chloro-3-(3-chloro-benzyl)-2-oxo-2,3-dihydro-1H-indol-3-yl]-cycloheptyl-amino}-acetic acid

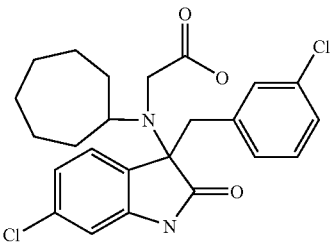

M. W. 460.13    C$_{24}$H$_{26}$Cl$_2$N$_2$O$_3$

The title compound was prepared by the same procedure for rac-{[6-chloro-3-(3-chloro-benzyl)-2-oxo-2,3-dihydro-1H-indol-3-yl]-cyclohexyl-amino}-acetic acid. MS: 461 (M+H)⁺.

EXAMPLE 357

Preparation of rac-6'-Chloro-3'-(3-chloro-benzyl)-6-methoxy-2'-oxo-2',3'-dihydro-1'H-[1,3']biindolyl-2-carboxylic acid

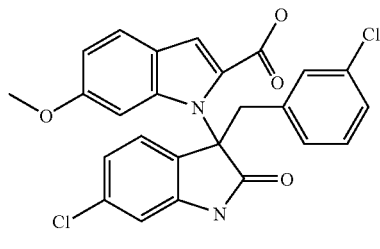

M. W. 481.34    C₂₅H₁₈Cl₂N₂O₄

The title compound was prepared by the same procedure for rac-{[6-chloro-3-(3-chloro-benzyl)-2-oxo-2,3-dihydro-1H-indol-3-yl]-cyclohexyl-amino}-acetic acid. MS: 481 (M+H)⁺.

EXAMPLE 358

Preparation of rac-2-{[6-Chloro-3-(3-chloro-benzyl)-2-oxo-2,3-dihydro-1H-indol-3-yl]-cyclohexyl-amino}-N,N-dimethyl-acetamide

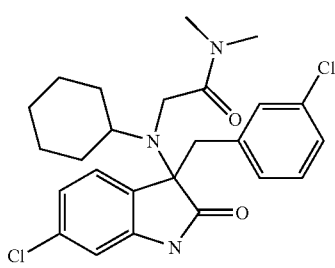

M. W. 474.43    C₂₅H₂₉Cl₂N₃O₂

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 474 (M+H)⁺.

EXAMPLE 359

Preparation of rac-2-{[6-Chloro-3-(3-chloro-benzyl)-2-oxo-2,3-dihydro-1H-indol-3-yl]-cyclohexyl-amino}-N-methyl-acetamide

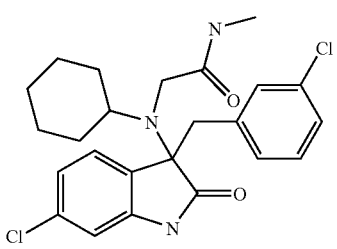

M. W. 460.41    C₂₄H₂₇Cl₂N₃O₂

The title compound was prepared by the same procedure for rac-6-chloro-3-(3-chloro-benzyl)-3-(4-propoxy-phenylamino)-1,3-dihydro-indol-2-one. MS: 460 (M+H)⁺.

EXAMPLE 360

Preparation of rac-6'-Chloro-3'-(3-chloro-benzyl)-6-methoxy-2'-oxo-2',3'-dihydro-1'H-[1,3']biindolyl-2-carboxylic acid cyclobutylamide

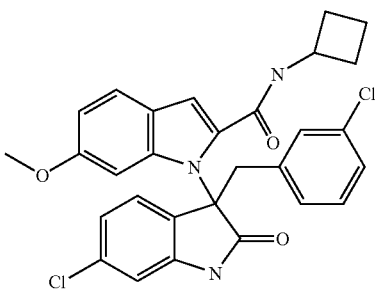

M. W. 534.45    C₂₉H₂₅Cl₂N₃O₃

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 534 (M+H)+.

EXAMPLE 361

Preparation of rac-6'-Chloro-3'-(3-chloro-benzyl)-6-methoxy-2'-oxo-2',3'-dihydro-1'H-[1,3']biindolyl-2-carboxylic acid cyclohexylamide

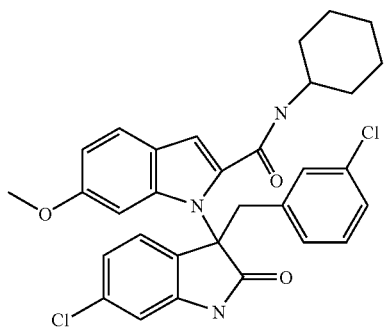

M. W. 562.50    $C_{31}H_{29}Cl_2N_3O_3$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 562 (M+H)+.

EXAMPLE 362

Preparation of rac-1-[6'-Chloro-3'-(3-chloro-benzyl)-6-methoxy-2'-oxo-2',3'-dihydro-1'H-[1,3']biindolyl-2-carbonyl]-piperidine-4-carboxylic acid amide

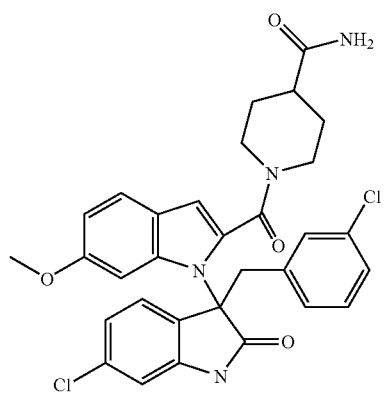

M. W. 591.50    $C_{31}H_{28}Cl_2N_4O_4$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 591 (M+H)+.

EXAMPLE 363

Preparation of rac-6'-Chloro-3'-(3-chloro-benzyl)-2-[4-(2-hydroxy-ethyl)-piperazine-1-carbonyl]-6-methoxy-1',3'-dihydro-[1,3']biindolyl-2'-one

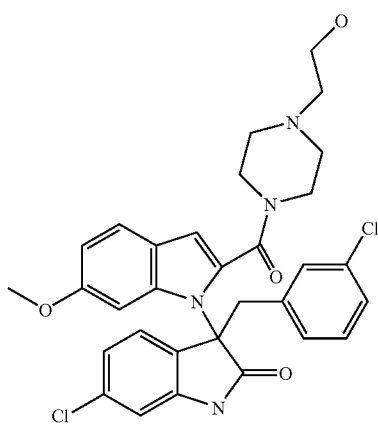

M. W. 593.52    $C_{31}H_{30}Cl_2N_4O_4$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 593 (M+H)+.

EXAMPLE 364

Preparation of rac-6'-Chloro-3'-(3-chloro-benzyl)-6-methoxy-2-(morpholine-4-carbonyl)-1',3'-dihydro-[1,3']biindolyl-2'-one

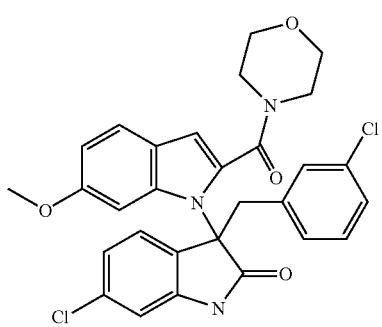

M. W. 550.45    $C_{29}H_{25}Cl_2N_3O_4$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 550 (M+H)⁺.

EXAMPLE 365

Preparation of rac-2-[6-Chloro-3-(3-chloro-benzyl)-2-oxo-2,3-dihydro-1H-indol-3-ylamino]-3-methyl-benzoic acid

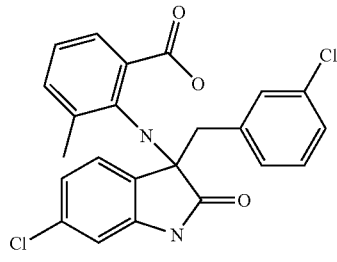

M. W. 441.32    C₂₃H₁₈Cl₂N₂O₃

The title compound was prepared by the same procedure for rac-3-[6-chloro-3-(3-chloro-benzyl)-2-oxo-2,3-dihydro-1H-indol-3-ylamino]-benzoic acid. MS: 441 (M+H)⁺.

EXAMPLE 366

Preparation of rac-2-[6-Chloro-3-(3-chloro-benzyl)-2-oxo-2,3-dihydro-1H-indol-3-ylamino]-4-fluoro-benzoic acid

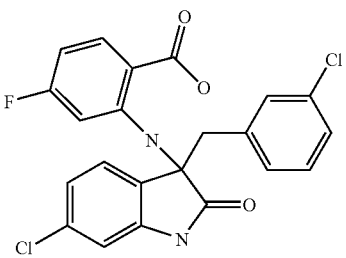

M. W. 445.28    C₂₂H₁₅Cl₂N₂O₃

The title compound was prepared by the same procedure for rac-3-[6-chloro-3-(3-chloro-benzyl)-2-oxo-2,3-dihydro-1H-indol-3-ylamino]-benzoic acid. MS: 445 (M+H)⁺.

EXAMPLE 367

Preparation of rac-2-[6-Chloro-3-(3-chloro-benzyl)-2-oxo-2,3-dihydro-1H-indol-3-ylamino]-N-cyclobutyl-3-methyl-benzamide

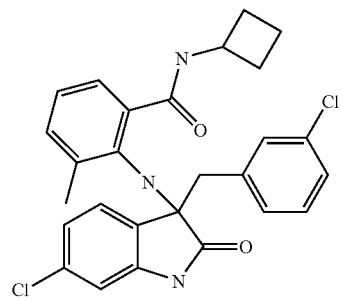

M. W. 494.43    C₂₇H₂₅Cl₂N₃O₂

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 494 (M+H)⁺.

EXAMPLE 368

Preparation of rac-6-Chloro-3-(3-chloro-benzyl)-3-[2-methyl-6-(morpholine-4-carbonyl)-phenylamino]-1,3-dihydro-indol-2-one

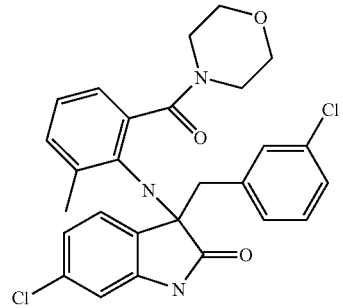

M. W. 510.42    C₂₇H₂₅Cl₂N₃O₃

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 510 (M+H)⁺.

EXAMPLE 369

Preparation of rac-2-[6-Chloro-3-(3-chloro-benzyl)-2-oxo-2,3-dihydro-1H-indol-3-ylamino]-N-cyclobutyl-4-fluoro-benzamide

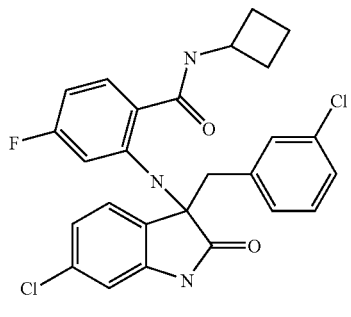

M. W. 498.39   C$_{26}$H$_{22}$Cl$_2$FN$_3$O$_2$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 498 (M+H)⁺.

EXAMPLE 370

Preparation of rac-6-Chloro-3-(3-chloro-benzyl)-3-[5-fluoro-2-(morpholine-4-carbonyl)-phenylamino]-1,3-dihydro-indol-2-one

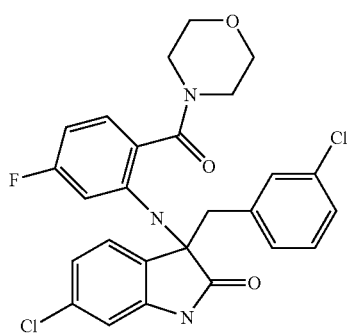

M. W. 514.39   C$_{26}$H$_{22}$Cl$_2$FN$_3$O$_2$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 514 (M+H)⁺.

EXAMPLE 371

Preparation of rac-3-[2-(4-Acetyl-piperazine-1-carbonyl)-5-fluoro-phenylamino]-6-chloro-3-(3-chloro-benzyl)-1,3-dihydro-indol-2-one

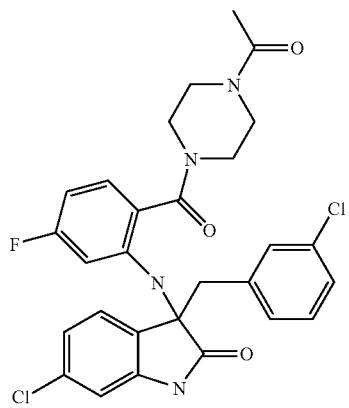

M. W. 555.44   C$_{28}$H$_{25}$Cl$_2$FN$_4$O$_3$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 555 (M+H)⁺.

EXAMPLE 372

Preparation of rac-2-[[6-Chloro-3-(3-chloro-benzyl)-2-oxo-2,3-dihydro-1H-indol-3-yl]-((R)-3-methyl-cyclohexyl)-amino]-N-cyclobutyl-acetamide

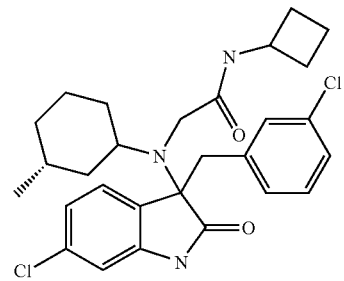

M. W. 514.50   C$_{28}$H$_{33}$Cl$_2$N$_3$O$_2$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 514 (M+H)⁺.

EXAMPLE 373

Preparation of rac-2-[[6-Chloro-3-(3-chloro-benzyl)-2-oxo-2,3-dihydro-1H-indol-3-yl]-((R)-3-methyl-cyclohexyl)-amino]-N-cyclohexyl-acetamide

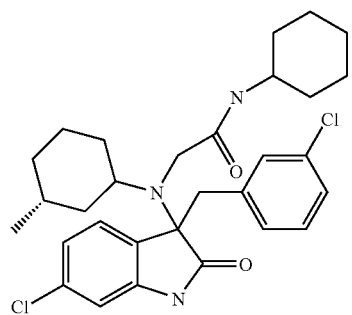

M. W. 542.55   $C_{30}H_{37}Cl_2N_3O_2$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 542 (M+H)⁺.

EXAMPLE 374

Preparation of rac-2-[[6-Chloro-3-(3-chloro-benzyl)-2-oxo-2,3-dihydro-1H-indol-3-yl]-((R)-3-methyl-cyclohexyl)-amino]-N-morpholin-4-yl-acetamide

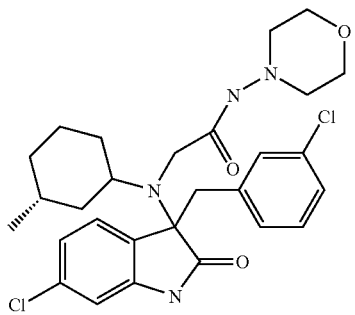

M. W. 545.51   $C_{28}H_{34}Cl_2N_2O_3$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 545 (M+H)⁺.

EXAMPLE 375

Preparation of rac-6-Chloro-3-(3-chloro-benzyl)-3-[((R)-3-methyl-cyclohexyl)-(2-morpholin-4-yl-2-oxo-ethyl)-amino]-1,3-dihydro-indol-2-one

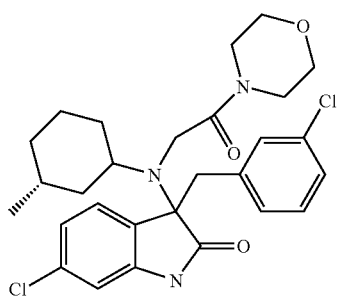

M. W. 530.50   $C_{28}H_{33}Cl_2N_3O_3$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 530 (M+H)⁺.

EXAMPLE 376

Preparation of rac-[[6-Chloro-3-(3-chloro-benzyl)-2-oxo-2,3-dihydro-1H-indol-3-yl]-((R)-3-methyl-cyclopentyl)-amino]-acetic acid

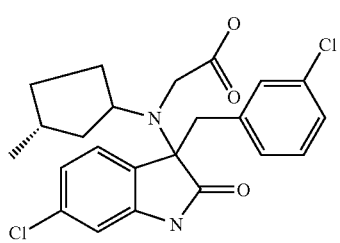

M. W. 447.37   $C_{23}H_{24}Cl_2N_2O_3$

The title compound was prepared by the same procedure rac-{[6-chloro-3-(3-chloro-benzyl)-2-oxo-2,3-dihydro-1H-indol-3-yl]-cyclohexyl-amino}-acetic acid. MS: 447 (M+H)$^+$.

EXAMPLE 377

Preparation of rac-2-[[6-Chloro-3-(3-chloro-benzyl)-2-oxo-2,3-dihydro-1H-indol-3-yl]-((R)-3-methyl-cyclopentyl)-amino]-N-cyclobutyl-acetamide

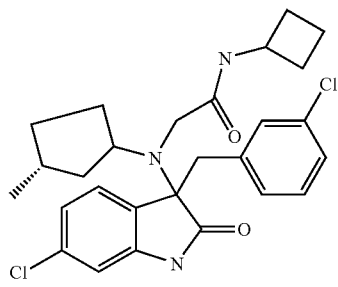

M. W. 500.47   $C_{27}H_{31}Cl_2N_3O_2$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 500 (M+H)$^+$.

EXAMPLE 378

Preparation of rac-2-[[6-Chloro-3-(3-chloro-benzyl)-2-oxo-2,3-dihydro-1H-indol-3-yl]-((R)-3-methyl-cyclopentyl)-amino]-N-cyclohexyl-acetamide

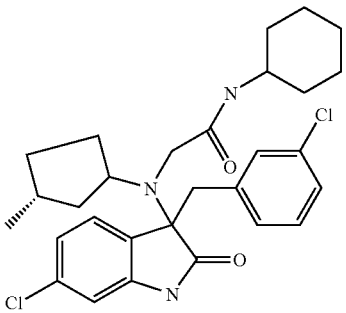

M. W. 528.53   $C_{29}H_{35}Cl_2N_3O_2$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 528 (M+H)$^+$.

EXAMPLE 379

Preparation of rac-2-[[6-Chloro-3-(3-chloro-benzyl)-2-oxo-2,3-dihydro-1H-indol-3-yl]-((R)-3-methyl-cyclopentyl)-amino]-N-morpholin-4-yl-acetamide

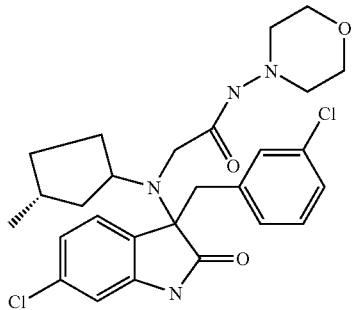

M. W. 531.49   $C_{27}H_{32}Cl_2N_4O_3$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 531 (M+H)$^+$.

EXAMPLE 380

Preparation of rac-6-Chloro-3-(3-chloro-benzyl)-3-[((R)-3-methyl-cyclopentyl)-(2-morpholin-4-yl-2-oxo-ethyl)-amino]-1,3-dihydro-indol-2-one

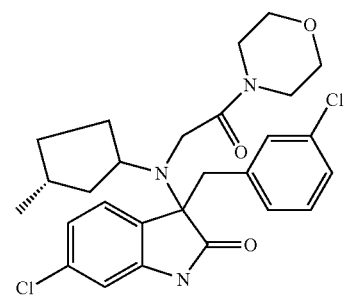

M. W. 516.47   $C_{27}H_{31}Cl_2N_3O_3$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 516(M+H)$^+$.

EXAMPLE 381

Preparation of rac-1-[6-Chloro-3-(3-chloro-benzyl)-2-oxo-2,3-dihydro-1H-indol-3-ylamino]-cyclohexanecarboxylic acid

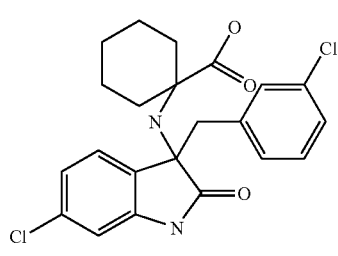

M. W. 433.34   $C_{22}H_{22}Cl_2N_2O_3$

The title compound was prepared by the same procedure for rac-1-[6-chloro-3-(3-chloro-benzyl)-2-oxo-2,3-dihydro-1H-indol-3-yl]-piperidine-3-carboxylic acid. MS: 433 (M+H)$^+$.

EXAMPLE 382

Preparation of rac2-[[6-Chloro-3-(3-chloro-benzyl)-2-oxo-2,3-dihydro-1H-indol-3-yl]-(2-methyl-cyclohexyl)-amino]-N-cyclobutyl-acetamide

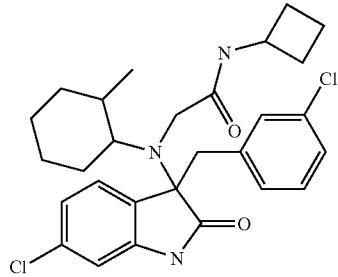

M. W. 514.50   $C_{28}H_{33}Cl_2N_3O_2$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 514 (M+H)$^+$.

EXAMPLE 383

Preparation of rac-1-[6-Chloro-3-(3-chloro-benzyl)-2-oxo-2,3-dihydro-1H-indol-3-ylamino]-cyclohexanecarboxylic acid cyclobutylamide

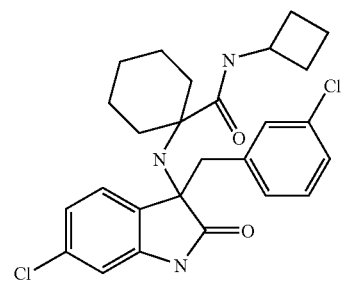

M. W. 486.45   $C_{26}H_{29}Cl_2N_3O_2$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 486 (M+H)$^+$.

EXAMPLE 384

Preparation of rac3-[1-(4-Acetyl-piperazine-1-carbonyl)-cyclohexylamino]-6-chloro-3-(3-chloro-benzyl)-1,3-dihydro-indol-2-one

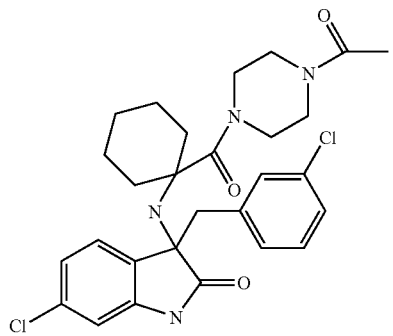

M. W. 543.50   $C_{28}H_{32}Cl_2N_4O_3$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 543 (M+H)$^+$.

EXAMPLE 385

Preparation of rac-2-{[6-Chloro-3-(3-chloro-benzyl)-2-oxo-2,3-dihydro-1H-indol-3-yl]-cyclopropylmethyl-amino}-N-cyclobutyl-acetamide

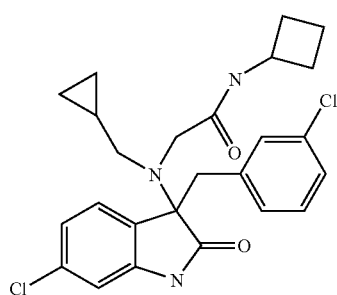

M. W. 472.42    $C_{25}H_{27}Cl_2N_3O_2$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 472 (M+H)$^+$.

EXAMPLE 386

Preparation of rac-2-[[6-Chloro-3-(3-chloro-benzyl)-2-oxo-2,3-dihydro-1H-indol-3-yl]-(3,3,5,5-tetramethyl-cyclohexyl)-amino]-N-cyclobutyl-acetamide

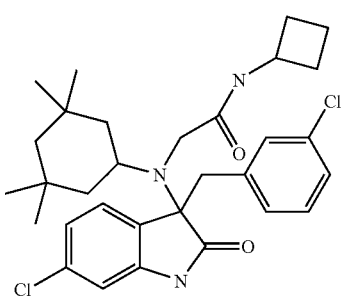

M. W. 556.58    $C_{31}H_{39}Cl_2N_3O_2$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 556 (M+H)$^+$.

EXAMPLE 387

Preparation of rac-2-{(R)-Bicyclo[2.2.1]hept-2-yl-[6-chloro-3-(3-chloro-benzyl)-2-oxo-2,3-dihydro-1H-indol-3-yl]-amino}-N-cyclobutyl-acetamide

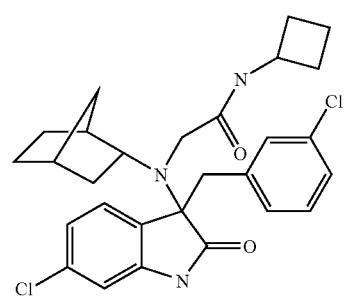

M. W. 512.48    $C_{28}H_{31}Cl_2N_3O_2$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 512 (M+H)$^+$.

EXAMPLE 388a

Preparation of Intermediate E/Z-6-chloro-3-cyclohexylmethylene-1,3-dihydro-indol-2-one

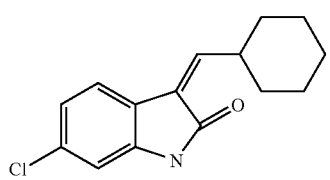

M. W. 261.75    $C_{15}H_{16}ClNO$

The title compound was prepared by the same procedure E/Z-6-chloro-3-(3-chloro-benzylidene)-1,3-dihydro-indol-2-one. MS: 262(M+H)⁺.

EXAMPLE 388b

Preparation of Intermediate rac-6-chloro-3-cyclohexylmethyle-1,3-dihydro-indol-2-one

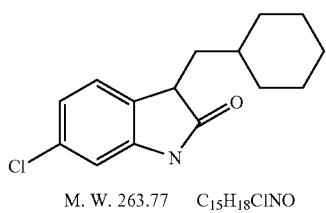

M. W. 263.77    $C_{15}H_{18}ClNO$

The title compound was prepared by the same procedure rac-6-chloro-3-(3-chloro-benzyl)-1,3-dihydro-indol-2-one. MS: 264(M+H)⁺.

EXAMPLE 388c

Preparation of Intermediate rac-3-bromo6-chloro-3-cyclohexylmethyle-1,3-dihydro-indol-2-one

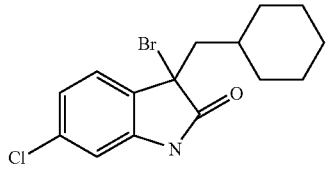

M. W. 342.67    $C_{15}H_{17}BrClNO$

The title compound was prepared by the same procedure rac-3-bromo-6-chloro-3-(3-chloro-benzyl)-1,3-dihydro-indol-2-one. MS: 342(M+H)⁺.

EXAMPLE 388d

Preparation of rac-2-[(6-Chloro-3-cyclohexylmethyl-2-oxo-2,3-dihydro-1H-indol-3-yl)-cyclohexyl-amino]-N-cyclobutyl-acetamide

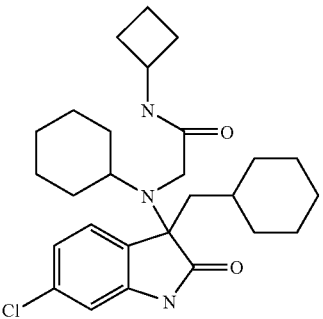

M. W. 472.08    $C_{27}H_{38}Cl_2N_3O_2$

To a solution of cyclohexylamine (61 μL, 0.80 mmol) and DIPEA (300 μL, 1.59 mmol) in dichloromethane (2 mL) was slowly added 2-bromo-N-cyclobytyl-acetamide (156 mg, 0.80 mmol) at 0° C. After the addition, the mixture was stirred at room temperature for 4 h. Then rac-3-bromo6-chloro-3-cyclohexylmethyle-1,3-dihydro-indol-2-one was added in the reaction mixture. The reaction mixture was stirred for 2 hour at room temperature.

And the mixture was washed with water (3×5 mL). The organic solution was dried with Na₂SO₄ and concentrated in vacuo. The residue was purified with chromatography to give white solid. MS: 472 (M+H)⁺.

EXAMPLE 389a

Preparation of Intermediate cyclohexyl-(2-morpholin-4-yl-ethyl)-amine

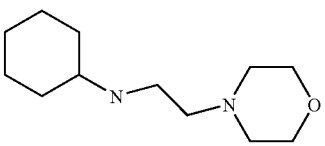

M. W. 212.34    $C_{12}H_{24}N_2O$

Cyclohexanone (2.00 g, 20.4 mmol) and 2-morpholin-4-yl-ethylamine (2.98 mL, 20.4 mmol) were dissolved in 10 mL methanol. The solution was stirred at room temperature for an hour. NaBH₃CN (1.62 g, 24.4 mmol) was slowly added portionwise in the solution. After the addition, the mixture was stirred at room temperature for 4 hour then concentrated under reduced pressure. To the residue was added 50 mL water and the mixture was adjusted to PH=10 with dilute aqueous KOH and extracted with ethyl acetate. The organic solution was dried with Na$_2$SO$_4$ and concentrated in vacuo to give an oil. MS: 213(M+H)$^+$.

EXAMPLE 389b

Preparation of rac-6-Chloro-3-(3-chloro-benzyl)-3-[cyclohexyl-(2-morpholin-4-yl-ethyl)-amino]-1,3-dihydro-indol-2-one

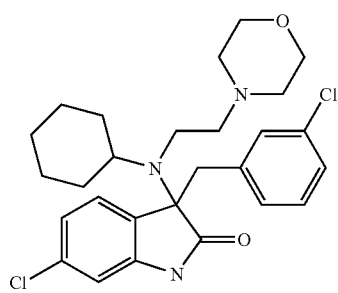

M. W. 502.49  C$_{27}$H$_{33}$Cl$_2$N$_3$O$_2$

The title compound was prepared by the same procedure rac-6-chloro-3-(3-chloro-benzyl)-3-cyclohexylamino-1,3-dihydro-1H-indol-2-one. MS: 502 (M+H)$^+$.

EXAMPLE 390

Preparation of rac-6-Chloro-3-(3-chloro-benzyl)-3-[cyclohexyl-(3-morpholin-4-yl-propyl)-amino]-1,3-dihydro-indol-2-one

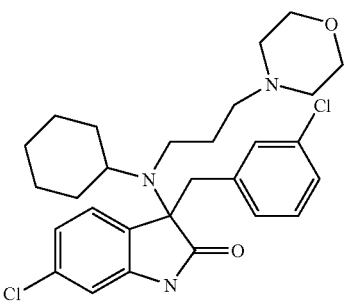

M. W. 516.52  C$_{28}$H$_{35}$Cl$_2$N$_3$O$_2$

The title compound was prepared by the same procedure for of rac-6-Chloro-3-(3-chloro-benzyl)-3-[cyclohexyl-(2-morpholin-4-yl-ethyl)-amino]-1,3-dihydro-indol-2-one MS: 516 (M+H)$^+$.

EXAMPLE 391

Preparation of rac-6-Chloro-3-(3-chloro-benzyl)-3-[isopropyl-(2-morpholin-4-yl-ethyl)-amino]-1,3-dihydro-indol-2-one

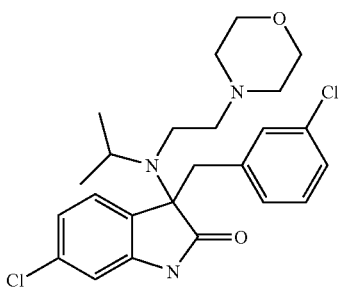

M. W. 462.42  C$_{24}$H$_{29}$Cl$_2$N$_3$O$_2$

The title compound was prepared by the same procedure for of rac-6-Chloro-3-(3-chloro-benzyl)-3-[cyclohexyl-(2-morpholin-4-yl-ethyl)-amino]-1,3-dihydro-indol-2-one. MS: 462 (M+H)$^+$.

EXAMPLE 392

Preparation of rac-6-Chloro-3-(3-chloro-benzyl)-3-[isopropyl-(3-morpholin-4-yl-propyl)-amino]-1,3-dihydro-indol-2-one

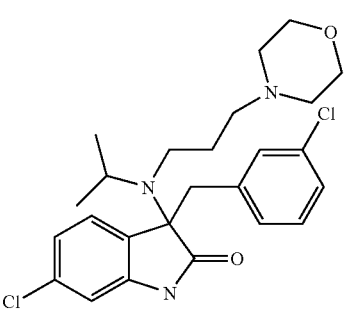

M. W. 476.45  C$_{25}$H$_{31}$Cl$_2$N$_3$O$_2$

The title compound was prepared by the same procedure of rac-6-Chloro-3-(3-chloro-benzyl)-3-[cyclohexyl-(2-morpholin-4-yl-ethyl)-amino]-1,3-dihydro-indol-2-one. MS: 476 (M+H)+.

EXAMPLE 393

Preparation of rac-2-[4-(2-{[6-Chloro-3-(3-chloro-benzyl)-2-oxo-2,3-dihydro-1H-indol-3-yl]-isopropyl-amino}-acetyl)-piperazin-1-yl]-N,N-dimethyl-2-oxo-acetamide

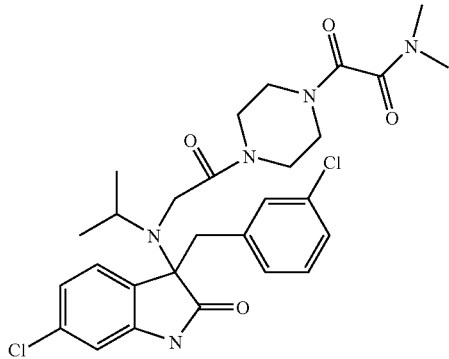

M. W. 574.51    C$_{28}$H$_{33}$Cl$_2$N$_5$O$_4$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 574(M+H)+

EXAMPLE 394

Preparation of rac-1-(2-{[6-Chloro-3-(3-chloro-benzyl)-2-oxo-2,3-dihydro-1H-indol-3-yl]-isopropyl-amino}-acetyl)-piperidine-4-carboxylic acid dimethylamide

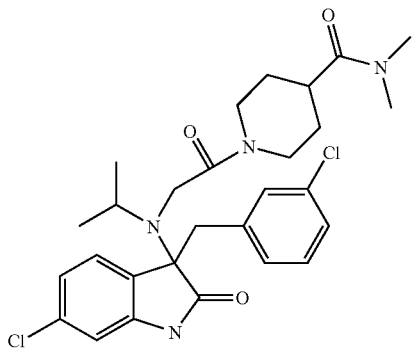

M. W. 545.51    C$_{28}$H$_{34}$Cl$_2$N$_4$O$_3$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 545 (M+H)+.

EXAMPLE 395

Preparation of rac-2-{sec-Butyl-[6-chloro-3-(3-chloro-benzyl)-2-oxo-2,3-dihydro-1H-indol-3-yl]-amino}-N-cyclobutyl-acetamide

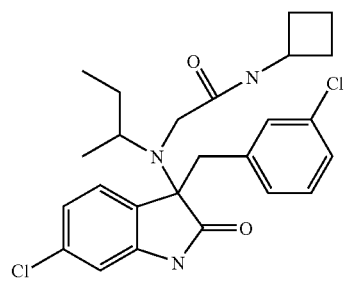

M. W. 474.43    C$_{25}$H$_{29}$Cl$_2$N$_3$O$_2$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 474 (M+H)+.

EXAMPLE 396

Preparation of rac-6-Chloro-3-(3-chloro-benzyl)-3-(isopropyl-{2-[4-(2-methanesulfonyl-ethyl)-piperazin-1-yl]-2-oxo-ethyl}-amino)-1,3-dihydro-indol-2-one

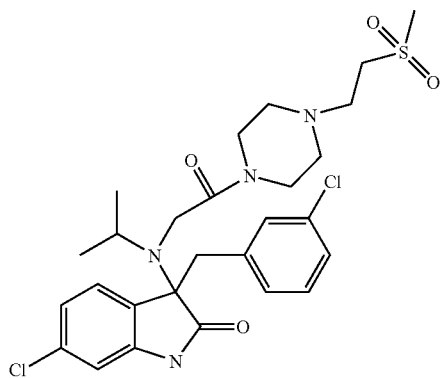

M. W. 581.57    C$_{27}$H$_{34}$Cl$_2$N$_4$O$_4$S

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 581 (M+H)+.

EXAMPLE 397

Preparation of rac-2-{[6-Chloro-3-(3-chloro-benzyl)-2-oxo-2,3-dihydro-1H-indol-3-yl]-isopropyl-amino}-N-[1-(propane-2-sulfonyl)-piperidin-4-yl]-acetamide

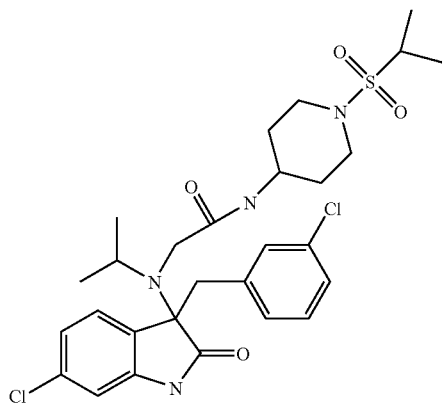

M. W. 595.59    C28H36Cl2N4OS

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 595(M+H)+.

EXAMPLE 398

Preparation of rac-2-{[6-Chloro-3-(3-chloro-benzyl)-2-oxo-2,3-dihydro-1H-indol-3-yl]-isopropyl-amino}-N-(2,2,2-trifluoro-ethyl)-acetamide

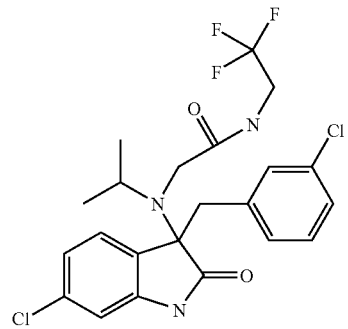

M. W. 488.34    C22H22Cl2F3N3O2

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 488 (M+H)+.

EXAMPLE 399a

Preparation of Intermediate cyclohexuyl-(2-methanesulfonyl-ethyl)amine

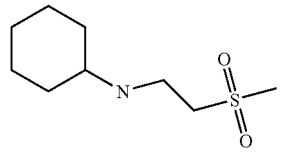

M. W. 205.32    C9H19NO2S

Methyl vinyl sulfone (5.7 mL, 64.8 mmol) was added to a solution of cyclohexylamine (6.2 mL, 54 mmol) in 50 mL DCM. The reaction mixture was stirred at room temperature for 4 hour and concentrated in vacuo, then purified by flash column chromatopgraphy to give oil. MS: 206 (M+H)+.

EXAMPLE 399b

Preparation of rac-6-Chloro-3-(3-chloro-benzyl)-3-[cyclohexyl-(2-methanesulfonyl-ethyl)-amino]-1,3-dihydro-indol-2-one

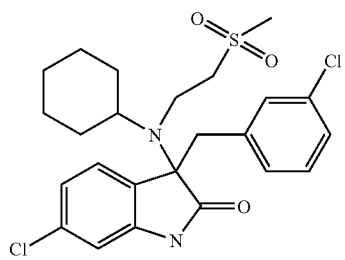

M. W. 495.47    C24H28Cl2N2O3S

The title compound was prepared by the same procedure for rac-6-chloro-3-(3-chloro-benzyl)-3-cyclohexylamino-1,3-dihydro-1H-indol-2-one. MS: 495(M+H)+.

EXAMPLE 400

Preparation of rac-6-Chloro-3-(3-chloro-benzyl)-3-[isopropyl-(2-methanesulfonyl-ethyl)-amino]-1,3-dihydro-indol-2-one

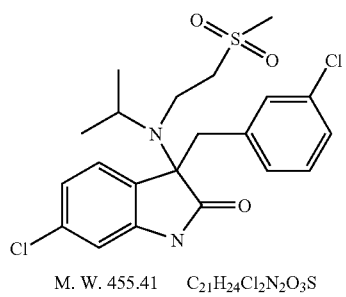

M. W. 455.41   $C_{21}H_{24}Cl_2N_2O_3S$

The title compound was prepared by the same procedure for rac-6-Chloro-3-(3-chloro-benzyl)-3-[cyclohexyl-(2-methanesulfonyl-ethyl)-amino]-1,3-dihydro-indol-2-one MS: 455 (M+H)+.

EXAMPLE 401

Preparation of rac-6-Chloro-3-(3-chloro-benzyl)-3-{isopropyl-[2-(4-methanesulfonyl-piperazin-1-yl)-2-oxo-ethyl]-amino}-1,3-dihydro-indol-2-one

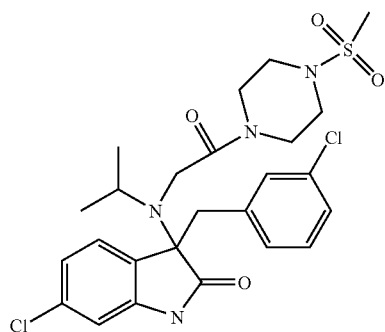

M. W. 553.51   $C_{25}H_{30}Cl_2N_4O_4S$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 553 (M+H)+.

EXAMPLE 402

Preparation of rac-2-{tert-Butyl-[6-chloro-3-(3-chloro-benzyl)-2-oxo-2,3-dihydro-1H-indol-3-yl]-amino}-N-cyclobutyl-acetamide

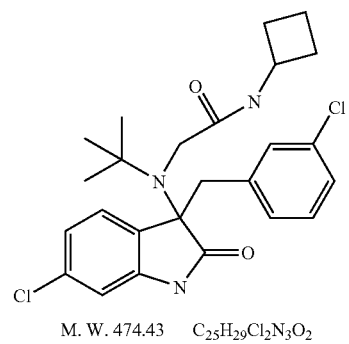

M. W. 474.43   $C_{25}H_{29}Cl_2N_3O_2$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 474 (M+H)+.

EXAMPLE 403

Preparation of rac-N-[1-(2-{[6-Chloro-3-(3-chloro-benzyl)-2-oxo-2,3-dihydro-1H-indol-3-yl]-isopropyl-amino}-acetyl)-piperidin-4-yl]-methanesulfonamide

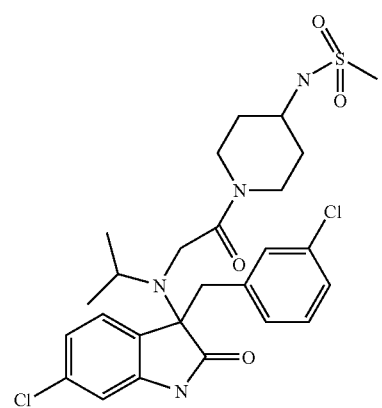

M. W. 567.54   $C_{26}H_{32}Cl_2N_4O_4S$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 567 (M+H)⁺.

EXAMPLE 404

Preparation of rac-2-[[6-Chloro-3-(3-chloro-benzyl)-2-oxo-2,3-dihydro-1H-indol-3-yl]-(1,2-dimethyl-propyl)-amino]-N-cyclobutyl-acetamide

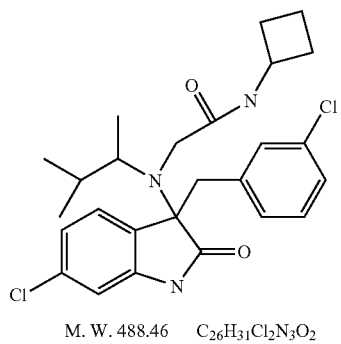

M. W. 488.46   C₂₆H₃₁Cl₂N₃O₂

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 488 (M+H)⁺.

EXAMPLE 405

Preparation of rac-6-Chloro-3-(3-chloro-benzyl)-3-((1,2-dimethyl-propyl)-{2-[4-(2-methanesulfonyl-ethyl)-piperazin-1-yl]-2-oxo-ethyl}-amino)-1,3-dihydro-indol-2-one

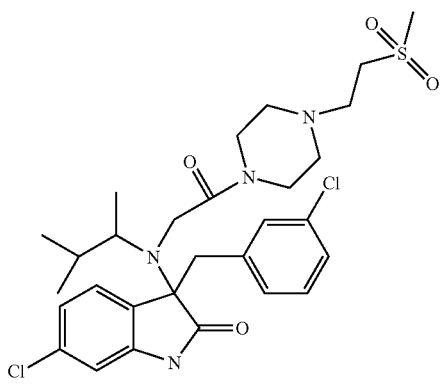

M. W. 609.62   C₂₉H₃₈Cl₂N₄O₄S

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 609(M+H)⁺.

EXAMPLE 406

Preparation of rac-2-[[6-Chloro-3-(3-chloro-benzyl)-2-oxo-2,3-dihydro-1H-indol-3-yl]-(1,2-dimethyl-propyl)-amino]-N-(1-methanesulfonyl-piperidin-4-yl)-acetamide

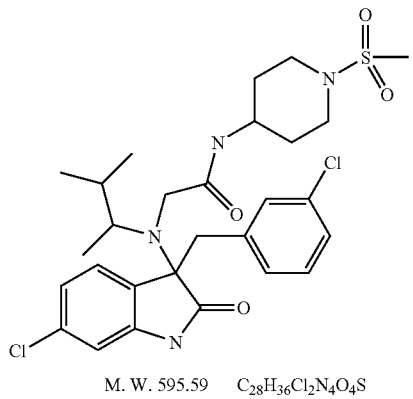

M. W. 595.59   C₂₈H₃₆Cl₂N₄O₄S

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 595 (M+H)⁺.

EXAMPLE 407

Preparation of rac-2-[[6-Chloro-3-(3-chloro-benzyl)-2-oxo-2,3-dihydro-1H-indol-3-yl]-(2,2-dimethyl-propyl)-amino]-N-cyclobutyl-acetamide

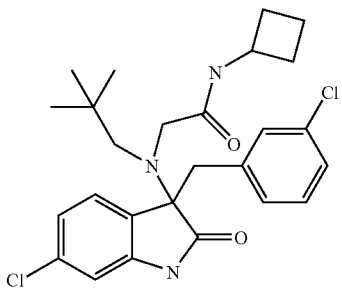

M. W. 488.46   C₂₆H₃₁Cl₂N₃O₂

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 488 (M+H)+.

EXAMPLE 408

Preparation of rac-6-Chloro-3-(3-chloro-benzyl)-3-((2,2-dimethyl-propyl)-{2-[4-(2-methanesulfonyl-ethyl)-piperazin-1-yl]-2-oxo-ethyl}-amino)-1,3-dihydro-indol-2-one

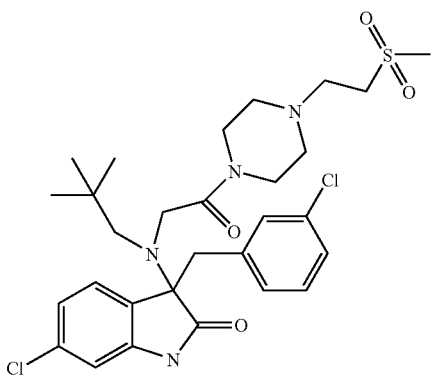

M. W. 609.62    C29H38Cl2N4O4S

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 609 (M+H)+.

EXAMPLE 409

Preparation of rac-1-{2-[[6-Chloro-3-(3-chloro-benzyl)-2-oxo-2,3-dihydro-1H-indol-3-yl]-(2,2-dimethyl-propyl)-amino]-acetyl}-piperidine-4-carboxylic acid amide

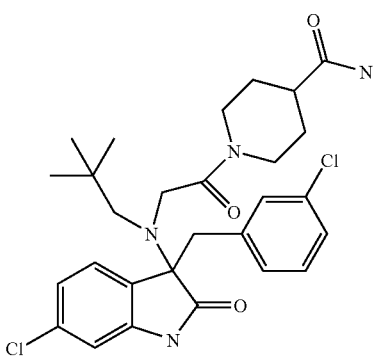

M. W. 545.51    C28H34Cl2N4O3

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 545 (M+H)+.

EXAMPLE 410a

Preparation of 3-(2,2-Dimethyl-propylamino)-propionic acid methyl ester

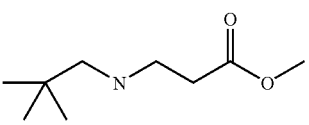

A mixture of 1.5 g 2,2-Dimethyl-propionaldehyde, 2.18 g 3-Amino-propionic acid methyl ester and 50 ml MeOH was stirred at room temperature for 30 min. 1.5 g NaCNBH3 was added in small portion. The mixture was stirred for another 3 hrs. The solvent was removed in vacuum. 50 mL Water was added to the residue and the mixture was basified to PH10 by 1N NaOH. The solution was extracted by EtOAc (30 mL×3). The organic phase was washed by 20 mL water, dried over Na2SO4. Removed the solvent gave 0.66 g target molecule as clear oil.

EXAMPLE 410b

Preparation of rac-3-[[6-Chloro-3-(3-chloro-benzyl)-2-oxo-2,3-dihydro-1H !-indol-3-yl]-(2,2-dimethyl-propyl)-amino]-propionic acid methyl ester

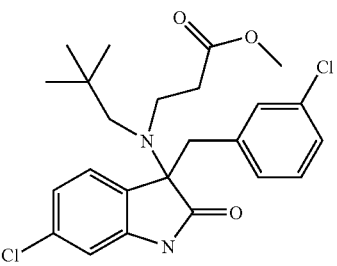

M. W. 463.4    C24H28Cl2N2O3

The title compound was prepared by the same procedure rac-(2-{[6-Chloro-3-(3-chloro-benzyl)-2-oxo-2,3-dihydro-1H-indol-3-yl]-isopropyl-amino}-ethyl)-carbamic acid tert-butyl ester. MS: 463 (M+H)+.

EXAMPLE 411

Preparation of rac-3-[[6-Chloro-3-(3-chloro-benzyl)-2-oxo-2,3-dihydro-1H!-indol-3-yl]-(2,2-dimethyl-propyl)-amino]-propionic acid

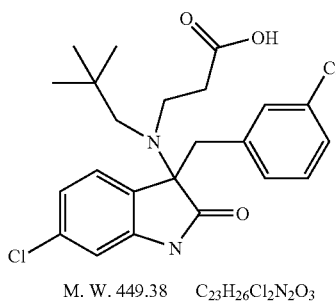

M. W. 449.38    $C_{23}H_{26}Cl_2N_2O_3$

To a mixture of 720 mg rac-3-[[6-Chloro-3-(3-chloro-benzyl)-2-oxo-2,3-dihydro-1H!-indol-3-yl]-(2,2-dimethyl-propyl)-amino]-propionic acid methyl ester in 10 mL MeOH was added 10 mL 1N NaOH. The mixture was heated at 90° C. for 3 hours. Most of the MeOH was removed in vacuum. 20 mL water was added into the residue. Acidigied to PH3 by 2N HCl. The precipitate was collected by filtration and washed by water gave 680 mg target molecule as light yellow solid. MS: 449 (M+H)+.

EXAMPLE 412

Preparation of rac-1-{3-[[6-Chloro-3-(3-chloro-benzyl)-2-oxo-2,3-dihydro-1H!-indol-3-yl]-(2,2-dimethyl-propyl)-amino]-propionyl}-piperidine-4-carboxylic acid amide

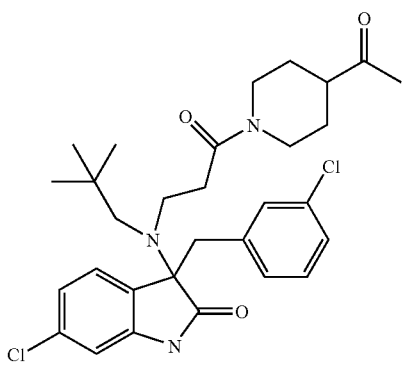

M. W. 559.53    $C_{30}H_{37}Cl_2N_3O_3$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 559 (M+H)+.

EXAMPLE 413

Preparation of rac-6-Chloro-3-(3-chloro-benzyl)-3-[(2,2-dimethyl-propyl)-(3-morpholin-4-yl-3-oxo-propyl)-amino]-1,3-dihydro-indol-2-one

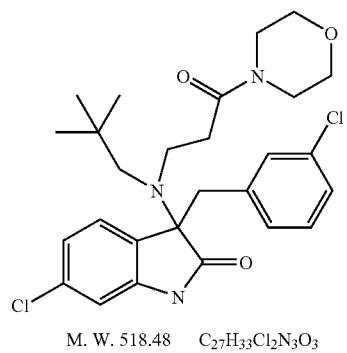

M. W. 518.48    $C_{27}H_{33}Cl_2N_3O_3$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 518 (M+H)+.

EXAMPLE 414

Preparation of rac-3-[[6-Chloro-3-(3-chloro-benzyl)-2-oxo-2,3-dihydro-1#H!-indol-3-yl]-(2,2-dimethyl-propyl)-amino]-N-methyl-propionamide

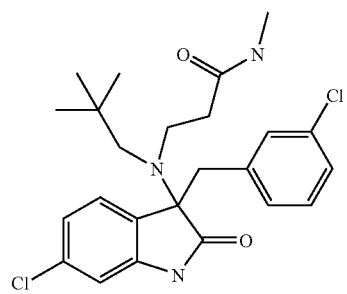

M. W. 462.41    $C_{24}H_{29}Cl_2N_3O_3$

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 462 (M+H)+.

EXAMPLE 415

Preparation of rac-3-[[6-Chloro-3-(3-chloro-benzyl)-2-oxo-2,3-dihydro-1H-indol-3-yl]-(2,2-dimethyl-propyl)-amino]-N,N-dimethyl-propionamide

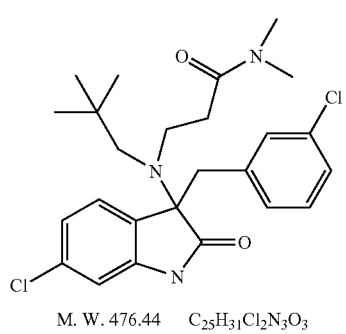

M. W. 476.44    C25H31Cl2N3O3

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 476 (M+H)+.

EXAMPLE 416

Preparation of rac-3-[[3-(4-Acetyl-piperazin-1-yl)-3-oxo-propyl]-(2,2-dimethyl-propyl)-amino]-6-chloro-3-(3-chloro-benzyl)-1,3-dihydro-indol-2-one

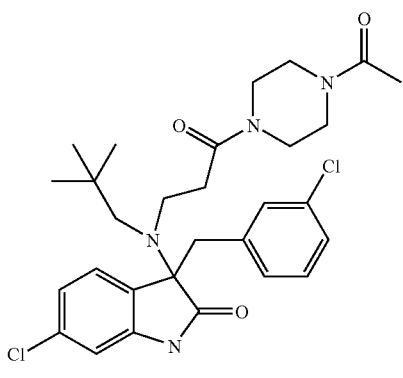

M. W. 559.53    C29H36Cl2N4O3

The title compound was prepared by the same procedure rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: 559 (M+H)+.

EXAMPLE 417

Preparation of rac-Morpholine-4-carboxylic acid (2-{[6-bromo-3-(3-chloro-benzyl)-2-oxo-2,3-dihydro-1H-indol-3-yl]-isopropyl-amino}-ethyl)-amide

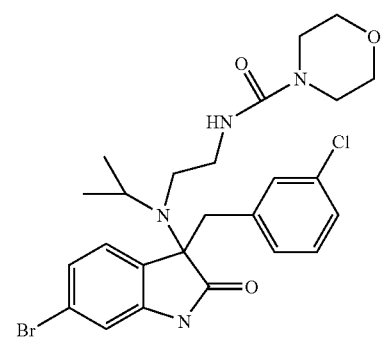

M. W. 549.89    C25H30BrClN4O3

The title compound was prepared following the similar procedure as rac-N-(2-{[6-Chloro-3-(3-chloro-benzyl)-2-oxo-2,3-dihydro-1H-indol-3-yl]-isopropyl-amino}-ethyl)-methanesulfonamide. MS: 549 (M+H)+.

EXAMPLE 418

Preparation of rac-N-{2-[[6-Chloro-3-(3-chloro-benzyl)-2-oxo-2,3-dihydro-1H!-indol-3-yl]-(2,2-dimethyl-propyl)-amino]-ethyl}-acetamide

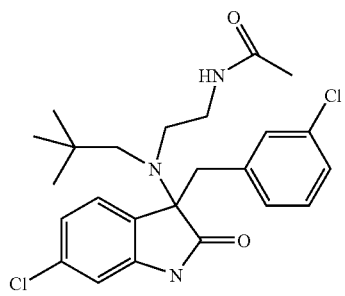

M. W. 462.42    C24H29Cl2N3O2

The title compound was prepared following the similar procedure as rac-N-(2-{[6-Chloro-3-(3-chloro-benzyl)-2- oxo-2,3-dihydro-1H-indol-3-yl]-isopropyl-amino}-ethyl)-methanesulfonamide. MS: 462 (M+H)+.

EXAMPLE 419

Preparation of rac-N-{2-[[6-Chloro-3-(3-chloro-benzyl)-2-oxo-2,3-dihydro-1H-indol-3-yl]-(1,2-dimethyl-propyl)-amino]-ethyl}-acetamide

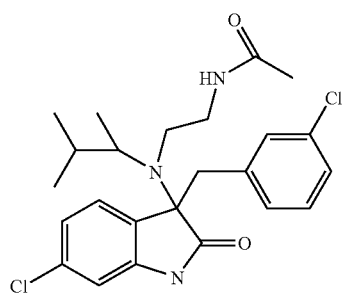

M. W. 462.42   C24H29Cl2N3O2

The title compound was prepared following the similar procedure as rac-N-(2-{[6-Chloro-3-(3-chloro-benzyl)-2-oxo-2,3-dihydro-1H-indol-3-yl]-isopropyl-amino}-ethyl)-methanesulfonamide. MS: 462 (M+H)+.

EXAMPLE 420

Preparation of (R)-1-{4-Bromo-2-[6-chloro-3-(3-chloro-benzyl)-2-oxo-2,3-dihydro-1H-indol-3-ylamino]-benzoyl}-pyrrolidine-2-carboxylic acid methyl ester

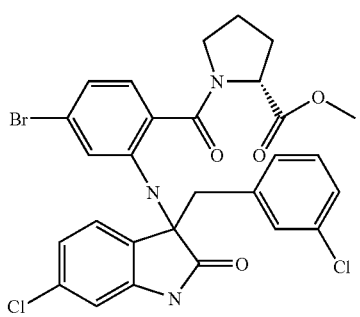

M. W. 617.33   C28H24BrCl2N3O4

The title compound was prepared following the similar procedure as rac-Cyclobutanecarboxylic acid (2-{[6-chloro- 3-(3-chloro-benzyl)-2-oxo-2,3-dihydro-1H-indol-3-yl]-isopropyl-amino}-ethyl)-amide. MS: [M+H]+=616.

EXAMPLE 421

Preparation of (R)-1-{4-Bromo-2-[6-chloro-3-(3-chloro-benzyl)-2-oxo-2,3-dihydro-1H-indol-3-ylamino]-benzoyl}-pyrrolidine-2-carboxylic acid

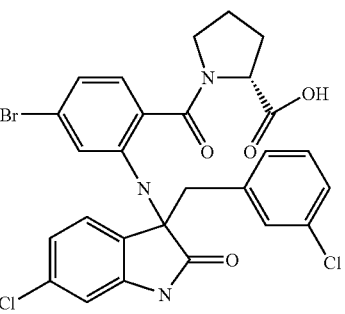

M. W. 603.30   C27H22BrCl2N3O4

The title compound was prepared following the similar procedure as rac-6'-Chloro-3'-(3-chloro-benzyl)-6-methoxy-2'-oxo-2,3,2',3'-tetrahydro-1'H-[1,3']biindolyl-2-carboxylic acid. MS: [M−H]−=600.

EXAMPLE 422

Preparation of (R)-1-{4-Bromo-2-[6-chloro-3-(3-chloro-benzyl)-2-oxo-2,3-dihydro-1H-indol-3-ylamino]-benzoyl}-pyrrolidine-2-carboxylic acid methylamide

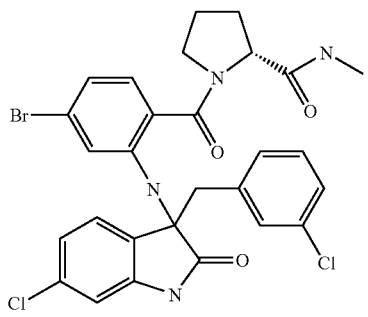

M. W. 616.35   C28H25BrCl2N4O3

The title compound was prepared following the similar procedure as rac-Cyclobutanecarboxylic acid (2-{[6-chloro- 3-(3-chloro-benzyl)-2-oxo-2,3-dihydro-1H-indol-3-yl]-isopropyl-amino}-ethyl)-amide. MS: [M+H]+=615.

EXAMPLE 423

Preparation of (R)-1-{4-Bromo-2-[6-chloro-3-(3-chloro-benzyl)-2-oxo-2,3-dihydro-1H-indol-3-ylamino]-benzoyl}-pyrrolidine-2-carboxylic acid dimethylamide

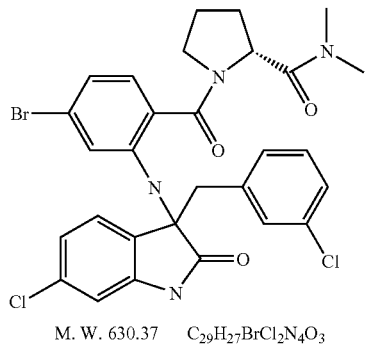

M. W. 630.37   C29H27BrCl2N4O3

The title compound was prepared following the similar procedure as rac-Cyclobutanecarboxylic acid (2-{[6-chloro-3-(3-chloro-benzyl)-2-oxo-2,3-dihydro-1H-indol-3-yl]-isopropyl-amino}-ethyl)-amide. MS: [M+H]+=629.

EXAMPLE 424

Preparation of 3-{5-Bromo-2-[(R)-2-(morpholine-4-carbonyl)-pyrrolidine-1-carbonyl]-phenylamino}-6-chloro-3-(3-chloro-benzyl)-1,3-dihydro-indol-2-one

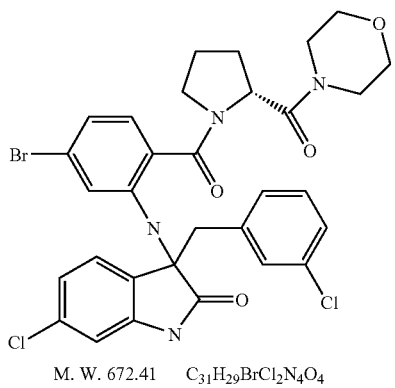

M. W. 672.41   C31H29BrCl2N4O4

The title compound was prepared following the similar procedure as rac-Cyclobutanecarboxylic acid (2-{[6-chloro- 3-(3-chloro-benzyl)-2-oxo-2,3-dihydro-1H-indol-3-yl]-isopropyl-amino}-ethyl)-amide. MS: [M+H]+=671.

EXAMPLE 425

Preparation of 3-{2-[(R)-2-(4-Acetyl-piperazine-1-carbonyl)-pyrrolidine-1-carbonyl]-5-bromo-phenylamino}-6-chloro-3-(3-chloro-benzyl)-1,3-dihydro-indol-2-one

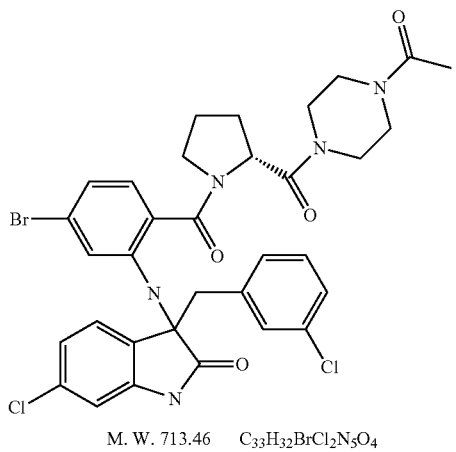

M. W. 713.46   C33H32BrCl2N5O4

The title compound was prepared following the similar procedure as rac-Cyclobutanecarboxylic acid (2-{[6-chloro-3-(3-chloro-benzyl)-2-oxo-2,3-dihydro-1H-indol-3-yl]-isopropyl-amino}-ethyl)-amide. MS: [M+H]+=712.

EXAMPLE 426

Preparation of 2-[6-Chloro-3-(3-chloro-benzyl)-2-oxo-2,3-dihydro-1H-indol-3-yloxy]-3-isopropyl-N-methyl-benzamide

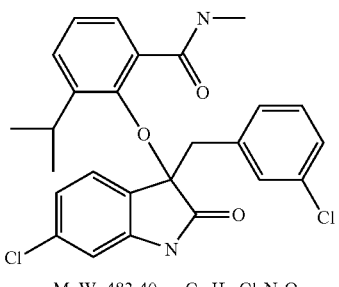

M. W. 483.40   C26H24Cl2N2O3

The title compound was prepared following the similar procedure as rac-Cyclobutanecarboxylic acid (2-{[6-chloro- 3-(3-chloro-benzyl)-2-oxo-2,3-dihydro-1H-indol-3-yl]-isopropyl-amino}-ethyl)-amide. MS: [M+H]+=483.

EXAMPLE 427

Preparation of 2-[6-Chloro-3-(3-chloro-benzyl)-2-oxo-2,3-dihydro-1H-indol-3-yloxy]-3-isopropyl-N!,N-dimethyl-benzamide

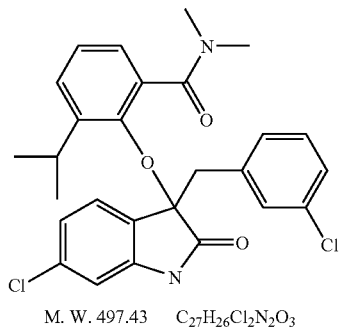

M. W. 497.43    C27H26Cl2N2O3

The title compound was prepared following the similar procedure as rac-Cyclobutanecarboxylic acid (2-{[6-chloro-3-(3-chloro-benzyl)-2-oxo-2,3-dihydro-1H-indol-3-yl]-isopropyl-amino}-ethyl)-amide. MS: [M+H]+=497.

EXAMPLE 428

Preparation of 2-[6-Chloro-3-(3-chloro-benzyl)-2-oxo-2,3-dihydro-1H-indol-3-yloxy]-N-(3-dimethylamino-propyl)-3-isopropyl-benzamide

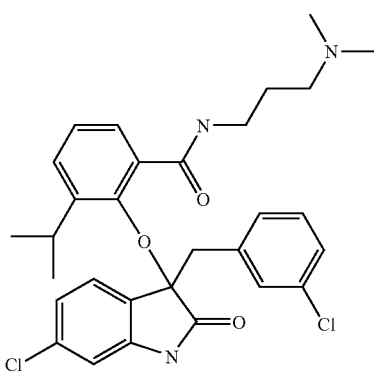

M. W. 554.52    C30H33Cl2N3O3

The title compound was prepared following the similar procedure as rac-Cyclobutanecarboxylic acid (2-{[6-chloro- 3-(3-chloro-benzyl)-2-oxo-2,3-dihydro-1H-indol-3-yl]-isopropyl-amino}-ethyl)-amide. MS: [M+H]+=554.

EXAMPLE 429

Preparation of 3-[6-Chloro-3-(3-chloro-benzyl)-2-oxo-2,3-dihydro-1H-indol-3-ylamino]-4-(morpholine-4-carbonyl)-benzonitrile

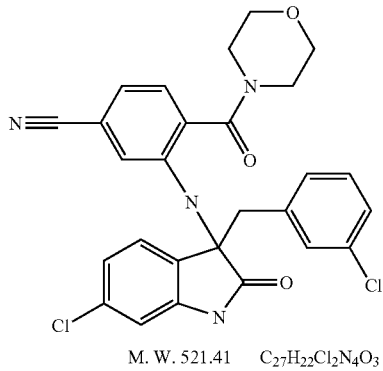

M. W. 521.41    C27H22Cl2N4O3

The title compound was prepared following the similar procedure as rac-Cyclobutanecarboxylic acid (2-{[6-chloro-3-(3-chloro-benzyl)-2-oxo-2,3-dihydro-1H-indol-3-yl]-isopropyl-amino}-ethyl)-amide. MS: [M+H]+=521.

EXAMPLE 430

Preparation of N-(3-{[6-Chloro-3-(3-chloro-benzyl)-2-oxo-2,3-dihydro-1H-indol-3-yl]-isopropyl-amino}-propyl)-acetamide

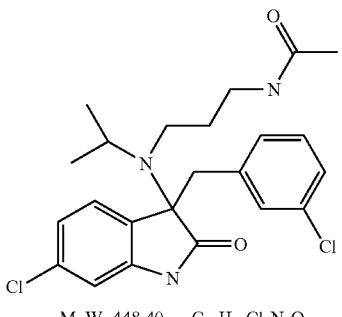

M. W. 448.40    C23H27Cl2N3O2

The title compound was prepared following the similar procedure as rac-N-(2-{[6-Chloro-3-(3-chloro-benzyl)-2- oxo-2,3-dihydro-1H-indol-3-yl]-isopropyl-amino}-ethyl)-acetamide. MS: [M+H]+=448.

EXAMPLE 431

Preparation of N-(3-{[6-Chloro-3-(3-chloro-benzyl)-2-oxo-2,3-dihydro-1H-indol-3-yl]-isopropyl-amino}-propyl)-methanesulfonamide

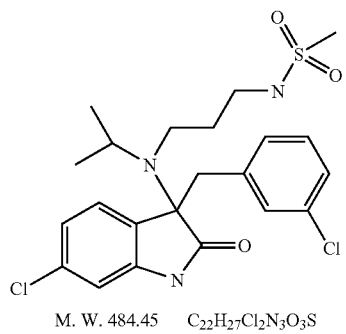

M. W. 484.45   $C_{22}H_{27}Cl_2N_3O_3S$

The title compound was prepared following the similar procedure as rac-N-(2-{[6-Chloro-3-(3-chloro-benzyl)-2-oxo-2,3-dihydro-1H-indol-3-yl]-isopropyl-amino}-ethyl)-methanesulfonamide. MS: [M+H]+=484.

EXAMPLE 432

Preparation of 6-Chloro-3-(3-chloro-benzyl)-3-[5-isopropyl-2-(morpholine-4-carbonyl)-phenylamino]-1,3-dihydro-indol-2-one

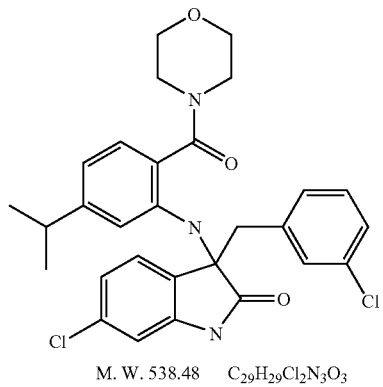

M. W. 538.48   $C_{29}H_{29}Cl_2N_3O_3$

The title compound was prepared following the similar procedure as rac-Cyclobutanecarboxylic acid (2-{[6-chloro-3-(3-chloro-benzyl)-2-oxo-2,3-dihydro-1H-indol-3-yl]-isopropyl-amino}-ethyl)-amide. MS: [M+H]+=538.

EXAMPLE 433

Preparation of (R)-6-Chloro-3-(3-chloro-benzyl)-3-((2,2-dimethyl-propyl)-{2-[4-(2-methanesulfonyl-ethyl)-piperazin-1-yl]-2-oxo-ethyl}-amino)-1,3-dihydro-indol-2-one

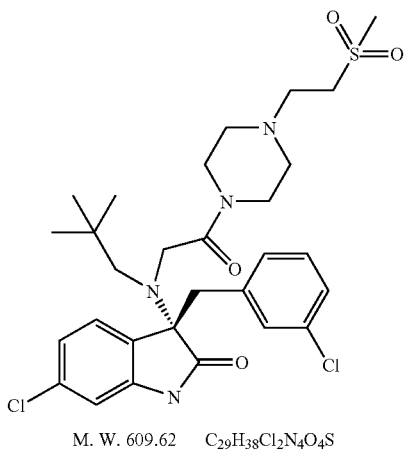

M. W. 609.62   $C_{29}H_{38}Cl_2N_4O_4S$

The title compound was separated from rac-6-Chloro-3-(3-chloro-benzyl)-3-((2,2-dimethyl-propyl)-{2-[4-(2-methanesulfonyl-ethyl)-piperazin-1-yl]-2-oxo-ethyl}-amino)-1,3-dihydro-indol-2-one by chiral prep-HPLC. MS: [M+H]+=609.

EXAMPLE 434

Preparation of 6-Chloro-3-(3-chloro-benzyl)-3-{5-isopropyl-2-[4-(2-methanesulfonyl-ethyl)-piperazine-1-carbonyl]-phenylamino}-1,3-dihydro-indol-2-one

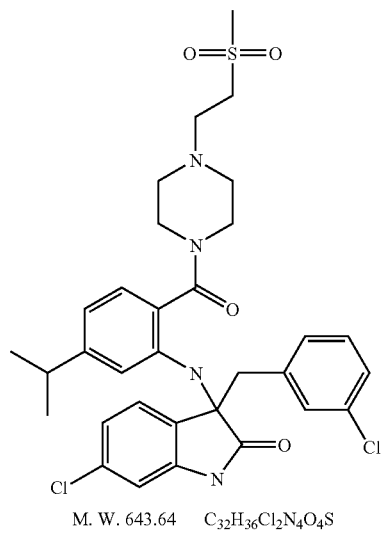

M. W. 643.64   $C_{32}H_{36}Cl_2N_4O_4S$

The title compound was prepared following the similar procedure as rac-Cyclobutanecarboxylic acid (2-{[6-chloro-3-(3-chloro-benzyl)-2-oxo-2,3-dihydro-1H-indol-3-yl]-isopropyl-amino}-ethyl)-amide. MS: [M+H]+=643.

EXAMPLE 435

Preparation of N-(2-Acetylamino-ethyl)-2-[6-chloro-3-(3-chloro-benzyl)-2-oxo-2,3-dihydro-1H-indol-3-ylamino]-4-isopropyl-benzamide

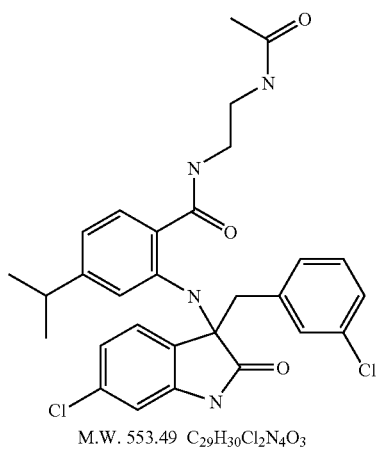

M.W. 553.49 $C_{29}H_{30}Cl_2N_4O_3$

The title compound was prepared following the similar procedure as rac-Cyclobutanecarboxylic acid (2-{[6-chloro-3-(3-chloro-benzyl)-2-oxo-2,3-dihydro-1H-indol-3-yl]-isopropyl-amino}-ethyl)-amide. MS: [M+H]+=553.

EXAMPLE 436

Preparation of 6-Chloro-4-[6-chloro-3-(3-chloro-benzyl)-2-oxo-2,3-dihydro-1H-indol-3-yl]-3,4-dihydro-1H-quinoxalin-2-one

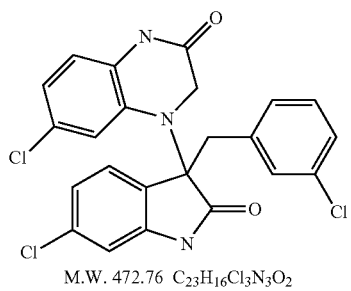

M.W. 472.76 $C_{23}H_{16}Cl_3N_3O_2$

The mixture of rac-3-bromo-6-chloro-3-(3-chloro-benzyl)-1,3-dihydro-indol-2-one (200 mg, 0.55 mmol) (from example 1c supra), 6-Chloro-3,4-dihydro-1H-quinoxalin-2-one (100 mg, 0.55 mmol) and $K_2CO_3$ (150 mg, 1.09 mmol) in acetonitrile (3 mL) was stirred at room temperature for 2 hour. The mixture was concentrated in vacuo and purified by flash column chromatography to give 110 mg 6-Chloro-4-[6-chloro-3-(3-chloro-benzyl)-2-oxo-2,3-dihydro-1H-indol-3-yl]-3,4-dihydro-1H-quinoxalin-2-one. MS: [M+H]+=472.

EXAMPLE 437

Preparation of 1-Acetyl-piperidine-4-carboxylic acid{2-[[(S)-6-chloro-3-(3-chloro-benzyl)-2-oxo-2,3-dihydro-1H-indol-3-yl]-(2,2-dimethyl-propyl)-amino]-ethyl}-amide

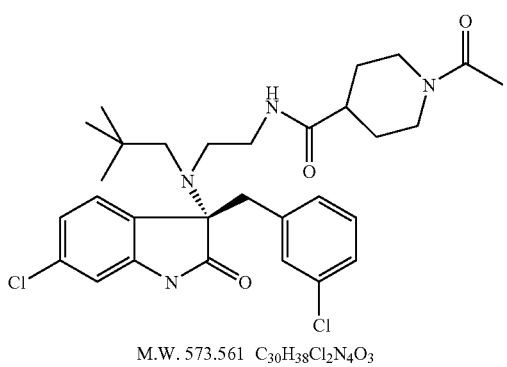

M.W. 573.561 $C_{30}H_{38}Cl_2N_4O_3$

The mixture 3-[(2-Amino-ethyl)-(2,2-dimethyl-propyl)-amino]-6-chloro-3-(3-chloro-benzyl)-1,3-dihydro-indol-2-one (120 mg, 0.286 mmol), 1-Acetyl-piperidine-4-carboxylic acid (59 mg, 0.344 mmol), EDC.HCl (66 mg, 0.344 mmol), HOBt (46 mg, 0.344 mmol) and DIPEA (111 mg, 0.860 mmol) in dichloro-methane (2 mL) was stirred at room temperature for overnight. The crude was then purified with Prep-HPLC to give 54 mg rac-1-Acetyl-piperidine-4-carboxylic acid{2-[[6-chloro-3-(3-chloro-benzyl)-2-oxo-2,3-dihydro-1H-indol-3-yl]-(2,2-dimethyl-propyl)-amino]-ethyl}-amide of as a white solid. Then 18 mg rac-1-Acetyl-piperidine-4-carboxylic acid{2-[[6-chloro-3-(3-chloro-benzyl)-2-oxo-2,3-dihydro-1H-indol-3-yl]-(2,2-dimethyl-propyl)-amino]-ethyl}-amide was separated by chiral preparative HPLC to obtain 7 mg 1-Acetyl-piperidine-4-carboxylic acid{2-[[(S)-6-chloro-3-(3-chloro-benzyl)-2-oxo-2,3-dihydro-1H-indol-3-yl]-(2,2-dimethyl-propyl)-amino]-ethyl}-amide MS: [M+H]+=573.

EXAMPLE 438

Preparation of 4-Acetyl-piperazine-1-carboxylic acid{2-[[(S)-6-chloro-3-(3-chloro-benzyl)-2-oxo-2,3-dihydro-1H-indol-3-yl]-(2,2-dimethyl-propyl)-amino]-ethyl}-amide

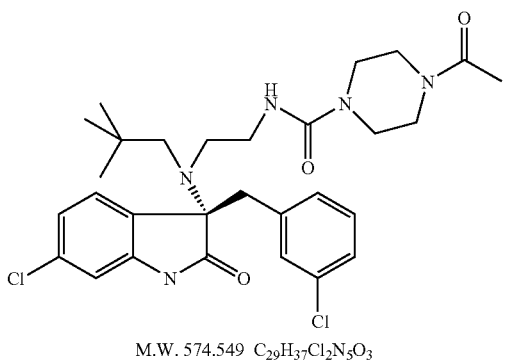

M.W. 574.549  $C_{29}H_{37}Cl_2N_5O_3$

The mixture 3-[(2-Amino-ethyl)-(2,2-dimethyl-propyl)-amino]-6-chloro-3-(3-chloro-benzyl)-1,3-dihydro-indol-2-one (75 mg, 0.179 mmol), 4-Acetyl-piperazine-1-carbonyl chloride (41 mg, 0.215 mmol) and $K_2CO_3$ (37 mg, 0.268 mmol) in dichloro-methane (2 mL) was stirred at room temperature for 2 h. Then the solution was concentrated and the crude product was purified by chromatography to give 42 mg rac-4-Acetyl-piperazine-1-carboxylic acid{2-[[6-chloro-3-(3-chloro-benzyl)-2-oxo-2,3-dihydro-1H-indol-3-yl]-(2,2-dimethyl-propyl)-amino]-ethyl}-amide of as a yellow solid. Then 15 mg rac-4-Acetyl-piperazine-1-carboxylic acid{2-[[6-chloro-3-(3-chloro-benzyl)-2-oxo-2,3-dihydro-1H-indol-3-yl]-(2,2-dimethyl-propyl)-amino]-ethyl}-amide was separated by chiral column to obtain 4 mg 4-Acetyl-piperazine-1-carboxylic acid{2-[[(S)-6-chloro-3-(3-chloro-benzyl)-2-oxo-2,3-dihydro-1H-indol-3-yl]-(2,2-dimethyl-propyl)-amino]-ethyl}-amide

MS: $[M+H]^+=574$.

EXAMPLE 439

Preparation of N-(S)-1-{4-Bromo-2-[6-chloro-3-(3-chloro-benzyl)-2-oxo-2,3-dihydro-1H-indol-3-ylamino]-benzoyl}-piperidin-3-yl)-acetamide

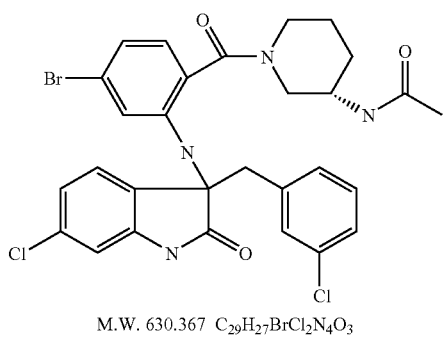

M.W. 630.367  $C_{29}H_{27}BrCl_2N_4O_3$

The mixture 4-Bromo-2-[6-chloro-3-(3-chloro-benzyl)-2-oxo-2,3-dihydro-1H-indol-3-ylamino]-benzoic acid (150 mg, 0.298 mmol), (S)-N-Piperidin-3-yl-acetamide (63 mg, 0.446 mmol), EDC.HCl (85 mg, 0.446 mmol), HOBt (60 mg, 0.446 mmol) and DIPEA (154 mg, 1.190 mmol) in dichloromethane (2 mL) was stirred at room temperature for overnight. The crude was then purified with Prep-HPLC to give 33 mg N-((S)-1-{4-Bromo-2-[6-chloro-3-(3-chloro-benzyl)-2-oxo-2,3-dihydro-1H-indol-3-ylamino]-benzoyl}-piperidin-3-yl)-acetamide as yellow solid.

MS: $[M+H]^+=629$.

EXAMPLE 440

Preparation of 3-((S)-1-{4-Bromo-2-[6-chloro-3-(3-chloro-benzyl)-2-oxo-2,3-dihydro-1H-indol-3-ylamino]-benzoyl}-piperidin-3-yl)-1,1-dimethyl-urea

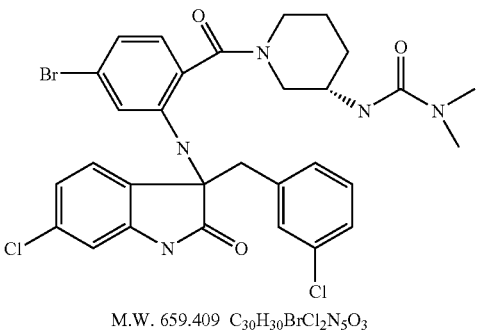

M.W. 659.409  $C_{30}H_{30}BrCl_2N_5O_3$

The title compound was prepared by the same procedure for N-((S)-1-{4-Bromo-2-[6-chloro-3-(3-chloro-benzyl)-2-oxo-2,3-dihydro-1H-indol-3-ylamino]-benzoyl}-piperidin-3-yl)-acetamide. MS: $[M+H]^+=658$

EXAMPLE 441

Preparation of Morpholine-4-carboxylic acid ((S)-1-{4-bromo-2-[6-chloro-3-(3-chloro-benzyl)-2-oxo-2,3-dihydro-1H-indol-3-ylamino]-benzoyl}-piperidin-3-yl)-amide

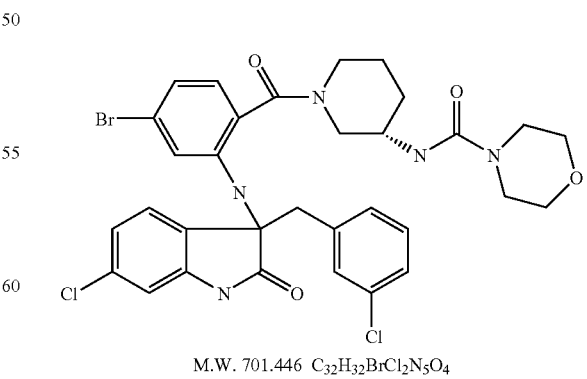

M.W. 701.446  $C_{32}H_{32}BrCl_2N_5O_4$

The title compound was prepared by the same procedure for N-(S)-1-{4-Bromo-2-[6-chloro-3-(3-chloro-benzyl)-2- oxo-2,3-dihydro-1H-indol-3-ylamino]-benzoyl}-piperidin-3-yl)-acetamide. MS: [M+H]$^+$=700.

EXAMPLE 442

Preparation of N-((S)-1-{4-Bromo-2-[6-chloro-3-(3-chloro-benzyl)-2-oxo-2,3-dihydro-1H-idol-3-ylamino]-benzoyl}-piperidin-3-yl)-methanesulfonamide

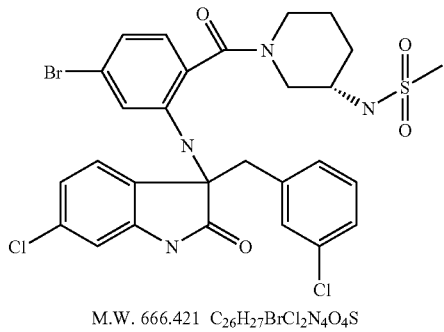

M.W. 666.421  $C_{26}H_{27}BrCl_2N_4O_4S$

The title compound was prepared by the same procedure for N-(S)-1-{4-Bromo-2-[6-chloro-3-(3-chloro-benzyl)-2-oxo-2,3-dihydro-1H-indol-3-ylamino]-benzoyl}-piperidin-3-yl)-acetamide. MS: [M+H]$^+$=665.

EXAMPLE 443

Preparation of (S)-1-{4-Bromo-2-[6-chloro-3-(3-chloro-benzyl)-2-oxo-2,3-dihydro-1H-indol-3-ylamino]-benzoyl}-pyrrolidine-2-carboxylic acid amide

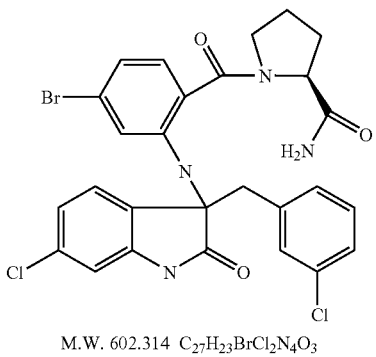

M.W. 602.314  $C_{27}H_{23}BrCl_2N_4O_3$

The title compound was prepared by the same procedure for N-((S)-1-{4-Bromo-2-[6-chloro-3-(3-chloro-benzyl)-2- oxo-2,3-dihydro-1H-indol-3-ylamino]-benzoyl}-piperidin-3-yl)-acetamide. MS: [M+H]$^+$=601.

EXAMPLE 444

Preparation of 4-Bromo-2-[6-chloro-3-(3-chloro-benzyl)-2-oxo-2,3-dihydro-1H-indol-3-ylamino]-N-(S)-piperidin-3-yl-benzamide

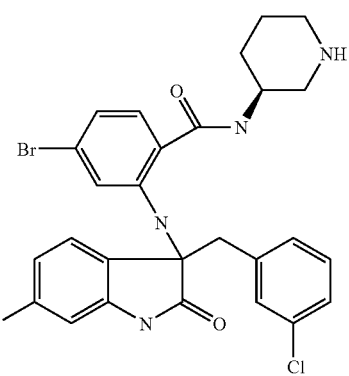

M.W. 588.331  $C_{27}H_{25}BrCl_2N_4O_2$

The mixture 4-Bromo-2-[6-chloro-3-(3-chloro-benzyl)-2-oxo-2,3-dihydro-1H-indol-3-ylamino]-benzoic acid (1.5 g, 0.003 mol), (S)-3-Amino-piperidine-1-carboxylic acid tert-butyl ester (0.72 g, 0.0036 mol), EDC.HCl (0.68 g, 0.0036 mol), HOBt (0.49 g, 0.0036 mol) and DIPEA (1.15 g, 0.0089 mol) in DMF (20 mL) was stirred at room temperature for overnight. Then the mixture was poured into water and the mixture solution was filtered to obtain the crude product. The crude product was purified by chromatography to obtain 1.2 g yellow solid 3-{4-Bromo-2-[6-chloro-3-(3-chloro-benzyl)-2-oxo-2,3-dihydro-1H-indol-3-ylamino]-benzoylamino}-(S)-piperidine-1-carboxylic acid tert-butyl ester. Then 100 mg 3-{4-Bromo-2-[6-chloro-3-(3-chloro-benzyl)-2-oxo-2,3-dihydro-1H-indol-3-ylamino]-benzoylamino}-(S)-piperidine-1-carboxylic acid tert-butyl ester was dissolved a mixture solution of CF$_3$COOH and CH$_2$Cl$_2$. After stirred 0.5 h, the solution was concentrated and the organic layer was washed with NaOH aqueous solution. The organic layer was dried, concentrated to obtain crude product. The crude product was purified by Prep-HPLC to obtain 31 mg 4-Bromo-2-

[6-chloro-3-(3-chloro-benzyl)-2-oxo-2,3-dihydro-1H-indol-3-ylamino]-N-(S)-piperidin-3-yl-benzamide. MS: 587 (M+H)⁺.

EXAMPLE 445

Preparation of N-((S)-1-Acetyl-piperidin-3-yl)-4-bromo-2-[6-chloro-3-(3-chloro-benzyl)-2-oxo-2,3-dihydro-1H-indol-3-ylamino]-benzamide

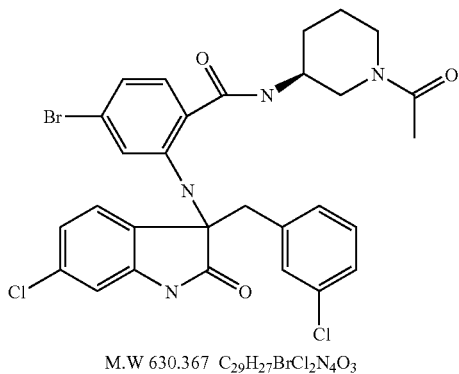

M.W 630.367  C$_{29}$H$_{27}$BrCl$_2$N$_4$O$_3$

Bromo-2-[6-chloro-3-(3-chloro-benzyl)-2-oxo-2,3-dihydro-1H-indol-3-ylamino]-N -(S)-piperidin-3-yl-benzamide (150 mg, 0.214 mmol), Acetic Anhydride (22 mg, 0.214 mmol) and DIPEA (111 mg, 0.859 mmol) were dissolved in 2 ml CH$_3$CN. After stirred for 2 h at r.t, the solution was concentrated and the crude product was purified by Prep-HPLC to obtain 32 mg N-((S)-1-Acetyl-piperidin-3-yl)-4-bromo-2-[6-chloro-3-(3-chloro-benzyl)-2-oxo-2,3-dihydro-1H-indol-3-ylamino]-benzamide as a white solid. MS: [M+H]⁺=629.

EXAMPLE 446

Preparation of 4-Bromo-2-[6-chloro-3-(3-chloro-benzyl)-2-oxo-2,3-dihydro-1H-indol-3-ylamino]-N-[(S)-1-(morpholine-4-carbonyl)-piperidin-3-yl]-benzamide

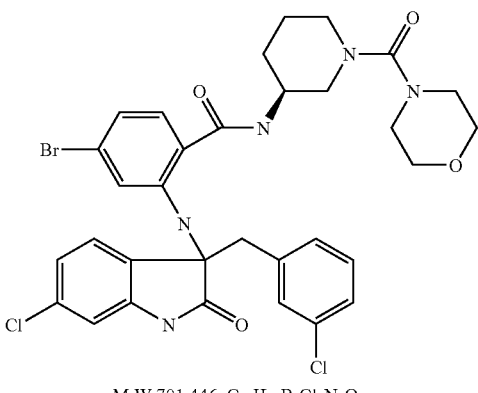

M.W 701.446  C$_{32}$H$_{32}$BrCl$_2$N$_5$O$_4$

The title compound was prepared by the same procedure for N-((S)-1-Acetyl-piperidin-3-yl)-4-bromo-2-[6-chloro-3-(3-chloro-benzyl)-2-oxo-2,3-dihydro-1H-indol-3-ylamino]-benzamide. MS: [M+H]⁺=700.

EXAMPLE 447

Preparation of (S)-3-{4-Bromo-2-[6-chloro-3-(3-chloro-benzyl)-2-oxo-2,3-dihydro-1H-indol-3-ylamino]-benzoylamino}-piperidine-1-carboxylic acid dimethylamide

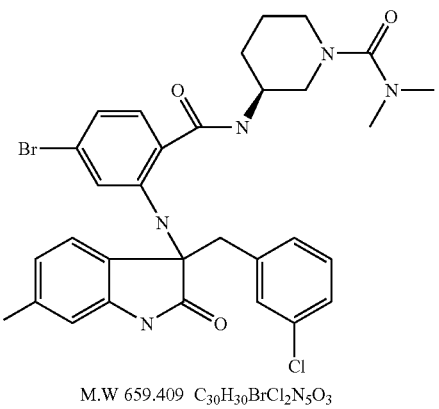

M.W 659.409  C$_{30}$H$_{30}$BrCl$_2$N$_5$O$_3$

The title compound was prepared by the same procedure for N-((S)-1-Acetyl-piperidin-3-yl)-4-bromo-2-[6-chloro-3-(3-chloro-benzyl)-2-oxo-2,3-dihydro-1H-indol-3-ylamino]-benzamide. MS: [M+H]⁺=658

EXAMPLE 448

Preparation of rac-3-[(2-Amino-ethyl)-(2,2-dimethyl-propyl)-amino]-6-chloro-3-(3-chloro-benzyl)-1,3-dihydro-indol-2-one

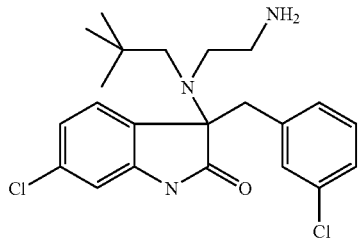

M.W 420.381  C$_{22}$H$_{27}$Cl$_2$N$_3$O (2-Amino-ethyl)-carbamic acid tert-butyl ester (1.2 g, 7.5 mmol) and 2,2-Dimethyl-propionaldehyde (0.65 g, 7.5 mmol) were dissolved in 20 ml methanol. After the mixture was stirred for 1 h at r.t, NaBH$_3$CN (0.6 g, 9 mmol) was added. Then the mixture was stirred overnight and concentrated under reduced pressure. To the residue was added 20 ml of water, and the mixture was adjusted to PH=10 with dilute aqueous NaOH and extracted with EtOAc. The combined organic layers were dried and concentrated to obtain 1.3 g oil. This oil, 3-Bromo-6-chloro-3-(3-chloro-benzyl)-1,3-dihydro-indol-2-one (2.1 g, 5.65 mmol) and K$_2$CO$_3$ (0.94 g, 6.78 mmol) were dissolved in 10 ml DMF. After stirred for about 3 h, the mixture was poured into water and the mixture solution was filtered to obtain the crude product. The crude product was purified by chromatography to obtain 1.8 g {2-[[6-Chloro-3-(3-chloro-benzyl)-2-oxo-2,3-dihydro-1H-indol-3-yl]-(2,2-dimethyl-propyl)-amino]-ethyl}-carbamic acid tert-butyl ester as a yellow solid. Then this 1.8 g yellow solid was dissolved in a mixture solution of $CF_3COOH$ and $CH_2Cl_2$. After stirred for 1 h, the solution was concentrated and the organic layer was washed with NaOH aqueous solution. The organic layer was dried, concentrated to obtain crude product. The crude product was purified by chromatography to obtain 566 mg rac-3-[(2-Amino-ethyl)-(2,2-dimethyl-propyl)-amino]-6-chloro-3-(3-chloro-benzyl)-1,3-dihydro-indol-2-one as a yellow solid. MS: $[M+H]^+=420$.

EXAMPLE 449

Preparation of rac-N-{2-[[6-Chloro-3-(3-chloro-benzyl)-2-oxo-2,3-dihydro-1H-indol-3-yl]-(2,2-dimethyl-propyl)-amino]-ethyl}-methanesulfonamide

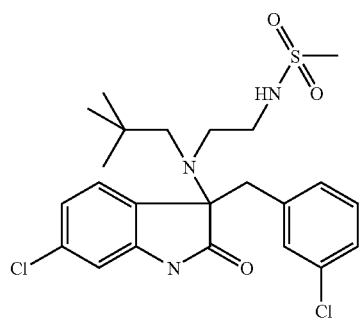

M.W 498.472  $C_{23}H_{29}Cl_2N_3O_3S$

The title compound was prepared by the same procedure 4-Acetyl-piperazine-1-carboxylic acid{2-[[(S)-6-chloro-3-(3-chloro-benzyl)-2-oxo-2,3-dihydro-1H-indol-3-yl]-(2,2-dimethyl-propyl)-amino]-ethyl}-amide. MS: $[M+H]^+=498$

EXAMPLE 450

Preparation of rac-morpholine-4-carboxylic acid{2-[[6-chloro-3-(3-chloro-benzyl)-2-oxo-2,3-dihydro-1H-indol-3-yl]-(2,2-dimethyl-propyl)-amino]-ethyl}-amide

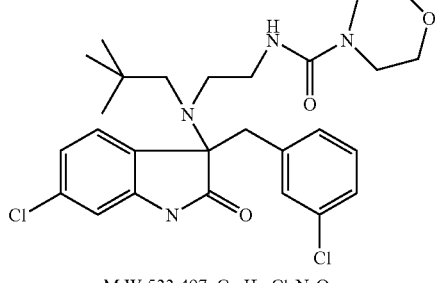

M.W 533.497  $C_{27}H_{34}Cl_2N_4O_3$

The title compound was prepared by the same procedure 4-Acetyl-piperazine-1-carboxylic acid{2-[[(S)-6-chloro-3-(3-chloro-benzyl)-2-oxo-2,3-dihydro-1H-indol-3-yl]-(2,2-dimethyl-propyl)-amino]-ethyl}-amide. MS: $[M+H]^+=533$.

EXAMPLE 451

Preparation of rac-1-Acetyl-piperidine-4-carboxylic acid{2-[[6-chloro-3-(3-chloro-benzyl)-2-oxo-2,3-dihydro-1H-indol-3-yl]-(2,2-dimethyl-propyl)-amino]-ethyl}-amide

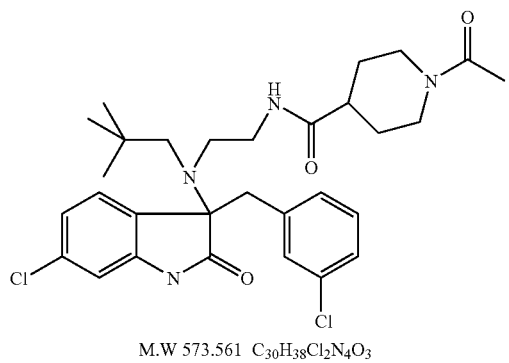

M.W 573.561  $C_{30}H_{38}Cl_2N_4O_3$

The title compound was prepared by the same procedure 1-Acetyl-piperidine-4-carboxylic acid{2-[[(S)-6-chloro-3-(3-chloro-benzyl)-2-oxo-2,3-dihydro-1H-indol-3-yl]-(2,2-dimethyl-propyl)-amino]-ethyl}-amide. MS: $[M+H]^+=573$.

EXAMPLE 452

Preparation of 1-Acetyl-piperidine-4-carboxylic acid{2-[[(R)-6-chloro-3-(3-chloro-benzyl)-2-oxo-2,3-dihydro-1H-indol-3-yl]-(2,2-dimethyl-propyl)-amino]-ethyl}-amide

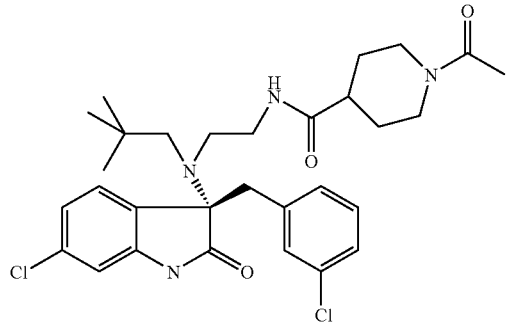

M.W 573.561  $C_{30}H_{38}Cl_2N_4O_3$ 18 mg rac-1-Acetyl-piperidine-4-carboxylic acid{2-[[6-chloro-3-(3-chloro-benzyl)-2-oxo-2,3-dihydro-1H-indol-3-yl]-(2,2-dimethyl-propyl)-amino]-ethyl}-amide was separated by chiral column to obtain 7 mg 1-Acetyl-piperidine-4-carboxylic acid{2-[[(S)-6-chloro-3-(3-chloro-benzyl)-2- oxo-2,3-dihydro-1H-indol-3-yl]-(2,2-dimethyl-propyl)-amino]-ethyl}-amide. MS: [M+H]⁺=573.

EXAMPLE 453

Preparation of 3-[(2-Amino-ethyl)-(1,2-dimethyl-propyl)-amino]-6-chloro-3-(3-chloro-benzyl)-1,3-dihydro-indol-2-one

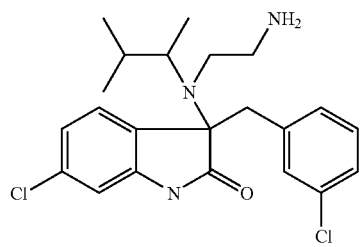

M.W 420.381  $C_{22}H_{27}Cl_2N_3O$

The title compound was prepared by the same procedure rac-3-[(2-Amino-ethyl)-(2,2-dimethyl-propyl)-amino]-6-chloro-3-(3-chloro-benzyl)-1,3-dihydro-indol-2-one  MS: [M+H]⁺=420.

EXAMPLE 454

Preparation of rac-4-Acetyl-piperazine-1-carboxylic acid{2-[[6-chloro-3-(3-chloro-benzyl)-2-oxo-2,3-dihydro-1H-indol-3-yl]-(1,2-dimethyl-propyl)-amino]-ethyl}-amide

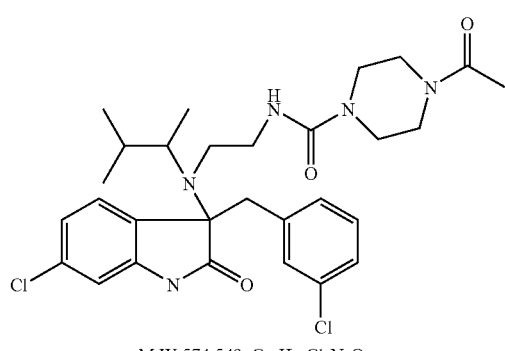

M.W 574.549  $C_{29}H_{37}Cl_2N_5O_3$

The title compound was prepared by the same procedure 4-Acetyl-piperazine-1-carboxylic acid{2-[[(S)-6-chloro-3-(3-chloro-benzyl)-2-oxo-2,3-dihydro-1H-indol-3-yl]-(2,2-dimethyl-propyl)-amino]-ethyl}-amide. MS: [M+H]⁺=574.

EXAMPLE 455

Preparation of rac-4-Acetyl-piperazine-1-carboxylic acid{2-[[6-chloro-3-(3-chloro-benzyl)-2-oxo-2,3-dihydro-1H-indol-3-yl]-(2,2-dimethyl-propyl)-amino]-ethyl}-amide

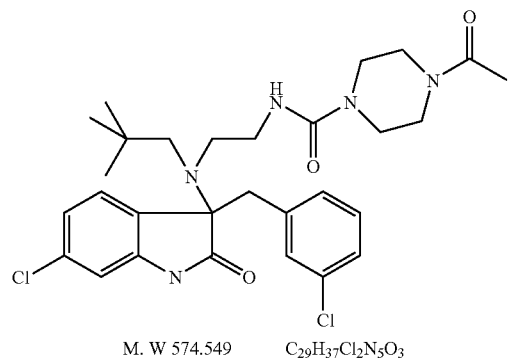

M. W 574.549  $C_{29}H_{37}Cl_2N_5O_3$

The title compound was prepared by the same procedure 4-Acetyl-piperazine-1-carboxylic acid{2-[[(S)-6-chloro-3-(3-chloro-benzyl)-2-oxo-2,3-dihydro-1H-indol-3-yl]-(2,2-dimethyl-propyl)-amino]-ethyl}-amide. MS: [M+H]⁺=574.

EXAMPLE 456

Preparation of rac-N-{2-[[6-Chloro-3-(3-chloro-benzyl)-2-oxo-2,3-dihydro-1H-indol-3-yl]-(1,2-dimethyl-propyl)-amino]-ethyl}-methanesulfonamide

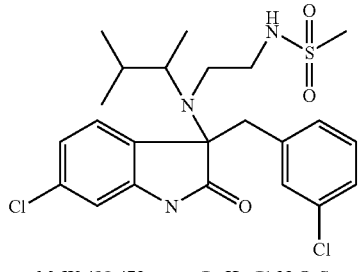

M. W 498.472  $C_{23}H_{29}Cl_2N_3O_3S$

The title compound was prepared by the same procedure 4-Acetyl-piperazine-1-carboxylic acid{2-[[(S)-6-chloro-3-

(3-chloro-benzyl)-2-oxo-2,3-dihydro-1H-indol-3-yl]-(2,2-dimethyl-propyl)-amino]-ethyl}-amide. MS: [M+H]⁺=498.

EXAMPLE 457

Preparation of rac-Morpholine-4-carboxylic acid{2-[[6-chloro-3-(3-chloro-benzyl)-2-oxo-2,3-dihydro-1H-indol-3-yl]-(1,2-dimethyl-propyl)-amino]-ethyl}-amide

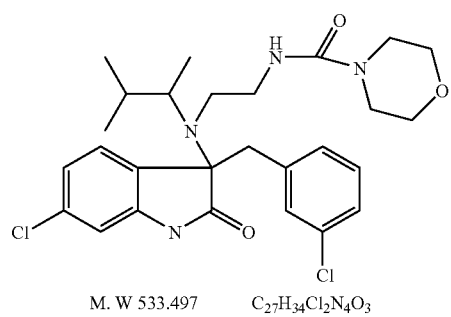

M. W 533.497    $C_{27}H_{34}Cl_2N_4O_3$

The title compound was prepared by the same procedure 4-Acetyl-piperazine-1-carboxylic acid{2-[[(S)-6-chloro-3-(3-chloro-benzyl)-2-oxo-2,3-dihydro-1H-indol-3-yl]-(2,2-dimethyl-propyl)-amino]-ethyl}-amide. MS: [M+H]⁺=533.

EXAMPLE 458

Preparation of rac-1-Acetyl-piperidine-4-carboxylic acid{2-[[6-chloro-3-(3-chloro-benzyl)-2-oxo-2,3-dihydro-1H-indol-3-yl]-(1,2-dimethyl-propyl)-amino]-ethyl}-amide

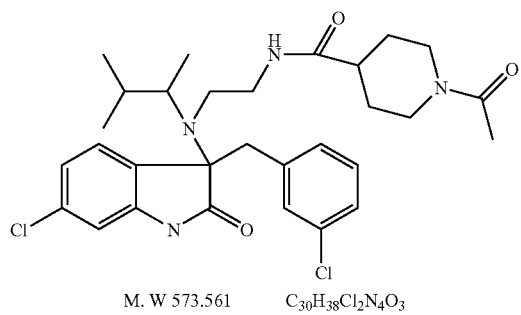

M. W 573.561    $C_{30}H_{38}Cl_2N_4O_3$

The title compound was prepared by the same procedure 1-Acetyl-piperidine-4-carboxylic acid{2-[[(S)-6-chloro-3-

(3-chloro-benzyl)-2-oxo-2,3-dihydro-1H-indol-3-yl]-(2,2-dimethyl-propyl)-amino]-ethyl}-amide. MS: [M+H]⁺=573.

EXAMPLE 459

Preparation of rac-4-Acetyl-piperazine-1-carboxylic acid{3-[[6-chloro-3-(3-chloro-benzyl)-2-oxo-2,3-dihydro-1H-indol-3-yl]-(2,2-dimethyl-propyl)-amino]-propyl}-amide

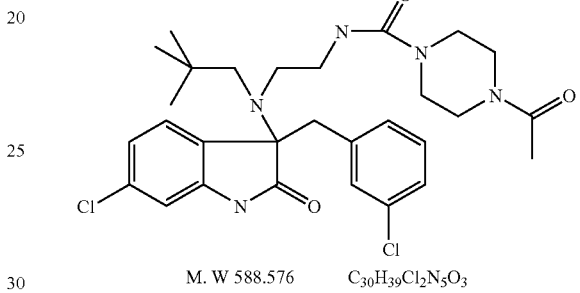

M. W 588.576    $C_{30}H_{39}Cl_2N_5O_3$

The title compound was prepared by the same procedure 4-Acetyl-piperazine-1-carboxylic acid{2-[[(S)-6-chloro-3-(3-chloro-benzyl)-2-oxo-2,3-dihydro-1H-indol-3-yl]-(2,2-dimethyl-propyl)-amino]-ethyl}-amide. MS: [M+H]⁺=588.

EXAMPLE 460

Preparation of rac-Morpholine-4-carboxylic acid{3-[[6-chloro-3-(3-chloro-benzyl)-2-oxo-2,3-dihydro-1H-indol-3-yl]-(2,2-dimethyl-propyl)-amino]-propyl}-amide

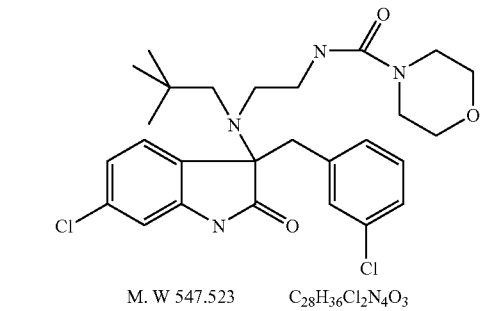

M. W 547.523    $C_{28}H_{36}Cl_2N_4O_3$

The title compound was prepared by the same procedure 4-Acetyl-piperazine-1-carboxylic acid{2-[[(S)-6-chloro-3-

(3-chloro-benzyl)-2-oxo-2,3-dihydro-1H-indol-3-yl]-(2,2-dimethyl-propyl)-amino]-ethyl}-amide. MS: [M+H]⁺=547.

EXAMPLE 461

Preparation of rac-N-{3-[[6-Chloro-3-(3-chloro-benzyl)-2-oxo-2,3-dihydro-1H-indol-3-yl]-(2,2-dimethyl-propyl)-amino]-propyl}-methanesulfonamide

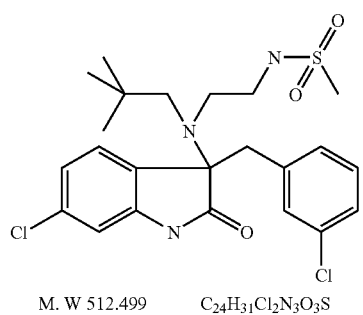

M. W 512.499    $C_{24}H_{31}Cl_2N_3O_3S$

The title compound was prepared by the same procedure 4-Acetyl-piperazine-1-carboxylic acid{2-[[(S)-6-chloro-3-(3-chloro-benzyl)-2-oxo-2,3-dihydro-1H-indol-3-yl]-(2,2-dimethyl-propyl)-amino]-ethyl}-amide. MS: [M+H]⁺=512

EXAMPLE 462

Preparation of rac-1-Acetyl-piperidine-4-carboxylic acid{3-[[6-chloro-3-(3-chloro-benzyl)-2-oxo-2,3-dihydro-1H-indol-3-yl]-(2,2-dimethyl-propyl)-amino]-propyl}-amide

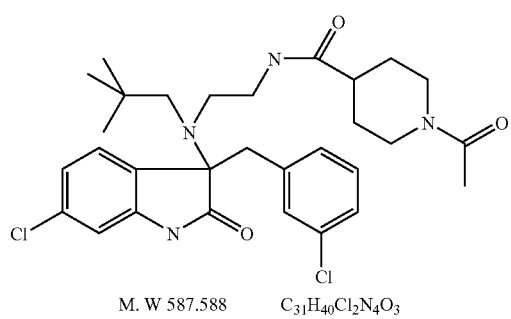

M. W 587.588    $C_{31}H_{40}Cl_2N_4O_3$

The title compound was prepared by the same procedure 1-Acetyl-piperidine-4-carboxylic acid{2-[[(S)-6-chloro-3-(3-chloro-benzyl)-2-oxo-2,3-dihydro-1H-indol-3-yl]-(2,2-dimethyl-propyl)-amino]-ethyl}-amide. MS: [M+H]⁺=587.

EXAMPLE 463

Preparation of rac-Morpholine-4-carboxylic acid (2-{sec-butyl-[6-chloro-3-(3-chloro-benzyl)-2-oxo-2,3-dihydro-1H-indol-3-yl]-amino}-ethyl)-amide

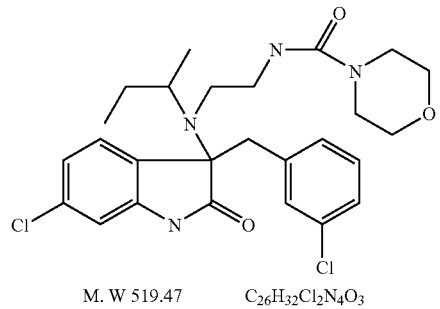

M. W 519.47    $C_{26}H_{32}Cl_2N_4O_3$

The title compound was prepared by the same procedure 4-Acetyl-piperazine-1-carboxylic acid{2-[[(S)-6-chloro-3-(3-chloro-benzyl)-2-oxo-2,3-dihydro-1H-indol-3-yl]-(2,2-dimethyl-propyl)-amino]-ethyl}-amide. MS: [M+H]⁺=519.

EXAMPLE 464

Preparation of rac-(R)-2-{4-Bromo-2-[6-chloro-3-(3-chloro-benzyl)-2-oxo-2,3-dihydro-1H-indol-3-ylamino]-benzoylamino}-propionic acid methyl ester

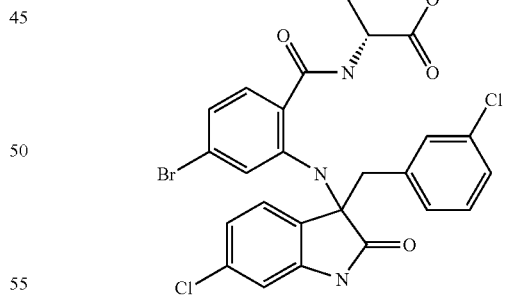

M. W. 591.29    $C_{26}H_{22}Cl_2BrN_3O_4$

The title compound was prepared following the similar procedure as rac-3-{[2-(4-acetyl-piperazin-1-yl)-2-oxoethyl]-cyclohexyl-amino}-6-chloro-3-(3-chloro-benzyl)-1,3-dihydro-indol-2-one. MS: [M+H]⁺=590.

EXAMPLE 465

Preparation of rac-(S)-2-{4-Bromo-2-[6-chloro-3-(3-chloro-benzyl)-2-oxo-2,3-dihydro-1H-indol-3-ylamino]-benzoylamino}-propionic acid tert-butyl ester

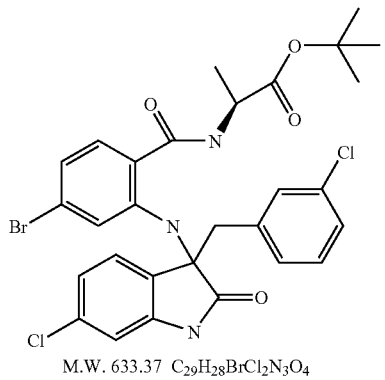

M.W. 633.37  $C_{29}H_{28}BrCl_2N_3O_4$

The title compound was prepared following the similar procedure as rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: [M+H]⁺=632.

EXAMPLE 466a

Preparation of rac-4-Bromo-2-[6-chloro-3-(3-chloro-benzyl)-2-oxo-2,3-dihydro-1H-indol-3-ylamino]-acetic acid ethyl ester

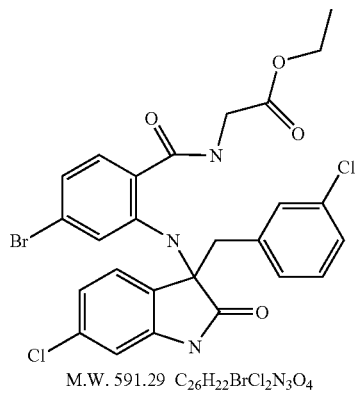

M.W. 591.29  $C_{26}H_{22}BrCl_2N_3O_4$

The title compound was prepared following the similar procedure as rac-3-{[2-(4-acetyl-piperazin-1-yl)-2-oxoethyl]-cyclohexyl-amino}-6-chloro-3-(3-chloro-benzyl)-1,3-dihydro-indol-2-one. MS: [M+H]⁺=590.

EXAMPLE 466b

Preparation of rac-4-Bromo-2-[6-chloro-3-(3-chloro-benzyl)-2-oxo-2,3-dihydro-1H-indol-3-ylamino]-acetic acid

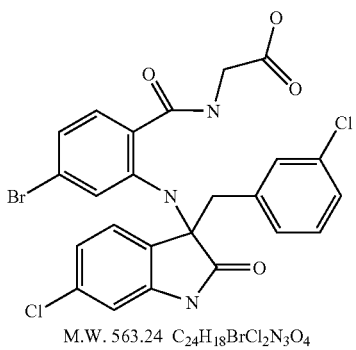

M.W. 563.24  $C_{24}H_{18}BrCl_2N_3O_4$

The title compound was prepared by the same procedure as rac-{[6-chloro-3-(3-chloro-benzyl)-2-oxo-2,3-dihydro-1H-indol-3-yl]-cyclohexyl-amino}-acetic acid. MS: 562 (M+H)⁺.

EXAMPLE 466c

Preparation of rac-4-Bromo-2-[6-chloro-3-(3-chloro-benzyl)-2-oxo-2,3-dihydro-1H-indol-3-ylamino]-N-methylcarbamoylmethyl-benzamide

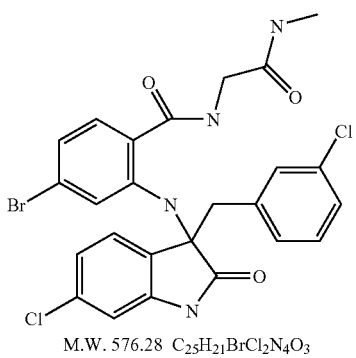

M.W. 576.28  $C_{25}H_{21}BrCl_2N_4O_3$

The title compound was prepared following the similar procedure as rac-4-Bromo-2-[6-chloro-3-(3-chloro-benzyl)-

2-oxo-2,3-dihydro-1H-indol-3-ylamino]-N-methylcarbamoylmethyl-benzamide MS: [M+H]$^+$=575.

EXAMPLE 467

Preparation of rac-4-Bromo-2-[6-chloro-3-(3-chlorobenzyl)-2-oxo-2,3-dihydro-1H-indol-3-ylamino]-N-dimethylcarbamoylmethyl-benzamide

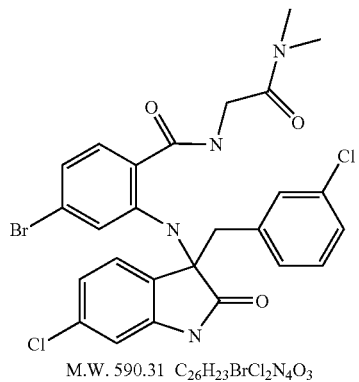

M.W. 590.31  $C_{26}H_{23}BrCl_2N_4O_3$

The title compound was prepared following the similar procedure as rac-4-Bromo-2-[6-chloro-3-(3-chloro-benzyl)-2-oxo-2,3-dihydro-1H-indol-3-ylamino]-N-methylcarbamoylmethyl-benzamide MS: [M+H]$^+$=589.

EXAMPLE 468

Preparation of rac-4-Bromo-2-[6-chloro-3-(3-chlorobenzyl)-2-oxo-2,3-dihydro-1H-indol-3-ylamino]-N-(2-morpholin-4-yl-2-oxo-ethyl)-benzamide

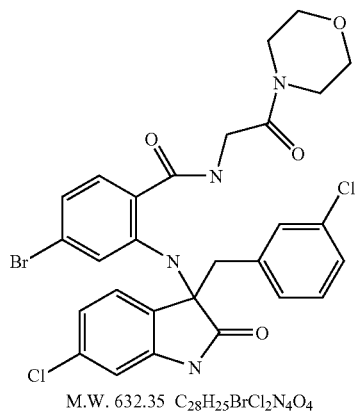

M.W. 632.35  $C_{28}H_{25}BrCl_2N_4O_4$

The title compound was prepared following the similar procedure as rac-4-Bromo-2-[6-chloro-3-(3-chloro-benzyl)-

2-oxo-2,3-dihydro-1H-indol-3-ylamino]-N-methylcarbamoylmethyl-benzamide MS: [M+H]$^+$=631.

EXAMPLE 469

Preparation of rac-4-Bromo-2-[6-chloro-3-(3-chlorobenzyl)-2-oxo-2,3-dihydro-1H-indol-3-ylamino]-N-{2-oxo-2-[4-(2-oxo-2-pyrrolidin-1-yl-ethyl)-piperazin-1-yl]-ethyl}-benzamide

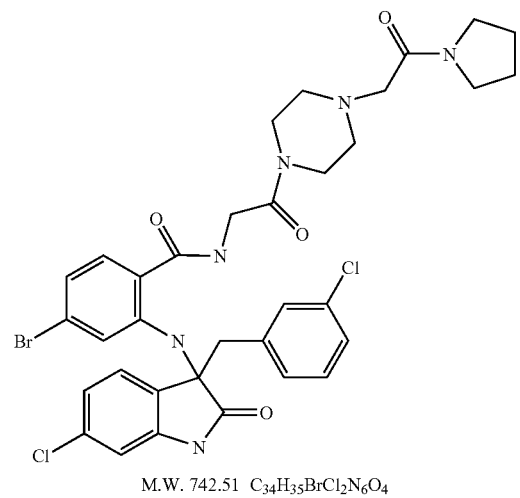

M.W. 742.51  $C_{34}H_{35}BrCl_2N_6O_4$

The title compound was prepared following the similar procedure as rac-4-Bromo-2-[6-chloro-3-(3-chloro-benzyl)-2-oxo-2,3-dihydro-1H-indol-3-ylamino]-N-methylcarbamoylmethyl-benzamide MS: [M+H]$^+$=741.

EXAMPLE 470a

Preparation of rac-(S)-6-Amino-2-(2-{4-bromo-2-[6-chloro-3-(3-chloro-benzyl)-2-oxo-2,3-dihydro-1H-indol-3-ylamino]-benzoylamino}-acetylamino)-6-tert-butoxycarbonylamino-hexanoic acid methyl ester

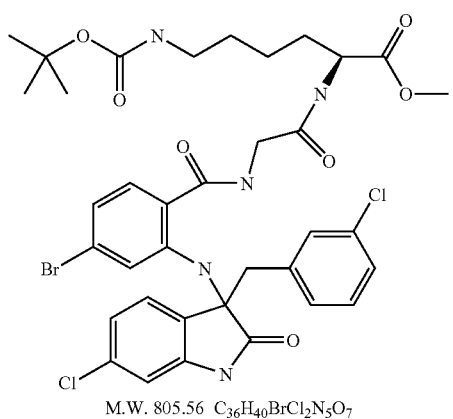

M.W. 805.56  $C_{36}H_{40}BrCl_2N_5O_7$

The title compound was prepared following the similar procedure as rac-3-{[2-(4-acetyl-piperazin-1-yl)-2-oxoethyl]-cyclohexyl-amino}-6-chloro-3-(3-chloro-benzyl)-1,3-dihydro-indol-2-one. MS: [M+H]⁺=804

EXAMPLE 470b

Preparation of rac-(S)-6-Amino-2-(2-{4-bromo-2-[6-chloro-3-(3-chloro-benzyl)-2-oxo-2,3-dihydro-1H-indol-3-ylamino]-benzoylamino}-acetylamino)-hexanoic acid methyl ester

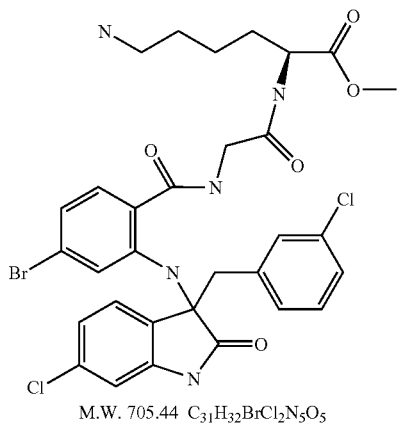

M.W. 705.44  $C_{31}H_{32}BrCl_2N_5O_5$

The rac-(S)-6-Amino-2-(2-{4-bromo-2-[6-chloro-3-(3-chloro-benzyl)-2-oxo-2,3-dihydro-1H-indol-3-ylamino]-benzoylamino}-acetylamino)-6-tert-butoxycarbonylamino-hexanoic acid methyl ester (200 mg, 0.25 mmol) in 5 mL of TFA was stirred at room temperature for 0.5 hour, and concentrated in vacuo. The residue was added by 10 mL of DCM, then rinsed with 20 mL of water. The organic layer was dried over $Na_2SO_4$, and concentrated in vacuo, then purified by flash column chromatopgraphy to 146 mg white solid. MS: 704 (M+H)⁺.

EXAMPLE 471

Preparation of rac-3-[5-Bromo-2-(morpholine-4-carbonyl)-phenylamino]-6-chloro-3-[1-(3-chloro-phenyl)-ethyl]-1,3-dihydro-indol-2-one

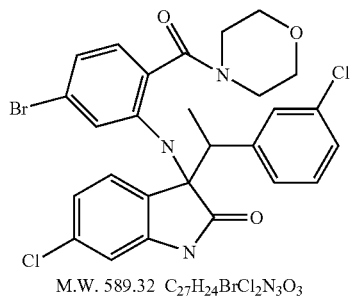

M.W. 589.32  $C_{27}H_{24}BrCl_2N_3O_3$

The title compound was prepared following the similar procedure as rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: [M+H]⁺=588.

EXAMPLE 472

Preparation of rac-4-Bromo-2-[6-bromo-3-(3-chloro-benzyl)-2-oxo-2,3-dihydro-1H-indol-3-ylamino]-N-(3-dimethylamino-propyl)-benzamide

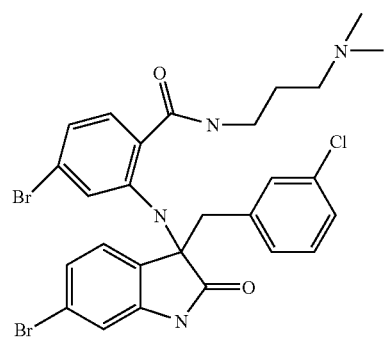

M. W. 634.80  $C_{27}H_{27}Br_2ClN_4O_2$

The title compound was prepared following the similar procedure as rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: [M+H]⁺=633.

EXAMPLE 473

Preparation of rac-3-[2-(4-Acetyl-piperazine-1-carbonyl)-5-bromo-phenylamino]-6-bromo-3-(3-chloro-benzyl)-1,3-dihydro-indol-2-one

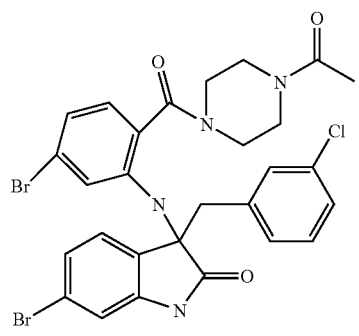

M. W. 660.80  $C_{28}H_{25}Br_2ClN_4O_3$

The title compound was prepared following the similar procedure as rac-3-{[2-(4-acetyl-piperazin-1-yl)-2-oxoethyl]-cyclohexyl-amino}-6-chloro-3-(3-chloro-benzyl)-1,3-dihydro-indol-2-one. MS: [M+H]⁺=659.

EXAMPLE 474a

Preparation of rac-(2-{[6-bromo-3-(3-chloro-benzyl)-2-oxo-2,3-dihydro-1H-indol-3-yl]-isopropyl-amino}-ethyl)-carbamic acid tert-butyl ester

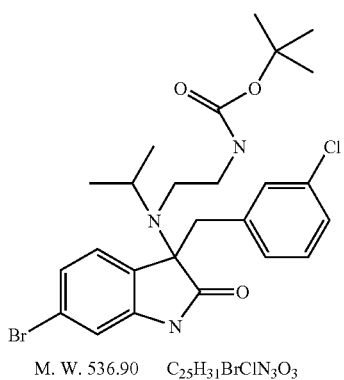

M. W. 536.90    $C_{25}H_{31}BrClN_3O_3$

The title compound was prepared by the same procedure as rac-6-chloro-3-(3-chloro-benzyl)-3-cyclohexylamino-1,3-dihydro-1H-indol-2-one. MS: 535 (M+H)⁺.

EXAMPLE 474b

Preparation of rac-3-[(2-Amino-ethyl)-isopropyl-amino]-6-bromo-3-(3-chloro-benzyl)-1,3-dihydro-indol-2-one

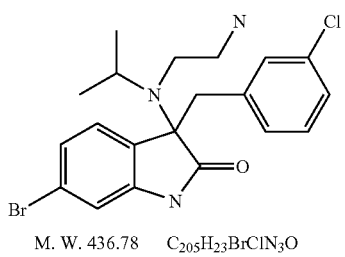

M. W. 436.78    $C_{205}H_{23}BrClN_3O$

The title compound was prepared by the same procedure as rac-(S)-6-Amino-2-(2-{4-bromo-2-[6-chloro-3-(3-chloro-benzyl)-2-oxo-2,3-dihydro-1H-indol-3-ylamino]-benzoylamino}-acetylamino)-hexanoic acid methyl ester. MS: 436 (M+H)⁺.

EXAMPLE 474c

Preparation of rac-4-Acetyl-piperazine-1-carboxylic acid (2-{[6-bromo-3-(3-chloro-benzyl)-2-oxo-2,3-dihydro-1H-indol-3-yl]-isopropyl-amino}-ethyl)-amide

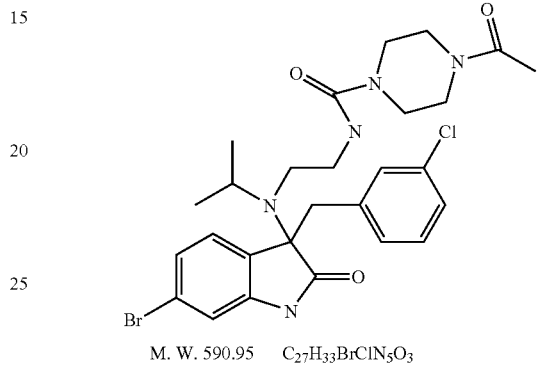

M. W. 590.95    $C_{27}H_{33}BrClN_5O_3$

To a solution of rac-3-[(2-Amino-ethyl)-isopropyl-amino]-6-bromo-3-(3-chloro-benzyl)-1,3-dihydro-indol-2-one (270 mg, 0.48 mmol) and DIPEA (167 uL, 0.96 mmol) in 5 mL of DCM was added 4-acetyl-piperazine-1-carbonyl chloride (137 mg, 0.72 mmol) at room temperature, and stirred at same temperature overnight. The reaction mixture was rinsed with 20 mL water. The organic layer was dried over Na₂SO₄, and concentrated in vacuo, then purified by flash column chromatopgraphy to 180 mg white solid. MS: [M+H]⁺=590.

EXAMPLE 475

Preparation of rac-Morpholine-4-carboxylic acid (2-{[4,6-dichloro-3-(3-chloro-benzyl)-2-oxo-2,3-dihydro-1H-indol-3-yl]-isopropyl-amino}-ethyl)-amide

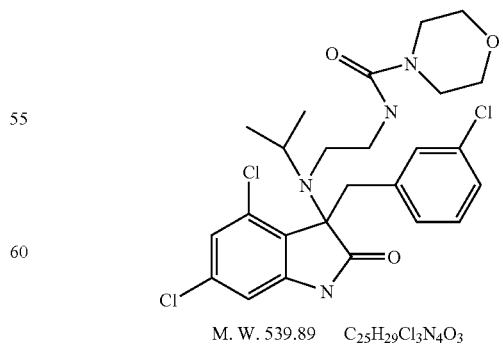

M. W. 539.89    $C_{25}H_{29}Cl_3N_4O_3$

The title compound was prepared following the similar procedure as rac-4-Acetyl-piperazine-1-carboxylic acid (2-{

[6-bromo-3-(3-chloro-benzyl)-2-oxo-2,3-dihydro-1H-indol-3-yl]-isopropyl-amino}-ethyl)-amide MS: [M+H]$^+$=539.

EXAMPLE 476

Preparation of rac-3-[2-(4-Acetyl-piperazine-1-carbonyl)-5-bromo-phenylamino]-4,6-dichloro-3-(3-chloro-benzyl)-1,3-dihydro-indol-2-one

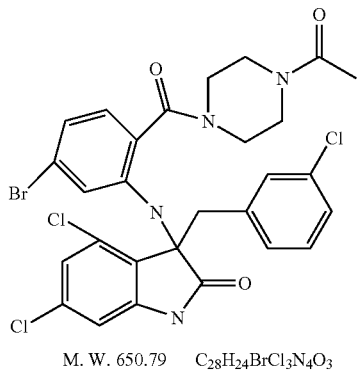

M. W. 650.79    $C_{28}H_{24}BrCl_3N_4O_3$

The title compound was prepared following the similar procedure as rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: [M+H]$^+$=649.

EXAMPLE 477

Preparation of rac-(S)-1-{4-Bromo-2-[6-chloro-3-(2-methyl-benzyl)-2-oxo-2,3-dihydro-1H-indol-3-ylamino]-benzoyl}-pyrrolidine-2-carboxylic acid amide

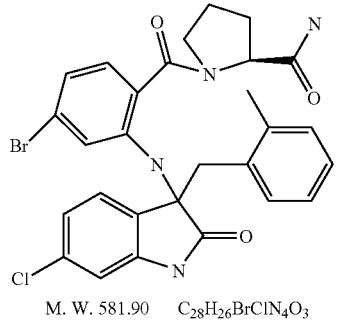

M. W. 581.90    $C_{28}H_{26}BrClN_4O_3$

The title compound was prepared following the similar procedure as rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: [M+H]$^+$=581.

EXAMPLE 478

Preparation of rac-1-{2-[[6-Chloro-3-(2-methyl-benzyl)-2-oxo-2,3-dihydro-1H-indol-3-yl]-(2,2-dimethyl-propyl)-amino]-acetyl}-piperidine-4-carboxylic acid amide

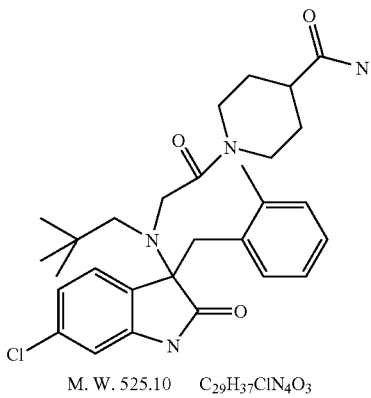

M. W. 525.10    $C_{29}H_{37}ClN_4O_3$

The title compound was prepared following the similar procedure as rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: [M+H]$^+$=525.

EXAMPLE 479

Preparation of rac-4-Bromo-2-[4,6-dichloro-3-(3-chloro-benzyl)-2-oxo-2,3-dihydro-1H-indol-3-ylamino]-N-(3-dimethylamino-propyl)-benzamide

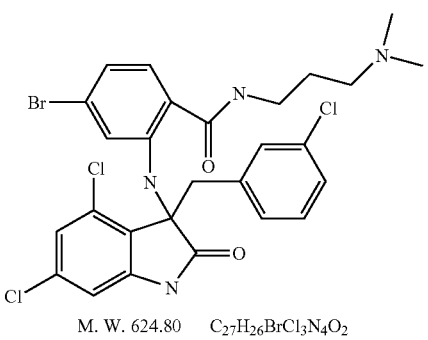

M. W. 624.80    $C_{27}H_{26}BrCl_3N_4O_2$

The title compound was prepared following the similar procedure as rac-3-{[2-(4-acetyl-piperazin-1-yl)-2-oxo-ethyl]-cyclohexyl-amino}-6-chloro-3-(3-chloro-benzyl)-1,3-dihydro-indol-2-one. MS: [M+H]$^+$=623.

EXAMPLE 480

In Vitro Assay

In a cell based assay, the ability of the compounds to inhibit the interaction between p53 and MDM2 proteins was measured. The ability of the compounds to inhibit the interaction between p53 and MDM2 proteins was measured by an HTRF (homogeneous time-resolved fluorescence) assay in which recombinant GST-tagged MDM2 binds to a peptide that resembles the MDM2-interacting region of p53 (Lane et al.). Binding of GST-MDM2 protein and p53-peptide (biotinylated on its N-terminal end) is registered by the FRET (fluorescence resonance energy transfer) between Europium (Eu)-labeled anti-GST antibody and streptavidin-conjugated Allophycocyanin (APC).

The test is performed in black flat-bottom 384-well plates (Costar) in a total volume of 40 uL containing: 90 nM biotinylate peptide, 160 ng/ml GST-MDM2, 20 nM streptavidin-APC (PerkinElmerWallac), 2 nM Eu-labeled anti-GST-antibody (PerkinElmerWallac), 0.2% bovine serum albumin (BSA), 1 mM dithiothreitol (DTT) and 20 mM Tris-borate saline (TBS) buffer as follows: Add 10 uL of GST-MDM2 (640 ng/ml working solution) in reaction buffer to each well. Add 10 uL diluted compounds (1:5 dilution in reaction buffer) to each well, mix by shaking. Add 20 uL biotinylated p53 peptide (180 nM working solution) in reaction buffer to each well and mix on shaker. Incubate at 37° C. for 1 h. Add 20 uL streptavidin-APC and Eu-anti-GST antibody mixture (6 nM Eu-anti-GST and 60 nM streptavidin-APC working solution) in TBS buffer with 0.2% BSA, shake at room temperature for 30 minutes and read using a TRF-capable plate reader at 665 and 615 nm (Victor 5, Perkin ElmerWallac). If not specified, the reagents were purchased from Sigma Chemical Co.

| Example | $IC_{50}$ (nM, 0.02% BSA) |
|---------|---------------------------|
| 6       | 1.1693                    |
| 11      | 3.7299                    |
| 19      | 2.561                     |
| 49      | 2.539                     |
| 62      | 3.6761                    |

What is claimed:
1. A compound of the formula

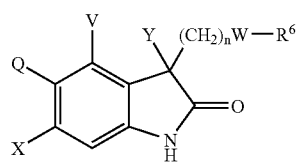

wherein X is selected from the group consisting of hydrogen, halogen, cyano, lower alkyl, lower alkenyl, lower alkynyl, lower alkoxy, nitro, methyl sulfonyl, sulfonamide and cyclopropyl,
V is hydrogen,
Q is hydrogen or halogen,
Y is

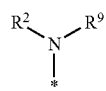

$R^2$ is selected from the group consisting of lower alkyl, substituted lower alkyl, aryl, substituted aryl, heteroaryl, substituted heteroaryl, cycloalkyl, substituted cycloalkyl, cycloalkenyl and substituted alkenyl,
$R^6$ is selected from the group consisting of aryl, substituted aryl,
$R^9$ is selected from the group consisting of hydrogen, substituted lower alkyl, lower alkoxy, substituted lower alkoxy,
and in the case of $R^2$ and $R^9$ they may independently link to form a cyclic structure selected from substituted or unsubstituted heteroaryl, or substituted or unsubstituted heterocycle, said heteroaryl or heterocycle selected from the group consisting of

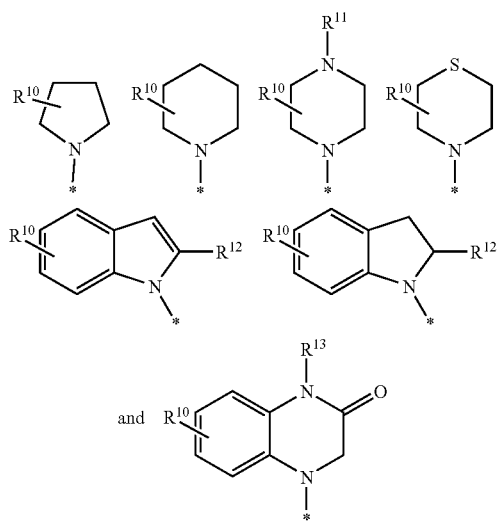

wherein
$R^{10}$ is selected from the group consisting of hydrogen, lower alkyl, lower-alkenyl, lower-alkynyl, dioxo-lower-alkylene, halogen, hydroxy, CN, $CF_3$, $NH_2$, heterocycloalkyl, N(H, lower-alkyl), N(lower-alkyl)$_2$, aminocarbonyl, carboxy, $NO_2$, lower-alkoxy, thio-lower-alkoxy, lower-alkylsulfonyl, aminosulfonyl, lower-alkylcarbonyl, lower-alkylcarbonyloxy, lower-alkoxycarbonyl, lower-alkyl-carbonyl-NH, fluoro-lower-alkyl, fluoro-lower-alkoxy, lower-alkoxy-carbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)$_2$-lower-alkoxy, benzyloxy-lower-alkoxy, mono- or di-lower alkyl substituted amino-sulfonyl and lower-alkyl which can optionally be substituted with halogen, hydroxy, $NH_2$, N(H, lower-alkyl) or N(lower-alkyl)$_2$,
$R^{11}$ is selected from the group consisting of hydrogen, lower alkyl, lower-alkenyl, lower-alkynyl, dioxo-lower-alkylene, hydroxy, CN, $CF_3$, $NH_2$, N(H, lower-alkyl), N(lower-alkyl)$_2$, lower-alkoxy, thio-lower-alkoxy, lower-alkylsulfonyl, aminosulfonyl, lower-alkylcarbonyl, lower-alkylcarbonyloxy, lower-alkoxycarbonyl, fluoro-lower-alkyl, fluoro-lower-alkoxy, lower-alkoxy-carbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)$_2$-lower-alkoxy, benzyloxy-lower-alkoxy, mono- or di-lower alkyl substituted amino-sulfonyl and lower-alkyl which can optionally be substituted with halogen, hydroxy, $NH_2$, $N(H, lower-alkyl)$ or $N(lower-alkyl)_2$, $N(H, lower-alkyl)$-carbonyl, $N(lower-alkyl)_2$-carbonyl, $R^{12}$ is selected from the group consisting of hydrogen, lower alkyl, aminocarbonyl, lower-alkylsulfonyl, aminosulfonyl, lower-alkylcarbonyl, lower-alkoxycarbonyl, fluoro-lower-alkyl, $N(H, lower-alkyl)$-carbonyl, $N(lower-alkyl)_2$-carbonyl, mono- or di-lower alkyl substituted amino-sulfonyl and lower-alkyl which can optionally be substituted with halogen, hydroxy, $NH_2$, $N(H, lower-alkyl)$ or $N(lower-alkyl)_2$, $R^{13}$ is selected from the group consisting of hydrogen, lower alkyl, lower-alkenyl, lower-alkynyl, dioxo-lower-alkylene, hydroxy, CN, $NH_2$, heterocycloalkyl, $N(H, lower-alkyl)$, $N(lower-alkyl)_2$, lower-alkoxy, thio-lower-alkoxy, lower-alkylcarbonyloxy, fluoro-lower-alkyl, fluoro-lower-alkoxy, lower-alkoxy-carbonyl-lower-alkoxy, carboxy-lower-alkoxy, carbamoyl-lower-alkoxy, hydroxy-lower-alkoxy, $NH_2$-lower-alkoxy, $N(H, lower-alkyl)$-lower-alkoxy, $N(lower-alkyl)_2$-lower-alkoxy, benzyloxy-lower-alkoxy, lower-alkyl which can optionally be substituted with halogen, hydroxy, $NH_2$, $N(H, lower-alkyl)$ or $N(lower-alkyl)_2$, $N(H, lower-alkyl)$-carbonyl, $N(lower-alkyl)_2$-carbonyl, W is a single bond, n is 1-3 with the proviso that when $R^9$ is hydrogen then $R^2$ is not substituted alkyl and the pharmaceutically acceptable salts thereof.

2. A compound of claim 1 selected from the group consisting of rac-6-chloro-3-(3-chloro-benzyl)-3-(2-fluoro-phenylamino)-1,3-dihydro-indol-2-one,
rac-6-chloro-3-(3-chloro-benzyl)-3-(4-fluoro-2-methyl-phenylamino)-1,3-dihydro-indol-2-one,
rac-6-chloro-3-(3-chloro-benzyl)-3-(4-chloro-3-methyl-phenylamino)-1,3-dihydro-indol-2-one,
rac-6-chloro-3-(3-chloro-benzyl)-3-(3,4,5-trifluoro-phenylamino)-1,3-dihydro-indol-2-one,
rac-6-chloro-3-(3-chloro-benzyl)-3-(2-chloro-phenylamino)-1,3-dihydro-indol-2-one,
rac-6-chloro-3-(3-chloro-benzyl)-3-(3-hydroxy-phenylamino)-1,3-dihydro-indol-2-one,
rac-6-chloro-3-(3-chloro-benzyl)-3-(3-methoxy-phenylamino)-1,3-dihydro-indol-2-one,
rac-6-chloro-3-(3-chloro-benzyl)-3-cyclohexylamino-1,3-dihydro-indol-2-one,
rac-6-chloro-3-(3-chloro-benzyl)-3-(2-methyl-pyrrolidin-1-yl)-1,3-dihydro-indol-2-one,
rac-6-chloro-3-(3-chloro-benzyl)-3-cyclobutylamino-1,3-dihydro-indol-2-one,
rac-1-[6-chloro-3-(3-chloro-benzyl)-2-oxo-2,3-dihydrol-indol-3-yl]-piperidine-3-carboxylic acid amide.
rac-6-chloro-3-(3-chloro-benzyl)-3-(3-isopropoxy-phenylamino)-1,3-dihydro-indol-2-one,
rac-6-chloro-3-(3-chloro-benzyl)-3-(2,6-difluoro-phenylamino)-1,3-dihydro-indol-2-one,
rac-3-(benzo[1,3]dioxo1-5-ylamino)-6-chloro-3-(3-chloro-benzyl)-1,3-dihydro-indol-2-one,
rac-6-chloro-3-(3-chloro-benzyl)-3-(4-fluoro-phenylamino)-1,3-dihydro-indol-2-one,
rac-6-chloro-3-(3-chloro-benzyl)-3-(2,4-difluoro-phenylamino)-1,3-dihydro-indol-2-one,
rac-6-chloro-3-(3-chloro-benzyl)-3-(4-chloro-2-fluoro-phenylamino)-1,3-dihydro-indol-2-one,
rac-3-(4-bromo-2-fluoro-phenylamino)-6-chloro-3-(3-chloro-benzyl)-1,3-dihydro-indol-2-one,
rac-6-chloro-3-(3-chloro-benzyl)-3-(3-ethyl-phenylamino)-1,3-dihydro-indol-2-one,
rac-6-chloro-3-(3-chloro-benzyl)-3-(4-isopropoxy-phenylamino)-1,3-dihydro-indol-2-one,
rac-6-chloro-3-(3-chloro-benzyl)-3-(3,4-difluoro-phenylamino)-1,3-dihydro-indol-2-one,
rac-6-chloro-3-(3-chloro-benzyl)-3-(3-hydroxymethyl-phenylamino)-1,3-dihydro-indol-2-one,
rac-6-chloro-3-(3-chloro-benzyl)-3-(4-difluoromethoxy-phenylamino)-1,3-dihydro-indol-2-one,
rac-6-chloro-3-(3-chloro-benzyl)-3-(3-difluoromethoxy-phenylamino)-1,3-dihydro-indol-2-one,
rac-6-chloro-3-(3-chloro-benzyl)-3-(4-trifluoromethyl-phenylamino)-1,3-dihydro-indol-2-one,
rac-3-(3-acetyl-phenylamino)-6-chloro-3-(3-chloro-benzyl)-1,3-dihydro-indol-2-one,
rac-6-chloro-3-(3-chloro-benzyl)-3-phenylamino-1,3-dihydro-indol-2-one,
rac-6-chloro-3-(3-chloro-benzyl)-3-(4-methoxy-phenylamino)-1,3-dihydro-indol-2-one,
rac-3-[6-chloro-3-(3-chloro-benzyl)-2-oxo-2,3-dihydro-indol-3-ylamino]-benzonitrile,
rac-6-chloro-3-(3-chloro-benzyl)-3-(3-chloro-phenylamino)-1,3-dihydro-indol-2-one,
rac-3-(4-bromo-2-methyl-phenylamino)-6-chloro-3-(3-chloro-benzyl)-1,3-dihydro-indol-2-one,
rac-6-chloro-3-(3-chloro-benzyl)-3-(5-fluoro-2-methyl-phenylamino)-1,3-dihydro-indol-2-one and
rac-6-chloro-3-(3-chloro-benzyl)-3-(2-trifluoromethyl-phenylamino)-1,3-dihydro-indol-2-one.

3. A compound selected from the group consisting of rac-1-(2-{[6-chloro-3-(3-chloro-benzyl)-2-oxo-2,3-dihydro-1H-indol-3-yl]-cyclohexyl-amino}-acetyl)-1,3-diisopropyl-urea,
rac-6-chloro-3-(3-chloro-benzyl)-3-{cyclohexyl-[2-oxo-2-(3-oxo-piperazin-1-yl)-ethyl]-amino}-1,3-dihydro-indol-2-one,
rac-6-chloro-3-(3-chloro-benzyl)-3-{cyclohexyl-[2-(4-isopropyl-piperazin-1-yl)-2-oxo-ethyl]-amino}-1,3-dihydro-indol-2-one,
rac-6-chloro-3-(3-chloro-benzyl)-3-(cyclohexyl-{2-[4-(3-hydroxy-propyl)-piperazin-1-yl]-2-oxo-ethyl}-amino)-1,3-dihydro-indol-2-one,
rac-2-{[6-chloro-3-(3-chloro-benzyl)-2-oxo-2,3-dihydro-1H-indol-3-yl]-cyclohexyl-amino}-N-(2-morpholin-4-yl-ethyl)-acetamide,
rac-2-{[6-chloro-3-(3-chloro-benzyl)-2-oxo-2,3-dihydro-1H-indol-3-yl]-cyclohexyl-amino}-N-[2-(3H-imidazol-4-yl)-ethyl]-acetamide,
rac-2-{[6-chloro-3-(3-chloro-benzyl)-2-oxo-2,3-dihydro-1H-indol-3-yl]-cyclohexyl-amino}-N-cyclobutyl-acetamide,
rac-2-{[6-chloro-3-(3-chloro-benzyl)-2-oxo-2,3-dihydro-1H-indol-3-yl]-cyclohexyl-amino}-N-(1,1-dimethyl-propyl)-acetamide,
rac-2-{[6-chloro-3-(3-chloro-benzyl)-2-oxo-2,3-dihydro-1H-indol-3-yl]-cyclohexyl-amino}-N-(2-dimethylamino-1-methyl-ethyl)-acetamide,
rac-2-{[6-chloro-3-(3-chloro-benzyl)-2-oxo-2,3-dihydro-1H-indol-3-yl]-cyclohexyl-amino}-N-piperidin-1-yl-acetamide,
rac-2-{[6-chloro-3-(3-chloro-benzyl)-2-oxo-2,3-dihydro-1H-indol-3-yl]-cyclohexyl-amino}-N-furan-2-ylmethyl-acetamide.
rac-6-chloro-3-(3-chloro-benzyl)-3-(3-hydroxy-pyrrolidin-1-yl)-1,3-dihydro-indol-2-one, rac-1[6-chloro-3-(3-chloro-benzyl)-2-oxo-2,3-dihydrol-1H-indol-3-yl]-piperidine-4-carboxylic acid amide,
rac-6-chloro-3-(3-chloro-benzyl)-3[4-(2-fluoro-phenyl)-piperazin-1-yl]-1,3-dihydro-indol-2-one,
rac-6-chloro-3-(3-chloro-benzyl)-3-[4-(3-trifluoromethyl-pyridin-2-yl)-piperazin-1-yl]-1,3-dihydro-indol-2-one,
rac-6-chloro-3-(3-chloro-benzyl)-3-thiomorpholin-4-yl-1,3-dihydro-indol-2-one,
rac-6-chloro-3-(3-chloro-benzyl)-3-cyclopropylamino-1,3-dihydro-indol-2-one,
rac-6-chloro-3-(3-chloro-benzyl)-3-(3-hydroxy-piperidin-1-yl)-1,3-dihydro-indol-2-one,
rac-6-chloro-3-(3-chloro-benzyl)-3-(2-hydroxy-cyclohexylamino)-1,3-dihydro-indol-2-one,
rac-(2S)[6-chloro-3-(3-chloro-benzyl)-2-oxo-2,3-dihydro-1H-indol-3-ylamino]-4-methyl-pentanoic acid tert-butyl ester,
rac-{[6-chloro-3-(3-chloro-benzyl)-2-oxo-2,3-dihydro-1H-indol-3-yl]-phenyl-amino}-acetic acid,
rac-6-chloro-3-(4-chloro-benzyl)-3-cyclohexylamino-1,3-dihydro-indol-2-one,
rac-5-bromo-6-chloro-3-(4-chloro-benzyl)-3-cyclohexylamino-1,3-dihydro-indol-2-one,
rac-6-chloro-3-(4-chloro-benzyl)-3-cyclohexylamino-1-(2-oxo-2-piperidin-1-yl-ethyl)-1,3-dihydro-indol-2-one,
rac-5-bromo-6-chloro-3-(4-chloro-benzyl)-3-cyclohexylamino-1-(2-oxo-2-piperidin-1-yl-ethyl)-1,3-dihydro-indol-2-one,
rac-{[6-chloro-3-(3-chloro-benzyl)-2-oxo-2,3-dihydro-1H-indol-3-yl]-cyclohexyl-amino}-acetic acid ethyl ester,
rac-{[6-chloro-3-(3-chloro-benzyl)-2-oxo-2,3-dihydro-1H-indol-3-yl]-cyclohexyl-amino}-acetic acid and
rac-3-{[2-(4-acetyl-piperazin-1-yl)-2-oxo-ethyl]-cyclohexyl-amino}-6-chloro-3-(3-chloro-benzyl)-1,3-dihydro-indol-2-one.

4. A compound selected from the group consisting of
rac-2-{[6-chloro-3-(3-chloro-benzyl)-2-oxo-2,3-dihydro-1H-indol-3-yl]-phenyl-amino}-N-cyclohexy-acetamide,
rac-2-{[6-chloro-3-(3-chloro-benzyl)-2-oxo-2,3-dihydro-1H-indol-3-yl]-phenyl-amino}-N-isopropoyl-acetamide,
rac-2-{[6-chloro-3-(3-chloro-benzyl)-2-oxo-2,3-dihydro-1H-indol-3-yl]-phenyl-amino}-N-cyclopentyl-acetamide,
rac-2-{[6-chloro-3-(3-chloro-benzyl)-2-oxo-2,3-dihydro-1H-indol-3-yl]-phenyl-amino}-N-cyclopropyl-acetamide,
rac-2-{[6-chloro-3-(3-chloro-benzyl)-2-oxo-2,3-dihydro-1H-indol-3-yl]-phenyl-amino}-N-phenyl-acetamide,
rac-6-chloro-3-(3-chloro-benzyl)-3-({2-[4-(3-hydroxy-propyl)-piperazin-1-yl]-2-oxo-ethyl}-phenyl-amino)-1,3-dihydro-indol-2-one,
rac-2-{[6-chloro-3-(3-chloro-benzyl)-2-oxo-2,3-dihydro-1H-indol-3-yl]-phenyl-amino}-N-cyclobutyl-acetamide,
rac-2-{[6-chloro-3-(3-chloro-benzyl)-2-oxo-2,3-dihydro-1H-indol-3-yl]-phenyl-amino}-N-[2-(3H-imidazol-4-yl)-ethyl]-acetamide,
rac-4-(2-{[6-chloro-3-(3-chloro-benzyl)-2-oxo-2,3-dihydro-1H-indol-3-yl]-phenyl-amino}-acetyl)-piperazine-1-carboxylic acid tert-butyl ester,
rac-2-{[6-chloro-3-(3-chloro-benzyl)-2-oxo-2,3-dihydro-1H-indol-3-yl]-phenyl-amino}-N-piperidin-1-yl-acetamide,
rac-(2S)-[6-chloro-3-(3-chloro-benzyl)-2-oxo-2,3-dihydro-1H-indol-3-ylamino]-N-(4-hydroxy-cyclohexyl)-3-phenyl-propionamide,
rac-2-{[6-chloro-3-(3-chloro-benzyl)-2-oxo-2,3-dihydro-1H-indol-3-yl]-cyclohexyl-amino}-N-(2-hydroxy-1,1-dimethyl-ethyl)-acetamide,
rac-6-chloro-3-(3-chloro-benzyl)-3-[cyclohexyl-(2-oxo-2-piperazin-1-yl-ethyl)-amino]-1,3-dihydro-indol-2-one,
rac-(2R)-[6-chloro-3-(3-chloro-benzyl)-2-oxo-2,3-dihydro-1H-indol-3-ylamino]-3-methyl-butyric acid,
rac-1-(2-{[6-chloro-3-(3-chloro-benzyl)-2-oxo-2,3-dihydro-1H-indol-3-yl]-phenyl-amino}-acetyl)-piperidine-4-carboxylic acid amide,
rac-6-chloro-3-(3-chloro-benzyl)-3-{[2-(4-hydroxy-piperidin-1-yl)-2-oxo-ethyl]-phenyl-amino}-1,3-dihydro-indol-2-one,
rac-2-{[6-chloro-3-(3-chloro-benzyl)-2-oxo-2,3-dihydro-1H-indol-3-yl]-phenyl-amino}-N-(4-hydroxy-cyclohexyl)-acetamide,
rac-6-chloro-3-(3-chloro-benzyl)-3-({2-[4-(2-hydroxy-ethyl)-piperazin-1-yl]-2-oxo-ethyl}-phenyl-amino)-1,3-dihydro-indol-2-one,
rac-6-chloro-3-(3-chloro-benzyl)-3-{[2-(3-hydroxy-pyrrolidin-1-yl)-2-oxo-ethyl]-phenyl-amino}-1,3-dihydro-indol-2-one,
rac-2-{[6-chloro-3-(3-chloro-benzyl)-2-oxo-2,3-dihydro-1H-indol-3-yl]-phenyl-amino}-N-(2-hydroxy-ethyl)-acetamide,
rac-{(2S)[6-chloro-3-(3-chloro-benzyl)-2-oxo-2,3-dihydro-1H-indol-3-ylamino]-4-methyl-pentanoyl}-piperidine-4-carboxylic acid amide,
rac-6-chloro-3-(3-chloro-benzyl)-3-[(1S)-(3-hydroxy-pyrrolidine-1-carbonyl)-3-methyl-butylamino]-1,3-dihydro-indol-2-one,
rac-6-chloro-3-(3-chloro-benzyl)-3-{(1S)-[4-(2-hydroxy-ethyl)-piperazine-1-carbonyl]-3-methyl-butylamino}-1,3-dihydro-indol-2-one,
rac-(2S)-[6-chloro-3-(3-chloro-benzyl)-2-oxo-2,3-dihydro-1H-indol-3-ylamino]-4-methyl-pentanoic acid (2-hydroxy-ethyl)-amide,
rac-6-chloro-3-(3-chloro-benzyl)-3-[(1S)-(4-hydroxy-piperidine-1-carbonyl)-3-methyl-butylamino]-1,3-dihydro-indol-2-one,
rac-2-{[6-chloro-3-(3-chloro-benzyl)-2-oxo-2,3-dihydro-1H-indol-3-yl]-cyclohexyl-amino}-N-cyclohexyl-acetamide,
rac-2-{[6-chloro-3-(3-chloro-benzyl)-2-oxo-2,3-dihydro-1H-indol-3-yl]-cyclohexyl-amino}-N-phenyl-acetamide,
rac-N-tert-butyl-2-([6-chloro-3-(3-chloro-benzyl)-2-oxo-2,3-dihydro-1H-indol-3-yl]-cyclohexyl-aminoyacetamide,
rac-2-{[6-chloro-3-(3-chloro-benzyl)-2-oxo-2,3-dihydro-1H-indol-3-yl]-cyclohexyl-amino}-N-cyclopropyl-acetamide,
rac-(2S)-[6-chloro-3-(3-chloro-benzyl)-2-oxo-2,3-dihydro-1H-indol-3-ylamino]-4-methyl-pentanoic acid methyl ester,
rac-6-chloro-3-(3-chloro-benzyl)-3-[4-(4-trifluoromethyl-phenyl)-piperazin-1-yl]-1,3-dihydro-indol-2-one,
rac-6-chloro-3-(3-chloro-benzyl)-3-[4-(3-chloro-phenyl)-piperazin-1-yl]-1,3-dihydro-indol-2-one and rac-6-chloro-3-(3-chloro-benzyl)-3-(4-phenyl-piperazin-1-yl)-1,3-dihydro-indol-2-one.

5. A compound selected from the group consisting of
rac-1-[6-chloro-3-(3-chloro-benzyl)-2-oxo-2,3-dihydro-1H-indol-3-yl]-piperidine-3-carboxylic acid (2-hydroxy-1-hydroxymethyl-ethyl)-amide,
rac-1-[6-chloro-3-(3-chloro-benzyl)-2-oxo-2,3-dihydro-1H-indol-3-yl]-piperidine-3-carboxylic acid (2-morpholin-4-yl-ethyl)-amide,
rac-{1-[6-chloro-3-(3-chloro-benzyl)-2-oxo-2,3-dihydro-1H-indol-3-yl]-piperidine-3-carbonyl}-amino)-acetic acid ethyl ester,
rac-1-{2-[6-chloro-3-(3-chloro-benzyl)-2-oxo-2,3-dihydro-1H-indol-3-ylamino]-benzoyl}-piperidine-4-carboxylic acid amide,
rac-1-{3-[6-chloro-3-(3-chloro-benzyl)-2-oxo-2,3-dihydro-1H-indol-3-ylamino]-benzoyl}-piperidine-4-carboxylic acid amide,
rac-6-chloro-3-(3-chloro-benzyl)-3-{3-[4-(2-methoxy-ethyl)-piperazine-1-carbonyl]-phenylamino}-1,3-dihydro-indol-2-one,
rac-6-chloro-3-(3-chloro-benzyl)-3-[3-(morpholine-4-carbonyl)-phenylamino]-1,3-dihydro-indol-2-one,
rac-(4-methyl-piperazine-1-carboxylic acid {1-[6-chloro-3-(3-chloro-benzyl)-2-oxo-2,3-dihydro-1H-indol-3-yl]-piperidin-(3S)-yl}-amide,
rac-4-(2-hydroxy-ethyl)-piperazine-1-carboxylic acid {1-[6-chloro-3-(3-chloro-benzyl)-2-oxo-2,3-dihydro-1H-indol-3-yl]-piperidin-(3S)-yl}-amide,
rac-morpholine-4-carboxylic acid {1-[6-chloro-3-(3-chloro-benzyl)-2-oxo-2,3-dihydro-1H-indol-3-yl]-piperidin-(3S)-yl}-amide,
rac-4-(2-methoxy-ethyl)-piperazine-1-carboxylic acid {1-[6-chloro-3-(3-chloro-benzyl)-2-oxo-2,3-dihydro-1H-indol-3-yl]-piperidin-(3S)-yl}-amide,
rac-(2S)-[6-chloro-3-(3-chloro-benzyl)-2-oxo-2,3-dihydro-1H-indol-3-ylamino]-N-(2-hydroxy-ethyl)-3-phenyl-propionamide,
rac-6-chloro-3-(3-chloro-benzyl)-3-[(2-oxo-2-piperazin-1-yl-ethyl)-phenyl-amino]-1,3-dihydro-indol-2-one,
rac-6-chloro-3-(3-chloro-benzyl)-3-piperazin-1-yl-1,3-dihydro-indol-2-one,
rac-3-(4-benzenesulfonyl-piperazin-1-yl)-6-chloro-3-(3-chloro-benzyl)-1,3-dihydro-indol-2-one,
rac-6-chloro-3-(3-chloro-benzyl)-3-[4-(thiophene-2-sulfonyl)-piperazin-1-yl]-1,3-dihydro-indol-2-one,
rac-2-[6-chloro-3-(3-chloro-benzyl)-2-oxo-2,3-dihydro-1H-indol-3-ylamino]-benzoic acid,
rac-1-[6-chloro-3-(3-chloro-benzyl)-2-oxo-2,3-dihydro-1H-indol-3-yl]-piperidine-3-carboxylic acid,
rac-6-chloro-3-(3-chloro-benzyl)-3-[3-(4-methyl-piperazine-1-carbonyl)-phenylamino]-1,3-dihydro-indol-2-one,
rac-3-[3-(4-acetyl-piperazine-1-carbonyl)-phenylamino]-6-chloro-3-(3-chloro-benzyl)-1,3-dihydro-indol-2-one,
rac-6-chloro-3-(3-chloro-benzyl)-3-{2[4-(2-hydroxy-ethyl)-piperazine-1-carbonyl]-phenylamino}-1,3-dihydro-indol-2-one,
rac-3[2-(4-acetyl-piperazine-1-carbonyl)-phenylamino]-6-chloro-3-(3-chloro-benzyl)-1,3-dihydro-indol-2-one,
rac-1-{[6-Chloro-3-(3-chloro-benzyl)-2-oxo-2,3-dihydro-1H-indol-3-yl]-piperidine-3-carbonyl}-piperidine-4-carboxylic acid amide,
rac-3-[3-(4-acetyl-piperazine-1-carbonyl)-piperidin-1-yl]-6-chloro-3-(3-chloro-benzyl)-1,3-dihydro-indol-2-one,
rac-6-chloro-3-(3-chloro-benzyl)-3-[3-(morpholine-4-carbonyl)-piperidin-1-yl]-1,3-dihydro-indol-2-one,
rac-6-chloro-3-(3-chloro-benzyl)-3-{3-[4-(2-hydroxy-ethyl)-piperazine-1-carbonyl]-phenylamino}-1,3-dihydro-indol-2-one,
rac-6-chloro-3-(3-chloro-benzyl)-3-[3-(4-methyl-piperazine-1-carbonyl)-piperidin-1-yl]-1,3-dihydro-indol-2-one,
rac-6-chloro-3-(3-chloro-benzyl)-3-{3[4-(2-hydroxy-ethyl)-piperazine-1-carbonyl]piperidin-1-yl}-1,3-dihydro-indol-2-one,
rac-6-chloro-3-(3-chloro-benzyl)-3-[2-(morpholine-4-carbonyl)-phenylamino]-1,3-dihydro-indol-2-one,
rac-6-(4-{1-[6-chloro-3-(3-chloro-benzyl)-2-oxo-2,3-dihydro-1H-indol-3-yl]-piperidine-3-carbonyl}-piperazin-1-yl)-nicotinonitrile,
rac-6-chloro-3-(3-chloro-benzyl)-3-[3-(4-pyridin-2-yl-piperazine-1-carbonyl)-piperidin-1-yl]-1,3-dihydro-indol-2-one,
rac-6-chloro-3-(3-chloro-benzyl)-3-[3-(4-pyrimidin-2-yl-piperazine-1-carbonyl)-piperidin-1-yl]-1,3-dihydro-indol-2-one and
rac-6-chloro-3-(3-chloro-benzyl)-3-{3-[4-(3-hydroxy-propyl)-piperazine-1-carbonyl]-piperidin-1-yl}-1,3-dihydro-indol-2-one.

6. A compound selected from the group consisting of
rac-6-Chloro-3-(3-chloro-benzyl)-3-[4,5-dimethoxy-2-(morpholine-4-carbonyl)-phenylamino]-1,3-dihydro-indol-2-one,
rac-6-Chloro-3-(3-chloro-benzyl)-3-[4-methoxy-2-(morpholine-4-carbonyl)-phenylamino]-1,3-dihydro-indol-2-one,
rac-2-[6-Chloro-3-(3-chloro-benzyl)-2-oxo-2,3-dihydro-1H-indol-3-ylamino]-4,5-difluoro-N,N!-dimethyl-benzamide,
rac-2-[6-Chloro-3-(3-chloro-benzyl)-2-oxo-2,3-dihydro-1H-indol-3-ylamino]-4,5-difluoro-N-methyl-benzamide,
rac-2-[6-Chloro-3-(3-chloro-benzyl)-2-oxo-2,3-dihydro-1H-indol-3-ylamino]-4,5-difluoro-N-(2-morpholin-4-yl-ethyl)-benzamide,
rac-2-[6-Chloro-3-(3-chloro-benzyl)-2-oxo-2,3-dihydro-1H-indol-3-ylamino]-4,5-difluoro-N-(2-morpholin-4-yl-propyl)-benzamide,
rac-4-Chloro-2-[6-chloro-3-(3-chloro-benzyl)-2-oxo-2,3-dihydro-1H-indol-3-ylamino]-N-cyclobutyl-benzamide,
rac-1-[6-Chloro-3-(3-chloro-benzyl)-2-oxo-2,3-dihydro-1H-indol-3-yl]-piperidine-3-carboxylic acid cyclobutylamide,
rac-6-Methoxy-2,3-dihydro-1H-indole-2-carboxylic acid ethyl ester,
rac-6'-Chloro-3'-(3-chloro-benzyl)-6-methoxy-2'-oxo-2,3,2',3'-tetrahydro-1'H-[1,3']biindolyl-2-carboxylic acid ethyl ester,
rac-6'-Chloro-3'-(3-chloro-benzyl)-6-methoxy-2'-oxo-2,3,2',3'-tetrahydro-1'H-[1,3']biindolyl-2-carboxylic acid.
rac-4-acetyl-piperazine-1-carboxylic acid {1-[6-chloro-3-(3-chloro-benzyl)-2-oxo-2,3-dihydro-1H-indol-3-yl]-piperidin-(3S)-yl}-amide,
rac-6-chloro-3-(3-chloro-benzyl)-3-(cyclopropylmethyl-amino)-1,3-dihydro-indol-2-one,
rac-6-chloro-3-(3-chloro-benzyl)-3-[cyclohexyl-(2-morpholin-4-yl-2-oxo-ethyl)-amino]-1,3-dihydro-indol-2-one, rac-6-chloro-3-(3-chloro-benzyl)-3-{cyclohexyl-[2-(4-methyl-piperazin-1-yl)-2-oxo-ethyl]-amino}-1,3-dihydro-indol-2-one,
rac-1-(2-{[6-chloro-3-(3-chloro-benzyl)-2-oxo-2,3-dihydro-1H-indol-3-yl]-cyclohexyl-amino}-acetyl)-piperidine-4-carboxylic acid amide,
rac-6-chloro-3-(3-chloro-benzyl)-3-(cyclohexyl-{2-[4-(2-hydroxy-ethyl)-piperazin-1-yl]-2-oxo-ethyl}-amino)-1,3-dihydro-indol-2-one,
rac-6-chloro-3-(3-chloro-benzyl)-3-(cyclohexyl-{2-[4-(2-methoxy-ethyl)-piperazin-1-yl]-2-oxo-ethyl}-amino)-1,3-dihydro-indol-2-one,
rac-4-chloro-2-[6-chloro-3-(3-chloro-benzyl)-2-oxo-2,3-dihydro-1H-indol-3-ylamino]-benzoic acid,
rac-6-chloro-3-(3-chloro-benzyl)-3-[5-chloro-2-(morpholine-4-carbonyl)-phenylamino]-1,3-dihydro-indol-2-one,
rac-1-{4-chloro-2[6-chloro-3-(3-chloro-benzyl)-2-oxo-2,3-dihydro-1H-indol-3-ylamino]-benzoyl}-piperidine-4-carboxylic acid amide,
rac-6-chloro-3-(3-chloro-benzyl)-3-[5-chloro-2-(4-methyl-piperazine-1-carbonyl)-phenylamino]-1,3-dihydro-indol-2-one,
rac-6-chloro-3-(3-chloro-benzyl)-3-{5-chloro-2-[4-(2-hydroxy-ethyl)-piperazine-1-carbonyl]-phenylamino}-1,3-dihydro-indol-2-one,
rac-6-chloro-3-(3-chloro-benzyl)-3-{5-chloro-2-[4-(2-methoxy-ethyl)piperazine-1-carbonyl]-phenylamino}-1,3-dihydro-indol-2-one,
rac-3-[2-(4-acetyl-piperazine-1-carbonyl)-5-chloro-phenylamino]-6-chloro-3-(3-chloro-benzyl)-1,3-dihydro-indol-2-one,
rac-6-chloro-3-(3-chloro-benzyl)-3-[(2-hydroxy-ethyl)-phenyl-amino]-1,3-dihydro-indol-2-one,
rac-2-{[6-chloro-3-(3-chloro-benzyl)-2-oxo-2,3-dihydro-1H-indol-3-yl]-phenyl-amino}-acetamide,
rac-[[6-chloro-3-(3-chloro-benzyl)-2-oxo-2,3-dihydro-1H-indol-3-yl]-(3-methoxy-phenyl)-amino]-acetic acid ethyl ester,
rac-6-Chloro-3-(3-chloro-benzyl)-3-[4-(2-ethoxy-phenyl)-piperazin-1-yl]-1,3-dihydro-indol-2-one,
rac-2-[6-Chloro-3-(3-chloro-benzyl)-2-oxo-2,3-dihydro-1H-indol-3-ylamino]-4,5-difluoro-benzoic acid,
rac-2-[6-Chloro-3-(3-chloro-benzyl)-2-oxo-2,3-dihydro-1H-indol-3-ylamino]-4,5-dimethoxyl-benzoic acid,
rac-2-[6-Chloro-3-(3-chloro-benzyl)-2-oxo-2,3-dihydro-1H-indol-3-ylamino]-4-methoxyl-benzoic acid and
rac-6-Chloro-3-(3-chloro-benzyl)-3-[4,5-difluoro-2-(morpholine-4-carbonyl)-phenylamino]-1,3-dihydro-indol-2-one.

7. A compound selected from the group consisting of
rac-2-{[6-Chloro-3-(3-chloro-benzyl)-2-oxo-2,3-dihydro-1H-indol-3-yl]-isopropyl-amino}-acetamide,
rac-3-[(2-Amino-ethyl)-isopropyl-amino]-6-chloro-3-(3-chloro-benzyl)-1,3-dihydro-indol-2-one,
rac-N-(2-{[6-Chloro-3-(3-chloro-benzyl)-2-oxo-2,3-dihydro-1H-indol-3-yl]-isopropyl-amino}-ethyl)-methanesulfonamide,
rac-N-(2-{[6-Chloro-3-(3-chloro-benzyl)-2-oxo-2,3-dihydro-1H-indol-3-yl]-isopropyl-amino}-ethyl)-acetamide,
rac-3-(2-{[6-Chloro-3-(3-chloro-benzyl)-2-oxo-2,3-dihydro-1H-indol-3-yl]-isopropyl-amino}-ethyl)-1,1-dimethyl-urea,
rac-4-Acetyl-piperazine-1-carboxylic acid (2-{[6-chloro-3-(3-chloro-benzyl)-2-oxo-2,3-dihydro-1H-indol-3-yl]-isopropyl-amino}-ethyl)-amide,
rac-Morpholine-4-carboxylic acid (2-{[6-chloro-3-(3-chloro-benzyl)-2-oxo-2,3-dihydro-1H-indol-3-yl]-isopropyl-amino}-ethyl)-amide,
rac-Cyclobutanecarboxylic acid (2-{[6-chloro-3-(3-chloro-benzyl)-2-oxo-2,3-dihydro-1H-indol-3-yl]-isopropyl-amino}-ethyl)-amide,
rac-1-Acetyl-piperidine-4-carboxylic acid (2-{[6-chloro-3-(3-chloro-benzyl)-2-oxo-2,3-dihydro-1H-indol-3-yl]-isopropyl-amino}-ethyl)-amide,
rac-N-(2-Acetylamino-ethyl)-2-[6-chloro-3-(3-chloro-benzyl)-2-oxo-2,3-dihydro-1H-indol-3-ylamino]-4-methoxy-benzamide,
rac-2-[6-Chloro-3-(3-chloro-benzyl)-2-oxo-2,3-dihydro-1H-indol-3-ylamino]-N-(3-dimethylamino-propyl)-4-methoxy-benzamide.
rac-6,6'-Dichloro-3'-(3-chloro-benzyl)-2-(morpholine-4-carbonyl)-2,3,1',3'-tetrahydro-[1,3']biindolyl-2'-one,
rac-6,6'-Dichloro-3'-(3-chloro-benzyl)-2'-oxo-2,3,2',3'-tetrahydro-1'H-[1,3']biindolyl-2-carboxylic acid cyclobutylamide,
rac-2-(4-Acetyl-piperazine-1-carbonyl)-6,6'-dichloro-3'-(3-chloro-benzyl)-2,3,1',3'-tetrahydro-[1,3']biindolyl-2'-one,
rac-6,6'-Dichloro-3'-(3-chloro-benzyl)-2'-oxo-2',3'-dihydro-1'H-[1,3']biindolyl-2-carboxylic acid cyclobutylamide,
rac-2-(4-Acetyl-piperazine-1-carbonyl)-6,6'-dichloro-3'-(3-chloro-benzyl)-1',3'-dihydro-[1,3]biindolyl-2'-one,
rac-2-[6-Chloro-3-(3-chloro-benzyl)-2-oxo-2,3-dihydro-1H-indol-3-ylamino]-4-ethynyl-benzoic acid,
rac-4-Bromo-2-[6-chloro-3-(3-chloro-benzyl)-2-oxo-2,3-dihydro-1H-indol-3-ylamino]-benzoic acid,
rac-3-[5-Bromo-2-(morpholine-4-carbonyl)-phenylamino]-6-chloro-3-(3-chloro-benzyl)-1,3-dihydro-indol-2-one,
rac-6-Chloro-3-(3-chloro-benzyl)-3-[5-ethynyl-2-(morpholine-4-carbonyl)-phenylamino]-1,3-dihydro-indol-2-one,
rac-2-[6-Chloro-3-(3-chloro-benzyl)-2-oxo-2,3-dihydro-1H-indol-3-yloxy]-3-isopropyl-benzoic acid,
rac-3-[2-(4-Acetyl-piperazine-1-carbonyl)-5-ethynyl-phenylamino]-6-chloro-3-(3-chloro-benzyl)-1,3-dihydro-indol-2-one,
rac-3-[2-(4-Acetyl-piperazine-1-carbonyl)-5-bromo-phenylamino]-6-chloro-3-(3-chloro-benzyl)-1,3-dihydro-indol-2-one,
rac-6-Chloro-3-(3-chloro-benzyl)-3-[2-isopropyl-6-(morpholine-4-carbonyl)-phenoxy]-1,3-dihydro-indol-2-one,
rac-3-[2-(4-Acetyl-piperazine-1-carbonyl)-6-isopropyl-phenoxy]-6-chloro-3-(3-chloro-benzyl)-1,3-dihydro-indol-2-one,
rac-6-Chloro-3-(3-chloro-benzyl)-3-[3-(morpholine-4-sulfonyl)-phenylamino]-1,3-dihydro-indol-2-one,
rac-4-{4-Chloro-2-[6-chloro-3-(3-chloro-benzyl)-2-oxo-2,3-dihydro-1H-indol-3-ylamino]-benzenesulfonylamino}-piperidine-1-carboxylic acid tert-butyl ester,
rac-4-Chloro-2[6-chloro-3-(3-chloro-benzyl)-2-oxo-2,3-dihydro-1H-indol-3-yloxy]-benzoic acid,
rac-4-{4-Bromo-2-[6-chloro-3-(3-chloro-benzyl)-2-oxo-2,3-dihydro-1H-indol-3-ylamino]-benzoylamino}-piperidine-1-carboxylic acid tert-butyl ester,
rac-6-Chloro-3-(3-chloro-benzyl)-3-[5-chloro-2-(morpholine-4-carbonyl)-phenoxy]-1,3-dihydro-indol-2-one, rac-3-[2-(4-Acetyl-piperazine-1-carbonyl)-5-chloro-phenoxy]-6-chloro-3-(3-chloro-benzyl)-1,3-dihydro-indol-2-one,
rac-4-Bromo-2-[6-chloro-3-(3-chloro-benzyl)-2-oxo-2,3-dihydro-1H-indol-3-ylamino]-N-piperidin-4-yl-benzamide and
rac-4-Bromo-2[6-chloro-3-(3-chloro-benzyl)-2-oxo-2,3-dihydro-1H-indol-3-ylamino]-N-(3-morpholin-4-yl-propyl)-benzamide.

8. A compound selected from the group consisting of
rac-6'-Chloro-3'-(3-chloro-benzyl)-2-(morpholine-4-carbonyl)-1',3'-dihydro-[1,3']biindolyl-2'-one,
rac-2-(4-Acetyl-piperazine-1-carbonyl)-6'-chloro-3'-(3-chloro-benzyl)-1',3'-dihydro-[1,3']biindolyl-2'-one,
rac-6'-Chloro-3'-(3-chloro-benzyl)-2'-oxo-2',3'-dihydro-1'H-[1,3']biindolyl-2-carboxylic acid cyclobutylamide,
rac-2-(4-Acetyl-piperazine-1-carbonyl)-6'-chloro-3'-(3-chloro-benzyl)-2,3,1',3'-tetrahydro-[1,3']biindolyl-2'-one,
rac-2-(4-Acetyl-piperazine-1-carbonyl)-6'-chloro-3'-(3-chloro-benzyl)-2,3,1',3'-tetrahydro-[1,3']biindolyl-2'-one,
rac-6'-Chloro-3'-(3-chloro-benzyl)-2-(morpholine-4-carbonyl)-2,3,1',3'-tetrahydro-[1,3']biindolyl-2'-one,
rac-3-[2-(4-Acetyl-piperazine-1-carbonyl)-6-ethoxy-phenylamino]-6-chloro-3-(3-chloro-benzyl)-1,3-dihydro-indol-2-one,
rac-6-Chloro-3-(3-chloro-benzyl)-3-[2-ethoxy-6-(morpholine-4-carbonyl)-phenylamino]-1,3-dihydro-indol-2-one,
rac-2-[6-Chloro-3-(3-chloro-benzyl)-2-oxo-2,3-dihydro-1H-indol-3-ylamino]-3-ethoxy-benzoic acid,
rac-6-Chloro-3-(3-chloro-benzyl)-3-[5-methoxy-2-(morpholine-4carbonyl)-phenylamino]-1,3-dihydro-indol-2-one,
rac-N-(2-Acetylamino-ethyl)-2,4-dichloro-6-[6-chloro-3-(3-chloro-benzyl)-2-oxo-2,3-dihydro-1H-indol-3-ylamino]-benzamide,
rac-2,4-Dichloro-6-[6-chloro-3-(3-chloro-benzyl)-2-oxo-2,3-dihydro-1H-indol-3-ylamino]-N-(3-dimethylamino-propyl)-benzamide,
rac-6-Chloro-3-(3-chloro-benzyl)-3-[3,5-dichloro-2-(morpholine-4-carbonyl)-phenylamino]-1,3-dihydro-indol-2-one,
rac-3-Chloro-2-[6-chloro-3-(3-chloro-benzyl)-2-oxo-2,3-dihydro-1H-indol-3-ylamino]-N-cyclohexyl-benzamide,
rac-3-Chloro-2-[6-chloro-3-(3-chloro-benzyl)-2-oxo-2,3-dihydro-1H-indol-3-ylamino]-N-cyclobutyl-benzamide,
rac-6-Chloro-3-(3-chloro-benzyl)-3-{2-chloro-6-[4-(2-hydroxy-ethyl)-piperazine-1-carbonyl]-phenylamino}-1,3-dihydro-indol-2-one,
rac-2-[6-Chloro-3-(3-chloro-benzyl)-2-oxo-2,3-dihydro-1 H-indol-3-ylamino]-N-cyclohexyl-3-methoxy-benzamide,
rac-2-[6-Chloro-3-(3-chloro-benzyl)-2-oxo-2,3-dihydro-1H-indol-3-ylamino]-N-cyclobutyl-3-methoxy-benzamide,
rac-6-Chloro-3-(3-chloro-benzyl)-3-{2-[4-(2-hydroxy-ethyl)-piperazine-1-carbonyl]-6-methoxy-phenylamino}-1,3-dihydro-indol-2-one,
rac-1-{2-[6-Chloro-3-(3-chloro-benzyl)-2-oxo-2,3-dihydro-1H-indol-3-ylamino]-3-methoxy-benzoyl}-piperidine-4-carboxylic acid amide,
rac-1-{2-[[6-Chloro-3-(3-chloro-benzyl)-2-oxo-2,3-dihydro-1H-indol-3-yl]-(3-chloro-phenyl)-amino]acetyl}-piperidine-4-carboxylic acid amide,
rac-6-Chloro-3-(3-chloro-benzyl)-3-((3-chloro-phenyl)-{2-[4-(2-hydroxy-ethyl)-piperazin-1-yl]-2-oxo-ethyl}-amino)-1,3-dihydro-indol-2-one,
rac-1-(2-{[6-Chloro-3-(3-chloro-benzyl)-2-oxo-2,3-dihydro-1H-indol-3-yl]-isopropyl-amino}-acetyl)-piperidine-4-carboxylic acid amide,
rac-2-[[6-Chloro-3-(3-chloro-benzyl)-2-oxo-2,3-dihydro-1H-indol-3-yl]-(1-ethyl-propyl)-amino]-N-cyclobutyl-acetamide,
rac-6-Chloro-3-(3-chloro-benzyl)-3-({2-[4-(2-hydroxy-ethyl)-piperazin-1-yl]-2-oxo-ethyl}-isopropyl-amino)-1,3-dihydro-indol-2-one,
rac-[[6-Chloro-3-(3-chloro-benzyl)-2-oxo-2,3-dihydro-1H-indol-3-yl]-(3-chloro-phenyl)-amino]-acetic acid and
rac-{[6-Chloro-3-(3-chloro-benzyl)-2-oxo-2,3-dihydro-1H-indol-3-yl]-isopropyl-amino}-acetic acid ethyl ester.

9. A compound selected from the group consisting of
rac-3-{5-Bromo-2-[(2,2-difluoro-ethylamino)-methyl]-phenylamino}-6-chloro-3-(3-chloro-benzyl)-1,3-dihydro-indol-2-one,
rac-3-{5-Bromo-2-[(3-imidazol-1-yl-propylamino)-methyl]-phenylamino}-6-chloro-3-(3-chloro-benzyl)-1,3-dihydro-indol-2-one,
rac-3-{5-Bromo-2-[(2,2,2-trifluoro-ethylamino)-methyl]-phenylamino}-6-chloro-3-(3-chloro-benzyl)-1,3-dihydro-indol-2-one,
rac-N-(2-Acetylamino-ethyl)-4-bromo-2-[6-chloro-3-(3-chloro-benzyl)-2-oxo-2,3-dihydro-1H-indol-3-ylamino]-benzamide,
rac-4-Bromo-2-[6-chloro-3-(3-chloro-benzyl)-2-oxo-2,3-dihydro-1H-indol-3-ylamino]-N-(2,2-difluoro-ethyl)-benzamide,
rac-4-Bromo-2-[6-chloro-3-(3-chloro-benzyl)-2-oxo-2,3-dihydro-1H-indol-3-ylamino]-N-(3-imidazol-1-yl-propyl)-benzamide,
rac-4-Bromo-2-[6-chloro-3-(3-chloro-benzyl)-2-oxo-2,3-dihydro-1H-indol-3-ylamino]-N-(3-dimethylamino-propyl)-benzamide,
rac-4-Bromo-2-[6-chloro-3-(3-chloro-benzyl)-2-oxo-2,3-dihydro-1H-indol-3-ylamino]-N-(2,2,2-trifluoro-ethyl)-benzamide,
rac-3-{5-Bromo-2-[(3-morpholin-4-yl-propylamino)-methyl]-phenylamino}-6-chloro-3-(3-chloro-benzyl)-1,3-dihydro-indol-2-one,
rac-3-{5-Bromo-2-[(2-morpholin-4-yl-ethylamino)-methyl]-phenylamino}-6-chloro-3-(3-chloro-benzyl)-1,3-dihydro-indol-2-one,
rac-3-{5-Bromo-2-[4-(2-methanesulfonyl-ethyl)-piperazine-1-carbonyl]-phenylamino}-6-chloro-3-(3-chloro-benzyl)-1,3-dihydro-indol-2-one,
rac-5-Chloro-2-[6-chloro-3-(3-chloro-benzyl)-2-oxo-2,3-dihydro-1 H-indol-3-ylamino]-benzoic acid,
rac-2-[6-Chloro-3-(3-chloro-benzyl)-2-oxo-2,3-dihydro-1 H-indol-3-ylamino]-5-methyl-benzoic acid,
rac-2-[6-Chloro-3-(3-chloro-benzyl)-2-oxo-2,3-dihydro-1 H-indol-3-ylamino]-3,5-dimethyl-benzoic acid,
rac-6'-Chloro-3'-(3-chloro-benzyl)-2'-oxo-2,3,2',3'-tetrahydro-1'H-[1,3']biindolyl-2-carboxylic acid,
rac-2-{[6-Chloro-3-(3-chloro-benzyl)-2-oxo-2,3-dihydro-1H-indol-3-yl]-piperidin-4-yl-amino}-N-cyclobutyl-acetamide, rac-4-{[6-Chloro-3-(3-chloro-benzyl)-2-oxo-2,3-dihydro-1H-indol-3-yl]-cyclobutylcarbamoylmethyl-amino}-piperidine-1-carboxylic acid dimethylamide,
rac-2-{(1-Acetyl-piperidin-4-yl)[6-chloro-3-(3-chloro-benzyl)-2-oxo-2,3-dihydro-1H-indol-3-yl]-amino}-N-cyclobutyl-acetamide,
rac-4-{[6-Chloro-3-(3-chloro-benzyl)-2-oxo-2,3-dihydro-1H-indol-3-yl]-cyclobutylcarbamoylmethyl-amino}-piperidine-1-carboxylic acid tert-butyl ester,
rac-3[2-(4-Acetyl-piperazine-1-carbonyl)-6-isopropyl-phenylamino]-6-chloro-3-(3-chloro-benzyl)-1,3-dihydro-indol-2-one,
rac-2-{[6-Chloro-3-(3-chloro-benzyl)-2-oxo-2,3-dihydro-1H-indol-3-yl]-isopropyl-amino}-N-(1-methane-sulfonyl-piperidin-4-yl)-acetamide,
rac-N-(1-Acetyl-piperidin-4-yl)-2-{[6-chloro-3-(3-chloro-benzyl)-2-oxo-2,3-dihydro-1H-indol-3-yl]-iso-propyl-amino}-acetamide,
rac-2-{[6-Chloro-3-(3-chloro-benzyl)-2-oxo-2,3-dihydro-1H-indol-3-yl]-isopropyl-amino}-N-piperidin-4-yl-acetamide,
rac-4-(2-{[6-Chloro-3-(3-chloro-benzyl)-2-oxo-2,3-dihydro-1H-indol-3-yl]-isopropyl-amino}acetylamino)-piperidine-1-carboxylic acid tert-butyl ester,
rac-3-{2-[(1-Acetyl-piperidin-4-ylamino)-methyl]-5-bromo-phenylamino}-6-chloro-3-(3-chloro-benzyl)-1,3-dihydro-indol-2-one,
rac-3-[2-(4-Acetyl-piperazin-1-ylmethyl)-5-bromo-phenylamino]-6-chloro-3-(3-chloro-benzyl)-1,3-dihydro-indol-2-one,
rac-3-{5-Bromo-2-[(1-methanesulfonyl-piperidin-4-ylamino)-methyl]-phenylamino}-6-chloro-3-(3-chloro-benzyl)-1,3-dihydro-indol-2-one,
rac-4-{4-Bromo-2-[6-chloro-3-(3-chloro-benzyl)-2-oxo-2,3-dihydro-1H-indol-3-ylamino]-benzylamino}-piperidine-1-carboxylic acid tert-butyl ester,
rac-3-(5-Bromo-2-cyclobutylaminomethyl-phenylamino)-6-chloro-3-(3-chloro-benzyl)-1,3-dihydro-indol-2-one,
rac-3-(5-Bromo-2-morpholin-4-ylmethyl-phenylamino)-6-chloro-3-(3-chloro-benzyl)-1,3-dihydro-indol-2-one,
rac-3-(5-Bromo-2-hydroxymethyl-phenylamino)-6-chloro-3-(3-chloro-benzyl)-1,3-dihydro-indol-2-one,
rac-4-Bromo-2-[6-chloro-3-(3-chloro-benzyl)-2-oxo-2,3-dihydro-1H-indol-3-ylamino]-N-(2-morpholin-4-yl-ethyl)-benzamide and
rac-N-(2-{4-Bromo-2-[6-chloro-3-(3-chloro-benzyl)-2-oxo-2,3-dihydro-1H-indol-3-ylamino]-benzylamino}-ethyl)-acetamide.

10. A compound selected from the group consisting of
rac-2-{[6-Chloro-3-(3-chloro-benzyl)-2-oxo-2,3-dihydro-1H-indol-3-yl]-cycloheptyl-amino}-N-cyclopentyl-acetamide,
rac-2-{[6-Chloro-3-(3-chloro-benzyl)-2-oxo-2,3-dihydro-1H-indol-3-yl]-cycloheptyl-amino}-N-cyclohexyl-acetamide,
rac-6-Chloro-3-(3-chloro-benzyl)-3-(cycloheptyl-{2-[4-(2-hydroxy-ethyl)-piperazin-1-yl]-2-oxo-ethyl}-amino)-1,3-dihydro-indol-2-one,
rac-1-(2-{[6-Chloro-3-(3-chloro-benzyl)-2-oxo-2,3-dihydro-1H-indol-3-yl]-cycloheptyl-amino}-acetyl)-piperidine-4-carboxylic acid amide,
rac-(S)-2-[6-Chloro-3-(3-chloro-benzyl)-2-oxo-2,3-dihydro-1H-indol-3-ylamino]-2,4-dimethyl-pentanoic acid cyclopropylamide,
rac-(S)-2-[6-Chloro-3-(3-chloro-benzyl)-2-oxo-2,3-dihydro-1H-indol-3-ylamino]-4-methyl-pentanoic acid cyclobutylamide,
rac-(S)-2-[6-Chloro-3-(3-chloro-benzyl)-2-oxo-2,3-dihydro-1H-indol-3-ylamino]-4-methyl-pentanoic acid cyclopentylamide,
rac-(S)-2-[6-Chloro-3-(3-chloro-benzyl)-2-oxo-2,3-dihydro-1H-indol-3-ylamino]-4-methyl-pentanoic acid cyclohexylamide,
rac-2-{[6-Chloro-3-(3-chloro-benzyl)-2-oxo-2,3-dihydro-1H-indol-3-yl]-cyclohexyl-amino}-acetamide,
rac-6'-Chloro-3'-(3-chloro-benzyl)-6-methoxy-2'-oxo-2',3'-dihydro-1'H-[1,3']biindolyl-2-carboxylic acid methyl ester,
rac-{[6-Chloro-3-(3-chloro-benzyl)-2-oxo-2,3-dihydro-1H-indol-3-yl]-cycloheptyl-amino}-acetic acid,
rac-4-Chloro-2-{[6-chloro-3-(3-chloro-benzyl)-2-oxo-2,3-dihydro-1H-indol-3-yl]-methyl-amino}-benzoic acid,
rac-6-Chloro-3-(3-chloro-benzyl)-3-{[5-chloro-2-(morpholine-4-carbonyl)-phenyl]-methyl-amino}-1,3-dihydro-indol-2-one,
rac-4-Chloro-2-{[6-chloro-3-(3-chloro-benzyl)-2-oxo-2,3-dihydro-1H-indol-3-yl]-methyl-amino}-N-(3-imidazol-1-yl-propyl)-benzamide,
rac-N-(2-Acetylamino-ethyl)-4-chloro-2-{[6-chloro-3-(3-chloro-benzyl)-2-oxo-2,3-dihydro-1H-indol-3-yl]-methyl-amino}-benzamide,
rac-4-Chloro-2-{[6-chloro-3-(3-chloro-benzyl)-2-oxo-2,3-dihydro-1H-indol-3-yl-methyl]-amino}-N-(3-dimethylamino-propyl)-benzamide,
rac-2-{[6-Chloro-3-(3-chloro-benzyl)-2-oxo-2,3-dihydro-1H-indol-3-yl]-cyclohexyl-amino}-N-cyclopentyl-acetamide,
rac-{[6-Chloro-3-(3-chloro-benzyl)-2-oxo-2,3-dihydro-1H-indol-3-yl]-cyclopentyl-amino}-acetic acid,
rac-{[6-Chloro-3-(3-chloro-benzyl)-2-oxo-2,3-dihydro-1H-indol-3-yl]-cyclobutyl-amino}-acetic acid,
rac-2-{[6-Chloro-3-(3-chloro-benzyl)-2-oxo-2,3-dihydro-1H-indol-3-yl]-cyclobutyl-amino}-N-cyclobutyl-acetamide,
rac-2-{[6-Chloro-3-(3-chloro-benzyl)-2-oxo-2,3-dihydro-1H-indol-3-yl]-cyclobutyl-amino}-N-cyclopentyl-acetamide,
rac-2-{[6-Chloro-3-(3-chloro-benzyl)-2-oxo-2,3-dihydro-1H-indol-3-yl]-cyclobutyl-amino}-N-cyclohexyl-acetamide,
rac-2-{[6-Chloro-3-(3-chloro-benzyl)-2-oxo-2,3-dihydro-1H-indol-3-yl]-cyclobutyl-amino}-N-cyclopropyl-acetamide,
rac-6-Chloro-3-(3-chloro-benzyl)-3-(cyclobutyl-{2-[4-(2-hydroxy-ethyl)-piperazin-1-yl]-2-oxo-ethyl}amino)-1,3-dihydro-indol-2-one,
rac-1-(2-{[6-Chloro-3-(3-chloro-benzyl)-2-oxo-2,3-dihydro-1H-indol-3-yl]-cyclobutyl-amino}-acetyl)-piperidine-4-carboxylic acid amide,
rac-2-{[6-Chloro-3-(3-chloro-benzyl)-2-oxo-2,3-dihydro-1H-indol-3-yl]-cyclopentyl-amino}-N-cyclopropyl-acetamide,
rac-2-{[6-Chloro-3-(3-chloro-benzyl)-2-oxo-2,3-dihydro-1H-indol-3-yl]-cyclopentyl-amino}-N-cyclobutyl-acetamide,
rac-2-{[6-Chloro-3-(3-chloro-benzyl)-2-oxo-2,3-dihydro-1H-indol-3-yl]-cyclopentyl-amino}-N-cyclopentyl-acetamide, rac-2-{[6-Chloro-3-(3-chloro-benzyl)-2-oxo-2,3-dihydro-1H-indol-3-yl]-cyclopentyl-amino}-N-cyclohexyl-acetamide, rac-6-Chloro-3-(3-chloro-benzyl)-3-(cyclopentyl-{2-[4-(2-hydroxy-ethyl)-piperazin-1-yl]-2-oxo-ethyl}amino)-1,3-dihydro-indol-2-one, rac-1-(2-{[6-Chloro-3-(3-chloro-benzyl)-2-oxo-2,3-dihydro-1H-indol-3-yl]-cyclopentyl-amino}-acetyl)-piperidine-4-carboxylic acid amide, rac-2-{[6-Chloro-3-(3-chloro-benzyl)-2-oxo-2,3-dihydro-1H-indol-3-yl]-cycloheptyl-amino}-N-cyclopropyl-acetamide and rac-2-{[6-Chloro-3-(3-chloro-benzyl)-2-oxo-2,3-dihydro-1H-indol-3-yl]-cycloheptyl-amino}-N-cyclobutyl-acetamide.

11. A compound selected from the group consisting of
rac-6-Chloro-3-(3-chloro-benzyl)-3-[((R)-3-methyl-cyclopentyl)-(2-morpholin-4-yl-2-oxo-ethyl)-amino]-1,3-dihydro-indol-2-one, rac-1-[6-Chloro-3-(3-chloro-benzyl)-2-oxo-2,3-dihydro-1H-indol-3-ylamino]-cyclohexanecarboxylic acid, rac-2-[[6-Chloro-3-(3-chloro-benzyl)-2-oxo-2,3-dihydro-1H-indol-3-yl]-(2-methyl-cyclohexyl)-amino]-N-cyclobutyl-acetamide, rac-1-[6-Chloro-3-(3-chloro-benzyl)-2-oxo-2,3-dihydro-1H-indol-3-ylamino]-cyclohexanecarboxylic acid cyclobutylamide, rac-3-[1-(4-Acetyl-piperazine-1-carbonyl)-cyclohexylamino]-6-chloro-3-(3-chloro-benzyl)-1,3-dihydro-indol-2-one, rac-2-{[6-Chloro-3-(3-chloro-benzyl)-2-oxo-2,3-dihydro-1H-indol-3-yl]-cyclopropylmethyl-amino}-N-cyclobutyl-acetamide, rac-2-[[6-Chloro-3-(3-chloro-benzyl)-2-oxo-2,3-dihydro-1H-indol-3-yl]-(3,3,5,5-tetramethyl-cyclohexyl)-amino]-N-cyclobutyl-acetamide, rac-2-{(R)-Bicyclo[2.2.1]hept-2-yl-[6-chloro-3-(3-chloro-benzyl)-2-oxo-2,3-dihydro-1H-indol-3-yl]-amino}-N-cyclobutyl-acetamide, rac-2-[(6-Chloro-3-cyclohexylmethyl-2-oxo-2,3-dihydro-1H-indol-3-yl)-cyclohexyl-amino]-N-cyclobutyl-acetamide, rac-6-Chloro-3-(3-chloro-benzyl)-3-[cyclohexyl-(2-morpholin-4-yl-ethyl)-amino]-1,3-dihydro-indol-2-one, rac-6-Chloro-3-(3-chloro-benzyl)-3-[cyclohexyl-(3-morpholin-4-yl-propyl)-amino]-1,3-dihydro-indol-2-one, rac-6'-Chloro-3'-(3-chloro-benzyl)-6-methoxy-2'-oxo-2',3'-dihydro-1'H-[1,3']biindolyl-2-carboxylic acid, rac-2{[6-Chloro-3-(3-chloro-benzyl)-2-oxo-2,3-dihydro-1H-indol-3-yl]-cyclohexyl-amino}-N,N-dimethyl-acetamide, rac-2-{[6-Chloro-3-(3-chloro-benzyl)-2-oxo-2,3-dihydro-1H-indol-3-yl]-cyclohexyl-amino}-N-methyl-acetamide, rac-6'-Chloro-3'-(3-chloro-benzyl)-6-methoxy-2'-oxo-2',3'-dihydro-1'[1,3']biindolyl-2-carboxylic acid cyclobutylamide, rac-6'-Chloro-3'-(3-chloro-benzyl)-6-methoxy-2'-oxo-2',3'-dihydro-1'H-[1,3']biindolyl-2-carboxylic acid cyclohexylamide, rac-1-[6'-Chloro-3'-(3-chloro-benzyl)-6-methoxy-2'-oxo-2',3'-dihydro-1'H-[1,3']biindolyl-2-carbonyl]-piperidine-4-carboxylic acid amide, rac-6'-Chloro-3'-(3-chloro-benzyl)-2-[4-(2-hydroxy-ethyl)-piperazine-1-carbonyl]-6-methoxy-1',3'-dihydro-[1,3']biindolyl-2'-one, rac-6'-Chloro-3'-(3-chloro-benzyl)-6-methoxy-2-(morpholine-4-carbonyl)-1',3'-dihydro-[1,3']biindolyl-2'-one, rac-2-[6-Chloro-3-(3-chloro-benzyl)-2-oxo-2,3-dihydro-1H-indol-3-ylamino]-3-methyl-benzoic acid, rac-2-[6-Chloro-3-(3-chloro-benzyl)-2-oxo-2,3-dihydro-1 H-indol-3-ylamino]-4-fluoro-benzoic acid, rac-6-Chloro-3-(3-chloro-benzyl)-3-[2-methyl-6-(morpholine-4-carbonyl)-phenylamino]-1,3-dihydro-indol-2-one, rac-2-[6-Chloro-3-(3-chloro-benzyl)-2-oxo-2,3-dihydro-1H-indol-3-ylamino]-N-cyclobutyl-4-fluoro-benzamide, rac-6-Chloro-3-(3-chloro-benzyl)-3-[5-fluoro-2-(morpholine-4-carbonyl)-phenylamino]-1,3-dihydro-indol-2-one, rac-3-[2-(4Acetyl-piperazine-l-carbonyl)-5-fluoro-phenylamino]-6-chloro-3-(3-chloro-benzyl)-1,3-dihydro-indol-2-one, rac-2-[[6-Chloro-3-(3-chloro-benzyl)-2-oxo-2,3-dihydro-1H-indol-3-yl]-((R)-3-methyl-cyclohexyl)-amino]-N-cyclobutyl-acetamide, rac-2-[[6-Chloro-3-(3-chloro-benzyl)-2-oxo-2,3-dihydro-1H-indol-3-yl]-((R)-3-methyl-cyclohexyl)-amino]-N-cyclohexyl-acetamide, rac-2-[[6-Chloro-3-(3-chloro-benzyl)-2-oxo-2,3-dihydro-1H-indol-3-yl]-((R)-3-methyl-cyclohexyl)-amino]-N-morpholin-4-yl-acetamide, rac-6-Chloro-3-(3-chloro-benzyl)-3-[((R)-3-methyl-cyclohexyl)-(2-morpholin-4-yl-2-oxo-ethyl)-amino]-1,3-dihydro-indol-2-one, rac-[[6-Chloro-3-(3-chloro-benzyl)-2-oxo-2,3-dihydro-1H-indol-3-yl]-((R)-3-methyl-cyclopentyl)-amino]-acetic acid, rac-2-[[6-Chloro-3-(3-chloro-benzyl)-2-oxo-2,3-dihydro-1H-indol-3-yl]-((R)-3-methyl-cyclopentyl)-amino]-N-cyclobutyl-acetamide, rac-2-[[6-Chloro-3-(3-chloro-benzyl)-2-oxo-2,3-dihydro-1H-indol-3-yl]-((R)-3-methyl-cyclopentyl)-amino]-N-cyclohexyl-acetamide and rac-2-[[6-Chloro-3-(3-chloro-benzyl)-2-oxo-2,3-dihydro-1H-indol-3-yl]-((R)-3-methyl-cyclopentyl)-amino]-N-morpholin-4-yl-acetamide.

12. A compound selected from the group consisting of
rac-2-{tert-Butyl-[6-chloro-3-(3-chloro-benzyl)-2-oxo-2,3-dihydro-1H-indol-3-yl]-amino}-N-cyclobutyl-acetamide, rac-N-[1-(2-{[6-Chloro-3-(3-chloro-benzyl)-2-oxo-2,3-dihydro-1H-indol-3-yl]-isopropyl-amino}-acetyl)-piperidin-4-yl]-methanesulfonamide, rac-2-[[6-Chloro-3-(3-chloro-benzyl)-2-oxo-2,3-dihydro-1H-indol-3-yl]-(1,2-dimethyl-propyl)-amino]-N-cyclobutyl-acetamide, rac-6-Chloro-3-(3-chloro-benzyl)-3-((1,2-dimethyl-propyl)-{2-[4-(2-methanesulfonyl-ethyl)-piperazin-1-yl]-2-oxo-ethyl}-amino)-1,3-dihydro-indol-2-one, rac-2-[[6-Chloro-3-(3-chloro-benzyl)-2-oxo-2,3-dihydro-1H-indol-3-yl]-(1,2-dimethyl-propyl)-amino]-N-(1-methanesulfonyl-piperidin-4-yl)-acetamide, rac-2-[[6-Chloro-3-(3-chloro-benzyl)-2-oxo-2,3-dihydro-1H-indol-3-yl]-(2,2-dimethyl-propyl)-amino]-N-cyclobutyl-acetamide, rac-6-Chloro-3-(3-chloro-benzyl)-3-((2,2-dimethyl-propyl)-{2-[4-(2-methanesulfonyl-ethyl)-piperazin-1-yl]-2-oxo-ethyl}-amino)-1,3-dihydro-indol-2-one, rac-1-{2-[[6-Chloro-3-(3-chloro-benzyl)-2-oxo-2,3-dihydro-1H-indol-3-yl]-(2,2-dimethyl-propyl)-amino]-acetyl}-piperidine-4-carboxylic acid amide,
rac-6-Chloro-3-(3-chloro-benzyl)-3-[isopropyl-(2-morpholin-4-yl-ethyl)-amino]-1,3-dihydro-indol-2-one,
rac-6-Chloro-3-(3-chloro-benzyl)-3-[isopropyl-(3-morpholin-4-yl-propyl)-amino]-1,3-dihydro-indol-2-one,
rac-2-[4-(2-{[6-Chloro-3-(3-chloro-benzyl)-2-oxo-2,3-dihydro-1H-indol-3-yl]-isopropyl-amino}-acetyl)-piperazin-1-yl]-N,N-dimethyl-2-oxo-acetamide,
rac-1-(2-{[6-Chloro-3-(3-chloro-benzyl)-2-oxo-2,3-dihydro-1H-indol-3-yl]-isopropyl-amino}acetyl)-piperidine-4-carboxylic acid dimethylamide,
rac-2-{sec-Butyl-[6-chloro-3-(3-chloro-benzyl)-2-oxo-2,3-dihydro-1H-indol-3-yl]-amino}-N-cyclobutyl-acetamide,
rac-6-Chloro-3-(3-chloro-benzyl)-3-(isopropyl-{2-[4-(2-methanesulfonyl-ethyl)-piperazin-1-yl]-2-oxo-ethyl}-amino)-1,3-dihydro-indol-2-one,
rac-2-{[6-Chloro-3-(3-chloro-benzyl)-2-oxo-2,3-dihydro-1H-indol-3-yl]-isopropyl-amino}-N-[1-(propane-2-sulfonyl)-piperidin-4-yl]acetamide,
rac-2-{[6-Chloro-3-(3-chloro-benzyl)-2-oxo-2,3-dihydro-1H-indol-3-yl]-isopropyl-amino}-N-(2,2,2-trifluoro-ethyl)-acetamide,
rac-6-Chloro-3-(3-chloro-benzyl)-3-[cyclohexyl-(2-methanesulfonyl-ethyl)-amino]-1,3-dihydro-indol-2-one,
rac-6-Chloro-3-(3-chloro-benzyl)-3-[isopropyl-(2-methanesulfonyl-ethyl)-amino]-1,3-dihydro-indol-2-one and
rac-6-Chloro-3-(3-chloro-benzyl)-3-{isopropyl-[2-(4-methanesulfonyl-piperazin-1-yl)-2-oxo-ethyl]-amino}-1,3-dihydro-indol-2-one.

13. A compound selected from the group consisting of
rac-6-chloro-3-(3-chloro-benzyl)-3-(1-hydroxymethyl-2-methyl-propylamino)-1,3-dihydro-indol-2-one,
rac-6-chloro-3-(3-chloro-benzyl)-3-(2-hydroxy-1-hydroxymethyl-1-methyl-ethylamino)-1,3-dihydro-indol-2-one,
rac-6-chloro-3-(3-chloro-benzyl)-3-[2-(2-hydroxyethoxy)-ethylamino]-1,3-dihydro-indol-2-one,
rac-6-chloro-3-(3-chloro-benzyl)-3-[(1R)-hydroxymethyl-2,2-dimethyl-propylamino]-1,3-dihydro-indol-2-one,
rac-2-[[6-Chloro-3-(3-chloro-benzyl)-2-oxo-2,3-dihydro-1H-indol-3-yl]-(1-ethyl-propyl)-amino]-N-cyclobutyl-acetamide,
rac-2-{[6-Chloro-3-(3-chloro-benzyl)-2-oxo-2,3-dihydro-1 H-indol-3-yl]-isopropyl-amino}-N-cyclohexyl-acetamide,
rac-[[6-Chloro-3-(3-chloro-benzyl)-2-oxo-2,3-dihydro-1H-indol-3-yl]-(1-ethyl-propyl)-amino]-acetic acid ethyl ester,
rac-2-{[6-Chloro-3-(3-chloro-benzyl)-2-oxo-2,3-dihydro-1H-indol-3-yl]-isopropyl-amino}-N-cyclobutyl-acetamide,
rac-2-[[6-Chloro-3-(3-chloro-benzyl)-2-oxo-2,3-dihydro-1H-indol-3-yl]-(1-ethyl-propyl)-amino]-N-cyclohexyl-acetamide,
rac-{[6-Chloro-3-(3-chloro-benzyl)-2-oxo-2,3-dihydro-1H-indol-3-yl]-isopropyl-amino}-acetic acid,
rac-6-chloro-3-(3-chloro-benzyl)-3-(isopropyl-methyl-amino)-1,3-dihydro-indol-2-one and
rac-[[6-Chloro-3-(3-chloro-benzyl)-2-oxo-2,3-dihydro-1H-indol-3-yl]-(1-ethyl-propyl)-amino]-acetic acid.

14. A compound of the formula

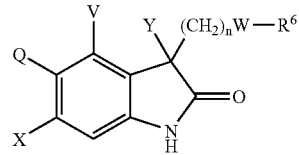

I wherein X is selected from the group consisting of hydrogen, halogen, cyano, lower alkyl, lower alkenyl, lower alkynyl, lower alkoxy, nitro, methyl sulfonyl, and cyclopropyl, V is hydrogen, Q is hydrogen or halogen, Y is selected from the group consisting of

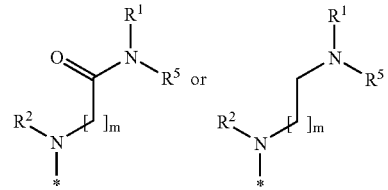

and

R$^1$ and R$^5$ are independently selected from the group consisting of hydrogen, lower alkyl, substituted lower alkyl, lower alkenyl, substituted lower alkenyl, lower alkynyl, substituted lower alkynyl, lower alkoxy, substituted lower alkoxy, aryl, substituted aryl, cycloalkyl, substituted cycloalkyl, cycloalkenyl, substituted cycloalkenyl, heterocycle and substituted heterocycle and in the case of R$^1$ and R$^5$ they may independently link to form a cyclic structure selected from substituted or unsubstituted heteroaryl, substituted or unsubstituted cycloalkyl, substituted or unsubstituted cycloalkenyl or substituted or unsubstituted heterocycle, R$^2$ is selected from cycloalkyl, phenyl,or substituted cycloalkyl, R$^6$ is a meta halogen substituted phenyl, X is Cl or Br, W is a bond, n is 1 and m is 1-3 and the pharmaceutically acceptable salts thereof.

15. A compound of the formula

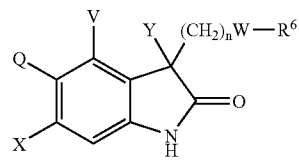

I wherein X is Cl or Br,
V is hydrogen,
Q is hydrogen or halogen,
Y is

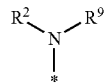

$R^2$ is

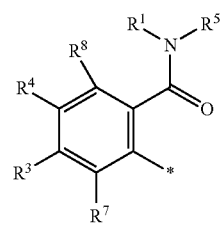

$R^6$ is a meta halogen substituted phenyl,
$R^9$ is hydrogen,
$R^1$ and $R^5$ are independently selected from the group consisting of hydrogen, lower alkyl, substituted lower alkyl, lower alkenyl, substituted lower alkenyl, lower alkynyl, substituted lower alkynyl, lower alkoxy, substituted lower alkoxy, aryl, substituted aryl, cycloalkyl, substituted cycloalkyl, cycloalkenyl, substituted cycloalkenyl, heterocycle and substituted heterocycle
and in the case of $R^1$ and $R^5$ they may independently link to form a cyclic structure selected from substituted or unsubstituted heteroaryl, substituted or unsubstituted cycloalkyl, substituted or unsubstituted cycloalkenyl or substituted or unsubstituted heterocycle,
$R^3$, $R^4$, $R^7$ and $R^8$ are selected from the group consisting of hydrogen, halogen, lower alkyl, lower alkenyl, lower alkynyl, lower alkoxy and cycloalkyl,
W is a bond,
n is 1,
m is 1-3,
and the pharmaceutically acceptable salts thereof.

16. The compound of claim 15 wherein
$R^7$ is hydrogen,
$R^8$ is hydrogen,
$R^3$ is selected from halogen, lower alkyl or lower alkoxy, and
$R^4$ is selected from hydrogen, halogen, lower alkyl or lower alkoxy.

17. A pharmaceutical formulation comprising a compound of the formula

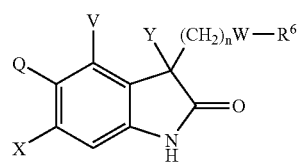

I wherein X is selected from the group consisting of hydrogen, halogen, cyano, lower alkyl, lower alkenyl, lower alkynyl, lower alkoxy, nitro, methyl sulfonyl, sulfonamide and cyclopropyl, V is hydrogen,
Q is hydrogen or halogen,
Y is selected from

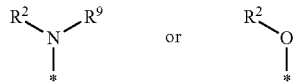

$R^2$ is selected from the group consisting of lower alkyl, substituted lower alkyl, aryl, substituted aryl, heteroaryl, substituted heteroaryl, cycloalkyl, substituted cycloalkyl, cycloalkenyl, substituted alkenyl,
$R^6$ is selected from the group consisting of aryl, substituted aryl,
$R^9$ is selected from the group consisting of hydrogen, lower alkyl, substituted lower alkyl, lower alkoxy and substituted lower alkoxy,
and in the case of $R^2$ and $R^9$ they may independently link to form a cyclic structure selected from substituted or unsubstituted heteroaryl, or substituted or unsubstituted heterocycle, said heteroaryl or heterocycle selected from the group consisting of

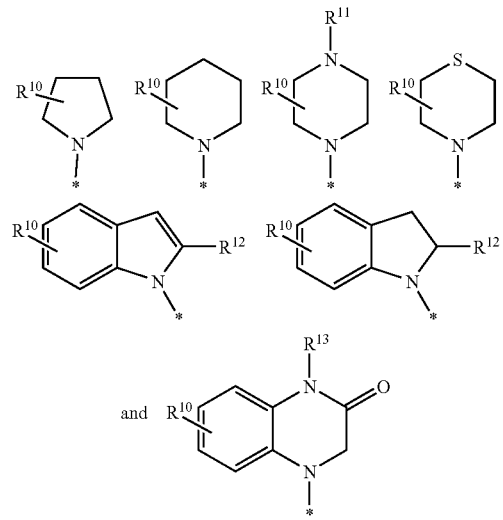

wherein
$R^{10}$ is selected from the group consisting of hydrogen, lower alkyl, lower-alkenyl, lower-alkynyl, dioxo-lower-alkylene, halogen, hydroxy, CN, $CF_3$, $NH_2$, heterocycloalkyl, N(H, lower-alkyl), N(lower-alkyl)$_2$, aminocarbonyl, carboxy, $NO_2$, lower-alkoxy, thio-lower-alkoxy, lower-alkylsulfonyl, aminosulfonyl, lower-alkylcarbonyl, lower-alkylcarbonyloxy, lower-alkoxycarbonyl, lower-alkyl-carbonyl-NH, fluoro-lower-alkyl, fluoro-lower-alkoxy, lower-alkoxy-carbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)$_2$-lower-alkoxy, benzyloxy-lower-alkoxy, mono- or di-lower alkyl substituted amino-sulfonyl and lower-alkyl which can optionally be substituted with halogen, hydroxy, $NH_2$, N(H, lower-alkyl) or N(lower-alkyl)$_2$,
$R^{11}$ is selected from the group consisting of hydrogen, lower alkyl, lower-alkenyl, lower-alkynyl, dioxo-lower-alkylene, hydroxy, CN, $CF_3$, $NH_2$, N(H, lower-alkyl), N(lower-alkyl)$_2$, lower-alkoxy, thio-lower-alkoxy, lower-alkylsulfonyl, aminosulfonyl, lower-alkylcarbonyl, lower-alkylcarbonyloxy, lower-alkoxycarbonyl, fluoro-lower-alkyl, fluoro-lower-alkoxy, lower-alkoxycarbonyl-lower-alkoxy, carboxy-lower-alkoxy, carbamoyl-lower-alkoxy, hydroxy-lower-alkoxy, NH$_2$-lower-alkoxy, N(H, lower-alkyl)-lower-alkoxy, N(lower-alkyl)$_2$-lower-alkoxy, benzyloxy-lower-alkoxy, mono- or di-lower alkyl substituted amino-sulfonyl and lower-alkyl which can optionally be substituted with halogen, hydroxy, NH$_2$, N(H, lower-alkyl) or N(lower-alkyl)$_2$, N(H, lower-alkyl)-carbonyl, N(lower-alkyl)$_2$-carbonyl, $R^{12}$ is selected from the group consisting of hydrogen, lower alkyl, aminocarbonyl, lower-alkylsulfonyl, aminosulfonyl, lower-alkylcarbonyl, lower-alkoxycarbonyl, fluoro-lower-alkyl, N(H, lower-alkyl)-carbonyl, N(lower-alkyl)$_2$-carbonyl, mono- or di-lower alkyl substituted amino-sulfonyl and lower-alkyl which can optionally be substituted with halogen, hydroxy, NH$_2$, N(H, lower-alkyl) or N(lower-alkyl)$_2$, $R^{13}$ is selected from the group consisting of hydrogen, lower alkyl, lower-alkenyl, lower-alkynyl, dioxo-lower-alkylene, hydroxy, CN, NH$_2$, heterocycloalkyl, N(H, lower-alkyl), N(lower-alkyl)$_2$, lower-alkoxy, thio-lower-alkoxy, lower-alkylcarbonyloxy, fluoro-lower-alkyl, fluoro-lower-alkoxy, lower-alkoxy-carbonyl-lower-alkoxy, carboxy-lower-alkoxy, carbamoyl-lower-alkoxy, hydroxy-lower-alkoxy, NH$_2$-lower-alkoxy, N(H, lower-alkyl)-lower-alkoxy, N(lower-alkyl)$_2$-lower-alkoxy, benzyloxy-lower-alkoxy, lower-alkyl which can optionally be substituted with halogen, hydroxy, NH$_2$, N(H, lower-alkyl) or N(lower-alkyl)$_2$, N(H, lower-alkyl)-carbonyl, N(lower-alkyl)$_2$-carbonyl, is a single bond, n is 1-3, with the proviso that when $R^9$ is hydrogen then $R^2$ is not substituted alkyl and the pharmaceutically acceptable salts thereof together with a pharmaceutically acceptable carrier.

\* \* \* \* \*